(12) United States Patent
Barnett

(10) Patent No.: US 8,609,416 B2
(45) Date of Patent: Dec. 17, 2013

(54) METHODS AND COMPOSITIONS COMPRISING HEAT SHOCK PROTEINS

(75) Inventor: Michael E. Barnett, Manhattan, KS (US)

(73) Assignee: Ventria Bioscience, Fort Collins, CO (US)

( * ) Notice: Subject to any disclaimer, the term of this patent is extended or adjusted under 35 U.S.C. 154(b) by 244 days.

(21) Appl. No.: 12/972,112

(22) Filed: Dec. 17, 2010

(65) Prior Publication Data

US 2011/0189751 A1 Aug. 4, 2011

Related U.S. Application Data

(60) Provisional application No. 61/288,234, filed on Dec. 18, 2009.

(51) Int. Cl.
*C12N 5/02* (2006.01)

(52) U.S. Cl.
USPC .......................................... 435/405; 435/407

(58) Field of Classification Search
USPC ................................................. 435/405, 407
See application file for complete search history.

(56) References Cited

U.S. PATENT DOCUMENTS

| | | |
|---|---|---|
| 2004/0072347 A1 | 4/2004 | Schuler et al. |
| 2010/0015713 A1 | 1/2010 | Deeter |
| 2012/0315697 A1 | 12/2012 | Pettit et al. |
| 2013/0157356 A1 | 6/2013 | Barnett |

OTHER PUBLICATIONS

Novoselova et al., "Treatment with extracellular HSP70/HSC70 protein can reduce polyglutamine toxicity and aggregation," J Neurochem 94:597-606, 2005.*
Johnson et al., (1993) Exogenous HSP70 becomes cell associated but not internalized, by stressed arterial smooth muscle cell. In vitro Cellular and Developmental Biology—Animal, vol. 29A, No. 10, pp. 807-821.
Bethke et al., (2002) Different efficiency of heat shock proteins (HSP) to activate human monocytes and dendritic cells; superiority of HSP60, The Journal of Immunology. vol. 169, pp. 6141-6148.
Khan et al., (2008) Toll-like receptor 4-mediated growth of endometriosis by human heat-shock protein 70, Human Reproduction, vol. 23, No. 10, pp. 2210-2219.
Lasunskaia E.B., et al., (2003) Transfection of NSO myeloma fusion partner cells with HSP70 gene results in higher hybridoma yield by improving cellular resistance to apoptosis, Biotechnology and Bioengineering 81(4):496-504.

* cited by examiner

*Primary Examiner* — Rosanne Kosson
(74) *Attorney, Agent, or Firm* — Dennis A. Bennett

(57) ABSTRACT

Compositions, and uses thereof, which are beneficial for eukaryotic cells in culture, and methods for their use in promoting cell growth, viability and recombinant protein expression. The methods disclosed in the present application are useful, for example, for improving cell viability and in accelerating the rate of cell growth of cells grown in culture. In one aspect, the supplements of the invention are useful for improving or enhancing the yield of the recombinant proteins from the cell cultures.

25 Claims, 15 Drawing Sheets

D

E

F

G

A

B

A

B

C

A

B

A

B

C

METHODS AND COMPOSITIONS COMPRISING HEAT SHOCK PROTEINS

CROSS-REFERENCE TO RELATED APPLICATIONS

This application claims the benefit of U.S. provisional patent application No. 61/288,234 filed on Dec. 18, 2009, the entire contents of which are incorporated herein by reference.

STATEMENT REGARDING FEDERALLY SPONSORED RESEARCH OR DEVELOPMENT

Not Applicable.

TECHNICAL FIELD

The invention relates to compositions, and uses thereof, which are beneficial for eukaryotic cells in culture, and methods for their use in promoting cell growth, viability and recombinant protein expression.

BACKGROUND

Investigation of biological processes often requires the examination of those processes in cells, tissues and organs that comprise less than the entire organism. For many years these cells, tissues and organs have been separated from the organism and studied independently under conditions that support their survival in an ex vivo or in vitro mode. Typically, the cells, tissues or organs are removed from the organism and are maintained in a culture media that supports the survival and/or biological process being studied. Given the large diversity of cell, tissue and organ types, the formulation of culture medium that support their survival, growth and biological properties outside of the intact organism are not trivial. Many cells and tissues are difficult to maintain in culture for reasons that are not entirely understood. In addition, cells and tissues are often used in processes involved in the manufacturing of recombinant proteins, vaccines, virus stocks and other products in vitro which are key to biomedical research and biologics-based medicaments. Therefore, there is a need to identify conditions and culture media components that support the growth and survival of cells, tissue and organ cultures under in vitro and ex vivo conditions.

Such cell components include for example, albumin, transferrin, glutathione S-transferees, superoxide dismutase, lactoferrin, and growth factors.

Albumin is the most abundant protein found in the plasma. It is produced by the liver in mammals and functions in a variety of capacities. Albumin is a soluble, monomeric protein which comprises about one-half of the blood serum protein. Albumin functions primarily as a carrier protein for steroids, fatty acids, and thyroid hormones and plays a role in stabilizing extracellular fluid volume. Albumin is a globular unglycosylated serum protein of molecular weight 67,000 and contains five or six internal disulphide bonds. Albumin is synthesized as preproalbumin which has an N-terminal peptide that is removed before the nascent protein is released from the rough endoplasmic reticulum. The product, proalbumin, is in turn cleaved in the Golgi vesicles to produce the secreted albumin.

Albumin is essential for maintaining the osmotic pressure needed for proper distribution of body fluids between intravascular compartments and body tissues. It also acts as a plasma carrier by non-specifically binding several hydrophobic steroid hormones and as a transport protein for hemin and fatty acids. Bovine serum albumin (BSA) has long been used as a supplement in cell culture media as it is a component of fetal bovine serum (FBS) which is commonly added to a basal media at 1-20% total volume. BSA is a major component in a number of defined serum free media formulations since it is readily available in bulk, is relatively cheap, and can be purified to homogeneity relatively easily. Representative sources of albumin include for example, plasma derived from bovine, horse, pig and other mammalian species.

With the advent of the large scale production of recombinant proteins, vaccines and other products destined for human clinical use, stricter requirements on the formulations used in the production of those products have been instigated. Because of the threat of animal-derived materials harboring pathogens that may affect the safety of the products, many existing recombinant production processes have been modified such that all materials or culture components used in the entire process are devoid of animal-derived products. That is, the cell culture components cannot have been isolated or purified from whole animal sources. Therefore, the recombinant production of media supplements, as an alternative to the purification of these supplements directly from the whole animal is preferred. Accordingly, human and cell culture components from other species can be manufactured using recombinant means, using defined tissue culture media, and using highly characterized tissue culture cells, which are certified to be free of viruses and toxins.

One method of preparing recombinant protein based cell culture components is to engineer yeast or plants to over express the protein and then to purify the protein. Plant derived recombinant proteins are particularly attractive as a source of cell culture components for recombinant protein production of human proteins that are intended for therapeutic uses since there are no examples of plant viruses that can also infect humans.

There is currently a high demand for recombinant cell culture components to support the recombinant production of human therapeutic proteins, as well as to grow & differentiate stem cells, and with the continued success and huge potential of such products in the market, more effective ways of producing recombinant cell culture components is desirable. In particular, existing processes for the recombinant production of proteins and the growth and differentiation of stem cells are slow, expensive and arduous. In part these processes are limited by fundamental aspects relating to the rate of cell growth and viability of the recombinant host cells or stem cells respectively. Key aspects of these limitations include i) the ability to rapidly isolate and expand single cell clones from complex mixtures of cells, ii) the ability to promote rapid cell growth, particularly at low densities and in serum free media, iii) the ability to sustain cell growth and viability at very high densities in bioreactors, iv) the ability to cryopreserve and thaw cells and cell banks while maintaining high viability, v) the ability to grow and differentiate stem cell cultures effectively. Accordingly there is a need for improved media and culturing conditions that address these needs and enable the improved growth and viability of cells in culture. The supplements and methods of the invention, by improving the viability and rate of cell growth meet these needs and can also result in an improved yield and quality of recombinant product obtained from a mammalian cell culture production process.

SUMMARY OF INVENTION

The present invention is based in part on the demonstration that the binding of long chain fatty acids to high affinity binding sites in albumin created via expression of the protein in plants provides unique biological functions and useful conformational stability. Without being bound by any one particular theory of operation, it is proposed that the enhanced stability of the plant produced albumin, derived from tightly bound fatty acids, promotes protease resistance, and stabilizes the protein against denaturation. Moreover the increased stability and hydrophobicity of the lipid bound albumin enhances protein uptake of both the albumin and bound heat shock proteins via endocytosis by enabling passage of the proteins through the endosome without degradation.

In one aspect, the invention is further based on the discovery that heat shock proteins co-purified, or co-mixed in solution with recombinant cell culture component proteins, result in the formation of protein complexes which are capable of significantly enhancing the cell culturing properties of the recombinant cell culture component proteins.

The methods disclosed in the present application are useful, for example, for improving cell viability and in accelerating the rate of cell growth of cells grown in culture. In one aspect, the supplements of the invention are useful for improving or enhancing the yield of the recombinant proteins from the cell cultures. Further improvements provided by the invention are described in detail below. In one embodiment, the present invention includes a supplement comprising a protein cell culture component and a heat shock protein, wherein the protein cell culture component comprises at least about 0.01% wt/wt of said heat shock protein, and wherein the protein cell culture component has less than about 1 EU of endotoxin,/mg of the protein cell culture component. In one aspect, of any of the supplements of the invention the heat shock protein is bound to the protein cell culture component. In one aspect, of any of the supplements of the invention the protein cell culture component further comprises at least about 1% wt/wt of bound long chain fatty acids.

In another aspect of any of the claimed supplements, the supplement provides for a cell viability of greater than about $10 \times 10^5$ cells/ml AE1 hybidoma cells after 70 hours culture when the AE1 cells are seeded at an initial density of $0.5 \times 10^5$ cells per ml in serum free DMEM with 5 mg/ml supplement and grown under standard culture conditions of humidity and temperature. In another aspect, the supplement provides a cell viability of greater than about $12 \times 10^5$ cells/ml AE1 hybidoma cells after 70 hours culture when said AE1 cells are seeded at an initial density of $0.5 \times 10^5$ cells per ml in serum free DMEM with 5 mg/ml supplement and grown under standard culture conditions of humidity and temperature. In another aspect, the supplement provides a cell viability of greater than about $13 \times 10^5$ cells/ml AE1 hybidoma cells after 70 hours culture when said AE1 cells are seeded at an initial density of $0.5 \times 10^5$ cells per ml in serum free DMEM with 5 mg/ml supplement and grown under standard culture conditions of humidity and temperature. In another aspect, the supplement provides a cell viability of greater than about $14 \times 10^5$ cells/ml AE1 hybidoma cells after 70 hours culture when said AE1 cells are seeded at an initial density of $0.5 \times 10^5$ cells per ml in serum free DMEM with 5 mg/ml supplement and grown under standard culture conditions of humidity and temperature. In another aspect, the supplement provides a cell viability of greater than about $15 \times 10^5$ cells/ml AE1 hybidoma cells after 70 hours culture when said AE1 cells are seeded at an initial density of $0.5 \times 10^5$ cells per ml in serum free DMEM with 5 mg/ml supplement and grown under standard culture conditions of humidity and temperature. In another aspect, the supplement provides a cell viability of greater than about $16 \times 10^5$ cells/ml AE1 hybidoma cells after 70 hours culture when said AE1 cells are seeded at an initial density of $0.5 \times 10^5$ cells per ml in serum free DMEM with 5 mg/ml supplement and grown under standard culture conditions of humidity and temperature.

In one embodiment of any of the claimed supplements, the protein cell culture component has less than about 200 ppm detergent, less than about 150 ppm detergent, less than about 100 ppm detergent, or less than about 80 ppm, or less than about 60 ppm, or less than about 40 ppm detergent. In one aspect the detergent is based on polyoxyethylene glycol. In one aspect the detergent is selected from a detergent sold under the trademarks TWEEN®, TRITON® or BRIJ®.

In one embodiment of any of the claimed supplements, the protein cell culture component is selected from the group consisting of albumin, transferrin, glutathione S-transferase, superoxide dismutase, and a human growth factor. In one aspect of any of the claimed supplements, the protein cell culture component is a recombinant protein produced in a plant. In one aspect the protein cell culture component is albumin. In another aspect the protein cell culture component is transferrin. In one aspect the protein cell culture component is albumin. In another aspect the protein cell culture component is glutathione S-transferase. In another aspect the protein cell culture component is transferrin. In another aspect the protein cell culture component is recombinant albumin. In another aspect the protein cell culture component is superoxide dismutase.

In another aspect of any of the claimed supplements, the heat shock protein is a HSP70 family member. In another aspect of any of the claimed supplements, the heat shock protein is a rice heat shock protein. In another aspect of any of the claimed supplements, the heat shock protein is selected from the group consisting of Rice HSP70 genes, and rice endosperm lumenal binding protein. In another aspect of any of the claimed supplements, the heat shock protein is selected from the group consisting of Rice (gb|ACJ54890.1|) (SEQ. ID. NO. 7), EEC69073/OsI_37938, (SEQ. ID. NO. 22) AAB63469 (SEQ. ID. NO. 18).

In another embodiment, the present invention includes a supplement for use in serum free culture consisting essentially of albumin and HSP70.

In another embodiment, the present invention includes a supplement for use in serum free culture consisting essentially of monomeric albumin to which is bound about 1% to about 2% long chain fatty acids and about 0.01% to about 0.1% heat shock proteins.

In another embodiment, the present invention includes a method for improving the viability of cells comprising the addition of a supplement of any of the claims to the cell culture medium.

In another embodiment, the present invention includes a method for improving the viability of cells grown under serum free conditions comprising the addition of a supplement of any of the claims to the cell culture medium.

In another embodiment, the present invention includes a method for improving the viability of cells when plated at low density comprising the addition of a supplement of any of the claims to the cell culture medium.

In another embodiment, the present invention includes a method for improving the viability of cells grown from single cell clones comprising the addition of a supplement of any of the claims to the cell culture medium.

In another embodiment, the present invention includes a method for improving the viability of primary cells grown in culture comprising the addition of a supplement of any of the claims to the cell culture medium.

In another embodiment, the present invention includes a method for improving the activity and/or stability of HSP70 comprising pre-mixing HSP70 with albumin in aqueous solution.

In another embodiment, the present invention includes a method for improving the yield of a recombinant product produced from cells in culture comprising the addition of a supplement of any of the claims to the cell culture medium.

In another embodiment, the present invention includes a method for improving the viability of cells after transfection comprising the addition of a supplement of any of the claims to the cell culture medium prior to, during, or immediately after transfection.

In another embodiment, the present invention includes a method for improving the viability of cells after cryopreservation comprising the addition of a supplement of any of the claims to the cell culture medium prior to, during, or immediately after cryopreservation or thawing.

In one aspect of any of these methods, the improvement in cell viability is greater than about 10% compared to cell viability of grown under identical conditions but without the hsp. In another aspect, improvement in cell viability is greater than about 20% compared to cell viability of grown under identical conditions but without the hsp. In another aspect, the improvement in cell viability is greater than about 30% compared to cell viability of grown under identical conditions but without the hsp. In another aspect the improvement in cell viability is greater than about 40% compared to cell viability of grown under identical conditions but without the hsp. In another aspect, the improvement in cell viability is greater than about 50% compared to cell viability of grown under identical conditions but without the hsp.

In one aspect of any of these methods, cells are embryonic stem cells. In one aspect of any of these methods, the cells are tissue culture cells. In one aspect of any of these methods, the cells are CHO cells. In one aspect of any of these methods, the cells are hybridoma cells. In one aspect of any of these methods, the cells are vero cells. In one aspect of any of these methods, the cells are sorted by flow cytometry. In one aspect of any of these methods, the cells are primary cells are B-cells. In one aspect of any of these methods, the cells primary cells are T-cells. In one aspect of any of these methods, the cells are isolated by flow cytometry. In one aspect of any of these methods, the cells are isolated by a micro fluidic device.

In another aspect of any of the claimed supplements, the supplement comprises albumin and HSP70 that have been premixed in aqueous solution. In one aspect the supplements of the invention are lyophilized.

In another aspect of the claimed invention, the heat shock protein is exogenously added to the protein cell culture component. In one aspect, the heat shock protein is bound to said protein cell culture component. In another aspect of any of the claimed supplements, the protein cell culture component is recombinant human serum albumin.

In another embodiment of any of the claimed supplements, the protein cell culture component comprises at least about 0.02% wt/wt HSP70. In another aspect, the protein cell culture component comprises at least about 0.04% wt/wt HSP70. In another aspect, the protein cell culture component comprises at least about 0.05% wt/wt HSP70. In another aspect, the protein cell culture component comprises at least about 0.06% wt/wt HSP70. In another aspect, the protein cell culture component comprises at least about 0.07% wt/wt HSP70. In another aspect, the protein cell culture component comprises at least about 0.08% wt/wt HSP70. In another aspect, the protein cell culture component comprises at least about 0.09% wt/wt HSP70. In another aspect, the protein cell culture component comprises at least about 0.15% wt/wt HSP70.

In another embodiment of any of the claimed supplements, the protein cell culture component comprises about 0.2% to about 2.5% long chain fatty acids. In another embodiment of any of the claimed supplements, the protein cell culture component comprises about 0.5% to about 2% long chain fatty acids. In another embodiment of any of the claimed supplements, the protein cell culture component comprises about 0.5% to about 1.5% long chain fatty acids. In another embodiment of any of the claimed supplements, the long chain fatty acids are selected from the group consisting of pamitic acid, oleic acid and linoleic acid, and mixtures thereof.

In another embodiment of any of the claimed supplements, the supplement comprises a plant HSP70. In another embodiment of any of the claimed supplements, the supplement comprises a vertebrate HSP70. In another embodiment of any of the claimed supplements, the supplement comprises a yeast HSP70. In another embodiment of any of the claimed supplements, the supplement comprises a insect HSP70. In another embodiment of any of the claimed supplements, the supplement comprises a human HSP70. In another embodiment of any of the claimed supplements, the supplement comprises a rice HSP70. In another embodiment of any of the claimed supplements, the supplement comprises a HSP70 which is non-phosphorylated. In another embodiment of any of the claimed supplements, the supplement comprises a recombinant Hsp70.

In another embodiment the present invention includes a method of isolating and maintaining a human pluripotent embryonic stem cell culture, comprising the steps of: a) isolating cells from the inner cell mass of a blastocyst; b) plating the inner cell mass cells on a human feeder cell, wherein inner cell mass-derived cell masses are formed; c) re-plating the colony in the absence of a feeder cell; and d) adding a human feeder cell conditioned medium to thereby isolate and maintain a human pluripotent embryonic stem cell in an undifferentiated state for at least two passages, wherein said stem cell culture comprises a supplement of the invention.

In another embodiment the present invention includes a human pluripotent stem cell culture, comprising a human embryonic stem cell and a human feeder cell conditioned medium, wherein the human feeder cell conditioned medium maintains the human embryonic stem cell in an undifferentiated state for at least two passages and comprises a supplement of the invention.

In another embodiment the present invention includes a method of maintaining a human pluripotent embryonic stem cell culture in an undifferentiated state for at least two passages, comprising culturing a human embryonic stem cell in a serum free medium comprising a supplement of the invention.

BRIEF DESCRIPTION OF FIGURES

A better understanding of the features and advantages of the present invention can be obtained by reference to the following detailed description that sets forth illustrative embodiments, in which the principles of the invention are utilized, and the accompanying drawings of which:

FIG. 1A shows the chromatogram for a serum derived (non-recombinant albumin). FIG. 1B shows the chromatogram for a rice recombinant albumin (Cellastim P0107) made using the "old process" B000 for purification. FIG. 1C shows the chromatogram for a rice recombinant albumin (Cellastim P0171) made using the "new process" B0000C for purification. FIG. 1D shows an overlay of the chromatograms for the serum derived albumin (1A; dotted line) and Cellastim prepared using the new process ((1C; solid line). FIG. 1E shows an overlay of the chromatograms for Cellastim prepared using the old process B000 (Cellastim P0107)(1B; dotted line) and Cellastim prepared using the new process B0000C (Cellastim P0171)(1C; solid line).

FIG. 1F shows the results of an HPLC-SEC analysis of Cellastim. FIG. 1G shows the results of a reverse phase HPLC analysis of Cellastim for 2 lots of Cellastim. The retention time for the dimer is 46.2 minutes in this chromatogram FIG. 2 Shows a comparison by SDS PAGE analysis of recombinant albumin produced from rice compared to other sources of albumin and methods of purification.

(FIG. 3A). FIG. 3B shows a comparison of the endotoxin levels in batches of albumin produced using the old (B000) and new processes (B0000C) for recombinant albumin production. FIG. 3C shows a comparison of cell growth and viability of cells grown in the presence of the Cellastim produced using the old (B000) and new processes (B0000C) for recombinant albumin production.

FIG. 4A Shows a western blot using an anti-heat shock protein antibody to show the heat shock protein content of different fractions obtained from recombinant albumin after ATP affinity chromatography. (See Example 3) FIG. 4B shows the results of SDS-PAGE analysis of various fractions from an ATP-agarose column. FIG. 4C shows ATPase activity in 2 affinity purified fractions from Cellastim.

FIG. 8A Shows a comparison of the cell growth and viability effect of Cellastim recombinant albumin after passing the albumin produced using the new process over an ATP affinity column to remove heat shock proteins. (See text for details). FIG. 8B shows that the addition of ATP-agarose affinity purified from Cellastim added back to depleted Cellastim restored the activity of the Cellastim.

FIG. 9A shows the results of lipid analysis for Cellastim compared plasma derived and yeast derived albumin preparations. FIG. 9B shows the specific long chain fatty acid content of Cellastim compared to plasma derived and yeast derived albumin. FIG. 9C shows the effect of adding exogenous lipids to defatted Cellastim and Novazyme recombinant albumins.

DETAILED DESCRIPTION OF INVENTION

Definitions

Figure 1:
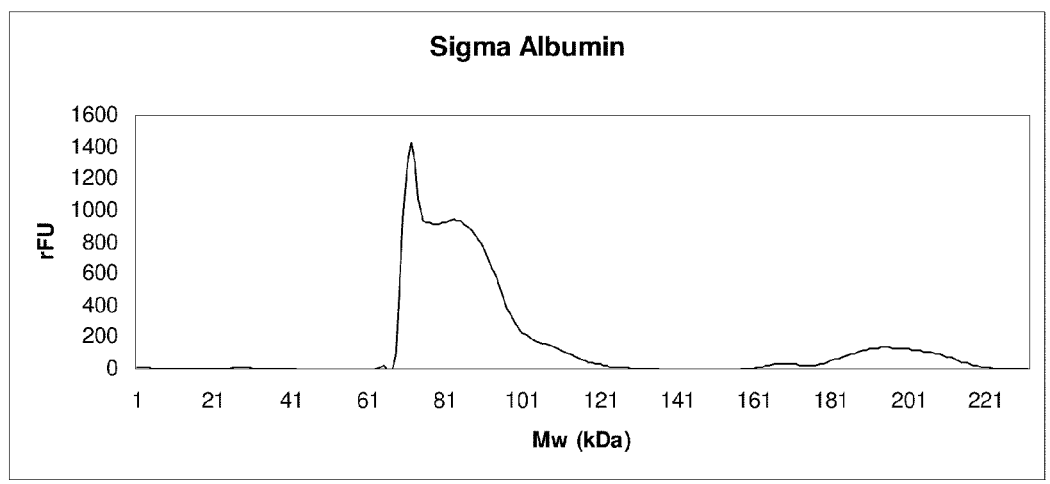
FIG. 1 Shows a comparison by HPLC size exclusion chromatography of recombinant albumin produced from rice compared to other sources of albumin and methods of purification.
Figure 1:
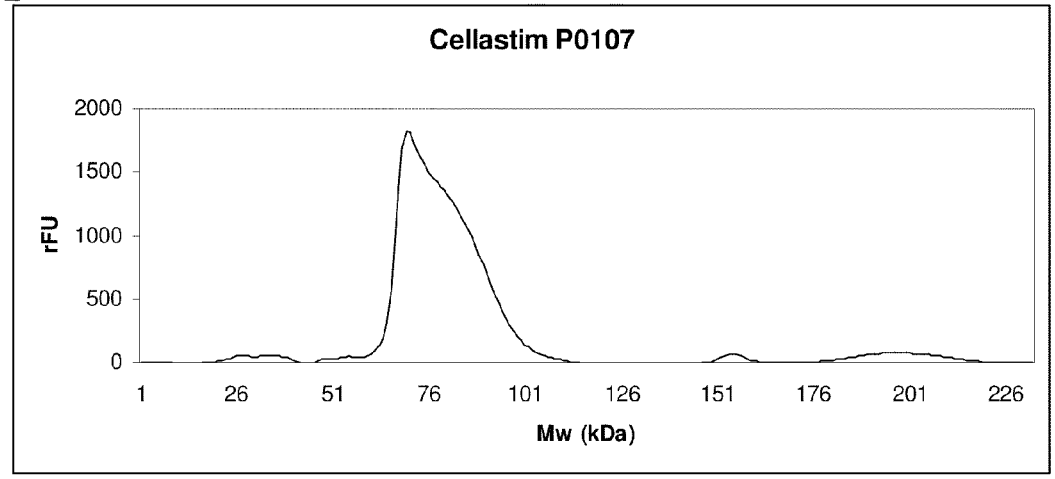
Figure 1:
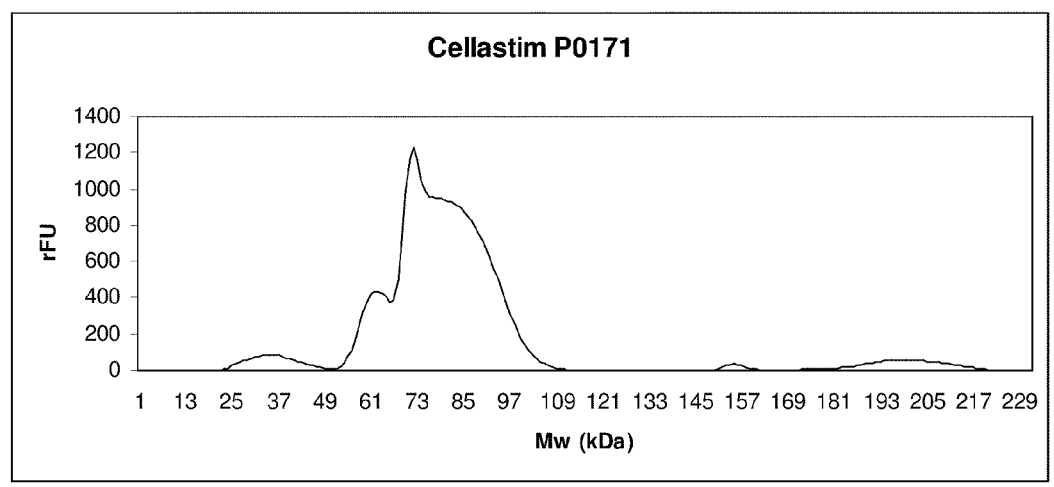
Figure 1:
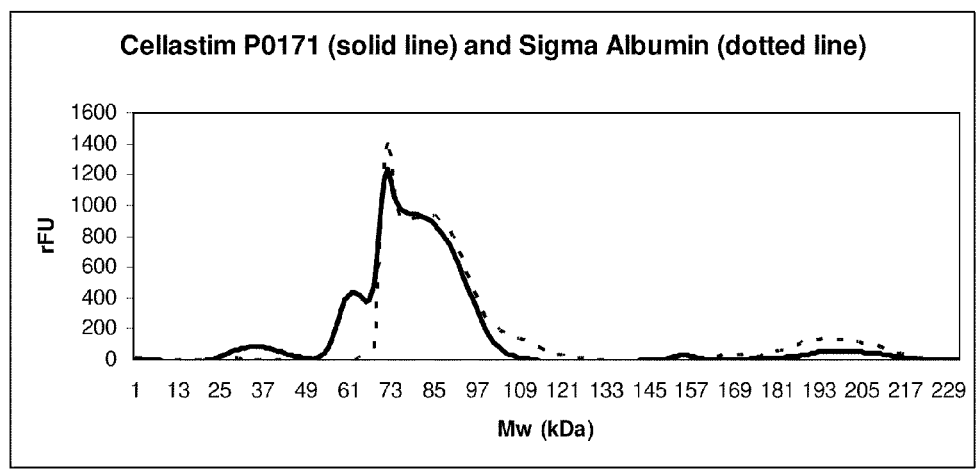
Figure 1:
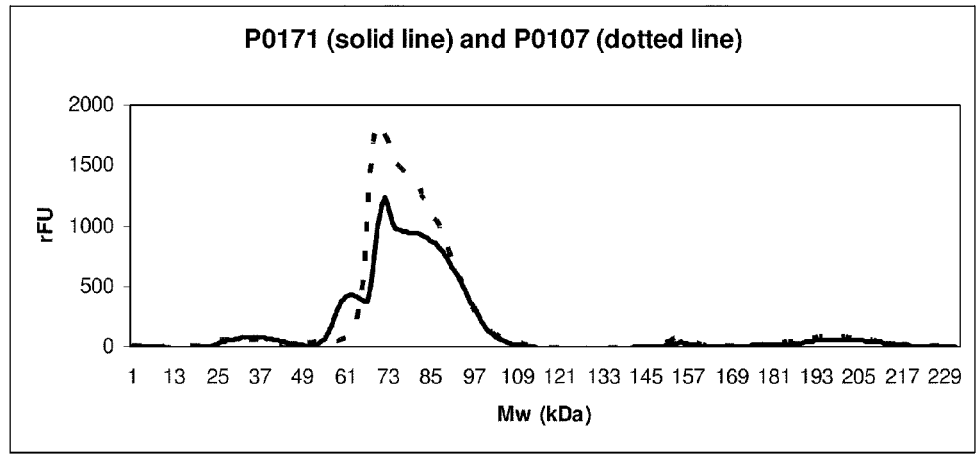
Figure 1:
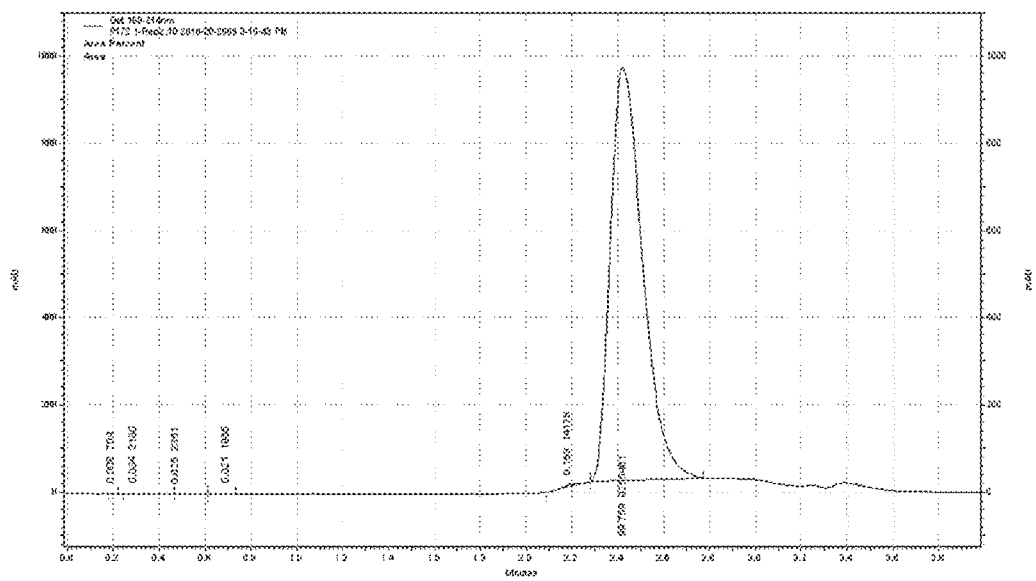
Figure 1:
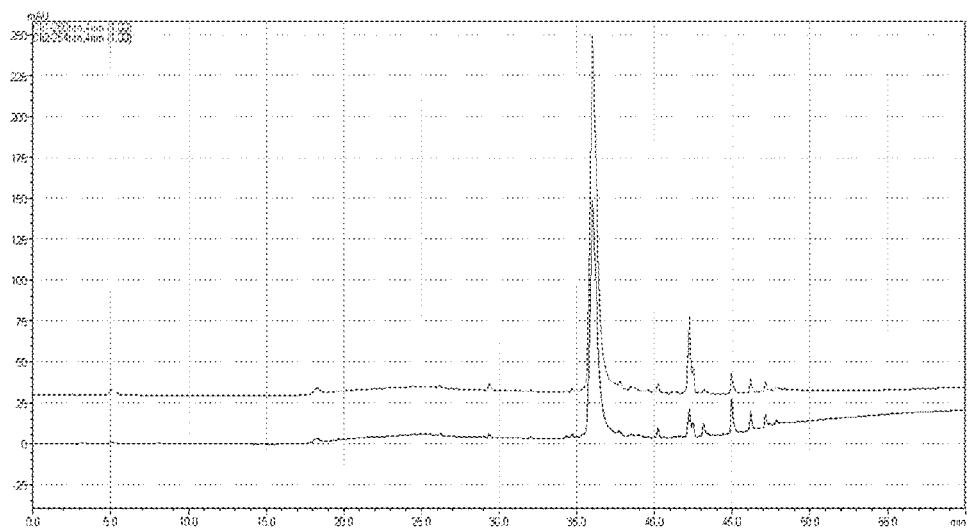

In order that the present disclosure may be more readily understood, certain terms are first defined. Additional definitions are set forth throughout the detailed description.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%. As used herein, the term "increase" or the related term "increased" refers to a statistically significant increase. For the avoidance of doubt, the terms generally refer to at least a 10% increase in a given parameter, and can encompass at least 20%, 50%, 75%, 100%, 150% or more.

The term "antigen-binding fragment" refers to a polypeptide portion of an immunoglobulin or antibody that binds antigen or competes with intact antibody (i.e., with the intact antibody from which they were derived) for antigen binding (i.e., specific binding). Binding fragments can be produced by recombinant DNA techniques, or by enzymatic or chemical cleavage of intact immunoglobulins. Binding fragments include Fab, Fab', $F(ab')_2$, Fabc, Fv, single chains, and single-chain antibodies.

The term "apoptosis" ("normal" or "programmed" cell death) refers to the physiological process by which unwanted or useless cells are eliminated during development and other normal biological processes. Apoptosis is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine dependent tissue atrophy. Apoptosis may also be triggered in cells grown under tissue culture conditions in response to stress. Cells undergoing apoptosis show characteristic morphological and biochemical features, which can be readily measured and quantified. These features include chromatin aggregation, nuclear and cytoplasmic condensation, partition of cytoplasm and nucleus into membrane bound vesicles (apoptotic bodies) which contain ribosomes, morphologically intact mitochondria and nuclear material. In vivo, these apoptotic bodies are rapidly recognized and phagocytized by either macrophages or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis".

As used herein, the terms "cell," "cells," "cell line," "host cell," and "host cells," are used interchangeably and, encompass plant, and animal cells and include invertebrate, non-mammalian vertebrate and mammalian cells. All such designations include cell populations and progeny. Thus, the terms "transformants" and "transfectants" include the primary subject cell and cell lines derived therefrom without regard for the number of transfers. Exemplary non-mammalian vertebrate cells include, for example, avian cells, reptilian cells and amphibian cells. Exemplary invertebrate cells include, but are not limited to, insect cells such as, for example, caterpillar (*Spodoptera frugiperda*) cells, mosquito (*Aedes aegypti*) cells, fruitfly (*Drosophila melanogaster*) cells, Schneider cells, and *Bombyx mori* cells. See, e.g., Luckow et al., Bio/Technology 6:47-55 (1988). The cells may be differentiated, partially differentiated or undifferentiated, e.g. stem cells, including embryonic stem cells and pluripotent stem cells. Additionally tissue samples derived from organs or organ systems may be used according to the invention. Exemplary mammalian cells include, for example, cells derived from human, non-human primate, cat, dog, sheep, goat, cow, horse, pig, rabbit, rodents including mouse, hamster, rat and guinea pig and any derivatives and progenies thereof.

The term "cell culture," refers to cells grown in suspension or grown adhered to a variety of surfaces or substrates in vessels such as roller bottles, tissue culture flasks, dishes, multi-well plates and the like. Large scale approaches, such as bioreactors, including adherent cells growing attached to microcarriers in stirred fermentors, are also encompassed by the term "cell culture." Moreover, it is possible not only to culture contact-dependent cells, but also to use suspension culture techniques in the methods of the claimed invention. Exemplary microcarriers include, for example, dextran, collagen, plastic, gelatin and cellulose and others as described in Butler, Spier & Griffiths, Animal cell Biotechnology 3:283-303 (1988). Porous carriers, such as, for example, Cytoline™ or Cytopore™, as well as dextran-based carriers, such as DEAE-dextran (Cytodex 1™ quaternary amine-coated dextran (Cytodex™) or gelatin-based carriers, such as gelatin-coated dextran (Cytodex 3™) may also be used. Cell culture procedures for both large and small-scale production of proteins are encompassed by the present invention. Procedures including, but not limited to, a fluidized bed bioreactor, hollow fiber bioreactor, roller bottle culture, or stirred tank bioreactor system may be used, with or without microcarriers, and operated alternatively in a batch, fed-batch, or perfusion mode.

The terms "cell culture medium," "cell culture media," and "culture medium" refer to the solutions used for growing, storing, handling and maintaining cells and cell lines. Such solutions generally include various factors necessary for cell attachment, growth, and maintenance of the cellular environment. For example, a typical solution may include a basal media formulation, various supplements depending on the cell type and, occasionally, antibiotics. In some embodiments, a solution may include at least one component from one or more of the following categories: 1) an energy source, usually in the form of a carbohydrate such as glucose; 2) all essential amino acids, and usually the basic set of twenty amino acids plus cystine; 3) vitamins and/or other organic compounds required at low concentrations; 4) free fatty acids; and 5) trace elements, where trace elements are defined as inorganic compounds or naturally occurring elements that are typically required at very low concentrations, usually in the micromolar range. The solution may optionally be supplemented with one or more components from any of the following categories: 1) hormones and other growth factors as, for example, insulin, transferrin, and epidermal growth factor; 2) salts and buffers as, for example, calcium, magnesium, phosphate, Tris, HEPES, and sodium bicarbonate; 3) nucleosides and bases such as, for example, adenosine and thymidine, hypoxanthine; and 4) protein and tissue hydrolysates. In general, any suitable cell culture medium may be used. The medium may be comprised of serum, e.g. fetal bovine serum, calf serum or the like. Alternatively, the medium may be serum free, animal free, or protein free.

The term "cell lineage" when referring to a stem cell culture refers to all of the stages of the development of a cell type, from the earliest precursor cell to a completely mature cell (i.e. a specialized cell).

The terms "cell viability" or "viability" refers to relative amounts of living and dead cells, present with a population of cells at any given time. Cell viability may be determined by measuring the relative numbers of living and dead cells in any given sample of the population. Cell viability may also be estimated by measuring the rate of cell proliferation of the entire population which represents the overall balance of the rates of cell growth and cell death. The concentration of viable cells may also be directly measured, by counting the number of viable cells, or by using any number of commercially available cell proliferation assays which directly scores the concentration of viable cells.

"Conditioned medium" refers to a cell culture medium that is obtained from a culture of a feeder cell that supports the growth of other cells. In one example, conditioned medium from feeder cells can be used for stem cells, which can be cultured and maintained in a pluripotent state. The feeder cell depletes the conditioned medium of some components, but also enriches the medium with cell-derived material, probably including small amounts of growth factors. The term "feeder cell factor" as used herein means the cell-derived material that is released into the conditioned medium by the feeder cell. The cell factor that is released into the cell culture medium is useful in enhancing the growth cells or embryonic stem cells, or in the maintenance of the embryonic stem cell in a pluripotent state. The feeder cell factor can be identified and purified using techniques that are known to one skilled in the art, and are described herein.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids can be defined where amino acids within a group exchange preferentially with each other, and therefore resemble each other most in their impact on the overall protein structure (Schulz, G. E. and R. H. Schirmer, Principles of Protein Structure, Springer-Verlag).

Examples of amino acid groups defined in this manner include: a "charged/polar group," consisting of Glu, Asp, Asn, Gln, Lys, Arg and His; an "aromatic, or cyclic group," consisting of Pro, Phe, Tyr and Trp; and an "aliphatic group" consisting of Gly, Ala, Val, Leu, Ile, Met, Ser, Thr and Cys.

Within each group, subgroups can also be identified, for example, the group of charged/polar amino acids can be sub-divided into the sub-groups consisting of the "positively-charged sub-group," consisting of Lys, Arg and His; the negatively-charged sub-group," consisting of Glu and Asp, and the "polar sub-group" consisting of Asn and Gln. The aromatic or cyclic group can be sub-divided into the sub-groups consisting of the "nitrogen ring sub-group," consisting of Pro, His and Trp; and the "phenyl sub-group" consisting of Phe and Tyr. The aliphatic group can be sub-divided into the sub-groups consisting of the "large aliphatic non-polar sub-group," consisting of Val, Leu and Ile; the "aliphatic slightly-polar sub-group," consisting of Met, Ser, Thr and Cys; and the "small-residue sub-group," consisting of Gly and Ala.

Examples of conservative mutations include substitutions of amino acids within the sub-groups above, for example, Lys for Arg and vice versa such that a positive charge can be maintained; Glu for Asp and vice versa such that a negative charge can be maintained; Ser for Thr such that a free —OH can be maintained; and Gln for Asn such that a free —NH$_2$ can be maintained.

The term "cytotoxicity" refers to the cell killing property of a chemical compound (such as a chemical or protein contaminant, detergent, or toxin). In contrast to necrosis and apoptosis, the term cytotoxicity need not necessarily indicate a specific cellular death mechanism.

As used herein, the term "decrease" or the related terms "decreased," "reduce" or "reduced" refers to a statistically significant decrease. For the avoidance of doubt, the terms generally refer to at least a 10% decrease in a given parameter, and can encompass at least a 20% decrease, 30% decrease, 40% decrease, 50% decrease, 60% decrease, 70% decrease, 80% decrease, 90% decrease, 95% decrease, 97% decrease, 99% or even a 100% decrease (i.e., the measured parameter is at zero).

As used herein, the terms "develop", "differentiate" and "mature", as used to describe a stem cell, refer to the progression of a cell from the stage of having the potential to differentiate into at least two different cellular lineages to becoming a specialized and terminally differentiated cell. Such terms can be used interchangeably for the purposes of the present application.

The term "expression" as used herein refers to transcription and/or translation of a nucleotide sequence within a host cell. The level of expression of a desired product in a host cell may be determined on the basis of either the amount of corresponding mRNA that is present in the cell, or the amount of the desired polypeptide encoded by the selected sequence. For example, mRNA transcribed from a selected sequence can be quantified by Northern blot hybridization, ribonuclease RNA protection, in situ hybridization to cellular RNA or by PCR. Proteins encoded by a selected sequence can be quantified by various methods including, but not limited to, e.g., ELISA, Western blotting, radioimmunoassays, immunoprecipitation, assaying for the biological activity of the protein, or by immunostaining of the protein followed by FACS analysis.

"Expression control sequences" are DNA regulatory sequences, such as promoters, enhancers, polyadenylation signals, terminators, internal ribosome entry sites (IRES) and the like, that provide for the expression of a coding sequence in a host cell. Exemplary expression control sequences are described in Goeddel; Gene Expression Technology: Methods in Enzymology 185, Academic Press, San Diego, Calif. (1990).

The term "feeder cell" refers to a culture of cells that grows in vitro and secretes at least one factor into the culture medium, and that can be used to support the growth of another cell of interest in culture. As used herein, a "feeder cell layer" can be used interchangeably with the term "feeder cell." A feeder cell can comprise a monolayer, where the feeder cells cover the surface of the culture dish with a complete layer before growing on top of each other, or can comprise clusters of cells.

The term "growth phase" of the cell culture refers to the period of exponential cell growth (the log phase) where cells are dividing at a constant rate. During this phase, cells are cultured for a period of time, and under such conditions that cell growth is maximized. The determination of the growth cycle for the host cell can be determined for the particular host cell envisioned without undue experimentation. "Period of time and under such conditions that cell growth is maximized" and the like, refer to those culture conditions that, for a particular cell line, are determined to be optimal for cell growth and division. During the growth phase, cells are cultured in nutrient medium containing the necessary additives usually at about 30-40° C., generally about 37° C., in a humidified, controlled atmosphere, such that optimal growth is achieved for the particular cell line, for instance a mammalian cell.

The term "homology" describes a mathematically based comparison of sequence similarities which is used to identify genes or proteins with similar functions or motifs. The nucleic acid and protein sequences of the present invention can be used as a "query sequence" to perform a search against public databases to, for example, identify other family members, related sequences or homologs. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and BLAST) can be used.

The term "homologous" refers to the relationship between two proteins that possess a "common evolutionary origin", including proteins from superfamilies (e.g., the immunoglobulin superfamily) in the same species of animal, as well as homologous proteins from different species of animal (for example, myosin light chain polypeptide, etc.; see Reeck et al., *Cell*, 50:667, 1987). Such proteins (and their encoding nucleic acids) have sequence homology, as reflected by their sequence similarity, whether in terms of percent identity or by the presence of specific residues or motifs and conserved positions.

The term growth factor refers to Amphiregulin, Angiopoietin, Betacellulin, (Bone Morphogenic protein-13, Bone Morphogenic protein-14, Bone Morphogenic protein-2, Human BMP-3, Bone Morphogenic protein-4, Human BMP-5, Bone Morphogenic protein-6, Bone Morphogenic protein-7, Human CD135 Ligand/Flt-3 Ligand, Human Granulocyte Colony Stimulating Factor (G-CSF), Human Granulocyte Macrophage Colony Stimulating Factor (GM-CSF), Human Macrophage Colony Stimulating Factor (M-CSF), Human Cripto-1, Human CTGF (Connective tissue growth factor), Human EGF (Epidermal Growth Factor), Human EG-VEGF (Endocrine-Gland-Derived Vascular Endothelial Growth Factor), Human Erythropoietin (EPO), Human FGF (Fibroblast Growth Factors 1-23), Human GDF-11, Human GDF-15, Human GDF-8, Human Growth Hormone Releasing Factor (GHRF, GRF, GHRH, Growth Hormone Releasing Hormone), Human Heparin Binding Epidermal Growth Factor (HB-EGF), Human Hepatocyte Growth Factor (HGF), Human Heregulin beta 1, Human insulin, Human IGF-1 (Insulin-like Growth Factor-1), Human IGF-2 (Insulin-like Growth Factor-2), Human IGFBP-1 (Insulin-like Growth Factor Binding Protein 1), Human IGFBP-3 (Insulin-like Growth Factor Binding Protein 3), intestinal trefoil factor (ITF), Human keratinocyte growth factors 1 & 2, Human Leukemia Inhibitory Factor (LIF), Human MSP, Human Myostatin, Human Myostatin, pro (propeptide), Human NRG1, Human NGF, Human Oncostatin M, Human Osteoblast Specific Factor 1 (OSF-1, Pleiotrophin), Human PD-ECGF (Platelet-derived endothelial cell growth factor), Human PDGF, Human P1GF, Human Placental Growth Factor 1 (PLGF1), Human Placental Growth Factor 2 (PLGF2), Human SCGF-a (Stem Cell Growth Factor-alpha), Human SCGF-b (Stem Cell Growth Factor-beta), Human Stem Cell Factor (SCF)/CD117 Ligand, Human Thrombopoietin (TPO, THPO), Human Transforming Growth Factor, Human TGF-alpha (Transforming Growth Factor-alpha, TGFa), Human TGF-beta 1 (Transforming Growth Factor-beta1, TGFb), Human TGF-beta 1.2 (Transforming Growth Factor-beta1, TGFb), Human TGF-beta 2 (Transforming Growth Factor-beta2, TGFb), Human TGF-beta 3 (Transforming Growth Factor-beta3, TGFb), Human VEGF (Vascular Endothelial Growth Factor), Human VEGF-121, Human VEGF-165, Human VEGF-A As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm can also be used to determine identity.

The terms "immunoglobulin" or "antibody" (used interchangeably herein) refers to a protein typically having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by beta-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains). Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments.

The term "isolated," when used to describe the cell culture components, or heat shock proteins disclosed herein, means protein that has been identified and separated and/or recovered from a component of its natural environment. Contaminant components of its natural environment are materials that would typically interfere with research, diagnostic or therapeutic uses for the protein, and may include enzymes, hormones, and other proteinaceous or non-proteinaceous solutes. In some embodiments, the protein will be purified to at least 95% homogeneity as assessed by SDS-PAGE under non-reducing or reducing conditions using Coomassie blue or, preferably, silver stain. Isolated protein includes protein in situ within recombinant cells, since at least one component of the protein of interest's natural environment will not be present. Ordinarily, however, isolated protein will be prepared by at least one purification step.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

Cells expressing "markers of pancreatic endocrine lineage" refer to cells with positive gene expression for the transcription factor PDX-1 and at least one of the following transcription factors: NGN-3, NRx2.2, NRx6.1, NeuroD, Isl-1, HNF-3 beta, MAFA, Pax4, and Pax6. Cells expressing markers characteristic of the pancreatic cell lineage include pancreatic β cells.

Cells expressing "markers characteristic of endoderm lineage" as used herein refer to cells expressing at least one of the following markers: SOX-17, GATA-4, HNF-3 beta, GSC, Cer1, Nodal, FGF8, Brachyury, Mix-like homeobox protein, FGF4 CD48, eomesodermin (EOMES), DKK4, FGF17, GATA-6, CXCR4, C-Kit, CD99, or OTX2. Cells expressing markers characteristic of the definitive endoderm lineage include primitive streak precursor cells, primitive streak cells, mesendoderm cells and definitive endoderm cells.

Cells expressing pluripotency markers derived by the methods of the present invention express at least one of the following pluripotency markers selected from the group consisting of: ABCG2, cripto, FoxD3, Connexin43, Connexin45, Oct4, SOX-2, Nanog, hTERT, UTF-1, ZFP42, SSEA-3, SSEA-4, Tral-60, and Tral-81.

Cells expressing "markers characteristic of mesoderm lineage" as used herein refers to a cell expressing at least one of the following markers: CD48, eomesodermin (EOMES), SOX-17, DKK4, HNF-3 beta, GSC, FGF17, GATA-6.

Cells expressing "markers characteristics of ectoderm lineage" as used herein refers to a cell expressing at least one of the following markers: BMP-4. Noggin, Chordin, Otx2, Fox J3, Nestin, p63/TP73L, beta-III Tubulin.

The terms "operably linked" and "operatively linked," as used interchangeably herein, refer to the positioning of two or more nucleotide sequences or sequence elements in a manner which permits them to function in their intended manner. In some embodiments, a nucleic acid molecule according to the invention includes one or more DNA elements capable of opening chromatin and/or maintaining chromatin in an open state operably linked to a nucleotide sequence encoding a recombinant protein. In other embodiments, a nucleic acid molecule may additionally include one or more nucleotide sequences chosen from: (a) a nucleotide sequence capable of increasing translation; (b) a nucleotide sequence capable of increasing secretion of the recombinant protein outside a cell; and (c) a nucleotide sequence capable of increasing the mRNA stability, where such nucleotide sequences are operatively linked to a nucleotide sequence encoding a recombinant protein. Generally, but not necessarily, the nucleotide sequences that are operably linked are contiguous and, where necessary, in reading frame. However, although an operably linked DNA element capable of opening chromatin and/or maintaining chromatin in an open state is generally located upstream of a nucleotide sequence encoding a recombinant protein; it is not necessarily contiguous with it. Operable linking of various nucleotide sequences is accomplished by recombinant methods well known in the art, e.g. using PCR methodology, by ligation at suitable restrictions sites or by annealing. Synthetic oligonucleotide linkers or adaptors can be used in accord with conventional practice if suitable restriction sites are not present.

The terms "polynucleotide" and "nucleic acid molecule," used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, "DNA" or "nucleotide sequence" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

The term "pluripotent stem cell" encompasses stem cells obtained from embryos, fetuses or adult tissues. In one preferred embodiment, the pluripotent stem cell is an embryonic stem cell. In another embodiment the pluripotent stem cell is a fetal stem cell, such as a primordial germ cell. In another embodiment the pluripotent stem cell is an adult stem cell.

As used herein, the term "pluripotent" refers to a cell capable of at least developing into one of ectodermal, endodermal and mesodermal cells. As used herein the term "pluripotent" includes cells that are totipotent and multipotent. As used herein, the term "totipotent cell" refers to a cell capable of developing into all lineages of cells. The term "multipotent" refers to a cell that is not terminally differentiated.

The term "produced in a plant" when used to describe the protein cell culture components disclosed herein, means that the protein has been obtained directly or indirectly from a plant cell. With respect to recombinant proteins, the term "produced in a plant" means that the recombinant protein has been expressed within a plant cell, and then purified from host cells proteins and lipids. Proteins that have been produced in a plant may be differentiated from proteins that have purified from other organisms by at least three criteria. 1) Proteins produced in a plant will typically comprise different patterns of post-translational modifications compared to proteins produced in different organisms, which may be readily identified by mass spectrum analysis. 2) Proteins produced in a plant will typically comprise a different set of bound co-factors, lipids and contaminating proteins compared to the same protein produced in a different expression system, or purified from a different source. 3) Proteins produced in a plant may exhibit a different biological activity compared to the same protein produced or purified from a different source. The difference in activity in the protein produced in a plant may arise from a difference in the conformation, folding, aggregation state, post-translational modifications, or bound factors or co-purified contaminating proteins of the protein produced in a plant compared to a protein produced or isolated from a different organism. In one aspect produced in a plant means produced in a higher plant. In one aspect, "produced in a plant" means produced in a higher plant selected from the group consisting of rice, barley, wheat, rye, corn, millet, triticale, and sorghum. Differences in the specific activity of a protein produced in a plant may be readily established by routine assays using defined concentrations and assay conditions, for example, using cell growth assays, as disclosed in Examples 3 and 4. Specifically a protein produced in a plant may exhibit at least at least 10% greater cell growth activity either alone, or in combination with other factors, compared to the same concentration of a non plant produced protein. Preferably, a protein produced in a plant may exhibit at least at least 20% greater cell growth activity either alone, or in combination with other factors, compared to the same concentration of a non plant produced protein. More preferably, a protein produced in a plant may exhibit at least at least 30% greater cell growth activity either alone, or in combination with other factors, compared to the same concentration of a non plant produced protein. More preferably, a protein produced in a plant may exhibit at least at least 40% greater cell growth activity either alone, or in combination with other factors, compared to the same concentration of a non plant produced protein. Even more preferably, a protein produced in a plant may exhibit at least at least 50% greater cell growth activity either alone, or in combination with other factors, compared to the same concentration of a non plant produced protein.

A "promoter" is a DNA regulatory region capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. A transcription initiation site (conveniently defined by mapping with nuclease S1) can be found within a promoter sequence, as well as protein binding domains (consensus sequences) responsible for the binding of RNA polymerase. Eukaryotic promoters can often, but not always, contain "TATA" boxes and "CAT" boxes. Prokaryotic promoters contain Shine-Dalgarno sequences in addition to the −10 and −35 consensus sequences.

A large number of promoters, including constitutive, inducible and repressible promoters, from a variety of different sources are well known in the art. Representative sources include for example, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter, the rice endosperm specific glutelin (Gt1) promoter, CaMV35S viral promoter. Inducible promoters include the Tet system, (U.S. Pat. Nos. 5,464,758 and 5,814,618), the Ecdysone inducible system (No et al., Proc. Natl. Acad. Sci. (1996) 93 (8): 3346-3351; the T-Re$_x$™ system (Invitrogen Carlsbad, Calif.), LacSwitch® (Stratagene, (San Diego, Calif.) and the Cre-ER$^T$ tamoxifen inducible recombinase system (Indra et al. Nuc. Acid. Res. (1999) 27 (22): 4324-4327; Nuc. Acid. Res. (2000) 28 (23): e99; U.S. Pat. No. 7,112,715; and Kramer & Fussenegger, Methods Mol. Biol. (2005) 308: 123-144) or any promoter known in the art suitable for expression in the desired cells.

The term "protein of interest" refers to any protein which may be useful for research, diagnostic or therapeutic purposes. The protein of interest may comprise a mammalian protein or non-mammalian protein, and may optionally comprise a receptor or a ligand. Exemplary proteins of interest include, but are not limited to, molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; members of the TNF and TNF receptor (TNFR) family, like tumor necrosis factor-alpha and -beta, CD40 ligand, Apo-2 ligand/TRAIL, DR4, DR5, DcR1, DcR2, DcR3, OPG, Fas ligand; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TG-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; thrombopoietin (TPO); interleukins (ILs), e.g., IL-1 to IL-10; superoxide dismutase; T-cell receptors; surface membrane proteins; decay accelerating factor; viral antigen such as, for example, a portion of the AIDS envelope, gp120; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and variants and/or fragments of any of the above-listed polypeptides; as well as antibodies against various protein antigens like CD proteins such as CD3, CD4, CD8, CD19, CD20 and CD34; members of the ErbB receptor family such as the EGF receptor, HER2, HER3 or HER4 receptor; cell adhesion molecules such as LFA-1, Mac1, p150.95, VLA-4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C; an Apo-2L receptor such as Apo-2 (DR5), DR4, DcR1, DcR2, DcR3; and variants and/or fragments of the above-identified antibodies etc. In one embodiment of the invention, a protein of interest will comprise a protein which itself is capable of inducing apoptosis in mammalian or non-mammalian cells in vitro or in vivo, such as Apo-2 ligand/TRAIL, Fas ligand, or TNF-alpha.

The term "production phase" of the cell culture refers to the period of time during which expression of protein is at the maximum. Typically, cell growth has reached a plateau. During the production phase, logarithmic cell growth has ended and protein production is primary. During this period of time the medium is generally supplemented to support continued protein production and to achieve the desired protein product.

The term "recombinant protein" or "recombinant polypeptide" refers to an exogenous, i.e., heterologous or foreign polypeptide, to the cells producing the polypeptide.

The term "stress" in the context of apoptosis or cell culture refers to non-optimal conditions for tissue culture including any combination of the following; the presence of toxins, nutrient or growth factor depletion or withdrawal, hypoxia, thermal stress (temperature is too high or too low compared to the preferred range), loss of cell-cell contacts, viral infection, osmotic stress (osmolality is too high or too low compared to the preferred range), oxidative stress, cell density (cell density is too high or too low compared to the preferred range), and pH stress (pH is too high or too low compared to the preferred range).

The term "transformation" refers to the transfer of one or more nucleic acid molecules into a host cell or organism. Methods of introducing nucleic acid molecules into host cells include, for instance, calcium phosphate transfection, DEAE-dextran mediated transfection, microinjection, cationic lipid-mediated transfection, electroporation, scrape loading, ballistic introduction or infection with viruses or other infectious agents. "Transformed", "transduced", "transgenic", and "recombinant" refer to a host cell or organism into which a recombinant or heterologous nucleic acid molecule (e.g., one or more DNA constructs or RNA, or siRNA counterparts) has been introduced. The nucleic acid molecule can be stably expressed (i.e. maintained in a functional form in the cell for longer than about three months) or non-stably maintained in a functional form in the cell for less than three months i.e. is transiently expressed. For example, "transformed," "transformant," and "transgenic" cells have been through the transformation process and contain foreign nucleic acid. The term "untransformed" refers to cells that have not been through the transformation process.

The term "transition phase" of the cell culture refers to the period of time during which culture conditions for the production phase are engaged. During the transition phase environmental factors such as pH, ion concentration, and temperature may shift from growth conditions to production conditions.

The term "serum free DMEM" refers to DMEM/F12+ITSE (10 mg/L insulin, 5.5 mg/L human transferrin, 0.0067 mg/L Sodium selenite, 2 mg/L ethanolamine).

The term "sequence similarity" refers to the degree of identity or correspondence between nucleic acid or amino acid sequences that may or may not share a common evolutionary origin (see Reeck et al., supra). However, in common usage and in the instant application, the term "homologous", when modified with an adverb such as "highly", may refer to sequence similarity and may or may not relate to a common evolutionary origin.

In specific embodiments, two nucleic acid sequences are "substantially homologous" or "substantially similar" when at least about 85%, and more preferably at least about 90% or at least about 95% of the nucleotides match over a defined length of the nucleic acid sequences, as determined by a sequence comparison algorithm known such as BLAST, FASTA, DNA Strider, CLUSTAL, etc. An example of such a sequence is an allelic or species variant of the specific genes of the present invention. Sequences that are substantially homologous may also be identified by hybridization, e.g., in a Southern hybridization experiment under, e.g., stringent conditions as defined for that particular system.

Similarly, in particular embodiments of the invention, two amino acid sequences are "substantially homologous" or "substantially similar" when greater than 80% of the amino acid residues are identical, or when greater than about 90% of the amino acid residues are similar (i.e., are functionally identical). Preferably the similar or homologous polypeptide sequences are identified by alignment using, for example, the GCG (Genetics Computer Group, Version 7, Madison, Wis.) pileup program, or using any of the programs and algorithms described above. The program may use the local homology algorithm of Smith and Waterman with the default values: Gap creation penalty=-(1+1/k), k being the gap extension number, Average match=1, Average mismatch=-0.333.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-3, 4-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The publications discussed above are provided solely for their disclosure before the filing date of the present application. Nothing herein is to be construed as an admission that the invention is not entitled to antedate such disclosure by virtue of prior invention.

I Methods for Using the Supplements of the Invention

The claimed supplements are useful in a wide range of applications for tissue culture and recombinant protein production where they provide for significant improvements in preventing apoptosis and improving cell viability during tissue culture, and in particular in response to stress.

Apoptosis involves a series of biochemical events leading to a characteristic cell morphology and death. These changes include, changes to the cell membrane such as loss of membrane asymmetry and attachment, cellular blebbing cell shrinkage, nuclear fragmentation, chromatin condensation, and chromosomal DNA fragmentation.

The process of apoptosis is controlled by a diverse range of cell signals, which may originate either extracellularly (extrinsic inducers) or intracellularly (intrinsic inducers). Extracellular signals may include toxins, hormones, growth factors, nitric oxide, cytokines, which may be present to different degrees in tissue culture media. These signals may positively (i.e., trigger) or negatively (i.e., repress, inhibit, or dampen) affect apoptosis, and thus influence overall cell viability. A number of intracellular components, including ATP content, calcium level, and a number of apoptotic and anti-apoptotic genes also help regulate apoptosis. A cell may initiate intracellular apoptotic signaling in response to a stress, which may bring about cell suicide. Stress inducing agents encountered during tissue culture include for example toxins, associated with tissue culture components such as endotoxins, and heavy metals that leach from plastic ware, transfection reagents (e.g. Lipofectamine and similar lipid based transfection reagents), viral transformation, nutrient and growth factor deprivation, associated with serum free culture, or cell differentiation protocols which include hypoxia and oxidative stress associated with high density culture in a bioreactor and increased intracellular calcium concentration, for example, by damage to the membrane caused by detergents and electroporation.

Before the actual process of cell death occurs, the apoptotic signals must overcome regulatory proteins which act as gatekeepers overseeing the activation of the apoptosis pathway. In vivo, this step allows the process to be stopped, should the cell no longer need to die. Several proteins are involved at this step, though two main mechanisms of regulation have been identified and include those associated with mitochondria functionality, and those directly involved in transducing the signal via adaptor proteins to the apoptotic mechanisms.

Cells grown under tissue culture conditions may experience cellular stresses associated with routine tissue culture procedures, as described above which may trigger apoptotic signals and increase the susceptibility of the cells to apoptosis. For example, nutrient deprivation associated with serum free culture, oxidative stress associated with high density growth in a bioreactor, the use of cytotoxic compounds associated with DNA transfection reagents, and thermal stresses associated with cryopreservation, may predispose the cell to enter apoptosis. By enhancing the ability of a cell to survive such signals it is possible to improve cell viability during these procedures, by preventing the cells commitment to cell death, thereby improving the success and utility of these approaches.

Recently a number of genes in eukaryotic cells have been identified which inhibit the onset or reduce the effects of apoptosis. Some of these genes inhibit caspase dependent apoptotic pathways in the cell, and in fact transfecting cells with anti-apoptotic genes may be useful in prolonging the life and productivity of transfected cells grown under biologically demanding conditions. (U.S. Pat. Nos., 6,586,206; 7,531,327; US Patent Application US 2009/0170165; US2009/0181426).

Additionally the addition of exogenous heat shock proteins has in some cases been shown to improve the survival of cells in culture under a variety of conditions. (Novoselova et al., J. Neurochem. 94 597-606 (2005); Tidwell et al., Cell Stress & Chap 9 (1) 88-90 (2004); Guzhova et al., Cell Stress & Chap. 3 (1) 67-77 (1998); Hounenou et al., Cell Stress & Chap 1 (3) 161-166 (1996); Johnson et al., In vitro Cell. Dev. Biol., 29A 807-812 (1993).

The present invention is based in part on the surprising demonstration that plant heat shock proteins co-purified, or co-mixed in solution with recombinant proteins such as human serum albumin and other protein tissue culture factors, result in the formation of active protein complexes which are capable of significantly enhancing the properties of the recombinant protein when added to cells in culture as a supplement. Specifically, such supplements result in improved culture viability, extended cell survival, improved rates of cell growth and improved yields of recombinant proteins produced from tissue culture bioreactors. Because the supplements show improved activity and stability they offer significant improvements compared to the use of purified heat shock proteins, which are costly to purify, relatively unstable, and exhibit low potency.

In one aspect, the binding of long chain fatty acids to high affinity binding sites in albumin created via expression of the protein in plants further enhances the utility of the albumin and bound heat shock proteins. Without being bound by any one particular theory of operation, it is proposed that the enhanced stability of the plant produced albumin, derived from tightly bound fatty acids, promotes protease resistance, and stabilizes the protein against denaturation. Moreover the increased stability and hydrophobicity of the lipid bound albumin enhances protein uptake of both the albumin and bound heat shock proteins via endocytosis by enabling passage of the proteins through the endosome without degradation.

Accordingly in one embodiment, the present invention includes a method for improving rate of cell growth, or viability of a cell population, comprising the addition of a supplement of the present invention to the cell culture media.

In another embodiment, the present invention includes a method for improving the rate of cell growth, or viability of a cell population, grown under serum free conditions comprising the addition of a supplement of the present invention to the cell culture media. In one aspect of this embodiment, the invention includes a method of adapting a cell population to serum free growth comprising the addition of a supplement of the present invention to the cell culture before serum withdrawal.

In another embodiment, the present invention includes a method for improving the rate of cell growth or viability of cells grown at low density comprising the addition of a supplement of the present invention to the cell culture media.

In another embodiment, the present invention includes a method for improving the rate of cell growth or viability of cells grown from single cell clones comprising the addition of a supplement of the present invention to the cell culture media into which the single cell is plated. In another embodiment, the present invention includes a method for improving the viability of cells after transfection comprising the addition of a supplement of the present invention to the cell culture media prior to, during, or immediately after transfection.

In another embodiment, the present invention includes a method for improving the viability of cells after cryopreservation comprising the addition of a supplement of the present invention prior to, during, or immediately after cryopreservation or thawing of the cells.

In another embodiment, the present invention includes a method for improving the rate of cell growth or viability of primary cells grown in culture comprising the addition of a supplement of the present invention to the cell culture media. In one aspect the primary cell is an embryonic stem cell.

In one embodiment, human embryonic stem cells are cultured in a culture system that is essentially free of feeder cells, but nonetheless supports proliferation of human embryonic stem cells without undergoing substantial differentiation, comprising a supplement of the invention. The growth of human embryonic stem cells in feeder-free culture without differentiation is supported using a medium conditioned by culturing previously with another cell type and further comprising a supplement of the present invention. Alternatively, the growth of human embryonic stem cells in feeder-free culture without differentiation is supported using a chemically defined medium comprising a supplement of the present invention. Examples of feeder-free, serum free culture systems in which embryonic stem cells are maintained in unconditioned serum replacement (SR) medium supplemented with different growth factors capable of triggering embryonic stem cell self-renewal include those disclosed in US patent applications, US20050148070, US20050244962, US20050233446, U.S. Pat. No. 6,800,480, and PCT publications WO2005065354 and WO2005086845.

In an alternate embodiment, human embryonic stem cells are initially cultured with a layer of feeder cells that support the human embryonic stem cells and further comprising a supplement of the present invention. The human embryonic are then transferred to a culture system that is essentially free of feeder cells, but nonetheless supports proliferation of human embryonic stem cells without undergoing substantial differentiation and which further comprises a supplement of the present invention. In any of these approaches, the use of the supplements of the invention results in significantly enhanced rates of cell growth and improved cell viability.

Examples of conditioned media suitable for use with the supplements of the present invention are disclosed in US20020072117, U.S. Pat. No. 6,642,048, WO2005014799, and Xu et al (Stem Cells 22: 972-980, 2004). An example of a chemically defined medium suitable for use with the supplements of the present invention may be found in US20070010011.

Examples of feeder cells include feeder cells selected from the group consisting of a fibroblast cell, a MRC-5 cell, an embryonic kidney cell, a mesenchymal cell, an osteosarcoma cell, a keratinocyte, a chondrocyte, a Fallopian ductal epithelial cell, a liver cell, a cardiac cell, a bone marrow stromal cell, a granulosa cell, a skeletal muscle cell, a muscle cell and an aortic endothelial cell. In a preferred embodiment, the MRC-5 cell, has ATCC Catalog Number 55-X; the transformed and has ATCC Accession Number CRL-2309; the human osteosarcoma cell has ATCC Accession Number HTB-96; and the mesenchymal cell is a human fetal palatal mesenchymal cell with ATCC Accession Number CRL-1486. In other preferred embodiments the human fibroblast cell is a skin keloid fibroblast, KEL FIB and has ATCC Accession Number CRL-1762, or is a fetal skin fibroblast cell; and the bone marrow stromal cell, HS-5, has ATCC Accession Number CRL-11882.

Suitable culture media may be made from the following components, such as, for example, Dulbecco's modified Eagle's medium (DMEM), Gibco # 11965-092; Knockout Dulbecco's modified Eagle's medium (KO DMEM), Gibco # 10829-018; Ham's F12/50% DMEM basal medium; 200 mM L-glutamine, Gibco #15039-027; non-essential amino acid solution, Gibco 11140-050; β-mercaptoethanol, Sigma # M7522; human recombinant basic fibroblast growth factor (bFGF), Gibco # 13256-029.

In one embodiment, the human embryonic stem cells are plated onto a suitable culture substrate that is treated prior to treatment according to the methods of the present invention, with a composition comprising a supplement of the present invention. In one embodiment, the treatment is an extracellular matrix component, such as, for example, those derived from basement membrane or that may form part of adhesion molecule receptor-ligand couplings. In one embodiment, the suitable culture substrate is MATRIGEL (Becton Dickenson). MATRIGEL is a soluble preparation from Engelbreth-Holm-Swarm tumor cells that gels at room temperature to form a reconstituted basement membrane.

Other extracellular matrix components and component mixtures are suitable as an alternative and can be used with the supplements of the present invention. This may include laminin, fibronectin, proteoglycan, entactin, heparan sulfate, and the like, alone or in various combinations with a supplement of the present invention.

In another embodiment, the invention encompasses an embryonic stem cell culture, comprising a human pluripotent stem cell and a feeder-free, serum free culture system comprising a supplement of the invention. In one embodiment the invention encompasses a human pluripotent stem cell culture, comprising a human pluripotent stem cell and a feeder-free, serum free culture system comprising a supplement of the invention.

In another embodiment the invention encompasses an embryonic stem cell culture, comprising a human embryonic stem cell and a human feeder cell culture comprising a supplement of the invention. In another embodiment the invention encompasses a human pluripotent stem cell culture, comprising a human pluripotent stem cell and a human feeder cell culture comprising a supplement of the invention.

In another embodiment, the present invention provides a method for deriving a population of cells comprising cells expressing pluripotency markers, comprising the steps of:
  a. Culturing human embryonic stem cells,
  b. Differentiating the human embryonic stem cells into cells expressing pluripotency markers, wherein the differentiation is conducted in the presence of a supplement of the present invention.

In another embodiment, the present invention provides a method for deriving a population of cells comprising cells expressing markers, characteristic of ectodermal, endodermal or mesodermal cells, comprising the steps of:
  a. Culturing pluripotency stem cells;
  b. Differentiating the pluripotency stem cells into cells expressing markers characteristic of ectodermal, endodermal or mesodermal cells, wherein the differentiation is conducted in the presence of a supplement of the present invention.

In any of these methods, the stem cells can be differentiated into cells expressing markers characteristic of an endodermal, ectodermal or mesodermal lineage by any method in the art. For example, cells expressing pluripotency markers may be differentiated into cells expressing markers characteristic of the definitive endoderm lineage according to the methods disclosed in D'Amour et al, Nature Biotechnology 23, 1534-1541 (2005), by Shinozaki et al, Development 131, 1651-1662 (2004), McLean et al., Stem Cells 25, 29-38 (2007), D'Amour et al., Nature Biotechnology 24, 1392-1401 (2006).

Cells expressing markers characteristic of the endoderm lineage may be further differentiated into cells expressing markers characteristic of the pancreatic endocrine lineage by any method in the art. For example, cells expressing markers characteristic of the pancreatic endoderm lineage may be differentiated into cells expressing markers characteristic of the pancreatic endocrine lineage according to the methods disclosed in D'Amour et al, Nature Biotechnology 24, 1392-1401 (2006), wherein the differentiation is conducted in the presence of a supplement of the present invention.

In one aspect of any of these methods of differentiation, the human embryonic stem cells are cultured and differentiated on a tissue culture substrate coated with an extracellular matrix. The extracellular matrix may be a solubilized basement membrane preparation extracted from mouse sarcoma cells (which is sold by BD Biosciences under the trade name MATRIGEL). Alternatively, the extracellular matrix may be growth factor-reduced MATRIGEL. Alternatively, the extracellular matrix may be fibronectin. In an alternate embodiment, the human embryonic stem cells are cultured and differentiated on tissue culture substrate coated with human serum. In one aspect, the tissue culture substrate is coated with extracellular matrix and a supplement of the present invention.

The extracellular matrix may be diluted prior to coating the tissue culture substrate. Examples of suitable methods for diluting the extracellular matrix and for coating the tissue culture substrate may be found in Kleinman, H. K., et al., Biochemistry 25:312 (1986), and Hadley, M. A., et al., J. Cell. Biol. 101:1511 (1985).

In one aspect of the methods of stem cell differentiation, the culture medium should contain sufficiently low concentrations of certain factors to allow the differentiation of human embryonic stem cells to cells of endoderm, ectoderm or mesoderm lineage, such as, for example insulin and IGF (as disclosed in WO2006020919). This may be achieved by lowering the serum concentration, or alternatively, by using chemically defined media that lacks insulin and IGF. Examples of chemically defined media are disclosed in Wiles et al (Exp Cell Res. 1999 Feb. 25; 247(1): 241-8.). In a preferred embodiment, of any of these methods, the culture media comprises a supplement of the present invention.

The culture medium may also contain at least one other additional factor that may enhance the formation of cells expressing markers characteristic of endoderm, mesoderm or ectoderm lineage from human embryonic stem cells. The at least one additional factor may be, for example, nicotinamide, members of TGF-β family, including TGF-β1, 2, and 3, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, retinoic acid, parathyroid hormone, insulin, progesterone, aprotinin, hydrocortisone, ethanolamine, beta mercaptoethanol, epidermal growth factor (EGF), gastrin I and II, copper chelators such as, for example, triethylene pentamine, forskolin, Na-Butyrate, activin, betacellulin, ITS, noggin, neurite growth factor, nodal, valproic acid, trichostatin A, sodium butyrate, hepatocyte growth factor (HGF), sphingosine 1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof. In a preferred embodiment, of any of these methods, the culture media containing at least one additional factor listed above, further comprises a supplement of the present invention.

The at least one other additional factor may be supplied by conditioned media obtained from pancreatic cells lines such as, for example, PANC-1 (ATCC No: CRL-1469), CAPAN-1 (ATCC No: HTB-79), BxPC-3 (ATCC No: CRL-1687), HPAF-II (ATCC No: CRL-1997), hepatic cell lines such as, for example, HepG2 (ATCC No: HTB-8065), and intestinal cell lines such as, for example, FHs 74 (ATCC No: CCL-241).

In a preferred embodiment, of any of these methods, the conditioned media further comprises a supplement of the present invention.

In another embodiment, the invention encompasses a method of using the cell or tissue of any of the aforementioned stem cells for the experimental, therapeutic and prophylactic treatment of a disease or condition in a human or animal. Preferably, the disease is selected from the group consisting of Parkinson's, Alzheimer's, Multiple Sclerosis, spinal cord injuries, stroke, macular degeneration, burns, liver failure, heart disease, diabetes, Duchenne's muscular dystrophy, osteogenesis imperfecta, osteoarthritis, rheumatoid arthritis, anemia, leukemia, breast cancer, solid tumors, and AIDS. In a preferred embodiment, the disease is Parkinson's or Alzheimer's. In a more preferred embodiment, the disease is Parkinson's.

In another aspect, the present invention includes a method for improving the yield of a recombinant product produced from cells in culture comprising the addition of a supplement of the present invention to the cell culture media during one or more of the growth phase, transition phase, or production phase of the culture.

In any of these methods, the supplements of the invention, by increasing host cell viability in culture (and during fermentation), provide for a simple and cost effective method to increase the yield of recombinant protein. Additionally, the supplements of the invention, by decreasing or inhibiting apoptosis in the cell culture, can decrease the number or presence of adverse proteases in the culture media and protect the expressed protein of interest against proteolytic degradation, thereby increasing the quality of the protein of interest produced, as evidenced by increased amounts of active protein, and increased yields of intact protein. Additionally Applicants have found that the supplements of the invention may protect the cells against potential adverse effects of agents like detergents, heavy metals and endotoxin contaminates present in the culture components, or protect the cells from toxic reagents introduced to the cells during transfection or cryopreservation.

In any of the claimed methods, the supplements of the invention can be added directly, or admixed, to the culture media at any convenient time, for example when changing the media, passaging the cells, or when plating out the cells at low density. Optionally, the supplement is added to the culture media at the beginning (at the time of initiating, day 0) of the cell culturing process. In one aspect the supplements of the invention may be added before an anticipated stressful event, for example before cryopreservation, transfection or serum withdrawal, etc.

In another aspect, the supplement is added to the culture media during the culturing of the cells prior to the point when induction of typically apoptosis occurs. For example, during a large scale cell culture, induction of apoptosis can be observed on about day 3 or day 4 of the culture, and therefore, the supplement will preferably be added prior to day 3 or day 4. Optionally, a desired quantity of the supplement is added throughout, or for the duration of, the cell culture, for instance, on a daily basis for the entire fermentation. As an example, for a 5 day culture, the supplement could be added at day 0, and every 24 hours thereafter until the culture is terminated.

Accordingly in one embodiment, the invention provides a method of improving the yield and quality of a recombinant protein produced in a bioreactor by adding a supplement of the invention to the bioreactor. In one embodiment, the bioreactor comprises bacterial cells. In another aspect the bioreactor comprises yeast cells. In another aspect the bioreactor comprises plant cells. In another aspect the bioreactor comprises mammalian cells.

In another embodiment, the invention provides a method of improving the yield and quality of a recombinant protein produced in bacterial cells, by adding the supplement of the invention to the cell culture. In another embodiment, the invention provides a method of improving the yield and quality of a recombinant protein produced in yeast cells by adding the supplement of the invention to the cell culture. In another embodiment, the invention provides a method of improving the yield and quality of a recombinant protein produced in a plant cells by adding the supplement of the invention to the cell culture. In another embodiment, the invention provides a method of improving the yield and quality of a recombinant protein produced in insect cells by adding the supplement of the invention to the cell culture. In another embodiment, the invention provides a method of improving the yield and quality of a recombinant protein produced in mammalian cells by adding the supplement of the invention to the cell culture.

In another embodiment, the invention provides a method to increase the yield of the production phase of a cell culture system and thereby increase the productivity of a bioreactor by adding the supplement of the invention to the cell culture system prior to, or during the production phase of the cell culture system. In one aspect of this method the yield of the production phase is increased by about 10%. In one aspect of this method the yield of the production phase is increased by about 20%. In one aspect of this method the yield of the production phase is increased by about 30%. In one aspect of this method the yield of the production phase is increased by about 40%. In one aspect of this method the yield of the production phase is increased by about 50%. In one aspect of this method the yield of the production phase is increased by about 60%. In one aspect of this method the yield of the production phase is increased by about 70%. In one aspect of this method the yield of the production phase is increased by about 80%. In one aspect of this method the yield of the production phase is increased by about 90%. In one aspect of this method the yield of the production phase is increased by about 100%. In one aspect of this method the yield of the production phase is increased by about 200%. In one aspect of this method the yield of the production phase is increased by about 500%.

In another embodiment, the invention provides a method to produce a protein of interest at a temperature that is elevated compared to normal growth conditions for the production of that protein, comprising the addition of a supplement of the invention to cells expressing the protein of interest.

In another embodiment, the invention provides a method to decrease the amount of aggregates formed in a cell culture expression system by aggregate prone proteins of interest comprising the addition of a supplement of the invention to the cell culture expression system, whereby the aggregation state of the protein is reduced.

In another embodiment, the invention provides a method to increase the activity of a protein of interest protein expressed by a cell by preventing the denaturation and aggregation of the recombinant protein comprising the addition of a supplement of the invention to the cell, whereby the specific activity of the protein of interest is increased.

In another embodiment, the invention provides a method to improve the expression of proteins in a cell culture expression system that are aggregation prone, cause precipitation to occur, or are toxic themselves to the cells comprising the addition of a supplement of the invention to the cell culture expression system, whereby the expression of the protein of interest is increased.

The amount of supplement to add in any of these methods will depend on various factors, for instance, the type of host cell, the cell density, protein of interest and culture conditions, etc. Determining the desired concentration of supplement to be added to the culture media is within the skill in the art and can be ascertained empirically by routine optimization and without undue experimentation.

The skilled artisan will readily appreciate that different cell types will have different magnitudes of responses to the supplement of the invention, and this will be determined, to some degree, by the amount or type of the HSPs in the supplement. Additionally different densities of cells will require appropriate adjustment in the total amount of supplement as well as the concentration of HSPs added to the culture to account for the increased cell number. Additionally cells grown in suspension culture or via adherent culture will have different membrane surface areas available for HSP entry and will typically exhibit different rates and degrees of response. Therefore, one should choose a concentration which provides for a sufficient inhibition of apoptosis, or increase in viability, or net cell growth. Typically the supplements of the invention will be added to a final concentration of about 0.1%, about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 40%, or about 50%. Wt/wt, or wt/volume.

There will typically be an upper range of concentration of HSP of the supplement beyond which further increases in cell survival do not occur. As described in the Examples below, Applicants have found that the HSP supplements of the invention can inhibit apoptosis when added to cell cultures at a concentration of about 0.2 to about 1000 ppm, or more preferably about 1 to about 500 ppm, or more preferable about 50 to about 500 ppm.

II. Supplements

In one aspect the supplements of the invention comprise one or more protein cell culture components and a heat shock protein. In one embodiment of the invention, the one or more cell culture components are independently selected from albumin, transferrin, glutathione S-transferase, superoxide dismutase or a growth factor.

In another aspect of the invention, the one or more cell culture components are independently selected from insulin, Epidermal Growth Factor (EGF), Fibroblast Growth Factors 1-23 (FGF), Insulin-like Growth Factor-1 (IGF), keratinocyte growth factors 1 & 2 (KGF), and Leukemia Inhibitory Factor (LIF).

In another aspect the supplements of the invention comprise at least one recombinant cell culture component and a rice heat shock protein. In another aspect the supplements of the invention comprise at least one recombinant cell culture component and a rice hsp70 homolog. In one aspect the rice hsp70 homolog is selected from HSP70, Bip and rice stromal protein. In one aspect the rice hsp70 homolog is substantially similar to a rice hsp 70 homolog. In another aspect the rice hsp70 homolog is substantially similar to a rice hsp 70 homolog selected from the group consisting of HSP70, Bip and rice stromal protein.

In one embodiment, the supplements of the invention comprise preparations of the co-purified recombinant cell culture components and rice hsps that are also essentially free of detergents and endotoxins which would otherwise mask or inhibit the positive impact of the Hsp proteins. In one aspect the supplements of the invention have less than about 1 EU of endotoxin per mg of purified protein, and said protein cell culture component is at least about 95% pure.

In any of these methods the supplements of the invention may be prepared by co-purifying, or mixing in aqueous solution the cell culture components with a heat shock protein.

In one aspect of the supplements of the invention, at least one of the recombinant cell culture components is albumin. In another aspect, the albumin comprises less than about 2% aggregated albumin. In another aspect the albumin comprises less than about 1% aggregated albumin.

The term "albumin" refers to all naturally-occurring and synthetic forms of albumin. Preferably, the term "albumin" refers to recombinant albumin. In one aspect the albumin is from a vertebrate. In one aspect the albumin is from a mammal. In a further embodiment the albumin is human. In another aspect, the recombinant albumin is produced from a plant cell. In one particularly preferred embodiment the recombinant albumin is produced from transgenic rice (*Oryza sativa*). Representative species and Gene bank accession numbers for various species of albumin are listed below in Table D1

TABLE D1

Exemplary Albumin genes

| Species | Gene Bank Accession number |
| --- | --- |
| Human | NP_000468.1 |
| Pan troglodytes | XP_517233.2 |
| Canis lupus familiaris | XP_855557.1 |
| Bos taurus | NP_851335.1 |
| Mus musculus | NP_033784.1 |
| Rattus norvegicus | NP_599153.1 |
| Gallus gallus | NP_990592.1 |

It will be understood that for the recombinant production of albumin in different species it will typically be necessary to codon optimize the nucleic acid sequence of the gene for the host organism in question. Such codon optimization can be completed by standard analysis of the preferred codon usage for the host organism in question, and the synthesis of an optimized nucleic acid via standard DNA synthesis. A number of companies provide such services on a fee for services basis and include for example, DNA2.0, (CA, USA) and Operon Technologies. (CA, USA).

The albumin may be in its native form, i.e., as different allelic variants as they appear in nature, which may differ in their amino acid sequence, for example, by truncation (e.g., from the N- or C-terminus or both) or other amino acid deletions, additions, insertions, substitutions, or post-translational modifications. Naturally-occurring chemical modifications including post-translational modifications and degradation products of the albumin, are also specifically included in any of the methods of the invention including for example, pyroglutamyl, iso-aspartyl, proteolytic, phosphorylated, glycosylated, reduced, oxidatized, isomerized, nitrosylated, and deaminated variants of the albumin.

Fragments of native or synthetic albumin sequences may also have the desirable functional properties of the peptide from which they derived and may be used in any of the methods of the invention. The term "fragment" as used herein thus includes fragments of albumin provided that the fragment retains the partial or full biological or therapeutically beneficial activity of the whole molecule.

For example, albumin contains at least 2 high affinity multi-metal binding sites for a number of physiologically important metals ions including copper, zinc, cadmium and nickel. (Carter et al., Advances in Protein Chemistry 45 153-203 (1994); Bai et al., J. Inorg Biochem 70 (1) 33-39 (1998), Blindauer et al., J. Biol. Chem. 284 (34) 23116-24 (2009); U.S. Pat. No. 6,787,636). Since trace amounts of these metals are typically present in the recombinant production of albumin, a significant amount of these metal ions can be become chelated to the protein. The binding of these ions, and in particular the binding of cadmium and nickel to recombinant albumin is associated with cellular toxicity of the protein when added to cells as a tissue culture component.

Accordingly, in one aspect, the term albumin can comprise a fragment of albumin that includes the deletion of one or more amino acids involved in the multi-metal binding sites of albumin. In one aspect the albumin fragment is created by the deletion of one or more amino acids at the N-terminus of the mature protein. In another aspect the albumin can comprise one or more deletions or mutations of any of the amino acids involved in the N-terminal metal binding site of albumin. In one aspect, the amino acids to be deleted or mutated are independently selected from the sequence 5' DAHKSEVAH 3' (SEQ. ID. NO. 1).

The term "derivative" as used herein thus refers to albumin sequences or fragments thereof, which have modifications as compared to the native sequence. Such modifications may be one or more amino acid deletions, additions, insertions and/or substitutions. These may be contiguous or non-contiguous. Representative variants may include those having 1 to 20, or more preferably 1 to 15, 1 to 10, or 1 to 5 amino acid substitutions, insertions, and/or deletions as compared to any of genes listed in Tables D1. The substituted amino acid may be any amino acid, particularly one of the well-known 20 conventional amino acids (Ala (A); Cys (C); Asp (D); Glu (E); Phe (F); Gly (G); His (H); Ile (I); Lys (K); Leu (L); Met (M); Asn (N); Pro (P); Gin (Q); Arg (R); Ser (S); Thr (T); Val (V); Trp (W); and Tyr (Y)). Any such variant or derivative of albumin may be used in any of the methods of the invention.

Accordingly, the albumin of the invention can comprise amino acid deletions, insertions or mutations in any of the functional binding domains of albumin. In one aspect the albumin may comprise a mutation in a binding domain of albumin. In one aspect the mutated binding domain is a domain involved in the binding of aspirin, warfarin, diazepam, digitoxin, dlofibrate, ibuprofen or AZT, as outlined is U.S. Pat. No. 5,780,593, or a multimetal binding site as outlined in Blindauer et al., J. Biol. Chem. 284 (34) 23116-24 (2009).

Thus, the albumin which may be used in any of the methods of the invention may have amino acid sequences which are substantially homologous, or substantially similar to the native albumin amino acid sequences, for example, to any of the native albumin gene sequences listed in Table D1. Alternatively, the albumin may have an amino acid sequence having at least 30% preferably at least 40, 50, 60, 70, 75, 80, 85, 90, 95, 98, or 99% identity with albumin listed in Table D1. In a preferred embodiment, the albumin for use in any of the methods of the present invention is at least 80% identical to the mature secreted human serum albumin as shown underlined in the below (Swiss-Prot P02768):

(SEQ. ID. NO. 2)
MKWVTFISLL FLFSSAYSRG VFRR<u>DAHKSE VAHRFKDLGE</u>

<u>ENFKALVLIA FAQYLQQCPF EDHVKLVNEV TEFAKTCVAD</u>

<u>ESAENCDKSL HTLFGDKLCT VATLRETYGE MADCCAKQEP</u>

```
ERNECFLQHK DDNPNLPRLV RPEVDVMCTA FHDNEETFLK

KYLYEIARRH PYFYAPELLF FAKRYKAAFT ECCQAADKAA

CLLPKLDELR DEGKASSAKQ RLKCASLQKF GERAFKAWAV

ARLSQRFPKA EFAEVSKLVT DLTKVHTECC HGDLLECADD

RADLAKYICE NQDSISSKLK ECCEKPLLEK SHCIAEVEND

EMPADLPSLA ADFVESKDVC KNYAEAKDVF LGMFLYEYAR

RHPDYSVVLL LRLAKTYETT LEKCCAAADP HECYAKVFDE

FKPLVEEPQN LIKQNCELFE QLGEYKFQNA LLVRYTKKVP

QVSTPTLVEV SRNLGKVGSK CCKHPEAKRM PCAEDYLSVV

LNQLCVLHEK TPVSDRVTKC CTESLVNRRP CFSALEVDET

YVPKEFNAET FTFHADICTL SEKERQIKKQ TALVELVKHK

PKATKEQLKA VMDDFAAFVE KCCKADDKET CFAEEGKKLV

AASQAALGL .
```

Fusion proteins of albumin to other proteins are also included, and these fusion proteins may enhance, activity, targeting, stability or potency.

Chemical modifications of the native albumin structure which retain or stabilize albumin activity or biological half-life may also be used with any of the methods described herein. Such chemical modification strategies include without limitation pegylation, glycosylation, and acylation (see Clark et al.: *J. Biol. Chem.* 271(36): 21969-21977, 1996; Roberts et al.: *Adv. Drug. Deliv. Rev.* 54(4): 459-476, (2002); Felix et al.: *Int. J. Pept. Protein. Res.* 46(3-4): 253-264, (1995); Garber Diabetes Obes. Metab. 7 (6) 666-74 (2005)) C- and N-terminal protecting groups and peptomimetic units may also be included.

Isomers of the native L-amino acids, e.g., D-amino acids may be incorporated in any of the above forms of albumin, and used in any of the methods of the invention. All such variants, derivatives, fusion proteins, or fragments of albumin are included, may be used in any of the methods claims or disclosed herein, and are subsumed under the term "albumin".

The term "transferrin" refers to all naturally-occurring and synthetic forms of transferrin. In one aspect, the term "transferrin" refers to recombinant transferrin. In one aspect the transferrin is from a vertebrate. In one aspect the transferrin is from a mammal. In a further embodiment the transferrin is human. In another aspect the recombinant transferrin is produced from a plant cell. In one particularly preferred embodiment the recombinant transferrin is produced from transgenic rice (*Oryza sativa*). Representative species and Gene bank accession numbers for various species of transferrin are listed below in Table D2.

TABLE D2

Exemplary Transferrin genes

| Species | Gene Bank Accession number |
| --- | --- |
| *Homo sapiens* | NP_001054.1 |
| *Canis lupus familiaris* | XP_864550.1 |
| *Bos taurus* | NP_803450.2 |
| *Mus musculus* | NP_598738.1 |
| *Rattus norvegicus* | NP_001013128.1 |

TABLE D2-continued

Exemplary Transferrin genes

| Species | Gene Bank Accession number |
| --- | --- |
| *Gallus gallus* | NP_990635.1 |
| *Danio rerio* | NP_001015057.1 |

The transferrin may be in its native form, i.e., as different apo forms, or allelic variants as they appear in nature, which may differ in their amino acid sequence, for example, by truncation (e.g., from the N- or C-terminus or both) or other amino acid deletions, additions, insertions, substitutions, or post-translational modifications. Naturally-occurring chemical modifications including post-translational modifications and degradation products of the transferrin, are also specifically included in any of the methods of the invention including for example, pyroglutamyl, iso-aspartyl, proteolytic, phosphorylated, glycosylated, reduced, oxidatized, isomerized, and deaminated variants of the transferrin.

The transferrin which may be used in any of the methods of the invention may have amino acid sequences which are substantially homologous, or substantially similar to the native transferrin amino acid sequences, for example, to any of the native transferrin gene sequences listed in Table D2. Alternatively, the transferrin may have an amino acid sequence having at least 30% preferably at least 40, 50, 60, 70, 75, 80, 85, 90, 95, 98, or 99% identity with transferrin listed in Table D2. In a preferred embodiment, the transferrin for use in any of the methods of the present invention is at least 80% identical to the mature human transferrin.

The term "Glutathione S-transferase" refers to all naturally-occurring and synthetic forms of Glutathione S-transferase. In one aspect, the term "Glutathione S-transferase" refers to recombinant Glutathione S-transferase. In one aspect the Glutathione S-transferase is from a vertebrate. In one aspect the Glutathione S-transferase is from a mammal. In a further embodiment the Glutathione S-transferase is human. In another aspect the recombinant Glutathione S-transferase is produced from a plant cell. In one particularly preferred embodiment the recombinant Glutathione S-transferase is produced from transgenic rice (*Oryza sativa*). Representative species and Gene bank accession numbers for various species of Glutathione S-transferase are listed below in Table D3.

TABLE D3

Exemplary Glutathione S-transferase genes

| Species | Gene Bank Accession number |
| --- | --- |
| *Homo sapiens* | NP_004519.1 |
| *Pan troglodytes* | XP_001174621.1 |
| *Canis lupus familiaris* | XP_536147.1 |
| *Canis lupus familiaris* | XP_851330.1 |
| *Bos taurus* | NP_001030218.1 |
| *Mus musculus* | NP_079845.1 |
| *Rattus norvegicus* | XP_213943.2 |
| *Gallus gallus* | XP_001232860.1 |
| *Danio rerio* | NP_998592.1 |
| *Arabidopsis thaliana* | NP_176758.1 |
| *Oryza sativa* | NP_001051042.1 |

The Glutathione S-transferase may be in its native form, i.e., as different apo forms, or allelic variants as they appear in nature, which may differ in their amino acid sequence, for example, by truncation (e.g., from the N- or C-terminus or both) or other amino acid deletions, additions, insertions, substitutions, or post-translational modifications. Naturally-occurring chemical modifications including post-translational modifications and degradation products of the Glutathione S-transferase, are also specifically included in any of the methods of the invention including for example, pyroglutamyl, iso-aspartyl, proteolytic, phosphorylated, glycosylated, reduced, oxidatized, isomerized, and deaminated variants of the Glutathione S-transferase. The Glutathione S-transferase which may be used in any of the methods of the invention may have amino acid sequences which are substantially homologous, or substantially similar to the native Glutathione S-transferase amino acid sequences, for example, to any of the native Glutathione S-transferase gene sequences listed in Table D2. Alternatively, the Glutathione S-transferase may have an amino acid sequence having at least 30% preferably at least 40, 50, 60, 70, 75, 80, 85, 90, 95, 98, or 99% identity with Glutathione S-transferase listed in Table D2. In a preferred embodiment, the Glutathione S-transferase for use in any of the methods of the present invention is at least 80% identical to the mature human Glutathione S-transferase.

The term "Superoxide Dismutase" refers to all naturally-occurring and synthetic forms of Superoxide Dismutase. In one aspect, the term "Superoxide Dismutase" refers to recombinant Superoxide Dismutase. In one aspect the Superoxide Dismutase is from a vertebrate. In one aspect the Superoxide Dismutase is from a mammal. In a further embodiment the Superoxide Dismutase is human. In another aspect the recombinant Superoxide Dismutase is produced from a plant cell. In one particularly preferred embodiment the recombinant Superoxide Dismutase is produced from transgenic rice (*Oryza sativa*). Representative species and Gene bank accession numbers for various species of Superoxide Dismutase are listed below in Table D4.

TABLE D4

Exemplary Superoxide Dismutase genes

| Species | Gene Bank Accession number |
|---|---|
| *Homo sapiens* | NP_000445.1 |
| *Pan troglodytes* | NP_001009025.1 |
| *Canis lupus familiaris* | NP_001003035.1 |
| *Bos taurus* | XP_584414.4 |
| *Bos taurus* | NP_777040.1 |
| *Mus musculus* | NP_035564.1 |
| *Mus musculus* | XP_994787.1 |
| *Rattus norvegicus* | NP_058746.1 |
| *Gallus gallus* | NP_990395.1 |
| *Danio rerio* | NP_571369.1 |
| *Drosophila melanogaster* | NP_476735.1 |
| *Anopheles gambiae* | XP_311594.2 |
| *Caenorhabditis elegans* | NP_494779.1 |
| *Caenorhabditis elegans* | NP_001021956.1 |
| *Schizosaccharomyces pombe* | NP_593163.1 |
| *Saccharomyces cerevisiae* | NP_012638.1 |
| *Kluyveromyces lactis* | XP_454197.1 |
| *Eremothecium gossypii* | NP_986346.1 |
| *Magnaporthe grisea* | XP_366549.2 |
| *Neurospora crassa* | XP_329323.1 |
| *Arabidopsis thaliana* | NP_001077494.1 |
| *Oryza sativa* | NP_001050118.1 |
| *Oryza sativa* | NP_001060564.1 |

The Superoxide dismutase may be in its native form, i.e., as different apo forms, or allelic variants as they appear in nature, which may differ in their amino acid sequence, for example, by truncation (e.g., from the N- or C-terminus or both) or other amino acid deletions, additions, insertions, substitutions, or post-translational modifications. Naturally-occurring chemical modifications including post-translational modifications and degradation products of the Superoxide dismutase, are also specifically included in any of the methods of the invention including for example, pyroglutamyl, iso-aspartyl, proteolytic, phosphorylated, glycosylated, reduced, oxidatized, isomerized, and deaminated variants of the Superoxide dismutase. The Superoxide dismutase which may be used in any of the methods of the invention may have amino acid sequences which are substantially homologous, or substantially similar to the native Superoxide dismutase amino acid sequences, for example, to any of the native Superoxide dismutase gene sequences listed in Table D2. Alternatively, the Superoxide dismutase may have an amino acid sequence having at least 30% preferably at least 40, 50, 60, 70, 75, 80, 85, 90, 95, 98, or 99% identity with Superoxide dismutase listed in Table D2. In a preferred embodiment, the Superoxide dismutase for use in any of the methods of the present invention is at least 80% identical to the mature human Superoxide dismutase.

In one aspect, the supplements of the invention may be prepared by mixing the isolated cell culture components with a purified, or semi purified preparation of one or more heat shock proteins in aqueous solution. Such heat shock proteins will be typically be mixed in a molar ratio of the cell culture component to hsp of about 1:1, about 1:10, about 1:20, about 1:50, about 1:100, about 1:200, about 1:500, about 1:1000, or about 1:10,000. In one aspect a mixture of the cell culture component and one or more heat shock proteins may be incubated together in an aqueous buffer at about 4° C. to 25° C. for a time ranging from a few minutes to overnight. In another aspect a mixture of cell culture component and one or more heat shock proteins may be incubated together in an aqueous buffer at about 20° C. to about 37° C. for a time ranging from a few minutes to overnight. In one aspect the cell culture component and hsp may be mixed in the presence of ATP to enable the hsp to undergo ATP-dependent conformation binding to the cell culture component. In one aspect of any of these methods, the aqueous buffer has a pH of about 6.5 to about 7.5. In another aspect of any of these methods, the aqueous buffer solution comprises a buffer selected from phosphate, TRIS, HEPES, and acetate. In one aspect of any of these methods the complex of the cell culture component and the heat shock protein is isolated.

In one aspect of any of the claimed methods the cell culture component is albumin. In one aspect of any of the claimed methods the cell culture component is transferrin. In one aspect of any of the claimed methods the cell culture component is a human growth factor.

Liquids of known concentration can also be combined containing one component part A (albumin or another cell culture component), to a liquid containing part B (such as a heat shock protein) to obtain a ratio that contains approximately 0.01% to 0.5% wt/wt hsp with respect to cell culture component. Powdered, lyophilized, or otherwise dried powder (Hsp) can be added directly to an aqueous solution containing the cell culture component in order to obtain a ratio based on dry weight of Hsp at 0.01% to 0.5% Hsp with respect to cell culture component. Powdered, lyophilized, or otherwise dried Hsp can also be blended with the cell culture component powder on a mass to mass basis to obtain a ratio that is completely based on gravimetrics. The resulting powder can be dissolved at concentrations ranging from very low (picomolar) to very high concentrations (millimolar) in suitable buffers that are common to the art to reconstitute the cell culture component/hsp complex.

In another embodiment, the present invention includes a method for improving the activity and or stability of a heat shock protein comprising the steps of contacting the heat shock protein with albumin in aqueous solution. In one aspect of this method the heat shock protein and albumin are contacted in the presence of ATP. In one aspect of this method, the albumin is recombinant albumin and the hsp is a native hsp to the host cell, and the method further comprises the step of purifying a protein fraction enriched in the complex of albumin and a heat shock protein.

In another embodiment, the present invention includes a method for improving the activity and or stability of the cell culture component comprising the steps of contacting the cell culture component with a hsp in aqueous solution. In one aspect of this method the heat shock protein and albumin are contacted in the presence of ATP. In one aspect of this method, the cell culture component is recombinant, and the albumin is recombinant, and the method further comprises the step of purifying a protein fraction enriched in the complex of albumin and a heat shock protein.

In one aspect, supplements of the present invention will accordingly comprise albumin and one or more heat shock proteins. Such supplements will commonly be prepared as sterile liquid or powder form. The total amount of hsp in the composition may vary from 1% to 0.001% of weight of the cell culture component. In other aspects the amount of hsp in the composition may vary from about 0.01% to about 0.02%, or about 0.01% to about 0.09%, or about 0.02% to about 0.04%, or about 0.02% to about 0.06% or about 0.02% to about 0.08%. In another aspect the amount of hsp in the composition is greater than about 0.02%, or more preferably greater than about 0.03%, or more preferably greater than about 0.04% wt/wt, or more preferably greater than about 0.05% wt/wt hsp with respect to the cell culture component.

In one aspect, supplements of the present invention will accordingly comprise transferrin and one or more heat shock proteins. Such supplements will commonly be prepared as sterile liquid or powder form. The total amount of hsp in any of the claimed compositions may vary from 5% to 0.001% of weight. In other aspects the amount of hsp in the composition may vary from about 5% to about 1%, In other aspects the amount of hsp in the composition may vary from about 4% to about 1%, In other aspects the amount of hsp in the composition may vary from about 3% to about 1%, In other aspects the amount of hsp in the composition may vary from about 2% to about 1%, In other aspects the amount of hsp in the composition may vary from about 1% to about 0.5%, In other aspects the amount of hsp in the composition may vary from about 0.5% to about 0.1%, In other aspects the amount of hsp in the composition may vary from about 0.1% to about 0.05%, wt/wt.

In other aspects the amount of hsp in any of the claimed compositions may vary from about 0.01% to about 0.02%, or about 0.01% to about 0.09%, or about 0.02% to about 0.04%, or about 0.02% to about 0.06%, or about 0.02% to about 0.08%. In another aspect the amount of hsp in the composition is greater than about 0.02%, or more preferably greater than about 0.03%, or even more preferably greater than about 0.04% wt/wt., or even more preferably greater than about 0.05% wt/wt.

In another aspect, supplements of the present invention will accordingly comprise a human growth factor and one or more heat shock proteins. Such supplements will commonly be prepared as sterile liquid or powder form. The total amount of hsp in the composition may vary from 1% to 0.001% of weight. In other aspects the amount of hsp in the composition may vary from about 0.01% to about 0.02%, or about 0.01% to about 0.09%, or about 0.02% to about 0.04%, or about 0.02% to about 0.06% or about 0.02% to about 0.08%. In another aspect the amount of hsp in the composition is greater than about 0.02%, or more preferably greater than about 0.03%, or more preferably greater than about 0.04% wt/wt or more preferably greater than about 0.05% wt/wt hsp with respect to the cell culture component.

In one aspect of any of the claimed supplements, the supplement is essentially free of endotoxin and detergents. In another aspect the supplement has less than about 1 EU/mg of endotoxin. In yet another aspect, the supplement contains less than about 10 ppm detergent. In another aspect of any of the claimed supplements, the cell culture component has a purity of greater than 95%.

In another of any of the claimed supplements, the supplement comprises a recombinant cell culture component which is bound to a rice heat shock protein, wherein the complex has less than about 1 EU of endotoxin and is at least 95% pure.

In another aspect of any of these methods the supplement contains albumin as the cell culture component, and the albumin is essentially free of aggregated albumin. In another aspect of any of these supplements the albumin has less than about 2% aggregated albumin.

III. Exemplary Heat Shock Proteins

The terms "heat shock protein", "HSP" or "hsp", as used herein includes all naturally-occurring and synthetic forms of the heat shock protein super family that retain anti-apoptotic activity. Such heat shock proteins include the small heat shock proteins/HSPB family, Hsp40/DnaJ family, HSP70/HSPA family, HSP90/HSPC family, HSP110/HSPH family and chapererone family, as well as peptide fragments and protein complexes of two or more heat shock proteins or nucleotide exchange factors (for example, complexes of HSP70 & HSP40) derived therefrom.

Heat shock genes from a large number of different species have been sequenced, and are known in the art to be at least partially functionally interchangeable. It would thus be a routine matter to select a variant being a heat shock protein from a family or species or genus other than rice heat shock protein. Several such variants of heat shock proteins (i.e., representative heat shock proteins) are shown in Tables D5-D11.

The heat shock proteins were originally identified as stress-responsive proteins required to adapt to thermal and other stresses. It became clear shortly thereafter that all HSP families also encode constitutively expressed members like Hsc70 (HSPA8) in the HSP70 family. The heat shock genes and the protein family members that they encode) that have been most extensively studied are those that are heat inducible, such as HSP70i (HSPA1A/B), HSP40 (DNAJB1), and HSP27 (HSPB1). Heat shock proteins, as a class, are among the most highly expressed cellular proteins across all species. As their name implies, heat shock proteins protect cells when stressed by elevated temperatures. They account for 1-2% of total protein in unstressed cells. However when cells are heated, the fraction of heat shock proteins increases to about 4-6% of cellular proteins.

The number of genes coding for the diverse HSP family members varies widely in different organisms. For example, in the HSPA (HSP70) family, the number of members varies from three in *Escherichia coli* to 13 in humans. Gene duplication during evolution likely satisfied the need for additional members in different intracellular compartments as well as for tissue specific or developmental expression. Moreover, gene duplication provides functional diversity for client specificity and/or processing.

All such homologues, orthologs, and naturally occurring isoforms of heat shock proteins from eukaryotes, prokaryotes, vertebrates, invertebrates, and plants as well as other species are included in any of the methods of the invention, as long as they retain detectable anti-apoptotic activity.

Since the annotation of the human genome, the names used for the Hsp family members in the literature have become chaotic and up to ten different names can be found for the same gene product. The nomenclature used in the tables below is based on the systematic gene symbols that have been assigned by the HUGO Gene Nomenclature Committee (HGNC) and are used as the primary identifiers in databases such as Entrez Gene and Ensemble. (Kaminga et al., Cell Stress 7 Chaperones 14 105-111 (2009)).

Small Hsps

The family of small HSPs consists presently of 11 members in man (Table D5) that are characterized by a signature conserved crystallin domain flanked by variable N- and C-termini. The best studied members are HSPB1 (HSP27), HSPB4 (αA crystallin), and HSPB5 (αB crystallin). The small HSPs are often found in oligomeric complexes involving one or more family members and as such may provide the cell with a large diversity in chaperone specificity.

which 23 are sHSPs. (Srakar et al., BMC Genomics 10 393 (2009) doi:10.1186/1471-2164-10-393). The majority of rice small HSP are expressed in seeds (Table D6).

sHsps

TABLE D6

| Rice small hsp genes | | |
|---|---|---|
| Gene Name | Protein Name | High expression in seeds |
| Os01g04340 | Hsp16.6-CVIII | + |
| Os01g04350 | Hsp17.9B-CIX | |
| Os01g04360 | Hsp16.9C-CI | |
| Os01g04370 | Hsp16.9A-CI | + |
| Os01g04380 | Hsp16.9B-CI | + |
| Os01g08860 | Hsp18.0-CII | |
| Os02g03570 | Hsp18.8-CX | |
| Os02g10710 | Hsp23.6-MII | |
| Os02g12610 | Hsp19.0-CII | |
| Os02g48140 | Hsp17.8-CXI | + |
| Os02g48140.2 | | |
| Os02g52150 | Hsp24.0-MI | |
| Os02g54140: | Hsp18.6-CIII | |
| Os03g14180 | Hsp26.7-P | + |
| Os03g15960 | Hsp17.9A-CI | |
| Os03g16020 | Hsp17.4-CI | + |
| Os03g16030 | Hsp18.0-CI | + |
| Os03g16040 | Hsp17.7-CI | |
| Os04g36750 | Hsp23.2-ER | |
| Os05g42120 | Hsp22.3-CVI | |
| Os06g11610 | Hsp26.2-MI | |
| Os06g14240 | Hsp16.0-Px | |
| Os07g33350 | Hsp18.8-CV | |
| Os07g33350.2 | | |
| Os11g13980 | Hsp21.8-ER | |

TABLE D5

| | Gene name | Protein name | Old names | Human gene ID | Mouse ortholog ID |
|---|---|---|---|---|---|
| | | | The HSPB family (small heat shock proteins) | | |
| 1 | HSPB1 | HSPB1 | CMT2F; HMN2B; HSP27; HSP28; HSP25; HS.76067; DKFZp586P1322 | 3315 | 15507 |
| 2 | HSPB2 | HSPB2 | MKBP; HSP27; Hs.78846; LOH11CR1K; MGC133245 | 3316 | 69253 |
| 3 | HSPB3 | HSPB3 | HSPL27 | 8988 | 56534 |
| 4 | HSPB4a | HSPB4 | crystallin alpha A; CRYAA, CRYA1 | 1409 | 12954 |
| 5 | HSPB5a | HSPB5 | crystallin alpha B, CRYAB; CRYA2 | 1410 | 12955 |
| 6 | HSPB6 | HSPB6 | HSP20; FLJ32389 | 126393 | 243912 |
| 7 | HSPB7 | HSPB7 | cvHSP; FLJ32733; DKFZp779D0968 | 27129 | 29818 |
| 8 | HSPB8 | HSPB8 | H11; HMN2; CMT2L; DHMN2; E2IG1; HMN2A; HSP22 | 26353 | 80888 |
| 9 | HSPB9 | HSPB9 | FLJ27437 | 94086 | 75482 |
| 10 | HSPB10a | HSPB10 | ODF1; ODF; RT7; ODF2; ODFP; SODF; ODF27; ODFPG; ODFPGA; ODFPGB; MGC129928; MGC129929 | 4956 | 18285 |
| 11 | HSPB11 | HSPB11 | HSP16.2; C1orf41; PP25 | 51668 | 72938 | aUnder consultation with HGNC and the scientific community

In plants, small heat shock proteins are encoded by nuclear multigene families which are localized in different cellular compartments. In *Arabidopsis* there are 19 genes coding for sHSPs and 25 genes encoding crystallin domain proteins. In rice genomic analysis reveals 40 crystallin domain proteins of Hsp40 Family The human Hsp40/DnaJ family of heat-shock proteins includes a large protein family that share a 70 amino-acid consensus sequence known as the J domain (Table D7).

TABLE D7

The DNAJ (HSP40) family

| | Gene name | Protein name | Old names | Human gene ID | Mouse ortholog ID |
|---|---|---|---|---|---|
| DnaJA | | | | | |
| 1 | DNAJA1 | DNAJA1 | DJ-2; DjA1; HDJ2; HSDJ; HSJ2; HSPF4; hDJ-2 | 3301 | 15502 |
| 2 | DNAJA2 | DNAJA2 | DNJ3; mDj3; Dnaj3; HIRIP4 | 10294 | 56445 |
| 3 | DNAJA3 | DNAJA3 | Tid-1; Tid11 | 9093 | 83945 |
| 4 | DNAJA4 | DNAJA4 | Dj4; Hsj4 | 55466 | 58233 |
| DnaJB | | | | | |
| 5 | DNAJB1 | DNAJB1 | HSPF1; HSP40 | 3337 | 81489 |
| 6 | DNAJB2 | DNAJB2 | HSJ1; HSPF3; Dnajb10; MDJ8 | 3300 | 56812 |
| 7 | DNAJB3 | DNAJB3 | Hsj3; Msj1; MSJ-1; Hcg3a | 414061a | 15504 |
| 8 | DNAJB4 | DNAJB4 | Hsc40 | 11080 | 67035 |
| 9 | DNAJB5 | DNAJB5 | Hsc40; HSP40-3 | 25822 | 56323 |
| 10 | DNAJB6 | DNAJB6 | Mrj; mDj4 | 10049 | 23950 |
| 11 | DNAJB7 | DNAJB7 | Dj5; mDj5 | 150353 | 57755 |
| 12 | DNAJB8 | DNAJB8 | mDj6 | 165721 | 56691 |
| 13 | DNAJB9 | DNAJB9 | Mdg1; mDj7; ERdj4 | 4189 | 27362 |
| 14 | DNAJB11 | DNAJB11 | Dj9; ABBP-2; Erdj3 | 51726 | 67838 |
| 15 | DNAJB12 | DNAJB12 | Dj10; mDj10 | 54788 | 56709 |
| 16 | DNAJB13 | DNAJB13 | Tsarg6; Tsarg 3 protein | 374407 | 69387 |
| 17 | DNAJB14 | DNAJB14 | EGNR9427; FLJ14281 | 79982 | 70604 |
| DnaJC | | | | | |
| 19 | DNAJC1 | DNAJC1 | MTJ1; ERdj1; ERj1p; Dnajl1 | 64215 | 13418 |
| 20 | DNAJC2b | DNAJC2 | Zrf1; Zrf2; MIDA1; M-phase phosphatase protein 11; MPP11; zuotin; ZUO1 | 27000 | 22791 |
| 21 | DNAJC3 | DNAJC3 | p58; mp58; Prkri; Dnajc3; p58IPK; Dnajc3b | 5611 | 100037258 |
| 22 | DNAJC4 | DNAJC4 | HSPf2; Mcg18 | 3338 | 57431 |
| 23 | DNAJC5 | DNAJC5 | Csp | 80331 | 13002 |
| 24 | DNAJC5B | DNAJC5B | CSP-beta | 85479 | 66326 |
| 25 | DNAJC5G | DNAJC5G | MGC107182; gamma-CSP | 285126 | 231098 |
| 26 | DNAJC6 | DNAJC6 | mKIAA0473; auxilin | 9829 | 72685 |
| 27 | DNAJC7 | DNAJC7 | Ttc2; mDj11; mTpr2 | 7266 | 56354 |
| 28 | DNAJC8 | DNAJC8 | AL024084; AU019262; splicing protein (spf31) | 22826 | 68598 |
| 29 | DNAJC9 | DNAJC9 | AU02008; RcDNAJ9 | 23234 | 108671 |
| 30 | DNAJC10 | DNAJC10 | JPDI; ERdj5; macrothioredoxin | 54431 | 66861 |
| 31 | DNAJC11 | DNAJC11 | FLJ10737; dJ126A5.1 | 55735 | 230935 |
| 32 | DNAJC12 | DNAJC12 | Jdp1; mJDP1 | 56521 | 30045 |
| 33 | DNAJC13 | DNAJC13 | Rme8; RME-8; Gm1124 | 23317 | 235567 |
| 34 | DNAJC14 | DNAJC14 | HDJ3; LIP6; DRIP78 | 85406 | 74330 |
| 35 | DNAJC15 | DNAJC15 | Dnajd1; MCJ; Cell growth-inhibiting 22 protein | 29103 | 66148 |
| 36 | DNAJC16 | DNAJC16 | mKIAA0962 | 23341 | 214063 |
| 37 | DNAJC17 | DNAJC17 | C87112 | 55192 | 69408 |
| 38 | DNAJC18 | DNAJC18 | MGC29463 | 202052 | 76594 |
| 39 | DNAJC19 | DNAJC19 | TIM14; TIMM14 | 131118 | 67713 |
| 40 | DNAJC20b | DNAJC20 | JAC1; HSC20; HscB | 150274 | 100900 |
| 41 | DNAJC21 | DNAJC21 | GS3; JJJ1; DNAJA5 | 134218 | 78244 |
| 42 | DNAJC22 | DNAJC22 | FLJ13236; Wurst | 79962 | 72778 |
| 43 | DNAJC23b | DNAJC23 | Sec63; AI649014 | 11231 | 140740 |
| 44 | DNAJC24b | DNAJC24 | DPH4; zinc finger, CSL-type containing 3 | 120526 | 99349 |
| 45 | DNAJC25 | DNAJC25 | bA16L21.2.1; DnaJ-like protein; AAH48318; LOC552891; G-protein gamma 10 | 548645 | 72429 |
| 46 | DNAJC26 | DNAJC26 | GAK; cyclin G associated kinase; auxilin- | 2 2580 | 231580 |
| 47 | DNAJC27b | DNAJC27 | RBJ; RabJ | 51277 | 217378 |
| 48 | DNAJC28 | DNAJC28 | Orf28 open reading frame 28; C21orf55, oculomedin | 54943 | 24738 |
| 49 | DNAJC29b | | Sacsin; SACS | 26278 | 50720 |
| 50 | DNAJC30 | DNAJC30 | WBSCR18; Williams-Beuren syndrome chromosome region 18 homolog (human) | 84277 | 66114 | aHcg3 is the closest human homologue of, and is syntenic with, MSJ-1 which encodes both N-and C-terminal domains in the same transcript but there is a reported frame shift between these domains
bUnder consultation with HGNC and the scientific community The J domain of Hsp40 interacts with Hsp70 heat shock proteins and plays a role in regulating the ATPase activity of Hsp70 heat-shock proteins while nucleotide exchange factors (NEFs) remove ADP after ATP hydrolysis, enabling a new Hsp70 interaction cycle with non-native protein substrate. The highly conserved ~70 amino acid J domain of HSP40 contacts Hsp70's nucleotide binding domain and enhances essential "house-keeping" HSPA member and is involved in co-translational folding and protein translocation across intracellular membranes. HSPA1L and HSPA2 are two cytosolic family members with high expression in the testis. HSPA9 is the mitochondrial housekeeping HSPA member (HSPA9 is also known as mortalin/mtHSP70/GRP75/PBP74).

TABLE D8

HSP70 superfamily: HSPA (HSP70)

| HSP A | Gene name | Protein name | Old names | Human gene ID | Mouse ortholog ID |
|---|---|---|---|---|---|
| 1 | HSPA1A | HSPA1A | HSP70-1; HSP72; HSPA1 | 3303 | 193740 |
| 2 | HSPA1B | HSPA1B | HSP70-2 | 3304 | 15511 |
| 3 | HSPA1L | HSPA1L | hum70t; hum70t; Hsp-hom | 3305 | 15482 |
| 4 | HSPA2 | HSPA2 | Heat-shock 70 kD protein-2 | 3306 | 15512 |
| 5 | HSPA5 | HSPA5 | BIP; GRP78; MIF2 | 3309 | 14828 |
| 6 | HSPA6 | HSPA6 | Heat shock 70 kD protein 6 (HSP70B') | 3310 | X |
| 7 | HSPA7a | HSPA7 | Heat shock 70 kD protein 7 | 3311 | X |
| 8 | HSPA8 | HSPA8 | HSC70; HSC71; HSP71; HSP73 | 3312 | 15481 |
| 9 | HSPA9 | HSPA9 | GRP75; HSPA9B; MOT; MOT2; PBP74; mot-2 | 3313 | 15526 |
| 10 | HSPA12A | HSPA12A | FLJ13874; KIAA0417 | 259217 | 73442 |
| 11 | HSPA12B | HSPA12B | RP23-32L15.1; 2700081N06Rik | 116835 | 72630 |
| 12 | HSPA13b | HSPA13 | Stch | 6782 | 110920 |
| 13 | HSPA14 | HSPA14 | HSP70-4; HSP70L1; MGC131990 | 51182 | 50497 | aAnnotated as pseudogene, but possibly a true gene
bUnder consultation with HGNC and the scientific community ATPase activity by inducing a conformational change. This leads to enhanced binding of Hsp70s to substrates. Moreover, some Hsp40 family members directly bind to unfolded regions on substrate proteins through their substrate binding domain and deliver the unfolded protein to the ATP bound form of their Hsp70 partner, while others contain atypical domains that specify exclusive functions.

Hsp40 members can be classified into three groups: DnaJA are most similar to DnaJ and contain a J domain followed by a glycine/phenylalanine-rich region and a cysteine-rich region with four repeats of a CxxCxGxG-type zinc finger; DnaJB lack the cysteine-rich region and are unable to coordinate Zn2+; DnaJC only have the J domain in common with DnaJ. Notably, the number of Hsp40 family members exceeds the number of Hsp70s in most organisms/organelles. In fact, a single Hsp70 can interact with different HSP40s to form unique Hsp70-Hsp40 pairs that participate in specific cellular functions. Despite the high conservation of the J domain, Hsp40 members are not necessarily interchangeable between organelles or organisms, further suggesting that there is specificity in the interaction between Hsp70s and Hsp40s. Specificity might be essential for substrate recognition and delivery, for the targeting of Hsp70 to distinct cellular locations, and/or for catalyzing protein folding in distinct chemical environments within organelles.

HSP70 Family

The human genome encodes 13 members of the HSPA family (Table D8), excluding the many pseudogenes. The most studied genes are HSPA1A and HSPA1B, the products of which only differ by two amino acids and which are believed to be fully interchangeable proteins. Together with HSPA6, these are the most heat-inducible family members. HSPA7 has long been considered to be a pseudogene, but recent analyses suggest that it might be a true gene that is highly homologous to HSPA6. HSPA8 is the cognate HSPA and was designated previously as Hsc70 (or HSP73). It is an Members of the Hsp70 family are strongly up-regulated by heat stress and toxic chemicals, particularly heavy metals such as arsenic, cadmium, copper, mercury, etc. Hsp70 was originally discovered by FM Ritossa in the 1960s when a lab worker accidentally boosted the incubation temperature of *Drosophila* (fruit flies). When examining the chromosomes, Ritossa found a "puffing pattern" that indicated the elevated gene transcription of an unknown protein. This was later described as the "Heat Shock Response".

Prokaryotes express three Hsp70 proteins: DnaK, HscA (Hsc66), and HscC (Hsc62). Eukaryotic organisms express several slightly different Hsp70 proteins. All share the common domain structure, but each has a unique pattern of expression or subcellular localization.

Hsc70 (Hsp73/HSPA8) is a constitutively expressed chaperone protein. It typically makes up one to three percent of total cellular protein.

Hsp72 (HSPA1A) is a stress-induced protein. High levels can be produced by cells in response to hyperthermia, oxidative stress, and changes in pH.

Binding immunoglobulin protein (BiP or Grp78) is a protein localized to the endoplasmic reticulum. It is involved in protein folding there, and can be up regulated in response to stress or starvation.

mtHsp70 or Grp75 is the mitochondrial Hsp70.

The Hsp70 proteins have three major functional domains:

An N-terminal ATPase domain—which drives conformational changes in the other two domains.

A substrate binding domain—contains a groove with an affinity for neutral, hydrophobic amino acid residues. The groove is long enough to interact with peptides up to seven residues in length.

The C-terminal domain—rich in alpha helical structure acts as a 'lid' for the substrate binding domain. When an Hsp70 protein is ATP bound, the lid is open and peptides bind and release relatively rapidly. When Hsp70 proteins are ADP bound, the lid is closed, and peptides are tightly bound to the substrate binding domain.

Hsp70 proteins play important roles in guiding the folding of new proteins, improving protein integrity, and also aid in the transmembrane transport of proteins, by stabilizing them in a partially-folded state. In addition to improving overall protein integrity, Hsp 70 also directly inhibits apoptosis, and participates in the recognition and disposal of damaged or defective proteins.

Consistent with Hsp70's central role in enhancing protein folding, the expression of Hsp 70 can also act to protect cells from thermal or oxidative stress during routine tissue culture processes such as cryopreservation and bio-processing. These stresses normally act to damage proteins, causing partial unfolding and possible aggregation. By temporarily binding to hydrophobic residues exposed by stress, Hsp70 prevents these partially-denatured proteins from aggregating, and allows them to refold. Low ATP which is characteristic of heat shock further enhances sustained binding of the HSP70 and further acts to enhance the ability of the HSPs to suppress aggregation. In a thermophile anaerobe (*Thermotoga maritima*) the Hsp70 demonstrates redox sensitive binding to model peptides, suggesting a second mode of binding regulation based on oxidative stress.

Hsp70 also inhibits apoptosis by blocking the recruitment of procaspase-9 leading to caspase 3 activation, and seems to be able to participate in disposal of damaged or defective proteins via interactions with CHIP (Carboxyl-terminus of Hsp70 Interacting Protein)—an E3 ubiquitin ligase.

Therefore, Hsp 70 proteins not only prevent damage to proteins, but also act to directly prevent programmed cell death under stressful conditions. The human aenome also encodes four HSP110 (HSPH; Table D9) genes which encode a family of HSPs with high homology to HSPA members except for the existence of a longer linker domain between the N-terminal ATPase domain and the C-terminal peptide binding domain. In fact, two members, HSPA4 (HSPH2) and HSPA4L (HSPH3), were previously named as HSPA members in the Entrez Gene database. Besides the three cytosolic members, one compartment-specific HSPH member (HYOU1/Grp170) is present in the ER, (HSPH4). Recent evidence shows that HSPH members are nucleotide exchange factors for the HSPA family.

TABLE D9

| | Gene name | Protein name | Old names | Human gene ID | Mouse ortholog ID |
|---|---|---|---|---|---|
| | | | HSP H superfamily: HSPH (HSP110) | | |
| 1 | HSPH1 | HSPH1 | HSP105 | 10808 | 15505 |
| 2 | HSPH2b | HSPH2 | HSPA4; APG-2; HSP110 | 3308 | 15525 |
| 3 | HSPH3b | HSPH3 | HSPA4L; APG-1 | 22824 | 18415 |
| 4 | HSPH4b | HSPH4 | HYOU1/Grp170; ORP150; HSP12A | 10525 | 12282 | a Annotated as pseudogene, but possibly a true gene
b Under consultation with HGNC and the scientific community Hsp90 Family Hsp90 was originally identified as one of several conserved heat shock proteins. Like the other major classes of heat shock proteins, Hsp90 exhibits general protective chaperone properties, such as preventing the unspecific aggregation of non-native proteins. However, Hsp90 seems to be more selective than the other promiscuous general chaperones, as it preferentially interacts with a specific subset of the proteome. Another specific feature of Hsp90 is its regulatory role of inducing conformational changes in folded, native-like substrate proteins that lead to their activation or stabilization.

In fact HSP90 controls the conformation, stability, activation, intracellular distribution, and turnover of numerous client proteins that are involved in cell growth, differentiation, and survival. Several kinases, hormone receptors, mutant p53, and the catalytic subunit of telomerase hTERT are HSP90 clients. HSP90 is a promising target for the development of cancer chemotherapeutics because its inhibition simultaneously affects multiple oncogenic proteins Hsp90 is a flexible dimer. Each monomer consists of three domains: the N-domain, connected by a long linker sequence (in eukaryotes) to an M-domain, which is followed by a C-terminal dimerization domain. Concomitant with the occurrence of a long charged linker connecting the N-3 and M-domains, the eukaryotic protein exhibits an extension of the C-terminal domain, which includes the conserved amino acid motif MEEVD at the C terminus. This region serves as the major interaction site for a family of co-chaperones, which appear to support Hsp90 in the folding and activation of its substrate proteins in eukaryotes. The N-domain possesses a deep ATP-binding pocket, where ATP is bound in an unusual kinked manner. ATP hydrolysis by Hsp90 is rather slow: Hsp90 from yeast hydrolyzes one molecule of ATP every 1 or 2 min and human Hsp90 hydrolyzes one molecule of ATP every 20 min.

TABLE D10

| | Gene name | Protein name | Old names | Human gene ID | Mouse ortholog ID |
|---|---|---|---|---|---|
| | | | The HSP90/HSPC family | | |
| 1 | HSPC1a | HSPC1 | HSP90AA1; HSPN; LAP2; HSP86; HSPC1; HSPCA; HSP89; HSP90; HSP90A; HSP90N; HSPCAL1; HSPCAL4; FLJ31884 | 3320 | 15519 |
| 2 | HSPC2a | HSPC2 | HSP90AA2; HSPCA; HSPCAL3; HSP90ALPHA; | 3324 | X |

TABLE D10-continued

The HSP90/HSPC family

| | Gene name | Protein name | Old names | Human gene ID | Mouse ortholog ID |
|---|---|---|---|---|---|
| 3 | HSPC3a | HSPC3 | HSP90AB1; HSPC2; HSPCB; D6S182; HSP90B; FLJ26984; HSP90-BETA | 3326 | 15516 |
| 4 | HSPC4a | HSPC4 | HSP90B1; ECGP; GP96; TRA1; GRP94; endoplasmin | 7184 | 22027 |
| 5 | HSPC5a | HSPC5 | TRAP1; HSP75; HSP90L | 10131 | 68015 | aUnder consultation with HGNC and the scientific community

The HSP90 family encodes five members (Table D10) with the exception of the so-called new member Hsp89-alpha-delta-N (HSP90N), which was found to be a chimera of two genes with its main part identical to HSPC1. The genes encoding these family members were initially annotated as HSPC members in Locuslink (the forerunner of the current Entrez Gene database). Up to now, more than a dozen distinct Hsp90 cofactors have been identified. Their large number is not paralleled by other chaperone systems. Most bind Hsp90 with submicromolar affinities. The major class of these is the TPR domain-containing cofactors, which include the proteins Hop/Sti1, PP5/Ppt1, and the large PPIases, among others.

The Human Chaperonin Families (HSPD/E and CCT)

In the mitochondria, single human orthologs of the *E. coli* GroEL (HSP60) and GroES (HSP10) are expressed and are annotated as HSPD and HSPE, respectively (Table D11). In the cytosol of human cells CCT (TRiC), a heterooligorneric chaperonin complex composed of eight different subunits, plays an essential role in folding newly synthesized cytosolic proteins and preventing protein aggregation. These subunits are encoded by separate genes and share approximately 30% amino acid sequence identity (approximately 15-20% identity to GroEL). There are two genes encoding CCT6 (zeta subunit): CCT6A (zeta-1) is constitutively expressed while CCT6B (zeta-2) is expressed in a testis-specific manner. None of them has been shown to be heat inducible.

TABLE D11

Chaperonins and related genes

| | Gene name | Protein name | Old names | Human gene ID | Mouse ortholog ID |
|---|---|---|---|---|---|
| | | | HSPD | | |
| 1 | HSPD1 | HSPD1 | HSP60; GroEL | 3329 | 15510 |
| | | | HSPE | | |
| 1 | HSPE1 | HSPE1 | HSP10; chaperonin 10; GroES | 3336 | 15528 |
| | | | CCT | | |
| 1 | CCT1a | CCT1 | TCP1; CCTA; CCT-alpha; TCP-1-alpha | 6950 | 21454 |
| 2 | CCT2 | CCT2 | CCTB; CCT-beta; TCP-1-beta | 10576 | 12461 |
| 3 | CCT3 | CCT3 | CCTG; CCT-gamma; TCP-1-gamma; TRiC-P5 | 7203 | 12462 |
| 4 | CCT4 | CCT4 | CCTD; CCT-delta,; TCP-1-delta; SRB | 10575 | 12464 |
| 5 | CCT5 | CCT5 | CCTE; CCT-epsilon; TCP-1-epsilon | 22948 | 12465 |
| 6 | CCT6A | CCT6A | CCT6; CCTZ; CCT-zeta; CCT-zeta1; TCP-1-zeta; HTR3; TCP20 | 908 | 12466 |
| 7 | CCT6B | CCT6B | CCTZ2; CCT-zeta2; TSA303 | 10693 | 12467 |
| 8 | CCT7 | CCT7 | CCTH; CCT-eta; TCP-1-eta | 10574 | 12468 |
| 9 | CCT8 | CCT8 | CCTQ; CCT-theta; TCP-1-theta; KIAA002 | 10694 | 12469 |
| | | | Other chaperonin-like | | |
| 1 | MKKS | MKKS | McKusick-Kaufman syndrome; MKS; Bardet-Biedl syndrome 6; BBS6 | 8195 | 59030 |
| 2 | BBS10 | BBS10 | Bardet-Biedl syndrome 10 | 79738 | 71769 |
| 3 | BBS12 | BBS12 | Bardet-Biedl syndrome 12 | 166379 | 241950 |

In normal cells, chaperonin genes such as HSP60 are mostly localized in the mitochondrial matrix and outer mitochondrial membrane. Hsp60 is constitutively expressed under normal conditions, and also induced by heat shock, mitochondrial damage, and mitochondrial DNA depletion. Human HSP60 may also trigger apoptosis through caspase cascade activation by an association between HSP60/HSP10 complex and pro-caspase-3 inside the mitochondria, resulting in a subsequent release of the HSP60 into the cytoplasm.

Under normal physiological conditions, HSP60 is a 60 kilodalton oligomer composed of monomers that form a complex arranged as two stacked heptameric rings. This double ring structure forms a large central cavity in which the unfolded protein binds via hydrophobic interactions. This structure is typically in equilibrium with each of its individual components: monomers, heptamers, and tetradeceamers.

Each subunit of HSP60 has three domains: the apical domain, the equatorial domain, and the intermediate domain. The equatorial domain contains the binding site for ATP and for the other heptameric ring. The intermediate domain binds the equatorial domain and the apical domain together.

In one embodiment of the any of the claims, the supplement of the invention comprises a Hsp selected from a small heat shock protein family member. In another aspect, the Hsp is selected from a HSP40/DnaJ family member. In another aspect, the Hsp is selected from a HSP70 family member. In another aspect, the Hsp is selected from a HSP90 family member. In another aspect, the Hsp is selected from a HSP110 family member. In another aspect, the Hsp is selected from a chapererone family member.

In one aspect of any the claims, the supplement of the invention comprises a Hsp superfamily member which is derived from a mammalian, insect, yeast or plant cell. In another aspect the Hsp superfamily member is derived from a plant cell. In yet another embodiment the HSP superfamily member is derived from rice (*Oryza sativa*).

In one aspect of any of these claims the supplement of the invention comprises a hsp superfamily member which is present in a protein complex with one or more other proteins. In a one aspect, the HSP superfamily member is complexed with another Hsp superfamily member of nucleotide exchange factor. In another aspect of any of these claims the Hsp superfamily member is bound to Albumin.

In one embodiment, the supplement of the invention comprises a HSP70 family member. In one aspect, the HSP70 family member is selected from HSPA1A (HSP72), HSPA8 (Hsc72) and HSPA9 (Grp78). In one aspect of any the claims, the HSP superfamily member is derived from a mammalian, insect, yeast or plant cell. In a preferred aspect the HSP superfamily member is derived from a plant cell. In one particularly preferred embodiment the HSP superfamily member is derived from rice (*Oryza sativa*).

In one aspect of any of the claims, the supplement of the invention comprises a HSP70 family member which is selected from a sequence from Table D12.

HSPA1A

TABLE D12

```
                                        HSPA1 HSP70 genes
Human               1 makaaaigid  lgttyscvgv  fqhgkgernv  lifdlgggtf  dvsiltiddg  ifevkatagd
CAM24989           61 thlggedfdn  rlvnhfveef  krkhkkdisq  nkravrrlrt  acerakrtls  sstqasleid
                  121 slfegidfyt  sitrarfeel  csdlfrstle  pvekalrdak  ldkaqihdlv  lvggstripk
                  181 vqkllqdffn  grdlnksinp  deavaygaav  qaailmgdks  envqdlllld  vaplslglet
                  241 aggvmtalik  rnstiptkqt  qifttysdnq  pgvliqvyeg  eramtkdnnl  lgrfelsgip
                  301 paprgvpqie  vtfdidangi  lnvtatdkst  gkankititn  dkgrlskeei  ermvqeaeky
                  361 kaedevqrer  vsaknalesy  afnmksaved  eglkgkisea  dkkkvldkcq  eviswldant
                  421 laekdefehk  rkeleqvcnp  iisglyqgag  gpgpggfgaq  gpkggsgsgp  tieevd
                  (SEQ. ID. NO. 3)

Insect              1 mpaigidlgt  tyscvgvyqh  gkveiiandq  gnrttpsyva  ftdserligd  paknqvamnp
NP_524798          61 rntvfdakrl  igrkyddpki  aedmkhwpfk  vvsdggkpki  gveykgeskr  fapeeissmv
                  121 ltkmketaea  ylgesitdav  itvpayfnds  qrqatkdagh  iaglnvlrii  neptaaalay
                  181 gldknlkger  nvlifdlggg  tfdvsiltid  egslfevrst  agdthlgged  fdnrlvthla
                  241 defkrkykkd  lrsnpralrr  lrtaaerakr  tlsssteati  eidalfegqd  fytkvsrarf
                  301 eelcadlfrn  tlqpvekaln  dakmdkgqih  divlvggstr  ipkvqsllqd  ffhgknlnls
                  361 inpdeavayg  aavqaailsg  dqsgkiqdvl  lvdvaplslg  ietaggvmtk  lierncripc
                  421 kqtktfstya  dnqpgvsiqv  yegeramtkd  nnalgtfdls  gippaprgvp  qievtfdlda
                  481 ngilnvsake  mstgkaknit  ikndkgrlsq  aeidrmvnea  ekyadedekh  rqritsrnal
                  541 esyvfnvkqa  veqapagkld  eadknsvldk  cndtirwlds  nttaekeefd  hkleeltrhc
                  601 spimtkmhqq  gagagaggpg  ancgqqaggf  ggysgptvee  vd
                  (SEQ. ID. NO. 4)

Yeast               1 msravgidlg  ttyscvahfs  ndrveiiand  qgnrttpsyv  aftdterlig  daaknqaain
NP_009478          61 phntvfdakr  ligrkfddpe  vttdakhfpf  kvisrdgkpv  vqveykgetk  tftpeeissm
                  121 vlskmketae  nylgttvnda  vvtvpayfnd  sqrqatkdag  tiagmnvlri  ineptaaaia
                  181 ygldkkgrae  hnvlifdlgg  gtfdvsllsi  degvfevkat  agdthlgged  fdnrlvnhla
                  241 tefkrktkkd  isnnqrslrr  lrtaaerakr  alssssqtsi  eidslfegmd  fytsltrarf
                  301 eelcadlfrs  tlepvekvlk  dskldksqid  eivlvggstr  ipkiqklvsd  ffngkepnrs
                  361 inpdeavayg  aavqaailtg  dqstktqdll  lldvaplslg  ietaggimtk  liprnstipt
                  421 kksetfstya  dnqpgvliqv  fegertrtkd  nnllgkfels  gippaprgvp  qidvtfdida
                  481 ngilnvsale  kgtgksnkit  itndkgrlsk  ddidrmvsea  ekyraddere  aervqaknql
                  541 esyaftlknt  ineasfkekv  geddakrlet  asqetidwld  asqaastdey  kdrqkelegi
                  601 anpimtkfyg  agagagpgag  esggfpgsmp  nsgatggged  tgptveevd
                  (SEQ. ID. NO. 5)

Rice                1 magkgegpai  gidlgttysc  vgvwqhdrve  iiandqgnrt  tpsyvgftds  erligdaakn
NP_001068540       61 qvamnpintv  fdakrligrr  fsdasvqsdi  klwpfkviag  pgdkpmivvq  ykgeekqfaa
                  121 eeissmvlik  mreiaeaylg  ttiknavvtv  payfndsqrq  atkdagviag  lnvmriinep
                  181 taaaiaygld  kkatsvgekn  vlifdlgggt  fdvslltiee  gifevkatag  dthlggedfd
                  241 nrmvnhfvqe  fkrknkkdit  gnpralrrlr  tacerakrtl  ssstaqttiei dslyegidfy
                  301 stitrarfee  lnmdlfrkcm  epvekclrda  kmdkssvhdv  vlvggstrip  rvqqllqdff
                  361 ngkelcknin  pdeavaygaa  vqaailsgeg  nekvqdlll   dvtplslgle  taggvmtvli
                  421 prnttiptkk  eqvfstysdn  qpgvliqvye  gertrtrdnn  llgkfelsgi  ppaprgvpqi
                  481 tvcfdidang  ilnvsaedkt  tgqknkitit  ndkgrlskee  iekmvqeaek  yksedeehkk
                  541 kvesknalen  yaynmrntik  dekiasklpa  adkkkiedai  dqaiqwldgn  qlaeadefdd
                  601 kmkelegicn  piiakmyqga  gadmaggmde  ddappaggsg  agpkieevd
                  (SEQ. ID. NO. 6)

Rice                1 magnkgegpa  igidlgttys  cvgvwqhdry  eiiandqgnr  ttpsyvaftd  terligdaak
Os03g0277300       61 nqvamnptnt  vfdakrligr  rfsdpsvgad  mkmwpfkvvp  gpadkpmivv  tykgeekkfs
NP_001049719.1|   121 aeeissmvlt  kmkeiaeafl  sttiknavit  vpayfndsqr  qatkdagvis  glnvmriine
                  181 ptaaaiaygl  dkkaastgek  nvlifdlggg  tfdvsiltie  egifevkata  gdthlggedf
                  241 dnrmvnhfvq  efkrkhkkdi  tgnpralrrl  rtacerakrt  lsstaqttie  idslyegidf
```

TABLE D12-continued

HSPA1 HSP70 genes

```
           301 yatitrarfe elnmdlfrrc mepvekclrd akmdkagihd vvlvggstri pkvqqllqdf
           361 fngkelcksi npdeavayga avqaailsge gnqrvqdlll ldvtplslgl etaggvmtvl
           421 iprnttiptk keqvfstysd nqpgvliqvy egertrtkdn nllgkfeltg ippaprgvpq
           481 invtfdidan gilnvsaedk ttgkknkiti tndkgrlske eiermvqeae kykaedeqvr
           541 hkvearnale nyaynmrntv rdekiasklp addkkkieda iedaikwldg nqlaeadefe
           601 dkmkeleslc npiiskmyqg gaggpagmde dapngsagtg ggsgagpkie evd
              (SEQ. ID. NO. 7)

Tobacco      1 magkgegpai gidlgttysc vgvwqhdrve iiandqgnrt tpsyvgftds erligdaakn
AAR17080    61 qvamnpintv fdakrligrr fsdasvqsdi klwpfkvisg pgdkpmivvn ykgeekqfaa
           121 eeissmvlik mkeiaeaflg stvknavvtv payfndsqrq atkdagvisg lnvmriinep
           181 taaaiaygld kkatsvgekn vlifdlgggt fdvslltiee gifevkatag dthlggedfd
           241 nrmvnhfvqe fkrkhkkdit gnpralrrlr tacerakrtl sstaqttiei dslyegvdfy
           301 stitrarfee lnmdlfrkcm epvekclrda kmdkstvhdv vlvggstrip kvqqllqdff
           361 ngkelcksin pdeavaygaa vqaailsgeg nekvqdllll dvtplslgle taggvmtvli
           421 prnttiptkk eqvfstysdn qpgvliqvye gerartrdnn llgkfelsgi ppaprgvpqi
           481 tvcfdidang ilnvsaedkt tgqknkitit ndkgrlskee iekmvqeaek ykaedeehkk
           541 kveaknalen yaynmrntik dekigsklss ddkkkiedai dqaiswldsn qlaeadefed
           601 kmkelesicn piiakmyqga ggeagapmdd dappaggssa gpkieevd
              (SEQ. ID. NO. 8)
```

The alignment of human and rice HSPA1 genes below shows that the two genes share approximately 73% identity (Identities=325/443 (73%), Positives=382/443 (86%), Gaps=7/443 (1%)). Consistent with the high degree of homology of this protein family, the present invention demonstrates that heat shock proteins as diverse as rice and human are functionally interchangeable, and suitable for use in any of the claimed methods.

HSPA8 Genes

In one aspect of any of the claims, the supplement of the invention comprises a HSP70 family member is selected from a sequence from Table D13.

TABLE D13

HSPA8/Hsc70/HSP70 genes

```
Human            1 amnptntvfd akrligrrfd davvqsdmkh wpfmvvndag rpkvqveykg etksfypeev
AAH07276        61 ssmvltkmke iaeaylgktv tnavvtvpay fndsqrqatk dagtiaglnv lriineptaa
               121 aiaygldkkv gaernvlifd lgggtfdvsi ltiedgifev kstagdthlg gedfdnrmvn
               181 hfiaefkrkh kkdisenkra vrrlrtacer akrtlsssstq asieidslye gidfytsitr
               241 arfeelnadl frgtldpvek alrdakldks qihdivlvgg stripkiqkl lqdffngkel
               301 nksinpdeav aygaavgaai lsgdksenvq dlllldvtpl slgietaggv mtvlikrntt
               361 iptkqtqtft tysdnqpgvl iqvyegeram tkdnnllgkf eltgippapr gvpqievtfd
               421 idangilnvs avdkstgken kititndkgr lskediermv qeaekykaed ekqrdkvssk
               481 nslesyafnm katvedeklq gkindedkqk ildkcneiin wldknqtaek eefehqqkel
               541 ekvcnpiitk lyqsaggmpg gmpggfpggg appsggassg ptieevd
                  (SEQ. ID. NO. 9)

Insect           1 msvigidfgn escyvaaars ggietlandy slratpsfva fdgkkriigv aaknqqvtnm
NP_648687       61 kntvggfkrl lgrkfndphv qheltsipar veargdgsig ikvnylgedq hfgpeqltam
               121 lftklketsa aamqtqvndc viacpvfftn aerkalldaa qiaglnvlrl mnettatala
               181 ygfykndlfe dkprnvifvd fghsslqasa caftkgklkm lastwdqigg rdidlalgdy
               241 fakefqeryk inaktnaran lrllteiekl kkqmsanstk lpiniecfld didvsssmqr
               301 sqmeelcapv lqrveqtfkr llaesklqld dihsveivgg ssripsvkql ieqvfnkpas
               361 ttlnqdeays rgaalqcaim spavrvrefg vtdignyavk vlwdsegsaa pgeieifpqy
               421 haspfsrllt inrkgpfnvs ivygqqvpyp dqtigvwkvk dvkptergeg qdvklkvrin
               481 nngivlissa tivekkeaee aaaaaeqaas eekpgdqtnn tgepadgqqe gadkkkkask
               541 atelplectt hgfspvdlsn ytqqeskmig ndqketerid aknaleefvy dmrnklqggp
               601 feryvveaer ekivsqlndl enwlyedged cerdiytsrl qalhqktdpi klrasdyeqg
               661 paafdelkns iaiarlavae frkgvpkydh ltetefinis etadkaqswl danlpkftqs
               721 prtadspvqi savrqevqtl nscvssvinr akpkptpakt atppkdeana eqnggepaan
               781 sgdkmdvdnn gqsaagndps meve
                  (SEQ. ID. NO. 10)

Yeast            1 gpmstpfgld lgnnnsvlav arnrgidivv nevsnrstps vvgfgpknry lgetgknkqt
Saccharomy      61 snikntvanl kriigldyhh pdfeqeskhf tsklvelddk ktgaevrfag ekhvfsatql
cescerevisiae  121 aamfidkvkd tvkqdtkani tdvciavppw yteeqrynia daariaglnp vrivndvtaa
YPL106C        181 gvsygifktd lpegeekpri vafvdighss ytcsimafkk gqlkvlgtac dkhfggrdfd
               241 laitehfade fktkykidir enpkaynril taaelkkvl santnapfsv esvmndvdvs
               301 sqlsreelee lvkpllervt epvtkalaqa klsaeevdfv eiiggttrip tlkqsiseaf
               361 gkplsttlnq deaiakgaaf icaihsptlr vrpfkfedih pysysyswdk qvededhmev
               421 fpagssfpst klitlnrtgd fsmaasytdi tqlppntpeq ianweitgvq lpegqdsvpv
               481 klklrcdpsg lhtieeayti edieveepip lpedapedae qefkkvtktv kkddltivah
               541 tfgldakkln eliekeneml aqdklvaete drkntleeyi ytlrgkleee yapfasdaek
               601 tklqgmlnka eewlydegfd sikakyiaky eelaslgnii rgrylakeee kkqairskqe
               661 asqmaama
                  (SEQ. ID. NO. 11)
```

TABLE D13-continued

HSPA8/Hsc70/HSP70 genes

| Rice EEE69961 | | | | | | |
|---|---|---|---|---|---|---|
| | 1 | maigsliasr | larstghala | saasqapmar | haaaspllsr | lgsvarafss kpaaadvigi |
| | 61 | dlgttnscvs | vmegktprvi | enaegarttp | sivaknqngd | llvgitasrq avtnaqntvr |
| | 121 | gskrligrtf | ddpqtqkemk | mvpykivrgp | ngdawvemgg | qqyspsqiga fvltkmketa |
| | 181 | eaflgktvsk | avitvpayfn | daqrqatkda | griaglevmr | iineptaaal sygmnnkegl |
| | 241 | iavfdlgggt | fdvsileisn | gvfevkatng | dtflggedfd | galldylvse fkksdnidls |
| | 301 | kdklalqrlr | eaaekakvel | sstmqteinl | pfitadatga | khfnitltrs kfeslvqsli |
| | 361 | ertripcvnc | lkdagvsakd | idevllvggm | trvpkvqdiv | sqifnktpsk gvnpdeavam |
| | 421 | gaaiqggilr | gdvkelllld | vtplslgiet | lggiftrlin | rnttiptkks qvfstaadnq |
| | 481 | tqvgikvlqg | erematdnkl | lgefqlegip | paprgmpqie | vtfdidangi vkvsakdkst |
| | 541 | gkeqeitiks | sgglsesdie | kmvreaelhs | qkdqerksli | dlknsadtti ysieksysey |
| | 601 | kdkvpaevtn | eiqsaysdlr | aamaeddlek | ikqkleaank | ayskigehmq qggggsggg |
| | 661 | ssssggdqt | peaeyqdaak | eakm | | |
| | (SEQ. ID. NO. 12) | | | | | |

| Tobacco HSp70 AAP04522 | | | | | | |
|---|---|---|---|---|---|---|
| | 1 | magkgegpai | gidlgttysc | vgvwqhdrve | iiandqgnrt | tpsyvgftds erligdaakn |
| | 61 | qvamnpintv | fdakrligrr | fsdasvqsdi | klwpfkgisg | pgdkpmivvn ykgeekqfaa |
| | 121 | eeissmglik | mkemaeaflg | stvknavvtv | payfndsqrq | atkdagvisg lnvmriinep |
| | 181 | taaaiaygld | kkatsvgekn | vlifdlgggt | fdvslltiee | gifevkatag dthlggedfd |
| | 241 | nrmvnhfvqe | fkrkhkkdit | gnpralrrlr | tacerakrtl | sstaqttiei dslyegvdfy |
| | 301 | stitrarfee | lnmdlfrkcm | epvekclrda | kmdkstvhdv | vlvggstrip kvqqllqdff |
| | 361 | ngkelcksin | pdeavaygaa | vqaailsgeg | nekvqdlllll | dvtplslgle taggvmtvli |
| | 421 | prnttiptkk | eqvfstysdn | qpgvliqvye | gerartrann | llgkfelsgi ppaprgvpqi |
| | 481 | tvcfdidang | ilnvsaedkt | tgqknkitit | ndkgrlskee | iekmvqeaek ykaedeehkk |
| | 541 | kveaknalen | yaynmrntik | dekigsklss | ddkkkiedai | dqaiswldsn qlaeadefed |
| | 601 | kmkelesicn | piiakmyqga | ggeagapmdd | dappaggssa | gpkieevd |
| | (SEQ. ID. NO. 13) | | | | | |

HSPA5/Grp78/Bip

In one aspect of any of the claims, the supplement of the invention comprises a HSP70 family member is selected from a sequence from Table D14.

TABLE D14

HSPA5/Bip/Grp78 HSP70 genes

| Human NP_005338 | | | | | | |
|---|---|---|---|---|---|---|
| | 1 | mklslvaaml | lllsaaraee | edkkedvgtv | vgidlgttys | cvgvfkngry eiiandqgnr |
| | 61 | itpsyvaftp | egerligdaa | knqltsnpen | tvfdakrlig | rtwndpsvqq dikflpfkvv |
| | 121 | ekktkpyiqv | digggqktf | apeeisamvl | tkmketaeay | lgkkvthavv tvpayfndaq |
| | 181 | rqatkdagti | aglnvmriin | eptaaaiayg | ldkregekni | lvfdlgggtf dvslltidng |
| | 241 | vfevvatngd | thlggedfdq | rvmehfikly | kkktgkdvrk | dnravqklrr evekakrals |
| | 301 | sqhqarieie | sfyegedfse | tltrakfeel | nmdlfrstmk | pvqkvledsd lkksdideiv |
| | 361 | lvggstripk | iqqlvkeffn | gkepsrginp | deavaygaav | qagvlsgdqd tgdlvlldvc |
| | 421 | pltlgietvg | gvmtklprn | tvvptkksqi | fstasdnqpt | vtikvyeger pltkdnhllg |
| | 481 | tfdltgippa | prgvpqievt | feidvngilr | vtaedkgtgn | knkititndq nrltpeeier |
| | 541 | mvndaekfae | edkklkerid | trnelesyay | slknqigdke | klggklssed ketmekavee |
| | 601 | kiewleshqd | adiedfkakk | keleeivqpi | isklygsagp | pptgeedtae kdel |
| | (SEQ. ID. NO. 14) | | | | | |

| Yeast EDN63302 | | | | | | |
|---|---|---|---|---|---|---|
| | 1 | mffnrlsagk | llvplsvvly | alfvvilplq | nsfhssnvlv | rgaddvenyg tvigidlgtt |
| | 61 | yscvavmkng | kteilaneqg | nritpsyvaf | tdderligda | aknqvaanpq ntifdikrli |
| | 121 | glkyndrsvq | kdikhlpfnv | vnkdgkpave | vsvkgekkvf | tpeeisgmil gkmkgiaedy |
| | 181 | lgtkvthavv | tvpayfndaq | rqatkdagti | aglnvlrrin | eptaaaiayg ldksdkehqi |
| | 241 | ivydlgggtf | dvsllsieng | vfevqatsgd | thlggedfdy | kivrqlikaf kkkhgidvsd |
| | 301 | nnkalaklkr | eaekakrals | sqmstrieid | sfvdgidlse | tltrakfeel nldlfkktlk |
| | 361 | pvekvlqdsg | lekkdvddiv | lvggstripk | vqqllesyfd | gkkaskginp deavaygaav |
| | 421 | qagvlsgeeg | vedivlldvn | altlgiettg | gvmtplirkn | taiptkksqi fstavdnqpt |
| | 481 | vmikvyeger | amskdnnllg | kfeltgippa | prgvpqievt | faldangilk vsatdkgtgk |
| | 541 | sesititndk | grltqeeidr | mveeaekfas | edasikakve | srnklenyah slknqvngdl |
| | 601 | gekleeedke | tlldaandvl | ewlddnfeta | iaedfdekfe | slskvaypit sklyggadgs |
| | 661 | gaadyddede | dddgdyfehd | el | | |
| | (SEQ. ID. NO. 15) | | | | | |

| Insect AAG22148 | | | | | | |
|---|---|---|---|---|---|---|
| | 1 | mpaigidlgt | tyscvgvyqh | gkveiiandq | gnrttpsyva | ftdserligd paknqvamnp |
| | 61 | rntvfdakrl | igrkyddpki | aedmkhwpfk | vvsdggkpki | gveykgeskr fapeeissmv |
| | 121 | ltkmketaea | ylgesitdav | itvpayfnds | qrqatkdagh | iaglnvlrii neptaaalay |
| | 181 | gldknlkger | nvlifdlggg | tfdvsiltid | egslfevrst | agdthlgged fdnrlvthla |
| | 241 | defkrkykkd | lrsnpralrr | lrtaaerakr | tlsssteati | eidalfegqd fytkvsrarf |
| | 301 | eelcadlfrn | tlqpvekaln | dakmdkgqih | divlvggstr | ipkvqsllqd ffhgknlnls |
| | 361 | inpdeavayg | aavqaailsg | dqsgkiqdvl | lvdvaplslg | ietaggvmtk lierncripc |
| | 421 | kqtktfstya | dnqpgvsiqv | yegeramtkd | nnalgtfdls | gippaprgvp qievtfdlda |
| | 481 | ngilnvsake | mstgkaknit | ikndkgrlsq | aeidrmvnea | ekyadedekh rqritsrnal |
| | 541 | esyvfnvkqa | veqapagkld | eadknsvldk | cndtirwlds | nttaekeefd hkleeltrhc |
| | 601 | spimtkmhqq | gagagaggpg | ancgqqaggf | ggysgptvee | vd |
| | (SEQ. ID. NO. 16) | | | | | |

TABLE D14-continued

HSPA5/Bip/Grp78 HSP70 genes

```
tobacco      1  maggawnrrt  slivfgivlf  gclfafsiat  eeatklgtvi  gidlgttysc  vgvyknghve
            61  iiandqgnri  tpswvaftdg  erligeaakn  laavnpertv  fdvkrligrk  fddkevqrdm
           121  klvpykivnk  dgkpyiqvki  kdgetkifsp  eeisamiltk  mketaeaylg  kkikdavvtv
           181  payfndaqrq  atkdagviag  lnvariinep  taaaiaygld  kkggeknilv  fdlgggtfdv
           241  siltidngvf  evlstngdth  lggedfdqri  meyfiklikk  khgkdiskdn  ralgklrrea
           301  erakralssq  hqvrveiesl  fdgvdfsepl  trarfeelnn  dlfrktmgpv  kkamddagle
           361  ktgideivlv  ggstripkvq  qllkdyfdgk  epnkgvnpde  avaygaavqg  gilsgeggde
           421  tkdillldva  pltlgietvg  gvmtkliprn  tviptkksqv  fttyqdqqtt  vtiqvfeger
           481  sltkdcrllg  kfdltgiapa  prgtpqievt  fevdangiln  vkaedkasgk  sekititndk
           541  grlsqeeier  mvkeaeefae  edkkvkerid  arnsletyvy  nmrnqindkd  kladklesde
           601  kekietatke  alewlddnqs  aekedyeekl  keveavcnpi  itavyqksgg  apggesgase
           661  dddhdel
           (SEQ. ID. NO. 17)

Rice         1  mdrvrgsafl  lgvllagslf  afsvakeetk  klgtvigidl  gttyscvgvy  knghveiian
AAB63469    61  dqgnritpsw  vaftdserli  geaaknqaav  npertifdvk  rdigrkfeek  evqrdmklvp
           121  ykivnkigkp  yiqvkikdge  nkvfspeevs  amilgkmket  aeaylgkkin  davvtvpayf
           181  ndagrqatkd  agviaglnva  riineptaaa  iaygldkkgg  eknilvfdlg  ggtfdvsilt
           241  idngvfevla  tngdthlgge  dfdqrimeyf  iklikkkysk  diskdnralg  klrreaerak
           301  ralsnqhqvr  veieslfdgt  dfsepltrar  feelnndlfr  ktmgpvkkam  ddagleksqi
           361  heivlvggst  ripkvqqllr  dyfegkepnk  gvnpdeavay  gaavqgsils  geggdetkdi
           421  llldvapltl  gietvggvmt  kliprntvip  tkksqvftty  qdqqttvsiq  vfegersmtk
           481  dcrllgkfdl  sgipaaprgt  pqievtfevd  angilnvkae  dkgtgkseki  titnekgrls
           541  qeeidrmvre  aeefaeedkk  vkeridarnq  letyvynmkn  tvgdkdklad  kleseekekv
           601  eealkealew  ldenqtaeke  eyeeklkeve  avcnpiisav  yqrtggapgg  rrrgrlddeh
           661  del
           (SEQ. ID. NO. 18)
```

The heat shock proteins may be in their native form, i.e., as different variants as they appear in nature in different species which may be viewed as functionally equivalent variants, or they may be functionally equivalent natural derivatives thereof, which may differ in their amino acid sequence, for example, by truncation (e.g., from the N- or C-terminus or both) or other amino acid deletions, additions, insertions, substitutions, or post-translational modifications. Naturally-occurring chemical derivatives, including post-translational modifications and degradation products of the HSPs, are also specifically included in any of the methods of the invention including for example, pyroglutamyl, iso-aspartyl, proteolytic, phosphorylated, glycosylated, oxidatized, isomerized, and deaminated variants of the HSP.

It is known in the art to synthetically modify the sequences of proteins or peptides, while retaining their useful activity and this may be achieved using techniques which are standard in the art and widely described in the literature, e.g., random or site-directed mutagenesis, cleavage, and ligation of nucleic acids, or via the chemical synthesis or modification of amino acids or polypeptide chains.

The term "derivative" as used herein thus refers to HSP sequences or fragments thereof, which have modifications as compared to the native sequence. Such modifications may be one or more amino acid deletions, additions, insertions and/or substitutions. These may be contiguous or non-contiguous. Representative variants may include those having 1 to 100, or more preferably 1 to 50, 1 to 25, or 1 to 10 amino acid substitutions, insertions, and/or deletions as compared to any of genes listed in Tables D5 to D14, or E3 to E6, or SEQ. ID. Nos 3 to 22. The substituted amino acid may be any amino acid, particularly one of the well-known 20 conventional amino acids (Ala (A); Cys (C); Asp (D); Glu (E); Phe (F); Gly (G); His (H); Ile (I); Lys (K); Leu (L); Met (M); Asn (N); Pro (P); Gin (Q); Arg (R); Ser (S); Thr (T); Val (V); Trp (W); and Tyr (Y)). Any such variant or derivative of a HSP may be used in any of the methods of the invention.

Thus, Hsps which may be used in any of the methods of the invention may have amino acid sequences which are substantially homologous, or substantially similar to the native HSP amino acid sequences, for example, to any of the native HSP gene sequences listed Tables D5 to D14, or E3 to E6, or SEQ. ID. Nos 3 to 22. Alternatively, the HSP may have an amino acid sequence having at least 30% preferably at least 40, 50, 60, 70, 75, 80, 85, 90, 95, 98, or 99% identity with the amino acid sequence of any one of genes shown in Tables D5 to D14, or E3 to E6. In a one embodiment, the HSP for use in any of the methods of the present invention is at least 80% identical to a sequence selected from Table D7. In another embodiment, the HSP for use in any of the methods of the present invention is at least 80% identical to a sequence selected from Tables D10 to D14. In another aspect, the HSP for use in any of the methods of the invention is at least 80% identical to an Hspa8 gene selected from Table D12. In another aspect, the HSP for use in any of the methods of the invention is at least 80% identical to an Hspa1 gene selected from Table D13. In another aspect, the HSP for use in any of the methods of the invention is at least 80% identical to an Hspa5 gene selected from Table D14. In another aspect, the HSP for use in any of the methods of the invention is at least 80% identical to any one of SEQ. ID. Nos 3 to 22.

Fusion proteins of HSP to other proteins are also included, and these fusion proteins may enhance HSP biological activity, targeting, biological life, or stability.

Chemical modifications of the native HSP structure which retain or stabilize HSP activity or biological half-life may also be used with any of the methods described herein. Such chemical modification strategies include without limitation pegylation, glycosylation, and acylation (see Clark et al.: *J. Biol. Chem.* 271(36): 21969-21977, 1996; Roberts et al.: *Adv. Drug. Deliv. Rev.* 54(4): 459-476, (2002); Felix et al.: *Int. J. Pept. Protein. Res.* 46(3-4): 253-264, (1995); Garber Diabetes Obes. Metab. 7 (6) 666-74 (2005)) C- and N-terminal protecting groups and peptomimetic units may also be included.

Isomers of the native L-amino acids, e.g., D-amino acids may be incorporated in any of the above forms of HSP, and used in any of the methods of the invention. Additional variants may include amino and/or carboxyl terminal fusions as well as intrasequence insertions of single or multiple amino acids. Longer peptides may comprise multiple copies of one or more of the HSP peptide sequences. Insertional amino acid sequence variants are those in which one or more amino acid residues are introduced at a site in the protein.

Fragments of native or synthetic HSP sequences may also have the desirable functional properties of the peptide from which they derived and may be used in any of the methods of the invention. The term "fragment" as used herein thus includes fragments of a HSP provided that the fragment retains the biological or therapeutically beneficial activity of the whole molecule. Deletional variants are characterized by the removal of one or more amino acids from the sequence. Variants may also include, for example, different allelic variants as they appear in nature, e.g., in other species or due to geographical variation. All such variants, derivatives, fusion proteins, or fragments of HSP are included, may be used in any of the methods claims or disclosed herein, and are subsumed under the terms "heat shock protein" or "hsp".

The variants, derivatives, and fragments are functionally equivalent in that they have detectable anti-apoptotic activity. More particularly, they exhibit at least 40%, preferably at least 60%, more preferably at least 80% of the activity of HSP70, particularly rice HSP70. Thus they are capable of functioning as anti-apoptotic agents when co-administered with albumin, i.e., can substitute for HSP70 itself.

Such activity means any activity exhibited by a native rice HSP, whether a physiological response exhibited in an in vivo or in vitro test system, or any biological activity or reaction mediated by a native HSP, for example, in an enzyme assay, cell growth assay or by testing the effect of the hsp on cell viability in the presence of stress.

Thus the activity of HSPs can be readily assessed using any previously disclosed methods to determine cell viability and apoptosis which are applicable to any cells grown in culture that can be conditioned to a serum free or low serum containing media or alternatively to media that contains components that are apoptotic or toxic in nature.

Additionally, growth rates may be determined using cells conditioned to grow in low serum or serum free conditions by plating defined numbers of the cells into multiwall plates. Cells may be seeded at different densities depending on the cells, and tissue culture plates employed. For example, hybridoma cells conditioned to serum free conditions can be seeded at an initial density of $0.5 \times 10^5$ cells per mL of media.

Typically the cells are initially washed three times, and specific ingredients required to support growth in culture such as albumin, candidate hsps, Glutathione S transferase, Superoxide Dismutase, or transferrin are added at the desired concentration in phosphate buffered saline up to about 1 part per 10 parts liquid media (for example, Dulbecos). At the end of the growth period at 37 C and 5% CO2, the cells are enumerated for viability. Dual label staining is the preferred method for determining viability in a mixture of viable and non-viable cells. The preferred method of determining the number of viable cells with respect to the total number of cells (percent viability) is to use a cell counting apparatus which is common to the art. Other methods that can be employed include dual label flow cytometry or alternatively manual counting of the cells utilizing a microscope, with stained with trypan blue and a cell counting device. Experimental sample viability and cell number are compared to the negative control, the media components minus the experimental factor(s), and the positive control (fetal bovine serum or other known cell culture supporting ingredients). In general, the statistical significance of the counts must be determined based on the signal to noise ratio of the replicate samples as well as the observed difference or lack of difference as compared to the positive and negative control. For those skilled in the art, with consideration that a stable cell platform must be established that allows serum free growth, a 20% change in viability versus the controls would be considered a significant difference with approximately 95% confidence provided a low signal to noise ratio for the replicate samples.

Performance of the potential factors may also be measured according to indicators of productivity including production of an endogenous or intentionally expressed protein or alternatively measured as a function of apoptotic indicators. Apoptosis assays are numerous and rely on upstream changes in the cell such as DNA fragmentation and nuclear degradation. Downstream assays rely on measurement of the activity of such apoptotic pathway components as Caspase 3. Cultured cells as conditioned in the previous method can also be assayed with a commercially available apoptosis assays to determine the effect of the added components to cell culture.

IV. Long Chain Fatty Acids

As used herein the term "long-chain fatty acids" or "LCFA" refers to fatty acids with aliphatic tails longer than 12 carbons. Such fatty acids comprise a carboxylic acid with an unbranched aliphatic tail (chain), which is either saturated or unsaturated. The term "unsaturated fatty acid refers to fatty acids, in which the aliphatic tail has one or more double-bonds between carbon atoms. Exemplary unsaturated fatty acids are listed in Table D15.

TABLE D15

Exemplary Unsaturated fatty acids

| Common name | Chemical structure | $\Delta^x$ | C:D | n-x |
|---|---|---|---|---|
| Myristoleic acid | $CH_3(CH_2)_3CH=CH(CH_2)_7COOH$ | cis-$\Delta^9$ | 14:1 | n-5 |
| Palmitoleic acid | $CH_3(CH_2)_5CH=CH(CH_2)_7COOH$ | cis-$\Delta^9$ | 16:1 | n-7 |
| Sapienic acid | $CH_3(CH_2)_8CH=CH(CH_2)_4COOH$ | cis-$\Delta^6$ | 16:1 | n-10 |
| Oleic acid | $CH_3(CH_2)_7CH=CH(CH_2)_7COOH$ | cis-$\Delta^9$ | 18:1 | n-9 |
| Linoleic acid | $CH_3(CH_2)_4CH=CHCH_2CH=CH(CH_2)_7COOH$ | cis,cis-$\Delta^9,\Delta^{12}$ | 18:2 | n-6 |
| α-Linolenic acid | $CH_3CH_2CH=CHCH_2CH=CHCH_2CH=CH(CH_2)_7COOH$ | cis,cis,cis,-$\Delta^9,\Delta^{12},\Delta^{15}$ | 18:3 | n-3 |
| Arachidonic acid | $CH_3(CH_2)_4CH=CHCH_2CH=CHCH_2CH=CHCH_2CH=CH(CH_2)_3COOH$ | cis,cis,cis,cis-$\Delta^5\Delta^8,\Delta^{11},\Delta^{14}$ | 20:4 | n-6 |

TABLE D15-continued

Exemplary Unsaturated fatty acids

| Common name | Chemical structure | $\Delta^x$ | C:D | n-x |
|---|---|---|---|---|
| Eicosapentaenoic acid | $CH_3CH_2CH=CHCH_2CH=CHCH_2CH=CHCH_2CH=CHCH_2CH=CH(CH_2)_3COOH$ | cis,cis,cis,cis,cis-$\Delta^5,\Delta^8,\Delta^{11},\Delta^{14},\Delta^{17}$ | 20:5 | n-3 |
| Erucic acid | $CH_3(CH_2)_7CH=CH(CH_2)_{11}COOH$ | cis-$\Delta^{13}$ | 22:1 | n-9 |
| Docosahexaenoic acid | $CH_3CH_2CH=CHCH_2CH=CHCH_2CH=CHCH_2CH=CHCH_2CH=CHCH_2CH=CH(CH_2)_2COOH$ | cis,cis,cis,cis,cis-$\Delta^4,\Delta^7,\Delta^{10},\Delta^{13},\Delta^{16},\Delta^{19}$ | 22:6 | n-3 |

Saturated fatty acids have no carbon-carbon double bonds within their aliphatic tails. Exemplary unsaturated fatty acids are listed in Table D16.

TABLE D16

Exemplary Saturated Fatty acids

| Common name | Chemical structure | C:D |
|---|---|---|
| Lauric acid | $CH_3(CH_2)_{10}COOH$ | 12:0 |
| Myristic acid | $CH_3(CH_2)_{12}COOH$ | 14:0 |
| Palmitic acid | $CH_3(CH_2)_{14}COOH$ | 16:0 |
| Stearic acid | $CH_3(CH_2)_{16}COOH$ | 18:0 |
| Arachidic acid | $CH_3(CH_2)_{18}COOH$ | 20:0 |
| Behenic acid | $CH_3(CH_2)_{20}COOH$ | 22:0 |
| Lignoceric acid | $CH_3(CH_2)_{22}COOH$ | 24:0 |
| Cerotic acid | $CH_3(CH_2)_{24}COOH$ | 26:0 |

In one aspect of any of the claimed compositions and methods the long chain fatty acids are selected from the group consisting of oleic acid, stearic acid, linoleic acid, palmitic acid and arcachidonic acid. In another aspect of any of the claimed compositions and methods, the long chain fatty acids are selected from the group consisting of palmitic acid, oleic acid and linoleic acid.

In another aspect of any of these composition and methods, the long chain fatty acids comprise a mixture of saturated and unsaturated fatty acids. In one aspect such mixture of fatty acids is selected from any combination of LCFAs selected from the group consisting of oleic acid, stearic acid, linoleic acid, palmitic acid and arcachidonic acid. In one aspect such mixture of fatty acids is selected from the group consisting of oleic acid, linoleic acid, and palmitic acid.

In one aspect, the long chain fatty acids comprise about 0.2% to about 2.5% (wt/wt) of the mass of the protein cell culture component. In one aspect, the long chain fatty acids comprise about 0.5% (wt/wt) to about 2.0% of the mass of the protein cell culture component. In one aspect, the long chain fatty acids comprise about 1.0% (wt/wt) to about 1.5% of the mass of the protein cell culture component.

In another aspect, the mixture of fatty acids comprises about 0.5% (wt/wt) to about 1% (wt/wt) linoleic acid, about 0.1% (wt/wt) to about 0.5% (wt/wt) oleic acid, and about 0.1% (wt/wt) to about 0.5% (wt/wt) palmitic acid with respect to the mass of the protein cell culture component respectively.

In another aspect of any of these composition and methods, the protein cell culture component is loaded with lipids via its expression in a plant. In one aspect, the plant is selected from the group consisting of rice, barley, wheat, rye, corn, millet, triticale, and sorghum. In one aspect the plant is rice.

Accordingly in another aspect, the current invention includes a method of producing fatty acid loaded albumin, comprising the steps of:

1) expressing the albumin in a plant expression system,
2) purifying the albumin; wherein the purified albumin comprises at least 1% bound fatty acids and at least 0.01 bound hsps.

In one aspect, the purification step involves the steps of 1) acid precipitation, 2) filtration, 3) anion exchange chromatography. In one aspect the purification step involves the method of Example 2.

V. Production of Tissue Components and Heat Shock Proteins

Heat shock proteins and albumin for use in the supplements of the present invention can be prepared in any suitable manner, for instance by isolation from naturally occurring sources, from genetically engineered host cells comprising expression systems (see below), or by chemical synthesis, using, for instance, automated peptide synthesizers, or any combination of such methods. The means for preparing such polypeptides are well understood in the art.

For recombinant production, host cells can be genetically engineered to incorporate nucleic acids encoding the culture component and/or a hsp of interest. Typically the nucleic acid will be codon optimized for high level expression in the expression system of choice, and incorporated into an expression vector to enable the expression of the protein of interest in the host cell. Vectors can exist as circular, double stranded DNA, and range in size from a few kilobases (kb) to hundreds of kb. Preferred cloning vectors have been modified from naturally occurring plasmids to facilitate the cloning and recombinant manipulation of polynucleotide sequences. Many such vectors are well known in the art and commercially available; see for example, by Sambrook (In. "Molecular Cloning: A Laboratory Manual," second edition, edited by Sambrook, Fritsch, & Maniatis, Cold Spring Harbor Laboratory, (1989)), Maniatis, In: Cell Biology: A Comprehensive Treatise, Vol. 3, Gene Sequence Expression, Academic Press, NY, pp. 563-608 (1980).

In one aspect, expression vectors are used to increase the expression of the culture component in the host cell, while the expression of the host cells endogenous heat shock proteins is accomplished by activating the expression of the host cells genes. In another aspect expression vectors are used to increase the expression of the heat shock protein. In another aspect expression vectors are used to increase the expression of the heat shock protein and the cell culture component. In another aspect the nucleic acid sequence encoding a heat shock protein and the cell culture component are located in the same expression vector.

Expression vectors include plasmids, episomes, cosmids retroviruses or phages; the expression vector can be used to express a DNA sequence encoding the cell culture component or a hsp, and in one aspect comprises an assembly of expression control sequences. The choice of promoter and other regulatory elements can vary according to the intended host cell, and many such elements are available commercially, and can be readily assembled from isolated components such as the Gateway system from Invitrogen, (CA, USA). Expression systems for hsps or tissue culture components can be stable, or transient expression systems.

In one aspect of any of these methods, hsp expression can be inducible, in another aspect, hsp expression can be constitutive. Inducible expression systems for hsps can be included in the expression vector for albumin, or can be included in a separate expression system or vector.

In one aspect of any of these methods, cell culture component expression can be inducible, in another aspect, hsp expression can be constitutive. Inducible expression systems for the tissue culture components can be included in the expression vector for the hsp, or can be included in a separate expression system or vector.

General and specific techniques for producing proteins from plant cells may be obtained from the following patents and applications, each of which is incorporated herein in its entirety by reference: U.S. Pat. Appi. Pub. No. 2003/0172403 A1 ("Plant Transcription Factors and Enhanced Gene Expression"); U.S. Pat. No. 6,991,824 ("Expression of Human Milk Proteins in Transgenic Plants"); U.S. Patent Application Publication No. Pub. No. 2003/0221223 ("Human Blood Proteins Expressed in Monocot Seeds"); U.S. Pat. Appl. Pub. No. 2004-0078851 ("Production of Human Growth Factors in Monocot Seeds"); U.S. Pat. Appl. Pub. No. 2004/0063617 ("Method of Making an Anti-infective Composition for Treating Oral Infections"); and international application no. PCT/US2004/041083 ("High-level Expression of Fusion Polypeptides in Plant Seeds Utilizing Seed-Storage Proteins as Fusion Carriers"). Other general and specific techniques for producing proteins from plant cells may be obtained, for example, from the following references, each of which is incorporated herein in its entirety by reference: U.S. Pat. No. 5,693,507, U.S. Pat. No. 5,932,479, U.S. Pat. Nos. 6,642,053, and 6,680,426 (each titled "Genetic Engineering of Plant Chloroplasts"); U.S. Pat. Appi. Pub. No. 2005/0066384 ("Site-Targeted Transformation Using Amplification Vectors"); U.S. Pat. Appi. Pub. No. 2005/0221323 ("Amplification Vectors Based on Trans-Splicing"); U.S. Pat. Appl. Pub. No. 2006/0026718 ("Method of Controlling Cellular Processes in Plants"); and U.S. Pat. Appi. Pub. No. 2006/0075524 (Method of Controlling A Cellular Process in a Multi-Cellular Organism"); Marillonnet et at., Systemic *Agrobacterium tumefaciens*-mediated transfection of viral replicons for efficient transient expression in plants, Nature Biotech. (2005) 23(6): 718-723.

Representative commercially available viral expression vectors include, but are not limited to, the adenovirus-based systems, such as the Per.C6 system available from Crucell, Inc., lentiviral-based systems such as pLP1 from Invitrogen, and retroviral vectors such as tobacco mosaic virus based vectors (Lindbo et al., BMC Biotechnol. (2007) 7 52-58).

An episomal expression vector is able to replicate in the host cell, and persists as an extrachromosomal episome within the host cell in the presence of appropriate selective pressure. (See for example, Conese et al., Gene Therapy 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP), specific examples include the vectors pREP4, pCEP4, pREP7 from Invitrogen. The host range of EBV based vectors can be increased to virtually any eukaryotic cell type through the co-expression of EBNA1 binding protein 2 (EPB2) (Kapoor et al., EMBO. J. 20: 222-230 (2001)), vectors pcDNA3.1 from Invitrogen, and pBK-CMV from Stratagene represent non-limiting examples of an episomal vector that uses T-antigen and the SV40 origin of replication in lieu of EBNA1 and oriP.

An integrating expression vector can randomly integrate into the host cell's DNA, or can include a recombination site to enable the specific recombination between the expression vector and the host cells chromosome. Such integrating expression vectors can utilize the endogenous expression control sequences of the host cell's chromosomes to effect expression of the desired protein. Examples of vectors that integrate in a site specific manner include, for example, components of the flp-in system from Invitrogen (e.g., pcDNA™5/FRT), or the cre-lox system, such as can be found in the pExchange-6 Core Vectors from Stratagene. Examples of vectors that integrate into host cell chromosomes in a random fashion include, for example, pcDNA3.1 (when introduced in the absence of T-antigen) from Invitrogen, pCI or pFN10A (ACT) Flexi® from Promega.

Alternatively, the expression vector can be used to introduce and integrate a strong promoter or enhancer sequences into a locus in the cell so as to modulate the expression of an endogenous gene of interest such as a heat shock protein (Capecchi MR. Nat Rev Genet. (2005); 6 (6):507-12; Schindehutte et al., Stem Cells (2005); 23 (1):10-5). This approach can also be used to insert an inducible promoter, such as the Tet-On promoter (U.S. Pat. Nos. 5,464,758 and 5,814,618), in to the genomic DNA of the cell so as to provide inducible expression of an endogenous gene of interest, such as a heat shock protein. The activating construct can also include targeting sequence(s) to enable homologous or non-homologous recombination of the activating sequence into a desired locus specific for the gene of interest (see for example, Garcia-Otin & Guillou, Front Biosci. (2006) 11:1108-36). Alternatively, an inducible recombinase system, such as the Cre-ER system, can be used to activate a transgene in the presence of 4-hydroxytamoxifen (Indra et al. Nuc. Acid. Res. (1999) 27 (22): 4324-4327; Nuc. Acid. Res. (2000) 28(23): e99; and U.S. Pat. No. 7,112,715).

Alternatively in one embodiment, the host cell may endogenously express the hsp of interest or be induced to express the hsp of interest by the means described above such as, but not limited to, heat elevation. Polynucleotides may be introduced into host cells by methods described in many standard laboratory manuals, such as Davis et al., Basic Methods in Molecular Biology (1986) and Sambrook et al., (In. "Molecular Cloning: A Laboratory Manual," second edition, edited by Sambrook, Fritsch, & Maniatis, Cold Spring Harbor Laboratory, (1989)), Maniatis, In: Cell Biology: A Comprehensive Treatise, Vol. 3, Gene Sequence Expression, Academic Press, NY, pp. 563-608 (1980). Exemplary methods of introducing polynucleotides into host cells include, for instance, calcium phosphate transfection, DEAE-dextran mediated transfection, transfection, microinjection, cationic lipid-mediated transfection, electroporation, transduction, scrape loading, ballistic introduction or infection.

Suitable cells for producing the tissue culture component and heat shock proteins include prokaryotic cells, yeasts, insect cells, plant expression systems and mammalian expression systems. Within these general guidelines, useful microbial hosts include, but are not limited to, bacteria from the genera *Bacillus, Escherichia* (such as *E. coli*), *Pseudomonas, Streptomyces, Salmonella, Erwinia, Bacillus subtilis, Bacillus brevis*, the various strains of *Escherichia coli* (e.g., HB101, (ATCC NO. 33694) DH5α, DH10 and MC1061 (ATCC NO. 53338)).

Many strains of yeast cells known to those skilled in the art are also available as host cells for the expression of albumin and hsps including those from the genera *Hansenula, Kluyveromyces, Pichia, Rhino-sporidium, Saccharomyces*, and *Schizosaccharomyces*, and other fungi. Preferred yeast cells include, for example, *Saccharomyces cerivisae* and *Pichia pastoris*.

Additionally, where desired, insect cell systems can be utilized in the methods of the present invention. Such systems are described, for example, by Kitts et al., Biotechniques, 14:810-817 (1993); Lucklow, Curr. Opin. Biotechnol., 4:564-572 (1993); and Lucklow et al. (J. Virol., 67:4566-4579 (1993). Preferred insect cells include Sf-9 and HI5 (Invitrogen, Carlsbad, Calif.).

Many suitable plant expression systems can be used for the expression of albumin and hsps examples includes for example, any monocot or dicot plant. Suitable moncot plants include without limitation, rice, barley, wheat, rye, corn, millet, triticale, or sorghum, preferably rice. Other suitable plants include *Arabidopsis*, Alfalfa, tobacco, peanut and soybean.

A number of suitable mammalian host cells are also known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61) CHO DHFR-cells (Urlaub et al., Proc. Natl. Acad. Sci. USA, 97:4216-4220 (1980)), human embryonic kidney (HEK) 293 or 293T cells (ATCC No. CRL1573), or 3T3 cells (ATCC No. CCL92). The selection of suitable mammalian host cells and methods for transformation, culture, amplification, screening and product production and purification are known in the art. Other suitable mammalian cell lines are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines.

Cell-free transcription and translation systems can also be employed to produce such proteins using the DNA constructs (or RNAs derived from the DNA constructs) of the present invention.

Accordingly, in another aspect, the invention comprises a method for producing a supplement with the ability to enhance survival and/or growth of cells or tissues in culture. The method comprises culturing a host cell of the invention under conditions sufficient for the expression of both cell culture component, and a heat shock protein and recovering the complex of albumin and the heat shock protein.

Production of recombinant proteins of the present invention may be prepared by processes well known in the art from genetically engineered host cells comprising expression systems. Accordingly, in a further aspect, the present invention relates to expression systems comprising a polynucleotide or polynucleotides encoding albumin and to host cells which are genetically engineered with such expression systems and to the production of such proteins by recombinant techniques. In one embodiment the host cell endogenously expresses a heat shock protein of interest.

In cases where purification of the expressed proteins of the supplement of the invention are necessary, proteins of the present invention can be recovered from either the cellular environment, before lysing the cells, or after cell lysis. The proteins can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography is also employed for purification.

Methods for the purification of heat shock proteins, including anion exchange chromatography and ATP agarose affinity chromatography are well known in the art. (Welch & Feramisco, J. Biol. Chem. 257 (24)14949-14959; (1982); Welch & Feramisco, Mol. Cell. Biol. 5 (6) 1229-1237 (1985). Well known techniques for refolding proteins may be employed to regenerate active conformation when the polypeptide is denatured during intracellular synthesis, isolation and/or purification.

A search of patents, published patent applications, and related publications will also provide those skilled in the art reading this disclosure with significant possible methods for preparing and purifying albumin. For example, U.S. Pat. Nos. 4,075,197; 4,086,222; 4,093,612; 4,097,473; 4,136,094; 4,228,154; 5,250,662; 5,656,729; 5,677,424; 5,710,253; 5,728,553; 5,994,507; 6,001,974; 6,638,740; 6,617,133 and 7,423,124 disclose various processes for purifying albumin. In one aspect, the albumin for use in the present invention is purified using any of these art recognized processes listed above, and then mixed in aqueous solution with a heat shock protein.

VI. Methods for Enriching Cell Culture Components with Heat Shock Proteins

In one preferred aspect the cell culture component is purified using procedures that enable the direct co-purification of both the cell culture component and a heat shock protein, or hsp protein complex. In one aspect, the cell culture component consists essentially of the cell culture component and the heat shock protein. In one aspect, the cell culture component is albumin, and the hsp is a rice HSP70 family member.

Due to the similar electronegativity of albumin and hsp70, anion exchange chromatography is the preferred method to prepare albumin enriched in Hsps. For example, both albumin and Hsp70 bind to anion exchange columns with resins consisting of either quaternary amine or diethylaminoethyl mounted on a bead that is suitable for the ion exchange of polypeptides (large molecular exclusion limit and of suitable size) at high pH (7.5 and above). Examples of such resins are General Electric (GE) Q Sepharose and GE DEAE Sepharose. Due to their similar electronegativity, utilizing low pH conditions (below pH 6.5) allows for the co-purification of the two molecules on cation exchangers as well. Examples of such cation exchangers are GE Carboxymethyl Sepharose and Sulfonic acid Sepharose based resins. Because the albumin and Hsp70 have similar isoelectric points, mixed mode resins may also be employed for the co-purification of albumin and Hsp70. Since both Hsp70 and Albumin are well known to bind to fatty acids and other hydrophobic molecules, it is also possible to co-purify albumin and Hsp70 on a hydrophobic based resin such as octyl sepharose (GE). Due the similar size of Hsp70 proteins and Albumin (65-75 kDa), co-purification of the two proteins and enrichment of Hsp70 by tangential flow ultrafiltration utilizing both higher and lower molecular exclusions than 65-75 kDa may also be employed to co-purify and thus enrich Albumin with hsps.

Also due to their similar molecular weights, any method that separates polypeptides based on size should effectively co-purify albumin and hsp70 such as molecular sieves and gel filtration or size exclusion chromatography. In addition, due to the similar nature of Hsp70 and Albumin in terms of hydrophobicity and electronegativity or surface charge may be co-purified by precipitation under a number of conditions. Some of those conditions are precipitation by ammonium sulfate, precipitation by denaturants such as urea, or precipitation based on isoelectric point and solubility.

The methods are also applicable to enrich albumin with hsps from other sources. For example albumin derived from native and transgenic animal feedstock serum, as well as albumin produced from recombinant organisms and tissue culture systems based on prokaryotic and eukaryotic cells, including, vertebrate cells such as mammalian cells, and non vertebrate cells, such as insects, as well as plant, and fungi such as yeast, and the like.

VII. Methods for Enriching Heat Shock Protein Expression

In contrast to serum feedstocks or other expression systems, the Hsp levels would be expected to be naturally elevated during seed ripening and drying in rice and other plants. Hsp content can be further increased in plants by using conditions that induce higher hsp expression prior to harvesting. Suitable conditions for increasing heat shock expression include water restriction (Jiang, Y., and Huang, B., Turfgrass Science, 32:202-207, 2002 and Bewley et al. Plant Physiology, 76, 270-274, 1984), the use of toxins such as pesticides fungicides, and herbicides (Nazir, A., et al., Biochimica et Biophysica Acta, 1621(2), 2003 and T Yoshimi et al. Env. Toxicology and Pharmacology 28(2), 294-301, 2009), chemical inducers of hsp expression such as ibuprofen (Bag J. et al. Human Mol. Genetics, 14(23), 3673-84, 2005 and Singleton, K. et al., J. Parenteral and Enteral Nutrition, 32(4), 371-376, 2008 and Wang, Q. et al. Biochemical and Biophysical Research Communications, 370(1), 11-15, 2008), as well as substances such as geranylgeranylacetone (Zhang et al. Cell Stress and Chaperones, 14(4), 407-415, 2009). Other known substances or conditions that induce hsp70 expression are Indomthacin (Asano, T. et al., J. of Pharm. And Exp. Ther. 330; 458-467, (2009), as well as heavy metals, osmotic stress, oxidative stress, low pH, and many others.

Hsp content can also be increased in other recombinant expression systems by inducing heat shock conditions to increase the endogenous expression of heat shock proteins. In one approach, this can be completed by increasing the incubation temperature of the culture prior to harvesting the cells, In general the temperature can be increased about 2° C. to about 25° C. higher than the normal incubation temperature of the organism. Typically such treat shock conditions can be maintained for about 1 minute, to about 24 hours depending upon the relative increase in temperature, and the organism in question. Typically the heat shock conditions will be applied about one hour to 72 hours prior to harvesting the albumin.

In another approach, hsp content can be increased in other recombinant expression systems by the addition of toxins, and known heat shock protein agents, specific for the organism or cell line in question. Representative examples of suitable inducing agents and conditions for hsp expression include heat, cold, osmotic shock, salt, drought, genotoxic stress, UV light, radiation, oxidative stress, wounding, pathogens, and infection.

For example during production of recombinant albumin in yeast, Hsp expression can be elevated during the production phase of albumin expression by transiently inducing heat shock conditions, that is raising the normal temperature of the bioreactor to a temperature that is about 5 to about 1° C. higher than the normal temperature, for about 1 to 60 minutes, and about one hour to 24 hours prior to harvesting the cells. This approach can be thus be employed as a method to increase the amount of Hsp in the crude cell lysate to be made available for co-purification.

It is also possible to add reagents to yeast culture to obtain higher Hsp70 expression. Similar to plant systems, Hsp70 levels in yeast are responsive to the same inducible factors with the addition of oxidative stress, since yeast exposed to either low or high levels of oxygen in culture are likely to express different levels of Hsp70.

During production in bacteria, the levels of Hsp70 may be elevated by raising the temperature as much as 20 C above the normal growth temperature of the organism. During this time, the temperature may be manipulated such as to condition the bacteria to heat shock and thus cause elevated Hsp70 levels.

Accordingly in one aspect the present invention includes a process for manufacturing albumin that is enriched in a heat shock protein comprising the steps of i) inducing the expression of a heat shock protein in a recombinant organism expressing albumin and, ii) co-purifying a fraction comprising the heat shock protein and the albumin.

During production in any expression system, the strategy to increase and control the levels of Hsp like proteins in combination or alone is beneficial to the production of the protein of interest.

Hsp70 has been successfully expressed in bacteria, yeast, and mammalian cell culture. Hsp70 expression has been widely examined in plants. Accordingly in one aspect the present invention includes an expression system in rice that promotes the production of a protein of interest by co-expressing a heat shock protein.

VIII. Exemplary Cells

Without wishing to be bound by theory, it is contemplated that any cell which is susceptible to apoptosis may be used in the methods of the invention, including primary cells, immortalized cells, differentiated cells, undifferentiated cells or cells, such as stem cells, with varying degrees of specialization. In a particular embodiment, cells used in the methods of the invention are transfected with a nucleic acid molecule comprising a nucleotide sequence encoding a protein of interest, e.g., a therapeutic protein or an antibody.

In a particular embodiment, the cells used in the methods of the invention are eukaryotic cells, e.g., mammalian cells. Examples of mammalian cells include, but are not limited to, for example, monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells/–DHFR(CHO, Urlaub and Chasin, Proc. Natl. Acad. Sci. USA, 77:4216 (1980)); CHO-K1 cell (ATCC CCL-61), human PER.C6 cells (Crucell, Nev.), mouse sertoli cells (TM4, Mather, Biol. Reprod., 23:243-251 (1980)); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; NSO mouse myeloma cells (ECACC; SIGMA), and a human hepatoma line (Hep G2). Additional examples of useful cell lines include, but are not limited to, HT1080 cells (ATCC CCL 121), MCF-7 breast cancer cells (ATCC BTH 22), K-562 leukemia cells (ATCC CCL 243), KB carcinoma cells (ATCC CCL 17), 2780AD ovarian carcinoma cells (see Van der Blick, A. M. et al., Cancer Res. 48:5927-5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), as well as heterohybridoma cells produced by fusion of human cells and cells of another species. These and other cells and cell lines are available commercially, for example from the American Type Culture Collection (Virginia, USA). Many other cell lines are known in the art and will be familiar to the ordinarily skilled artisan; such cell lines therefore can be used equally well in the methods of the present invention. In a particular embodiment, cells used in the methods of the invention are CHO cells or NSO cells. Hybridomas and antibody-producing cells may also be used in the methods of the invention.

In another embodiment, cells used in any of the methods of the invention are stem cells. Stem cells are undifferentiated cells defined by their ability at the single cell level to both self-renew and differentiate to produce progeny cells, including self renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Types of human embryonic stem cells that may be used in any of the methods of the invention include established lines of human embryonic cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.). In one embodiment, Human embryonic stem cells are prepared as described by Thomson et al. (U.S. Pat. No. 5,843,780; Science 282: 1145, 1998; Curr. Top. Dev. Biol. 38:133 ff., 1998; Proc. Natl. Acad. Sci. U.S.A. 92:7844, 1995).

Additionally, hybridoma cells can also be used in the methods of the invention. The term "hybridoma" refers to a hybrid cell line produced by the fusion of an immortal cell line of immunologic origin and an antibody producing cell. The term encompasses progeny of heterohybrid myeloma fusions, which are the result of a fusion with human cells and a murine myeloma cell line subsequently fused with a plasma cell, commonly known as a trioma cell line. Furthermore, the term is meant to include any immortalized hybrid cell line which produces antibodies such as, for example, quadromas. See, e.g., Milstein et al., Nature, 537:3053 (1983). The hybrid cell lines can be of any species, including human, rabbit and mouse.

In some embodiments, a cell line used in the methods of the invention is an antibody-producing cell line. Antibody-producing cell lines may be selected and cultured using techniques well known to the skilled artisan. See, e.g., Current Protocols in Immunology, Coligan et al., Eds., Green Publishing Associates and Wiley-Interscience, John Wiley and Sons, New York (1991) which is herein incorporated by reference in its entirety, including supplements. In general, any cell suitable for recombinant protein expression in cell culture can be used in the methods of the invention.

In some embodiments, the cells used in the methods of the present invention may include a heterologous nucleic acid molecule which encodes a desired recombinant protein, e.g., a therapeutic protein or antibody which is desired to be produced using the methods of the invention. In a particular embodiment, the methods of the present invention are useful for producing high titers of a desired recombinant protein, e.g., a therapeutic protein or antibody, in the presence of reduced levels of one or more contaminants.

IX. Cell Culture Media

Any suitable culture medium or feed medium suitable for cell growth and protein production may be used in the methods of the invention. Suitable culture or feed mediums are chosen for their compatibility with the host cells and process of interest. Suitable culture or feed mediums are well known in the art and include, but are not limited to, commercial media such as Ham's F10 (SIGMA), Minimal Essential Medium (SIGMA), RPMI-1640 (SIGMA), and Dulbecco's Modified Eagle's Medium SIGMA) are suitable for culturing the animal cells. In addition, any of the media described in Ham and Wallace, (1979) Meth. Enz., 58:44; Barnes and Sato, (1980) Anal. Biochem., 102:255; U.S. Pat. Nos. 4,767, 704; 4,657,866; 4,927,762; 5,122,469 or 4,560,655; International Publication Nos. WO 90/03430; and WO 87/00195 may be used.

Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. The necessary growth factors for a particular cell are readily determined empirically without undue experimentation, as described for example in Mammalian Cell Culture (Mather, J. P. ed., Plenum Press, N.Y. (1984), and Barnes and Sato, Cell, 22:649 (1980).

Other methods, vectors, and host cells suitable for adaptation to the synthesis of the protein of interest in recombinant vertebrate cell culture are described in Gething et al., Nature, 293:620-625 (1981); Mantei et al., Nature, 281:40-46 (1979); EP 117,060; and EP 117,058. In general, principles, protocols, and practical techniques for maximizing the productivity of mammalian cell cultures can be found in Mammalian Cell Biotechnology: A Practical Approach, M. Butler, ed. (IRL Press, 1991).

X. Exemplary Cell Culture Expression Products

In one aspect of any of the claimed methods, the supplements of the invention are used to improve the viability and growth of a cell which is used to express and produce a protein of interest. The cell may express the protein of interest endogenously or may be an engineered cell line that has been modified genetically to express the protein of interest at levels above background for that cell.

Cells may be genetically modified to express a protein by transformation with a nucleic acid encoding the protein of interest, or by transformation of an activating sequence that promotes the expression of an endogenous gene. In one aspect the protein of interest may be expressed from an expression vector, in which a coding sequence for the protein of interest is operably linked to a expression control sequences, to enable either constitutive or inducible expression, as is known in the art.

The protein of interest may be any protein, or fragment thereof, which is of commercial, therapeutic or diagnostic value including without limitation cytokines, chemokines, hormones, antibodies, anti-oxidant molecules, engineered immunoglobulin-like molecules, a single chain antibodies, a humanized antibodies, fusion proteins, enzymes, immune co-stimulatory molecules, immunomodulatory molecules, trans-dominant negative mutants of a target protein, toxins, conditional toxins, antigens, a tumor suppresser proteins, growth factors, membrane proteins, vasoactive proteins and peptides, anti-viral proteins and ribozymes, and derivatives thereof (such as with an associated reporter group). The protein of interest may also comprise pro-drug activating enzymes.

In some embodiments, the protein of interest comprises a glycoprotein, or any other protein which has one or more post-translational modifications. For example, any protein which is suitable for production in a eukaryotic host may be expressed using the methods and compositions described here.

The methods of the invention can be used to produce any desired recombinant protein or fragment thereof. In some embodiments, a recombinant protein produced using the methods described herein is a therapeutic protein. In other embodiments, the recombinant protein is an antibody or functional fragment thereof. Antibodies which may be produced using the methods of the invention include, for example, polyclonal, monoclonal, monospecific, polyspecific, fully human, humanized, single-chain, chimeric, hybrid, CDR grafted. It may comprise a full length IgG1 antibody or an antigen-binding fragments thereof, such as, for example, Fab, F(ab')$_2$, Fv, and scfv.

Antibodies within the scope of the present invention include, but are not limited to: anti-HER2 antibodies including Trastuzumab (HERCEPTIN™) (Carter et al., Proc. Natl. Acad. Sci. USA, 89:4285-4289 (1992), U.S. Pat. No. 5,725,856); anti-CD20 antibodies such as chimeric anti-CD20"C2B8" as in U.S. Pat. No. 5,736,137 (RITUXAN™), a chimeric or humanized variant of the 2H7 antibody as in U.S. Pat. No. 5,721,108, B1, or Tositumomab (BEXXAR™); anti-IL-8 (St John et al., Chest, 103:932 (1993), and International Publication No. WO 95/23865); anti-VEGF antibodies including humanized and/or affinity matured anti-VEGF antibodies such as the humanized anti-VEGF antibody huA4.6.1 AVASTIN™. (Kim et al., Growth Factors, 7:53-64 (1992), International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., Transplant Intl. 4:3-7 (1991), and Hourmant et al., Transplantation 58:377-380 (1994)); anti-IgE (Presta et al., J. Immunol. 151: 2623-2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-.alpha. antibodies including cA2 (REMICADE™), CDP571 and MAK-195 (See, U.S. Pat. No. 5,672,347 issued Sep. 30, 1997, Lorenz et al. J. Immunol. 156(4):1646-1653 (1996), and Dhainaut et al. Crit. Care Med. 23(9):1461-1469 (1995)); anti-Tissue Factor (TF) (European Patent No. 0 420 937 B1 granted Nov. 9, 1994); anti-human .alpha.4.beta.7 integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT™) and (ZENAPAX™) (See U.S. Pat. No. 5,693,762 issued Dec. 2, 1997); anti-CD4 antibodies such as the cM-7412 antibody (Choy et al. Arthritis Rheum 39(1):52-56 (1996)); anti-CD52 antibodies such as CAMPATH-1H (Riechmann et al. Nature 332:323-337 (1988)); anti-Fc receptor antibodies such as the M22 antibody directed against Fc.gamma.RI as in Graziano et al. J. Immunol. 155(10):4996-5002 (1995); anti-carcinoembryonic antigen (CEA) antibodies such as hMN-14 (Sharkey et al. Cancer Res. 55(23Suppl): 5935s-5945s (1995); antibodies directed against breast epithelial cells including huBrE-3, hu-Mc 3 and CHL6 (Ceriani et al. Cancer Res. 55(23): 5852s-5856s (1995); and Richman et al. Cancer Res. 55(23 Supp): 5916s-5920s (1995)); antibodies that bind to colon carcinoma cells such as C242 (Litton et al. Eur J. Immunol. 26(1):1-9 (1996)); anti-CD38 antibodies, e.g. AT 13/5 (Ellis et al. J. Immunol. 155(2):925-937 (1995)); anti-CD33 antibodies such as Hu M195 (Jurcic et al. Cancer Res 55(23 Suppl):5908s-5910s (1995) and CMA-676 or CDP771; anti-CD22 antibodies such as LL2 or LymphoCide (Juweid et al. Cancer Res 55(23 Suppl):5899s-5907s (1995)); anti-EpCAM antibodies such as 17-1A (PANOREX™); anti-GpIIb/IIIa antibodies such as abciximab or c7E3 Fab (RE-OPRO™ anti-RSV antibodies such as MEDI-493 (SYN-AGIS™); anti-CMV antibodies such as PROTOVIR™; anti-HIV antibodies such as PRO542; anti-hepatitis antibodies such as the anti-Hep B antibody OSTAVIR™; anti-CA 125 antibody OvaRex; anti-idiotypic GD3 epitope antibody BEC2; anti-.alpha.v.beta.3 antibody VITAXIN™; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2 receptor, VEGF, IgE, CD20, CD11a, and CD40.

The recombinant protein may be a cellular protein such as a receptor (e.g., membrane bound or cytosolic) or a structural protein (e.g. a cytoskeleton protein). The recombinant protein may be cellular factor secreted by the cell or used internally in one or more signal transduction pathways. Non limiting examples include, but are not limited to, CD2, CD3, CD4, CD8, CD11a, CD14, CD18, CD20, CD22, CD23, CD25, CD33, CD40, CD44, CD52, CD80 (B7.1), CD86 (B7.2), CD147, IL-1, IL-2, IL-3, IL-7, IL-4, IL-5, IL-8, IL-10, IL-2 receptor, IL-4 receptor, IL-6 receptor, IL-13 receptor, IL-18 receptor subunits, PDGF, EGF receptor, VEGF receptor, hepatocyte growth factor, osteoprotegerin ligand, interferon gamma, B lymphocyte stimulator C5 complement TAG-72, integrin alpha 4 beta 7, the integrin VLA-4, B2 integrins, TRAIL receptors 1, 2, 3, and 4, RANK, RANK ligand, TNF, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2, and CTLA4 (which is a cytotoxic T lymphocyte-associated antigen).

The recombinant protein may also be derived from an infectious agent such as a virus, a bacteria, or fungus. For example, the protein may be derived from a viral coat or may be a viral enzyme or transcription factor. The protein may be derived from a bacterial membrane or cell wall, or may be derived from the bacterial cytosol. The protein may be a yeast enzyme, transcription factor, or structural protein. The yeast protein may be membrane bound, cytsolic, or secreted. Examples of infectious agents include, but are not limited to, respiratory syncitial virus, human immunodeficiency virus (HIV), hepatitis B virus (HBV), hepatitis C virus (HCV), *Streptococcus mutans*, and *Staphlycoccus aureus*, and *Candida albicans*. Moreover, the product of the cell culture system may be a virus such as any of those noted above. These viruses include live viruses, attenuated viruses and otherwise inactivated viruses or components thereof such as viral particles or virus-like-particles. The virus can also be pseudotyped viruses in which the components of the virus are comprised of components of two or more different viruses. In addition, the product of the cell culture can be a vaccine. Vaccines can be therapeutic or prophylactic in nature. Vaccines produced in cultures are often live or attenuated viruses or components thereof as exemplified by subunit vaccines or can be recombinant viruses or virus-like particles comprising components of more than one virus.

The methods of the invention can also be used to produce recombinant fusion proteins comprising all or part of any of the above-mentioned proteins. For example, recombinant fusion proteins comprising one of the above-mentioned proteins plus a multimerization domain, such as a leucine zipper, a coiled coil, an Fc portion of an antibody, or a substantially similar protein, can be produced using the methods of the invention. See e.g. International Application No. WO 94/10308; Lovejoy et al. (1993), Science 259:1288-1293; Harbury et al. (1993), Science 262: 1401-05; Harbury et al. (1994), Nature 371:80-83; Hang.kansson et al. (1999), Structure 7:255-64.

Also encompassed by this invention are pharmaceutical compositions including one or more recombinant proteins produced by the methods described herein. In some embodiments, pharmaceutical compositions further include a pharmaceutically acceptable carrier. The term "pharmaceutically-acceptable carrier" as used herein means one or more compatible solid or liquid filler, diluents or encapsulating substances which are suitable for administration into a subject.

XI. Large Scale Production of Recombinant Proteins

In one embodiment, the supplements of the present invention can be used to produce a protein of interest by growing host cells in the presence of the supplement. In one embodiment, the cell culture is performed in a stirred tank bioreactor system and a fed batch culture procedure is employed. In another embodiment a wave disposable bioreactor is employed. In the bioreactor system, the size of the bioreactors are sufficiently large to produce the desired amount of protein of interest, such as 1,000 Liter or 12,000 Liter sizes, but are not limited to such sizes as much smaller (i.e., 2 Liter, 400 Liter) or larger (i.e., 25,000 Liter, 50,000 Liter) bioreactor vessels may be appropriate. In the preferred fed batch culture, the mammalian host cells and culture medium are supplied to a culturing vessel initially and additional culture nutrients are fed, continuously or in discrete increments, to the culture during culturing, with or without periodic cell and/or product harvest before termination of culture. The fed batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernatant is not removed from the culturing vessel during the process but at the termination of the culture process (in perfusion culturing, the cells are restrained in the culture by, e.g., filtration, encapsulation, anchoring to microcarriers etc. and the culture medium is continuously or intermittently introduced and removed from the culturing vessel).

Further, the cultured cells may be propagated according to any scheme or routine that may be suitable for the particular host cell and the particular production plan contemplated. Therefore, the present invention contemplates a single step or multiple step culture procedure. In a single step culture, the host cells are inoculated into a culture environment and the method steps of the instant invention are employed during a single production phase of the cell culture. Alternatively, a multi-stage culture is envisioned. In the multi-stage culture, cells may be cultivated in a number of steps or phases. For instance, cells may be grown in a first step or growth phase culture wherein cells, possibly removed from storage, are inoculated into a medium comprising a supplement of the present invention suitable for promoting growth and high viability. The cells may be maintained in the growth phase for a suitable period of time by the addition of fresh medium to the host cell culture.

According to a preferred aspect of the invention, fed batch or continuous cell culture conditions are devised to enhance growth of the mammalian cells in the growth phase of the cell culture. In the growth phase, cells are grown under conditions and for a period of time that is maximized for growth. Culture conditions, such as temperature, pH, dissolved oxygen ($dO_2$) and the like, are those used with the particular host and will be apparent to the ordinarily skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30 to 38° C. and preferably about 37° C. and a suitable $dO_2$ is between 5-90% of air saturation.

At a particular stage the cells may be used to inoculate a production phase or step of the cell culture. Alternatively, as described above, the production phase or step may be continuous with the inoculation or growth phase or step.

According to the present invention, the cell culture environment during the production phase of the cell culture is controlled. According to the steps of the presently disclosed methods, the addition of the supplements of the invention can be coordinated such that the desired content and quality of the protein of interest is achieved and maintained in the resulting cell culture fluid. In a preferred aspect, the production phase of the cell culture is preceded by a transition phase of the cell culture in which the addition of the supplements of the invention initiates the production phase of the cell culture.

In any of the above-described methods, it is contemplated that it may be desirable to include a desired amount of agent like butyrate or Trichostatin A in the cell culture medium in combination with a supplement of the invention. Various forms of butyrate and its salts are known in the art, such as butyric acid and sodium butyrate, and are publicly available from sources such as Sigma Chemical Co. Butyrate has been reported in the literature to enhance the productivity and protein expression of cell cultures [Arts et al., Biochem J., 310:171-176 (1995); Gorman et al., Nucleic Acids Res., 11:7631-7648 (1983); Krugh, Mol. Cell. Biochem., 42:65-82 (1982); Lamotte et al., Cytotechnology, 29:55-64 (1999);

Chotigeat et al., Cytotechnology, 15:217-221 (1994)]. Trichostatin A (TSA) is an inhibitor of histone deacetylase and may act similarly to butyrate in enhancing the productivity and protein expression in cell cultures [Medina et al., Cancer Research, 57:3697-3707 (1997)]. Although butyrate has some positive effects on protein expression, it is also appreciated in the art that at certain concentrations, butyrate can induce apoptosis in the cultured cells and thereby decrease viability of the culture as well as viable cell density [Hague et al., Int. J. Cancer, 55:498-505 (1993); Calabresse et al., Biochim. Biophys. Res. Comm., 195:31-38 (1993); Fillipovich et al., Biochim. Biophys. Res. Comm., 198:257-265 (1994); Medina et al., Cancer Research, 57:3697-3707 (1997)]. In the methods of the present invention, a desired amount of butyrate or TSA may be added to the cell culture at the onset of the production phase and more preferably, may be added to the cell culture after a temperature shift has been implemented. Butyrate or TSA can be added in a desired amount determined empirically by those skilled in the art, but preferably, butyrate is added to the cell culture at a concentration of about 1 to about 25 mM, and more preferably, at a concentration of about 1 to about 6 mM.

Expression of the protein of interest may be measured in a sample directly, for example, by ELISA, conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe. Various labels may be employed, most commonly radioisotopes, and particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionucleotides, fluorescers or enzymes. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like.

Antibodies useful for immunohistochemical staining and/or assay of sample fluids may be either monoclonal or polyclonal, and may be prepared in any mammal. Many are commercially available.

The supplements claimed herein can also be used to increase transfection efficiency and viability of cells during transfection. Conditions and reagents used in various transfection techniques, such as Lipofectamin are relatively toxic to the cells, while electroporation can severely stress a cell. The use of higher concentrations of transfection reagents, and more extensive electroporation conditions is preferred to achieve higher transfection efficiencies. Thus the addition of the supplements of the invention prior, with, and after transfection can result in higher transfection efficiencies, and higher yields of recombinant proteins.

The supplements of the invention can be used to express proteins of interest which induce apoptosis, such as Apo-2 ligand/TRAIL or Fas ligand. The presence of the supplements of the invention may block such apoptotic activity and allow for improved expression of the protein of interest.

In addition, the methods can be used to increase the viability of cells undergoing freezing/storage/thawing procedures. During these procedures generally cells can lose viability. The presence of apoptosis inhibitors added to the cell culture media can provide for increased cell viability and aid in reducing or eliminating the variability in cell viabilities between aliquots or vials of cells.

XII. Kits

Also encompassed by the present invention are kits for promoting the viability of cells. In one embodiment, a kit according to the present invention comprises: (a) one or more reagents or devices for transfection and (b) a supplement of the present invention. In some embodiments, kits featured herein include instructions and/or promotional materials including details regarding using the transfection device, transfection agent and supplement.

In another embodiment a kit according to the present invention comprises: (a) one or more reagents or devices for freezing or thawing cells and (b) a supplement of the present invention. In some embodiments, kits featured herein include instructions and/or promotional materials including details regarding protocols for freezing or thawing cell lines and the use of the reagents.

In another embodiment a kit according to the present invention comprises: (a) one or more tissue culture products for culturing cells and (b) a supplement of the present invention. In some embodiments, kits featured herein include instructions and/or promotional materials including details regarding protocols for dilution cloning techniques and the use of the reagents in such approaches.

EXAMPLES

Example 1

Production of Recombinant Rice Flour

Methods: Protein sequences of human serum albumin from various data bases were compared. The consensus sequence represented by accession number P02768 was used as base for gene codon-optimization for suitable expression of human serum albumin in rice grain as described previously in WO2007/002762. Gene synthesis was carried out by Blue Heron (Seattle, Wash.) and the synthetic fragment was inserted into a pUC based vector to create pUC-HSA. After confirmation of the correct DNA sequences, the vector was digested with Mly1 and Xho1. The fragment containing the codon-optimized HSA gene was inserted into pAP1405, which had been precut with Nae1 and Xho1. Plasmid AP1405 was a derivate of vector pAP1441 (WO2007/002762) which includes a Gt1 promoter, Gt1 signal sequence and a nos terminator. Insertion of Mly/Xho1 fragment into pAP1405 resulted in vector pAP1504 which was used for transfection by bombardment as described below.

The basic procedures of particle bombardment-mediated rice transformation and plant regeneration were carried out as described previously (Yi Chuan Xue Bao. 2001; 28(11):1012-8. Chinese and Biotechnol Prog. 2001; 17(1): 126-33). Rice variety TP309 seeds were dehusked, sterilized in 50% (v/v) commercial bleach for 25 min and washed with sterile water. The sterilized seeds were placed on rice callus induction medium (RCI) plates containing [N6 salts (Sigma), B5 vitamins (Sigma), 2 mg/l 2,4-D and 3% sucrose]. The rice seeds were incubated for 10 days to induce callus formation. Primary callus was dissected from the seeds and placed on RCI for 3 weeks. This was done twice more to generate secondary and tertiary callus which was used for bombardment and continued subculture. A callus of 1-4 mm diameter was placed in a 4 cm circle on RCI with 0.3M mannitol 0.3M sorbitol for 5-24 hrs prior to bombardment. Microprojectile bombardment was carried out using the Biolistic PDC-1000/He system (Bio-Rad). The procedure requires 1.5 mg gold particles (60 ug/ml) coated with 2.5 ug DNA. DNA-coated gold particles were bombarded into rice calli with a He pressure of 1100 psi.

After bombardment, the callus was allowed to recover for 48 hrs and then transferred to RCI with 30 mg/l hygromycin B for selection and incubated in the dark for 45 days at 26.degree. C. Transformed calli were selected and transferred to RCI (minus 2,4-D) containing 5 mg/l ABA, 2 mg/l BAP, 1 mg/l NAA and 30 mg/l hygromycin B for 9-12 days. Transformed calli were transferred to regeneration medium consisting of RCI (minus 2,4-D), 3 mg/l BAP, and 0.5 mg/l NAA without hygromycin B and cultured under continuous lighting conditions for 2-4 weeks. Regenerated plantlets (1-3 cm high) were transferred to rooting medium whose concentration was half that of MS medium (Sigma) plus 1% sucrose and 0.05 mg/l NM. After 2 weeks on rooting medium, the plantlets developed roots and the shoots grew to about 10 cm. The plants were transferred to a 6.5.times.6.5 cm pots containing a mix of 50% commercial soil (Sunshine #1) and 50% soil from rice fields. The plants were covered by a plastic container to maintain nearly 100% humidity and grown under continuous light for 1 week. The transparent plastic cover was slowly shifted over a 1 day period to gradually reduce humidity and water and fertilizers added as necessary. When the transgenic R0 plants were approximately 20 cm in height, they were transferred to a greenhouse where they grew to maturity.

Individual R1 seed grains from the individual R0 regenerated plants were dissected into embryos and endosperms. Expression levels of recombinant albumin in the isolated rice endosperms were determined. Embryos from the individual R1 grains with high recombinant protein expression were sterilized in 50% bleach for 25 min and washed with sterile distilled water. Sterilized embryos were placed in a tissue culture tube containing 1/2 MS basal salts with the addition of 1% sucrose and 0.05 mg/l NAA. Embryos were germinated and plantlets having .about.7 cm shoots and healthy root systems were obtained in about 2 weeks. Mature R1 plants were obtained as regenerants.

Transgenic rice containing heterologous polypeptides can be converted to rice extracts by either a dry milling or wet milling process. In the dry milling process, transgenic rice seeds containing the heterologous polypeptides are dehusked with a dehusker. The dehusked rice was then ground into a fine flour though a dry milling process, for example, in one experiment, at speed 3 of a model 91 Kitchen Mill from K-TEC.

Example 2

Purification of Recombinant Albumin (B0000C)

Methods: For Ventria grown rice, the rice was harvested by combine or by hand. During this process the mature seeds were separated from the vegetative plant matter by the combine separator or by manual labor. The harvested rice was dried to approximately 12% moisture at which point it is suitable for storage in a clean grain bin, storage tote, supersack, or other container that will protect the grain from birds, rodents, lizards, insects and other pests. When the rice grain is needed for flour, it is first dehusked or dehulled. This process is done under vacuum such that debris and the outer part of the seed are swept away from the endosperm and germ or bran layer. The dehusked grain is then either washed and dried, or washed and processed directly as in wet homogenization, or processed further in the dry, dehusked state. The dry, dehusked material may be debranned by a rice polishing or debranning machine which are common to white rice producers.

Debranned, dehusked rice may be washed at this point and wet-milled or dried for dry milling or processed directly by grinding into flour. Milling with the least amount of shear and heat is preferred as such with a roller mill or pin mill. A hammermill is also suitable. The flour should be ground such that the protein can be extracted to 90% in less than 5 minutes in water with hard agitation. Normally that requires a size of particle that is smaller than 400 micrometers or 4 mm. However, larger particles can be extracted if given longer time. Alternatively, the grain can be washed and wet milled with a liquid homogenizer set up such that 90% of the extractable protein is solubilized.

The flour slurry is typically mixed at a ratio of at least 3 parts water to 1 part flour and up to 20 parts water to 1 part flour. The water typically contains suitable buffers such as Tris/HCl, Citrate, Phosphate, HEPES, or the like, such that the pH is maintained around pH 7 and a small amount of salt such as 100 mM NaCl. After the slurry is homogenized in the case of wet milling, or mixed thoroughly for dry flour, the bulk solids are removed from the slurry by way of solid liquid separation. This is carried out by decanting, centrifugation, or filtration; for example using plate and frame with pads, pressure filter, belt filter, vacuum flask, hydroclone, or vacuum belt filter. After filtration, the compressed cake should be washed with extraction buffer to recover protein from the cake. The addition of diatomateous earth or other filter media is useful in promoting the clarity of the filtrate but is not necessary given the right equipment. Alternatively, a flocculating agent may be used to aid in clarification. The clarified filtrate should be checked for its albumin content and verified that the recovery is consistent with the determined expression level in the rice seed.

In order to remove starches, precipitable proteins, viruses, and other contaminants, 5 M acetic acid is added to the clarified filtrate until the pH reaches 5.0 and the solution turns white. The white solution is agitated for at least 20 minutes to encourage precipitation of insoluble materials. The precipitated solution is then filtered through a depth filter, such as a canister filter, cartridge filter or other filtration device to reach a clarity that is suitable for ultrafiltration, or less that 10 NTU (nephelometry turbidity units). It can also be clarified with a filter press, pressure filter, or alternatively by using a ceramic filter or other material that utilizes cross-flow. In addition, this material is suitable for direct application to an expanded bed chromatography column.

In a preferred method, the clarified filtrate is clarified via filtration through a 0.2 micron filter, and neutralized to pH 7.0 with 1M NaOH. This material is then suitable for ultrafiltration by hollow fiber, flat sheet, or spiral wound cross flow filtration. The material can be passed through a membrane of 100 kilodalton (kD) size or larger to remove viruses, unwanted larger contaminants, and aggregates. The material that passes through the membrane can be concentrated by a 10 or 30 kD crossflow membrane and then the same membrane can be used to prepare the solution for chromatography. The concentrated material can then diafiltered with column equilibration buffer until the conductivity and the pH are equalized.

The preferred buffer for anion exchange chromatography on GE DEAE sepharose or GE Q sepharose is 10 or 20 mM Tris/HCl buffer pH balanced to pH 8.0. In contrast, the preferred buffer for cation exchange, for example via the use of for negatively charged resins or negatively charged resins mixed with a hydrophobic linker (mixed mode absorbents), or alternatively blue Cibicron such Blue Sepharose (GE) is acetate or citrate buffer pH balanced to 4.8 to 5.0.

For either system the albumin and other similarly charged proteins will be retained by the matrix and washing is conducted to remove loosely bound material by washing with at least 5 column volumes of loading buffer, which may also include detergents, salts, octanoic acid, or other agents as deemed necessary to help remove hydrophobic and protein impurities. The material can be eluted by charging the column with the same or modified buffers with the pH increased 2-4 units for cation exchange or decreased 2-4 units for anion exchange. The resulting change in pH will allow for the exchange of ions and the protein will be eluted in a sharp band. To increase the purity of the elution fraction, the elution peak can be scrutinized such that the first portion (10%) or last (10%) or both portions can be excluded from the main elution peak. In the preferred method, a solution containing phosphate at 100 mM and pH adjusted to pH 4.0 including 10 mM NaCl is used to elute the protein from GE Q sepharose (Fast Flow). In this instance, pH and conductivity are used to elute the material allowing the discrimination between non-binding contaminants (flow through and wash) and tighter binding contaminants (those that are retained on the column in 100 mM Phosphate, 10 mM NaCl, and pH adjusted to 4.0).

After elution, If the pH of the eluted material has a pH of less than 6.0, then it is neutralized with 1M NaOH. The resulting solution is then diafiltered against the same buffer for the next chromatography step, which in a preferred method involves flowing the elutent through a column of the same matrix (i.e. Q sepharose) except in the non-binding mode with 100 mM Phosphate, 10 mM NaCl, and pH 7.0.

The second column step uses the same principles as the first but in reverse mode such that the contaminants that were co-eluted on the binding column have an opportunity to be retained on the matrix at a neutral pH. The flow through material from the first capture column can also be treated with a variety of alternative types of chromatography approaches, for example, cation exchange, hydrophobic, mixed mode, or gel filtration chromatography.

In a preferred method, the flow through material from the Q sepharose non-binding column is concentrated on a 10 kD or 30 kD crossflow membrane until the concentration is between 15 and 25% albumin. The buffer is then changed by diafiltration into a suitable buffer for cell culture such as Dulbeccos PBS or alternatively 20 mM Phosphate, 50 mM NaCl, and pH 7.0. The material is then sterile grade filtered into a sterile container. The sterile filtered material may be treated with detergent to destroy enveloped viruses and to aid in the removal of hydrophobic toxins and contaminants. In a preferred method, 0.5% v/v Triton X-114 or X-100 is added to the 15 to 25% albumin solution at room temperature (less than 23° C. and greater than 18° C.) and the solution is agitated or stirred for at least 1 hour. The material is then passed over a hydrophobic resin with a molecular weight exclusion limit that is much less than the molecular weight of albumin. Many commercially available resins are available including those from Biorad and Pall Corporation.

The material that is passed over the column may then be tested in cells that are sensitive to detergent to confirm biological activity. The residual detergent that remains should typically be less than 0.005% with respect to the albumin solution. The detergent free flow through can then be sterile filtered into containers for direct shipment, or can have stabilizers added, or can be subjected to pasteurization with stabilizers, or can have stabilizers added before drying or dried directly. The material may be dried by lyophilization or spray drying. Prior to drying, in some instances, it may be useful to subject the material to a virus filtration step using a disposable, validated, virus removing capsule such as is available from GE, Pall, and Millipore. It is common in the art to understand that a prefiltration step may be necessary in order to effectively and economically pass the concentrated material through a 20 nm filter.

Results: Rice flour was extracted at 1:5 ratio in phosphate buffered saline and mixed for 20 minutes. The liquid was clarified using a Nalgene filter flask. The subsequent clarified extract was subjected to acid precipitation as is described in the methods. The solution was then filtered and neutralized to give a clarified filtrate. This material was diafiltered against 50 mM Tris/Cl pH 8.0 until the material and buffer were equilibrated. The material was then loaded (300-600 cmh) on a pre-equilibrated GE Q-sepharose column to allow for 50 g/L binding capacity. The loaded material was washed with the same buffer and the material was then eluted with 100 mM Phosphate, 10 mM NaCl, and pH 4.0 as described above. The material eluted in a sharp peak and the collected eluate had a stable pH of about 5.8. Albumin produced using this method was compared to other sources of Albumin as more fully disclosed below: The eluate was collected in a pool and 1M NaOH was added until the pH was greater than 6.0. The material was then concentrated on a 10 kDa regenerated cellulose membrane approximately 5 fold and approximately five equal volume diafiltrations were carried out with 100 mM phosphate, 10 mM NaCl, pH 7.0. The final diafiltered material was checked for albumin protein content (in relation to the expression level in the starting material should be greater than 80%) and endotoxin level (should be less than 100 EU/mg depending on the feed material). This material was passed (60-160 cmh) over a Q-sepharose column, equilibrated with 100 mM phosphate, 10 mM NaCl, pH 7.0, of sufficient size to allow for approximately 2-3 times loading volume. The material was washed through the resin with the same buffer and collected. The collected material was diafiltered on a 10 kDa regenerated cellulose membrane and concentrated approximately 10 fold or until the albumin concentration reaches at least 10% or not more than 20% and five equal volume diafiltrations were performed with 20 mM phosphate, 50 mM NaCl, pH 7.0. After sterile grade filtration (0.2 μm), the solution was agitated for 1 hour with 0.5% (v/v) Triton X-100 at 20+/−2° C. After the incubation, the material was passed through Pall SDR resin according to the manufacturer's directions. The flow through material was sterile grade filtered into sterile containers and refrigerated or freeze dried as is common for protein and salt solutions.

Example 3

Comparison of Recombinant Albumin Produced from Rice Using B0000C Process Compared to Other Sources of Albumin and Previous Methods for the Production of Albumin Methods: Albumin prepared using the method described in Example 2, was compared to albumin prepared using an alternative process (B000) which was previously used to prepare Cellastim (Batches B202 to B217).

Albumin Production (Old Process, B000):

Rice flour and 25 mM Sodium phosphate, 50 mM Sodium Chloride, was pH balanced to 6.5 with NaOH and mixed for 20 minutes at room temperature with a S/L ratio of approximately 1:10. Filter aid (Cellpure 300) was added at 10 g/L and the slurry was filtered by filter press, vacuum filtration, or centrifugation. The clarified filtrate was acid precipitated to pH 5.0 with 1 M acetic acid. The resulting solution was filtered as described above with the addition of 5 g/L filter aid (Cellpure 300). The material was neutralized immediately to pH 6.5 to 7.0 with 1M NaOH. The material was diafiltered (10 kDa regenerated cellulose for all UFDF steps) with 5 equal diavolumes of the same buffer used for extraction. The material was loaded on a pre equilibrated Q-sepharose column (GE Healthcare) to allow for 8 g albumin binding per liter of resin at 60 cmh.

After washing the column with 5 column volumes of the same buffer, the albumin was eluted by increasing the salt concentration to 250 mM NaCl in one step. The resulting material was diafiltered against 100 mM Sodium Phosphate, 10 mM NaCl, pH 7.0 with 5-7 equal diavolumes. The resulting material was passed over a Q-sepharose column equilibrated with the 100 mM Sodium Phosphate, 10 mM NaCl, pH 7.0, and collected as flow-through. The flow-through material was then concentrated and diafiltered against 20 mM sodium phosphate, 10 mM NaCl, pH 7.0 with 5 diavolumes. The final concentrated material was sterile filtered and incubated with 10 g/L of the detergent CHAPS ((3-Cholamidopropyl)dimethylammonio)-1-Propanesulfonic Acid) and mixed at room temperature for 1 hour. After the one hour incubation, the material was passed over a Biorad SM-2 column. The material was sterile filtered and freeze dried.

Size Exclusion Chromatography Analysis.

Purity analysis by HPLC was carried out in 100 mM phosphate, pH 7.0 on a GF-250 column (Agilent Technologies) at a flow rate of 1 ml/min with the detector set at 214 and 280 nm. A standard curve was developed by injecting 5 different dilutions made by dry powder with a correction factor of 0.92 for salt and moisture. The main peak from 214 nm was integrated either by retention time or alternatively baseline. The unknown sample was injected at a concentration that is within the range of the standard injections. The unknown concentration of albumin per dry powder weight (purity) was calculated from the standard curve. In a typical experiment, the 0, 5, 8, 10, 15, and 20 μg of the standard was injected followed by approximately 10 μg of unknown sample in approximately 50 μL injection volume. The correlation coefficient for the standard curve after integrating the peaks was typically above 0.98.

SDS PAGE and Densitometry: (Sodium Dodecyl Sulfate Polyacrylamide Gel Electrophoresis).

Samples were prepared by diluting the protein solutions to 1-2 mg/ml to enable a defined amount of each protein to be loaded on to each well. The sample was mixed 1:1 with Tris-Glycine SDS sample buffer (LC2673 Novex) containing reducing agent (Invitrogen NP0004) and heated to 70° C. for 5 minutes. The sample was loaded (10, 20, or 30 μg) onto a Novex 4-20% precast gel and separated at constant voltage (130V) in standard Tris-Glycine-SDS running buffer. The electrophoresis was ended when the tracking dye reached the end of the gel. A molecular weight marker was included in the first lane as a reference.

The gel was stained with G Bioscience (786-35G) and destained with water. A digital image was obtained with a Hewlett Packard Scanner (G4010). The image file was then opened with UN-SCAN-IT (Silk Scientific Corp.). The densitometry was carried out with positive image analysis in 256 grayscale in which all visible bands were included as individual segments. The background noise was corrected by four corner interpolation as specified in the software for each segment. The signal for each segment or band was then calculated from the product of the # of pixels and the average pixel intensity (0-255). The sum of the signals for an entire lane (all visible segments or bands) was taken as 100% and the impurity bands were subtracted to calculate the albumin purity. The percent of each contaminating protein in each band was calculated as the number of peptides identified for that contaminat protein as determined by peptide mapping divided by the total number of all peptides identified in a particular band. The image analysis was repeated 3 times such that the standard deviation is less than 0.5% out of 100%.

Determination of Endotoxin by the Pyrogene rFC Method.

Endotoxin content was determined by the Pyrogene rFC method. Lyophilized endotoxin standard was mixed with endotoxin free water as specified by the manufacturer (Lonza) to develop a standard curve. The protein samples were either diluted as is for liquid or alternatively, reconstituted with endotoxin free water for powder. Different dilutions were prepared such that the readings should appear within the range of the standard curve. The samples were heated to 100° C. for 10 minutes to dissociate unwanted molecular interactions. In a typical experiment, the sample and standard were added at 100 μl per well, with 0, 0.001, 0.005, 0.01, 0.05, and 0.1 endotoxin units per well. The samples were also added at 100 μl and extra samples were included such that spiking with 0.001-0.01 endotoxin units per well were added to test for assay inhibition or interference. The working reagent was prepared according to the manufacturer (Lonza) by mixing the rFC enzyme, assay buffer, and substrate in a 1:4:5 ratio, respectively. The working reagent was added to the wells at equal volume to the sample or standards. The fluorescence plate reader (Biotek FLX 800T) was set for excitation at 380 nm (bandwidth=20 nm) and the emission wavelength was set at 440 nm (bandwidth=30 nm). The reading taken at time zero is subtracted from the reading taken after 1 hour at 37° C. The readings were considered valid if the correlation coefficient, slope, and Y-intercept for the standards was within the set limits, and the spiking experiments show that the spiked endotoxin was measureable and recoverable within the set limits. In addition, the standard deviation for duplicate samples should be in reasonable agreement such that the standard deviation was within a specified arbitrarily chosen limit. All samples were collected aseptically and the tubes/vials/containers used for testing were verified to be extremely low endotoxin following good laboratory practices as they relate to accurate and precise endotoxin testing.

Determination of Cell Viability

The hybridoma cell line AE1 (ATCC) was maintained in DMEM/F12+ITSE basic media containing 1% fetal bovine serum (FBS). Albumin was tested in serum-free base medium composed of DMEM/F12+ITSE. Cells were seeded at a density of $0.5 \times 10^5$ viable cells/ml. The cells were grown under standard culture conditions (5% $CO_2$ and 37° C.) for approximately 70 hours after which the concentration of viable cells for the cultures was measured. The experiments were conducted in duplicate. The data shows the number of viable cells/ml multiplied by $10^5$.

Analysis of Purity by RP-HPLC

Cellastim was analyzed by RP-HPLC with an Agilent C8 column with I.D. of 4.6 mm. (SB-C8) The flow rate was 0.3 ml/min and the protein was injected into the system equilibrated in buffer A (distilled water, 0.1% TFA), and separated on a linear gradient from 0 to 60% B (99.9% acetonitrile, 0.1% TFA) over 60 minutes. The chromatogram and subsequent analysis (peak integration and retention times) were generated using software that came with the instrument (Shimadzu LC20 with diode array detection).

Analysis of Purity by Agilent 2100 Bioanalyzer

Purity was determined using an Agilent Protein 230 Assay protocol with an Agilent 2100 Bioanalyzer. The samples were loaded at 20 mg/ml according to the instructions given as part of the Protein 230 kit (Item # 5067-1517). The resulting data was analyzed with the instrument software 2100 expert and used to produce the electropherograms which present the band intensity as a function of molecular weight.

Determination of Detergent

The detergent concentration for the albumin was determined by a detergent (cell based) assay. Briefly, detergent sensitive cells were spiked with different amounts of detergent and the resulting cell viability cell determination used to generate a standard curve based on 16 independent data points from 32 1 ml cultures. The change in viability with respect to the change in detergent concentration was plotted and fitted with a logarithmic function. This equation was then used to calculate the unknown detergent concentrations in samples tested in the same cell based assay. The correlation coefficient for the standard curve for the data given was 0.9816. Typically detergent concentrations of greater than about 200 ppm per Cellastim dry weight, result in a 10 to 20% loss (significant) in average viable cell concentration for 4 different concentrations of albumin. By comparison in a 10% albumin solution, a similar level of toxic effects of detergent typically becomes apparent when the detergent concentration is above about 25 ppm to 50 ppm or 0.0025% to 0.005% (v/v).

Results & Discussion:

I Analysis by Agilent Bioanalyzer of plasma derived serum (Sigma Albumin), and recombinant HSA (Cellastim) produced using the process of Example 2 (Cellastim P0171) and the old process (Cellastime P0107).

The Agilent Bioanalyzer size exclusion profiles (FIGS. 1A, C & D) for the three types of albumin show that in terms of overall purity the different albumin preparations are generally similar. Specifically, the peaks at around 4.5 kDa and 240 kDa are the internal controls, while all three products contain a very small amount of an off main peak signal at about 10-12 kDa.

While the human serum derived albumin (Sigma Albumin) (FIG. 1A), contains a contaminant at around 17 kDa, the recombinant rice derived albumin using the new process (Cellastim P0171)(FIG. 1C) contains two protein contaminants of around 44 KDa and 55 kDa that occur in Cellastim made with the new process at significantly higher levels than when using the old process (Cellastim P0107)(FIG. 1B). These peaks are not completely resolved in the electropherograms, but can be seen as more clearly in the overlaid profiles of Cellastim P0171 and Sigma albumin (FIG. 1D) and Cellastim made using the old and new processes shown in FIG. 1E. FIGS. 1F and 1G verify that the purity of Cellastim is high, measuring more than 97% pure by SEC-HPLC (FIG. 1F) with greater than 94% albumin, and with 80.7% purity for the monomer (n=3) by RP-HPLC (FIG. 1G).

The proteins corresponding to these minor peaks represent about 5% of all of the contaminant proteins present within the main albumin peak in Cellastim produced using the process described in Example 2. The major contaiminating proteins present were identified by Peptide Mass Fingerprinting analysis as discussed further below.

All albumin products tested also contained a peak at around 130 kDa that most likely represents albumin dimers, it is noticeable that the Cellastim dimer peak is significantly smaller than the plasma derived albumin. The creation of aggregated albumin is an indicator of protein degradation which is used as one marker for degradation or loss of stability industry wide. It is likely that the Hsps present in Cellastim promote the disaggregation of the albumin, therefore reducing the number of dimers, since it is a commonly known function of Hsp 70 and other Hsp proteins.

RP-HPLC shows that the average dimer content for 3 lots of Cellastim was 0.6% of the total protein (FIG. 1G). There were at least eight peaks identified by RP-HPLC and these are shown in FIG. 1G. The 4 largest peaks were identified and associated with the 67 kDa Rt=36.0, the 55 kDa Rt=44.9, the 44 kDa Rt=42.3, and the dimer at 46.2 minutes.

II. Analysis by SDS PAGE of Cellastim batch P0171 (New process) compared to albumin produced by Millipore/Novozymes (Cat No. 9301-01).

Figure 2:
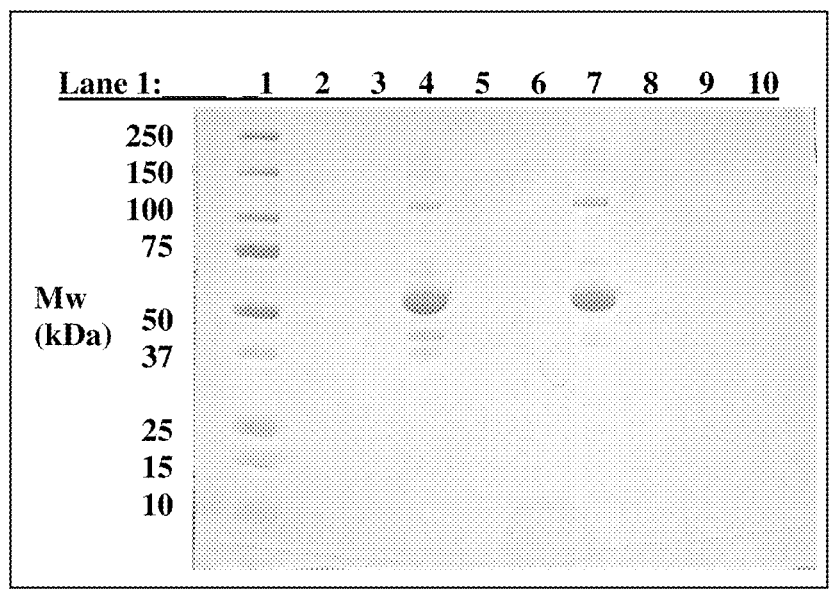
FIG. 2A shows a comparison of Cellastim P0171 and Cellprime albumin (Millipore/Novozymes). Lane 1 is the molecular weight marker. Lane 4 is the Cellastim albumin (10 µg) and Lane 7 is the Cellprime albumin (10 µg).
FIG. 2B shows a comparison by SDS PAGE analysis of three Cellastim lots from the previous process (B000) (Lane 2, 3, and 4), and the new Cellastim Process (B0000C) (Lane 6, 7, and 8). The six samples were loaded at 20 µg per lane.
Figure 2:
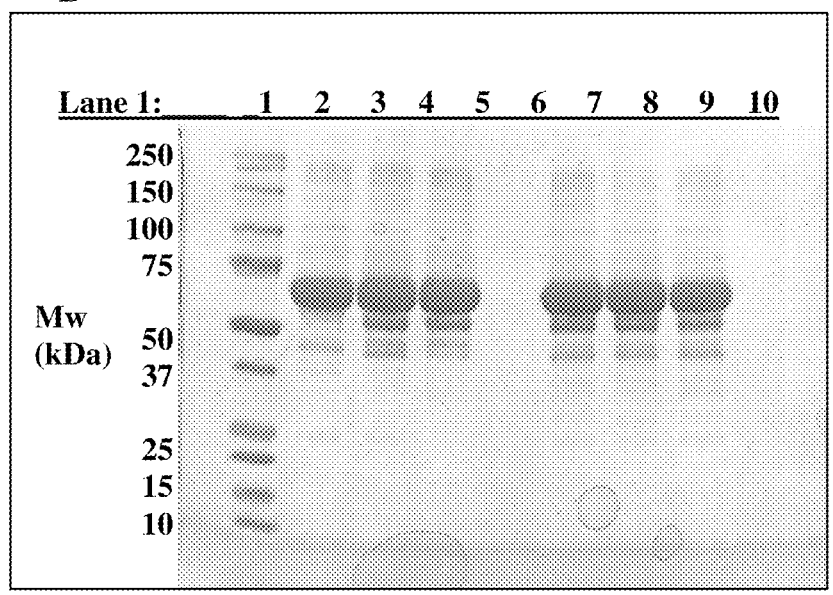

Results: SDS-PAGE analysis (FIGS. 2A & B) shows that in terms of overall purity the products are generally similar. FIG. 2A shows a comparison of Cellastim P0171 and Cellprime albumin (Millipore/Novozymes). Lane 1 is the molecular weight marker. Lane 4 is the Cellastim albumin (10 µg) and Lane 7 is the Cellprime albumin (10 µg). FIG. 2B shows a comparison by SDS PAGE analysis of three Cellastim lots from the previous process (B000) (Lane 2, 3, and 4), and the new Cellastim Process (B0000C) (Lane 6, 7, and 8). The six samples were loaded at 20 µg per lane.

Visual inspection of the gel shows that the new process which meets more rigorous specifications is more consistent among the 3 lots tested. (FIG. 2B, lane 2, 3, 4 vs. lane 6, 7, 8). The banding pattern is significantly different among the three samples from the previous process as compared to the new process. Importantly, the new process samples have significantly less aggregates at around 250 KDa than the old process samples have. (Average greater than 2% for the old process, and average less than 1% for the new process). The identity of the protein contaminates was that are enriched in Cellastim produced using the new process is discussed further below.

III. Analysis of endotoxin, detergent and growth promoting abilities of old and new batches of Cellastim. A comparison of the performance of the two different processes for preparing several different lots of albumin (Tables E1 and E2) demonstrates that the old process produced recombinant albumin that contained significantly more endotoxin, and detergent compared to the new process described in Example 2, and resulted in a product that significantly enhanced cell viability.

TABLE E1

| Cellastim - Old Process B000 | | | | | | | | |
|---|---|---|---|---|---|---|---|---|
| Production Date | Batch Number | Grams product | EU/mg Dry Material | Detergent (ppm) | Viability (number of viable cells/ml/$10^5$) | | | |
| | | | | | 1 mg/ml | 2 mg/ml | 5 mg/ml | 10/mg ml |
| Feb. 27, 2008 | B202 | 70.6 | 25.3 | 3313 | 15 | 7.9 | 4.1 | 0.9 |
| Feb. 27, 2008 | B203 | 58.8 | 23.1 | 946 | 15.8 | 12.4 | 6.5 | 4.1 |
| Feb. 28, 2008 | B204 | 59.9 | 29.2 | 1371 | 16.3 | 11.1 | 5.2 | 2.9 |
| Feb. 28, 2008 | B205 | 63 | 64.3 | 1250 | 14 | 11.6 | 6.9 | 3.8 |
| Mar. 3, 2008 | B206 | 41.1 | 35.1 | 11602 | 14.9 | 2.3 | 0.0 | 0.0 |

TABLE E1-continued

Cellastim - Old Process B000

| Production Date | Batch Number | Grams product | EU/mg Dry Material | Detergent (ppm) | Viability (number of viable cells/ml/$10^5$) | | | |
|---|---|---|---|---|---|---|---|---|
| | | | | | 1 mg/ml | 2 mg/ml | 5 mg/ml | 10/mg ml |
| Mar. 3, 2008 | B207 | 94.2 | 28.7 | 750 | 16.5 | 12.7 | 7.6 | 4 |
| Mar. 4, 2008 | B208 | 24.5 | >80 | 1250 | 15.3 | 11.4 | 7.1 | 2.7 |
| Mar. 4, 2008 | B209 | 66.1 | 91.8 | 595 | 16.7 | 15.2 | 6.9 | 4.1 |
| Mar. 4, 2008 | B210 | 87.3 | 67.8 | 77 | 17.5 | 19.1 | 15.4 | 8.5 |
| Mar. 11, 2008 | B217 | 62.09 | 4.4 | 430.5 | 16.7 | 18.7 | 13.2 | 6.6 |
| Averages | | | 44.97 | 2158.5 | 15.87 | 12.24 | 7.29 | 3.76 |

TABLE E2

Cellastim - New Process B0000C

| Production Date | Batch Number | Grams product | EU/mg Dry Material | Detergent (ppm) | Viability (number of viable cells/ml/$10^5$) | | | |
|---|---|---|---|---|---|---|---|---|
| | | | | | 0.5 mg/ml | 2 mg/ml | 5 mg/ml | 10/mg ml |
| Feb. 2, 2009 | B0032C | 209.4 | 0.35 | 170 | 13.1 | 15.7 | 13.4 | 11.2 |
| Feb. 2, 2009 | B0033C | 271.4 | 0.26 | not det. | 18.4 | 17.4 | 15.1 | 14.3 |
| Feb. 10, 2009 | B0041C | 247.1 | 0.18 | 93 | 15.4 | 17.2 | 14.1 | 12.1 |
| Apr. 27, 2009 | B0118C | 617.4 | 0.11 | not det. | 15.7 | 15.4 | 19.2 | 16.8 |
| May 14, 2009 | B0138C | 610.6 | 0.48 | 102 | 12.5 | 15.8 | 15.1 | 14.6 |
| Jun. 9, 2009 | B0158C | 598.0 | 0.13 | 141 | 13.7 | 17.1 | 13.2 | 11 |
| Jun. 15, 2009 | B0162C | 618.6 | 0.20 | not det. | 15.5 | 17.5 | 17.2 | 14.7 |
| Jul. 28, 2009 | B0196C | 507.0 | 0.36 | not det. | 17.4 | 17.3 | 18.8 | 14.8 |
| Aug. 26, 2009 | B0219C | 851.4 | 0.86 | not det. | 17.9 | 16.3 | 16.6 | 13.7 |
| Aug. 31, 2009 | B0220C | 897.8 | 0.93 | 77 | 13.5 | 16 | 15.5 | 15.1 |
| Sep. 9, 2009 | B0227C | 929.9 | 0.13 | 270 | 11.1 | 14.4 | 12.5 | 11.4 |
| Averages | | | 0.36 | 142.2 | 14.92 | 16.37 | 15.52 | 13.6 |

Discussion: Re-engineering the old process to create the new process described in Example 2 resulted in significant changes in both overall product purity, and performance, as described more fully below.

The changes made it possible to make products that were lower in detergent, lower in endotoxin, and increased purity. Specifically, the new process routinely produced recombinant albumin with an overally purity of greater than about 95%. By comparison the old method routinely produced albumin with a maximum purity of about 90%. Surprisingly, despite the increased product purity, these changes in processing also resulted in enhanced co-purification of heat shock proteins, (see below) with the recombinant albumin. Without being bound by any particular theory of operation, it is believed that the combination of high albumin purity, relative lack of endotoxin and/or detergent, and co-purification of heat shock proteins results in a product that significantly out performs previous methods for preparing albumin.

Specifically Tables E1 and E2 demonstrate that the new process for producing Cellastim results in a product that, for example at 5 mg/ml, results in an average batch to batch 100 percent improvement in cell viability (at 5 mg/ml), and also results in a product with an average 100-fold less endotoxin, and more than 10 fold less detergent than the old process.

Example 4

Analysis of the Effects on Cell Growth and Viability

To compare the cell growth promoting abilities of the supplements of the invention, to other commercially available albumin products, the different sources of albumin they were compared side by side in a cell growth and viability assay. The three products tested were (Cellastim, Lot # P0153) Cellprime albumin (Millipore/Novozymes Cat No. #9301-01), and plasma derived albumin (Seracare Cat No. #1 S-400-60 F.

Figure 3:
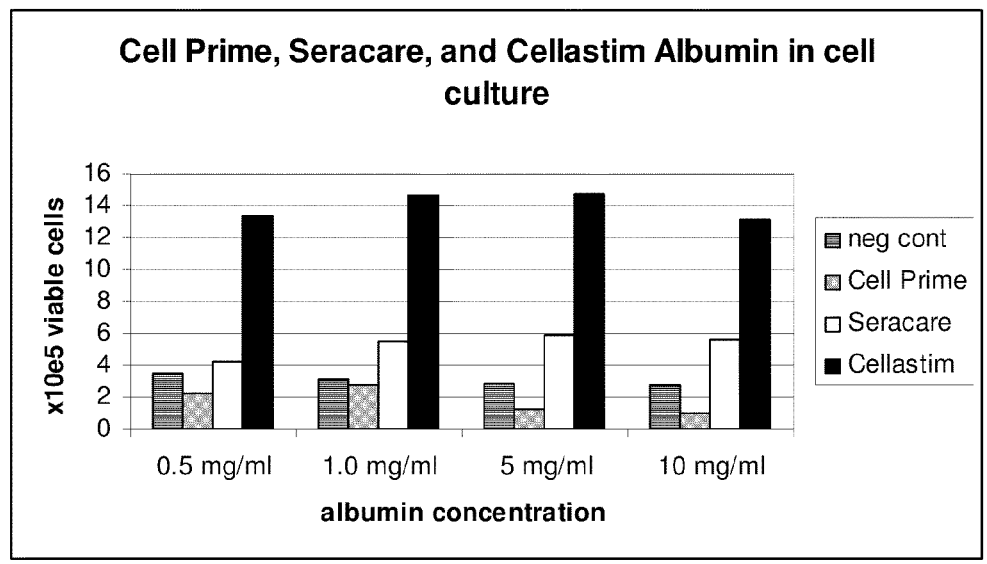
FIG. 3: Shows a comparison of the effects of yeast recombinant (Cellprime), human derived, (Seracare) and plant recombinant albumin (Cellastim P0171) with respect to cell growth and viability.
Figure 3:
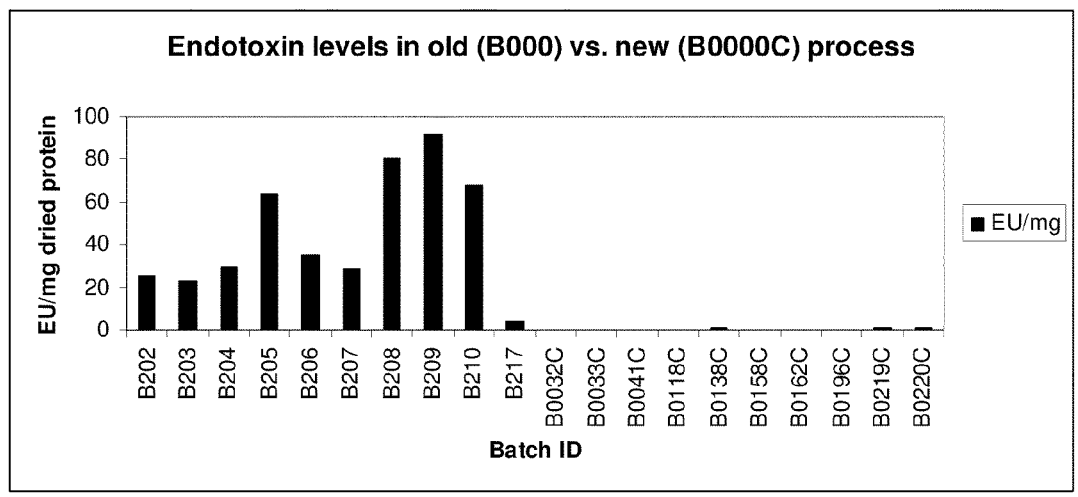
Figure 3:
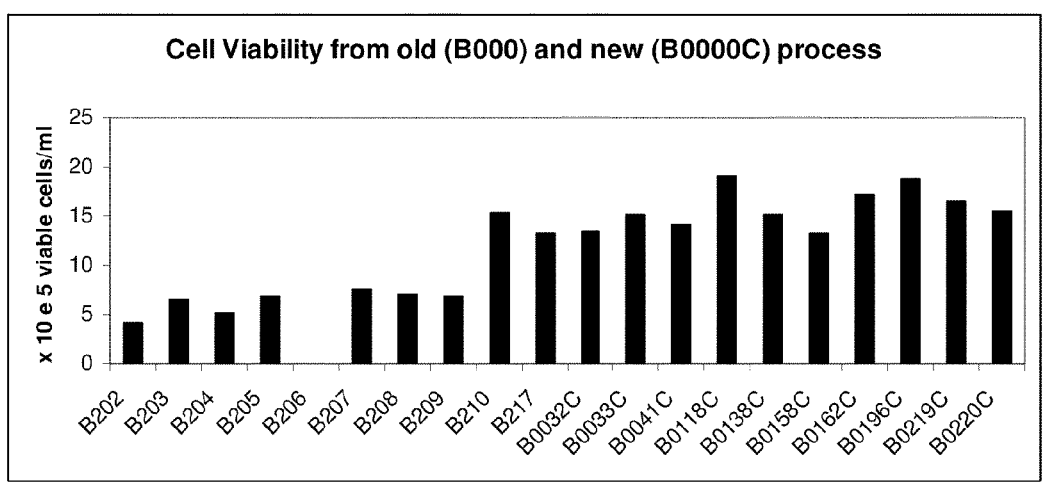

Methods: Hybridoma cells AE1 were seeded in serum-free base medium composed of DMEM/F12+ITSE at a density of $0.5 \times 10^5$ cells per ml of media after washing twice with same media to remove residual media. The media and cells were then left untreated (negative control), treated with Seracare albumin, treated with Cellprime albumin, and treated with Cellastim at the concentrations shown in the figure legend. The cells were grown under standard culture conditions (5% $CO_2$ and 37° C.) for approximately 70 hours after which the concentration of viable cells for the cultures was measured. The experiments were conducted in duplicate. Results are shown in FIG. 3.

Results: Novazyme's Cellprime caused a loss in viable cell concentration (cross-hatch bars). Seracare albumin (white bars) caused a measureable increase in viable cell concentration but not as large an increase as is seen with the supplement of the invention comprising recombinant albumin with rice hsps (black bars). Under these conditions Cellastim was approximately 5 times as active in promoting the number of viable cells compared to any of the other albumin products, at any concentration tested. The negative control is represented by the striped bars.

Discussion: Given the possibility that the other commercially available albumin products may have similar overall purity, endotoxin and detergent levels to Cellastim, the dramatically superior performance of the recombinant albumin of the invention compared to other commercially available albumins suggests that the previously un-identified protein contaminants identified in Cellastim compared to the serum derived albumin (Example 2) could be having a positive impact on cell viability and the concentration of viable cells. To identify and then characterize the impact of these proteins on the properties of Cellastim, a sample of the recombinant albumin was subjected to peptide mass finger printing, as described below.

Example 5

Peptide Mass Finger Printing of Recombinant Human Serum Albumin

Methods: Samples of albumin were analyzed to determine significant protein contaminants using a NanoLCMS/MS peptide sequencing system (ProtTech, Inc.), and proprietary software to identify the proteins based on the molecular weight of the peptide fragments. In brief, samples of albumin were analyzed by SDS-PAGE, and each major band gel band was destained, cleaned, and digested in-gel with sequencing grade modified trypsin. The resulting peptide mixture was analyzed by a LC-MS/MS system, in which a high pressure liquid chromatography (HPLC) with a 75 micrometer inner diameter reverse phase C18 column was used in-line coupled with an ion trap mass spectrometer. The mass spectrometric data acquired was used to search the most recent non-redundant protein database with ProtTech's proprietary software suite. The output from the database search was manually validated before reporting.

Results: Upon testing of three representative lots of recombinant albumin, three Hsp70 proteins were identified by Peptide Mass Fingerprinting (Table E3). The three specific sequences identified: ABF95267, ABA97211, and BAD 07938 were compared to the non redundant database to identify highly related and homologous proteins. The results of the top hits from each of these comparisons is shown in Tables E4, E5 and E6

TABLE E3

| Peptides identified from Cellastim by mass finger printing | |
|---|---|
| Sequence | Peptide |
| ABF95267 | ATAGDTHLGGEDFDNRVVPGPADKSPMIVVTYKGEEK NAVITVPAYFN DSQRIINEPTAAAIAYGLDKK (SEQ. ID. NO. 19) |
| AAB63469 BAD07938 BAD07713 | NQAAVNPER NGHVEIIANDQGNRIVNKDGKPYIQVK IINEPTAAAIAYGLDKK KLGTVIGIDLGTTYSCVGVYK VEIESLFDGTDSFSEPLTR (SEQ. ID. NO. 20) |
| ABA97211 | NQADSVVYQTEK KQDITITGASTLPKDEVERDVVLLDVTPLSLSLGLET LGGVMTK (SEQ. ID. NO. 21) |

Results of sequence comparisons to ABF95267 sequences in the non redundant database of protein sequences in GenBank® (Nucleic Acids Research, (2008) 36 (Database issue): D25-30) are shown in Table E4 below.

TABLE E4

| Sequences producing significant alignments with ABF95267: | | | |
|---|---|---|---|
| Gene Refs | Gene description | (Bits) | Value |
| ref|NP_001140835.1| | hypothetical protein LOC100272911 [*Zea ma* . . . | 79.7 | 8e-14 |
| ref|XP_002465468.1| | hypothetical protein SORBIDRAFT_01g039390 . . . | 79.7 | 9e-14 |
| ref|NP_001049719.1| | Os03g0277300 [*Oryza sativa (japonica* cult . . . | 79.7 | 9e-14 |
| gb|ACJ54890.1| | heat shock protein 70 [*Oryza sativa Japonica* G . . . | 79.7 | 9e-14 |
| sp|P09189.1| | HSP7C_PETHY RecName: Full = Heat shock cognate 70 k . . . | 77.0 | 5e-13 |
| emb|CAA31663.1| | hsp70 (AA 6-651) [*Petunia x hybrida*] | 77.0 | 5e-13 |
| ref|XP_002312089.1| | predicted protein [*Populus trichocarpa*] > . . . | 77.0 | 5e-13 |
| sp|P24629.1| | HSP71_SOLLC RecName: Full = Heat shock cognate 70 k . . . | 77.0 | 5e-13 |
| gb|AAB99745.1| | HSP70 [*Triticum aestivum*] | 76.6 | 6e-13 |
| gb|AAB42159.1| | Hsc70 [*Lycopersicon esculentum*] | 76.6 | 7e-13 |
| gb|ACD45076.1| | heat-shock protein 70 [*Dactylis glomerata*] | 76.3 | 8e-13 |
| ref|XP_002512741.1| | heat shock protein, putative [*Ricinus* com . . . | 75.9 | 1e-12 |
| ref|XP_002512742.1| | heat shock protein, putative [*Ricinus* com . . . | 75.9 | 1e-12 |
| gb|AAA82975.1| | PsHSP71.2 >emb|CAA67867.1| heat shock protein . . . | 75.9 | 1e-12 |
| gb|AAS09825.1| | heat shock cognate protein 70 [*Thellungiella* h . . . | 75.9 | 1e-12 |
| emb|CAA44820.1| | heat shock protein 70 [*Nicotiana tabacum*] | 75.5 | 2e-12 |
| ref|NP_001055754.1| | Os05g0460000 [*Oryza sativa (japonica* cult . . . | 75.5 | 2e-12 |
| ref|NP_001051724.1| | Os03g0821100 [*Oryza sativa (japonica* cult . . . | 75.1 | 2e-12 |
| ref|XP_002456611.1| | hypothetical protein SORBIDRAFT_03g039360 . . . | 75.1 | 2e-12 |
| ref|NP_001044757.1| | Os01g0840100 [*Oryza sativa (japonica* cult . . . | 75.1 | 2e-12 |
| gb|ACR35910.1| | unknown [*Zea mays*] | 75.1 | 2e-12 |
| ref|XP_002284017.1| | PREDICTED: similar to HSC70-1 (heat shock . . . | 75.1 | 2e-12 |
| ref|XP_002532297.1| | heat shock protein, putative [*Ricinus* com . . . | 75.1 | 2e-12 |
| ref|XP_002284008.1| | PREDICTED: similar to HSC70-1 (heat shock . . . | 75.1 | 2e-12 |
| ref|XP_002283532.1| | PREDICTED: similar to HSC70-1 (heat shock . . . | 74.7 | 3e-12 |
| ref|XP_002332067.1| | predicted protein [*Populus trichocarpa*] | 74.7 | 3e-12 |
| gb|AAF34134.1| | high molecular weight heat shock protein [Malu . . . | 74.7 | 3e-12 |
| gb|EEC76425.1| | hypothetical protein OsI_14101 [*Oryza sativa* I . . . | 74.7 | 3e-12 |
| ref|XP_002316294.1| | predicted protein [*Populus trichocarpa*] > . . . | 74.7 | 3e-12 |
| ref|XP_002283516.1| | PREDICTED: similar to HSC70-1 (heat shock . . . | 74.3 | 3e-12 |
| ref|XP_002441219.1| | hypothetical protein SORBIDRAFT_09g022580 . . . | 74.3 | 4e-12 |

Results of sequence comparisons of ABB63469 to sequences in the non redundant database of protein sequences in GenBank® are shown in Table E5 below.

TABLE E5

Sequences producing significant alignments with AAB63469:

| Gene Refs | Gene description | (Bits) | Value |
|---|---|---|---|
| emb\|CAP31983.1\| | C. briggsae CBR-HSP-4 protein [Caenorhabditis . . . | 50.1 | 7e-05 |
| dbj\|BAG60366.1\| | unnamed protein product [Homo sapiens] | 49.7 | 8e-05 |
| ref\|YP_002421952.1\| | chaperone protein DnaK [Methylobacterium . . . | 49.7 | 9e-05 |
| ref\|YP_001640420.1\| | chaperone protein DnaK [Methylobacterium . . . | 49.7 | 9e-05 |
| ref\|NP_001105893.1\| | Binding protein homolog1 precursor [Zea m . . . | 49.3 | 1e-04 |
| gb\|AAA62325.1\| | HSP70 | 49.3 | 1e-04 |
| ref\|YP_001756576.1\| | chaperone protein DnaK [Methylobacterium . . . | 49.3 | 1e-04 |
| gb\|AAB63469.1\| | endosperm lumenal binding protein [Oryza sativa] | 49.3 | 1e-04 |
| ref\|YP_001925829.1\| | chaperone protein DnaK [Methylobacterium . . . | 49.3 | 1e-04 |
| ref\|NP_001105894.1\| | Binding protein homolog2 precursor [Zea m . . . | 49.3 | 1e-04 |
| gb\|ACF86491.1\| | unknown [Zea mays] | 49.3 | 1e-04 |
| ref\|NP_001045675.1\| | Os02g0115900 [Oryza sativa (japonica cult . . . | 49.3 | 1e-04 |
| ref\|ZP_02191025.1\| | Molecular chaperone [alpha proteobacterium . . . | 49.3 | 1e-04 |
| ref\|XP_001701685.1\| | binding protein 1 [Chlamydomonas reinhard . . . | 48.5 | 2e-04 |
| ref\|XP_001701884.1\| | binding protein 2 [Chlamydomonas reinhard . . . | 48.5 | 2e-04 |
| emb\|CAC37635.1\| | luminal binding protein, BiP [Scherffelia dubia] | 48.1 | 3e-04 |
| gb\|AAM93256.1\| | heat shock protein 70-C [Heterodera glycines] . . . | 48.1 | 3e-04 |

Results of sequence comparisons of sequence ABA97211 to sequences in the non redundant database of protein sequences in GENBANK® are shown in Table E6 below.

TABLE E6

Sequences producing significant alignments with ABA97211

| Gene Refs | Gene description | (Bits) | Value |
|---|---|---|---|
| gb\|AAK13022.1\| | heat shock protein 70 [Fibrobacter succinogene . . . | 44.3 | 0.004 |
| ref\|XP_002442079.1\| | hypothetical protein SORBIDRAFT_08g009580 . . . | 44.3 | 0.004 |
| gb\|EEC69073.1\| | hypothetical protein OsI_37938 [Oryza sativa I . . . | 44.3 | 0.004 |
| ref\|XP_001752769.1\| | predicted protein [Physcomitrella patens . . . | 44.3 | 0.004 |
| ref\|NP_001066486.1\| | Os12g0244100 [Oryza sativa (japonica cult . . . | 44.3 | 0.004 |
| gb\|ACT65562.1\| | 70 kDa heat shock protein [Triticum aestivum] | 43.9 | 0.005 |
| ref\|NP_001152528.1\| | stromal 70 kDa heat shock-related protein . . . | 43.9 | 0.005 |
| gb\|ACN31310.1\| | unknown [Zea mays] | 43.9 | 0.005 |
| ref\|XP_001772650.1\| | predicted protein [Physcomitrella patens . . . | 43.9 | 0.005 |
| ref\|NP_001146752.1\| | hypothetical protein LOC100280354 [Zea ma . . . | 43.9 | 0.005 |
| gb\|ABP65327.1\| | chloroplast heat shock protein 70 [Pennisetum . . . | 43.9 | 0.005 |
| gb\|AAO72585.1\| | heat shock-related protein [Oryza sativa (japo . . . | 43.5 | 0.007 |
| ref\|YP_001740846.1\| | Chaperone protein dnaK (Heat shock protei . . . | 43.5 | 0.008 |
| ref\|ZP_03728467.1\| | chaperone protein DnaK [Dethiobacter alkal . . . | 43.1 | 0.009 |

Discussion: Peptide Mass Fingerprinting identified 3 rice heat shock protein super family members that co-purify with albumin, 2 Rice HSP70 genes, (gb|ACJ54890.1|), EEC69073, and AAB63469—a BiP homolog from rice endosperm tissue (endosperm lumenal binding protein). The complete amino acid sequences coded by these genes are listed below:

Gene gb|ACJ54890.1| (NP_001045675.1) heat shock protein 70 [Oryza sativa Japonica Group] HSP70 was found to occur in recombinant albumin in Cellastim at approximately 0.07% wt/wt. Its complete amino acid coding sequence is provided below:

```
                                                  (SEQ. ID. NO. 7)
  1 magnkgegpa igidlgttys cvgvwqhdry eiiandqgnr ttpsyvaftd terligdaak 61 nqvamnptnt vfdakrligr rfsdpsvqad mkmwpfkvvp gpadkpmivv tykgeekkfs 121 aeeissmvlt kmkeiaeafl sttiknavit vpayfndsqr qatkdagvis glnvmriine 181 ptaaaiaygl dkkaastgek nvlifdlggg tfdvsiltie egifevkata gdthlggedf 241 dnrmvnhfvq efkrkhkkdi tgnpralrrl rtacerakrt lsstaqttie ieslyegidf 301 yatitrarfe elnmdlfrrc mepvekclrd akmdkaqihd vvlvggstri pkvqqllqdf 361 fngkelcksi npdeavayga avqaailsge gnqrvqdlll ldvtplslgl etaggvmtvl
```

-continued

```
421 iprnttiptk keqvfstysd nqpgvliqvy egertrtkdn nllgkfeltg ippaprgvpq 481 invtfdidan gilnvsaedk ttgkknkiti tndkgrlske eiermvqeae kykaedeqvr 541 hkvearnale nyaynmrntv rdekiasklp addkkkieda iedaikwldg nqlaeadefe 601 dkmkeleslc npiiskmyqg gaggpagmde dapngsagtg ggsgagpkie evd
```

AAB63469 BiP homolog from rice endosperm tissue (endosperm lumenal binding protein [*Oryza sativa*]) BiP was found to occur in recombinant albumin in Cellastim at about 0.09% wt/wt. Its complete amino acid coding sequence is provided below:

```
                                                   (SEQ. ID. NO. 18)
  1 mdrvrgsafl lgvllagslf afsvakeetk klgtvigidl gttyscvgvy knghveiian 61 dqgnritpsw vaftdserli geaaknqaav npertifdvk rdigrkfeek evqrdmklvp 121 ykivnkigkp yiqvkikdge nkvfspeevs amilgkmket aeaylgkkin davvtvpayf 181 ndaqrqatkd agviaglnva riineptaaa iaygldkkgg eknilvfdlg ggtfdvsilt 241 idngvfevla tngdthlgge dfdqrimeyf iklikkkysk diskdnralg klrreaerak 301 ralsnqhqvr veieslfdgt dfsepltrar feelnndlfr ktmgpvkkam ddagleksqi 361 heivlvggst ripkvqqllr dyfegkepnk gvnpdeavay gaavqgsils geggdetkdi 421 llldvapltl gietvggvmt kliprntvip tkksqvftty qdqqttvsiq vfegersmtk 481 dcrllgkfdl sgipaaprgt pqievtfevd angilnvkae dkgtgkseki titnekgrls 541 qeeidrmvre aeefaeedkk vkeridarnq letyvynmkn tvgdkdklad kleseekekv 601 eealkealew ldenqtaeke eyeeklkeve avcnpiisav yqrtggapgg rrrgrlddeh 661 del
```

EEC69073/OsI_37938 [*Oryza sativa* Indica Group] The stromal HSP70 was found to occur in recombinant albumin in Cellastim at about 0.06% wt/wt. Its complete amino acid coding sequence is provided below:

```
                                                   (SEQ. ID. NO. 22)
  1 masftsqlga macgaapsts plaarrsgql fvgrkpaaas vqmrvpragr argvamrvac 61 ekvvgidlgt tnsavaameg gkptvitnae gqrttpsvva ytkggerlvg qiakrqavvn 121 pentffsvkr figrkmaevd deakqvsyhv vrddngnvkl dcpaigkqfa aeeisaqvlr 181 klvddaskfl ndkitkavvt vpayfndsqr tatkdagria glevlriine ptaaslaygf 241 ekknnetilv fdlgggtfdv svlevgdgvf evlstsgdth lggddfdkfy fcwvfyfgam 301 thetpkvvdw lasnfkkdeg idllkdkqal qrlteaaeka kmelstlsqt nislpfitat 361 adgpkhiett lsrakfeelc sdlidrlktp vtnalrdakl svdnldevil vggstripsv 421 qelvkkitgk dpnvtvnpde vvslgaavqg gvlagdvkdv vlldvtplsl gletlggvmt 481 kiiprnttlp tsksevfsta adgqtsvein vlqgerefvr dnkslgsfrl dgippaprgv 541 pqievkfdid angilsvaai dkgtgkkqdi titgastlpk devermveea dkfaqedkek 601 rdaidtknqa dsvvyqtekq lkelgdkvpa pvkekvdakl nelkeaiagg stqsmkdama 661 alneevmqig qamynqqpna gaagptpgad agptssggkg pndgdvidad ftdsn
```

Because these proteins only occur at low levels in the new batches of Cellastim relative to albumin, a pre-requisite for confirming that these contaminants are actually responsible for the superior growth promoting effects of the new batches of Cellastim is to determine whether the addition back of these components to albumin restores or enhances the growth promoting activities of the albumin at levels which are comparable to those actually identified for each component in Cellastim. It seems clear that other similar sequences also exist in the data bases which are substantially similar to or substantially identical to the three proteins given previously such as CAA47948, ABF95267, and NP_001049719.

Example 6

Separation of Heat Shock Proteins from Recombinant Albumin by Affinity Chromatography Methods: Cellastim produced using the new process [Lots P0153, P0156, and or P0171] powder was mixed with purified water at approximately 20 g/L. The resulting solution was diafiltered against 50 mM Tris/Cl, pH 7.0 with at least 5 equal volumes of buffer. The resulting solution was passed over an ATP agarose column and the resulting flow through was labeled as fraction A. The column was washed with 5 column volumes of the equilibration buffer and the material bound to the ATP-agarose was eluted with 50 mM Tris/Cl, 1M KCl, pH7.0. The eluted material was labeled as fraction B. The wash was kept as fraction C. Fraction A was directly concentrated to 100 g/L and diafiltered with d-PBS. Fraction B was concentrated significantly, up to 20 fold or 100 fold in 50 mM Tris/Cl for further analysis. The wash fraction C was kept for further reference.

For Western blotting, 10 µg of each protein fraction (by A280, where the e.c. (extinction coefficient) of albumin is 0.53 cm$^2$/mg and e.c. of Hsp70 is 0.41 cm$^2$/mg) were loaded on a 4-20% SDS PAGE gel in 2×SDS loading buffer. The samples were heated to 80° C. for approximately 5 minutes before loading. The separation was done at 200V (constant voltage) and ran for approximately 90 minutes. The resulting gel was rinsed in water for 30 minutes to 2 hours and then the proteins were transferred to a Nitrocellulose membrane at 30 mA (constant current) for 2 hours. The resulting blot contained the molecular weight marker proteins as a transfer control and was then blocked in 5% (w/v) milk powder in water. The primary monoclonal antibody (a mouse anti-bovine Hsp70(Sigma/Aldrich #H5147)) was added in 5% milk solution to the blot (1:2500) and the blot was incubated on a rocker with gentle rocking overnight at 4° C. The blot was then washed 4 times for 10 minutes each in TDN and the secondary antibody (Pierce anti-mouse HRP conjugated) in 5% milk solution which was added at a dilution of 1:2500. After incubation at 4° C. for 2 to 3 hours, the blot was washed 4 times with TDN for 10 minutes each. The resulting blot was then incubated with pico (Pierce) chemiluminescent substrate for 5 minutes. Kodak photographic film was exposed to the blot in a dark room and the subsequent film was developed, rinsed, fixed, rinsed, and dried. To determine accurate transfer of the molecular weight marker position onto the film, a light emitting label was used.

To determine the approximate enzyme activity of fraction B, affinity purified and concentrated Hsp70 from Cellastim was buffer exchanged using Pall spin filters with a molecular cutoff of 10,000 Daltons to remove residual phosphate. The final dialysate was used as a reference buffer and the signal for the buffer was subtracted from the sample signal. ATPase activity was determined using the BioVision inorganic phosphate quantitative assay after the 30 minute enzymatic reaction in 50 mM Tris/Cl, pH 7.5, 10 mM MgC$_2$, and 0.05 mM ATP at 37° C. The approximate concentration of the affinity purified Hsp70 samples were 10 mg/ml (estimated by the absorbance at A280 and the purity by SDS PAGE) and the reaction volumes were 1 mL. The sample activity was determined by using a standard curve generated according to the manufacturer's directions with 5, 10, 15, and 20 nmol/ml phosphate standards. The sample absorbance at 660 was corrected for background signal by subtracting the signal of the final dialysate from the sample signal. The signal for the 10,000 Dalton final dialysate is given in FIG. 4C for reference.

Peptide Mass Fingerprinting of ATP-agarose affinity purified Hsp70 protein The Peptide Mass Fingerprinting of the Hsp70 enriched fraction was conducted similarly to the that described for Cellastim above. In this case, eight separate bands were subjected to Trypsin digestion, followed by LC-MS and standard database matching and scoring of the peptide masses.

Figure 4:
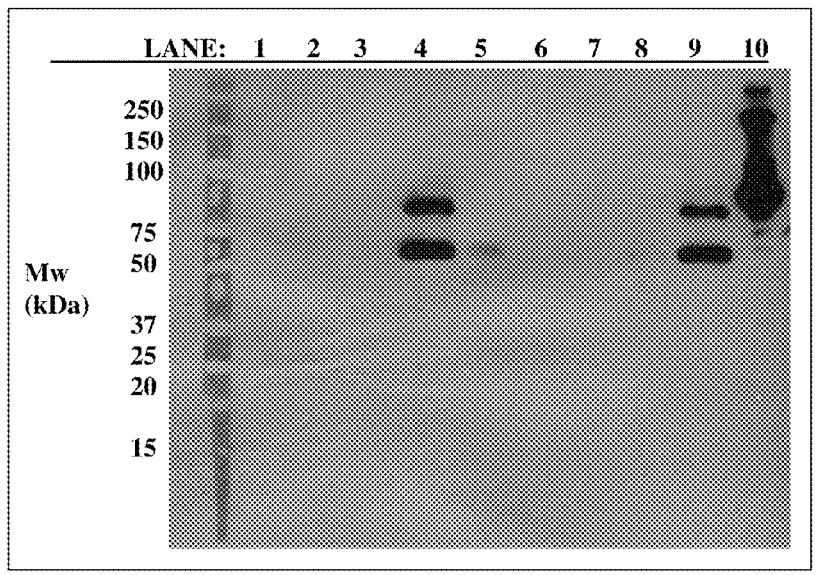
FIG. 4.
Figure 4:
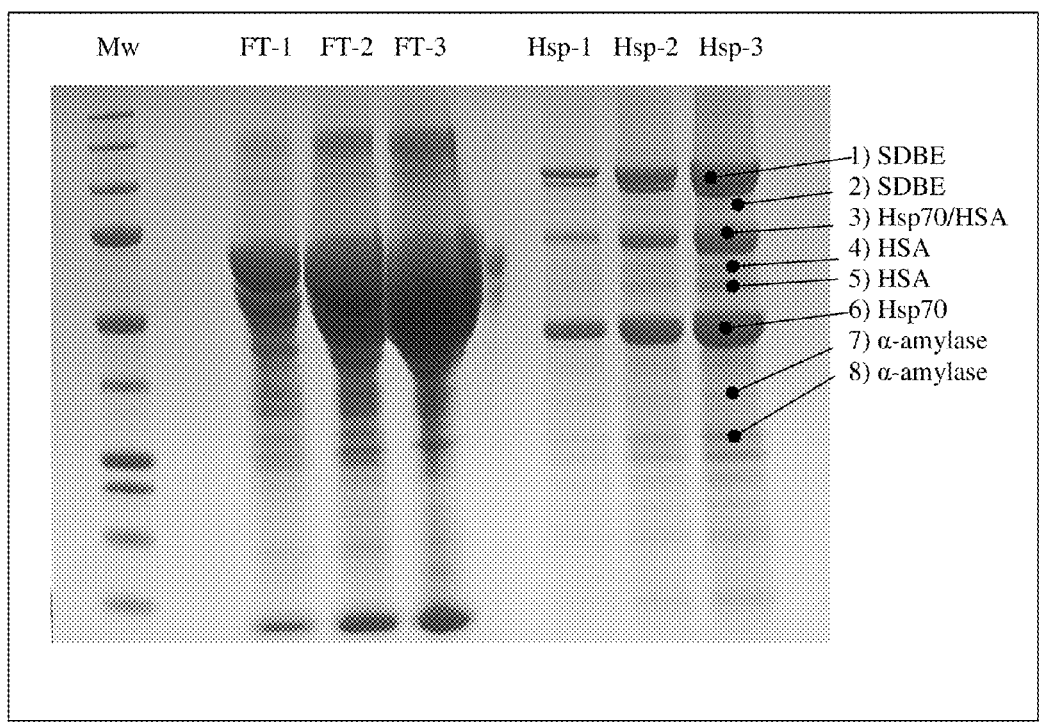
Figure 4:
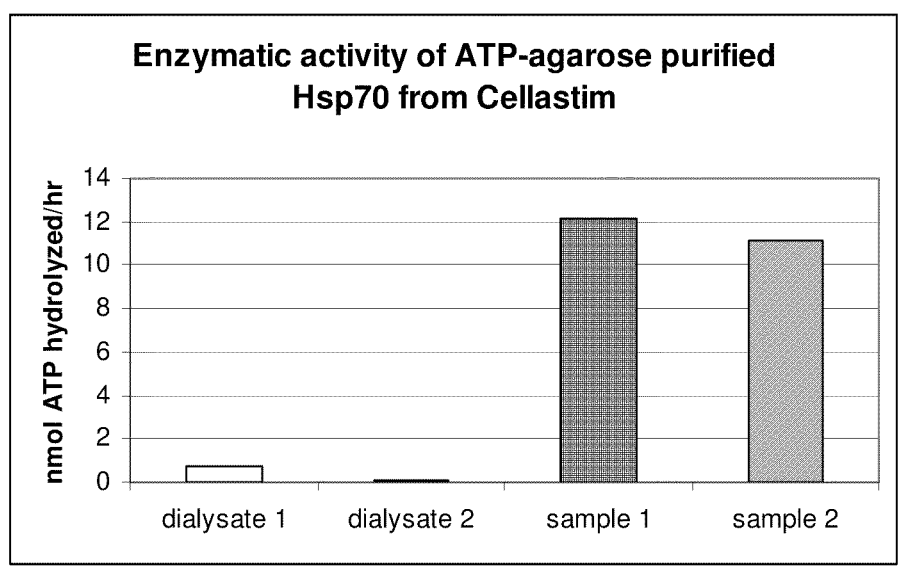

Results: The results are shown in FIG. 4A. The Western blot pictured shows that the separation scheme produces two populations of proteins in the A (flowthrough) and B (ATP binding) fractions. The starting material, (lane 2) the fraction A flowthrough, (lane 3) fraction C wash, (lane 4) and fraction B (lane 5) were tested for the ability to react to the monoclonal antibody. In addition, a commercially available Hsp70 protein that serves as a positive control was loaded in the last lane (lane 10). As shown in the blot in FIG. 4, the flow through fraction A (lane 3) does not contain significant amounts of Hsp70. The eluted and concentrated fraction B (lane 4) is highly reactive to the antibody as shown in the blot and indicates at least two distinct bands centered around the 75 kDa molecular weight marker. The wash fraction C (lane 5), indicates the presence of two bands that run at slightly below 75 kDa. In a separate independent experiment, the flowthrough fraction A (lane 7) again is not reactive to the antibody, and the wash fraction C (lane 8) is also not reactive to the antibody, but the fraction enriched in ATP binding proteins (Fraction B) shown in lane 9 gives the same banding pattern as was seen from the first separation.

FIG. 4B shows the results of SDS-PAGE analysis of the flow through fractions loaded at protein concentrations of 5, 10 and 20 µg, and the ATP-agarose affinity purified fraction loaded at protein concentrations of approximately 1, 5, and 10 µg. Identified to the right of the fractions obtained after elution with ATP are the proteins identified after peptide mass fingerprinting. The three amino acid sequences identified for the two HSP immunoreactive bands were Bip-AAB63469 (SEQ. ID. NO. 18), Hsp70-ABF95267 (SEQ. ID. NO. 19) and chaperone DNAK like protein EEC69073 (SEQ. ID. NO. 22). Also identified in the ATP agarose purified fractions were alpha-amylase and Starch De-Branching Enzyme (SDBE).

The gel also reveals a significant amount of contaminating albumin even though albumin does not bind ATP-agarose to any extent. The most likely explanation for this contaminating albumin is that it binds to the Hsps and other proteins, enabling the albumin to be co-purified with hsps.

FIG. 4C confirms that the ATP agarose affinity purified fractions retain enzymatic ATPase activity. To eliminate the possibility of a false positive, the samples were compared directly to their respective 10,000 Da final dialysate. The specific activity calculated for these two samples based on the estimated protein concentration was 6.09 and 5.56 nmol ATP/mg Hsp70/hr.

Discussion: A separation protocol was developed to separate HSP70 proteins based on their ability to bind to ATP agarose affinity resin, and, was tested for its effectiveness. The procedure involved only minimal sample manipulation, using only ATP agarose, and ultrafiltration to concentrate and conduct buffer changes, and an anti-hsp70 antibody to detect the presence of hsps. The results of the procedure (FIG. 4) clearly demonstrates that while in 10 µg of starting material, 10 µg of flowthrough, or 10 µg of wash fraction there is insufficient hsp70 to be detected by the ant-Hsp antibody. By contrast, in the fraction eluted from the ATP agarose column, contains at least two proteins that clearly are recognized by the anti-Hsp70 antibody. The results therefore show that the separation scheme was successful and predictable on two independent chromatography runs and diafiltrations. Furthermore, the data substantiates the identification of heat shock proteins made by Peptide Mass Finger printing and demonstrates that these proteins are functional and can be readily isolated and enriched by simple ATP agarose chromatography followed with diafiltration. It is concluded that the heat shock proteins co-purify with the recombinant albumin. Such co-purification is consistent with the hypothesis that the heat shock proteins are bound to the albumin, and that the albumin acts to stabilize the heat shock proteins in a stable conformation. Surprisingly, the recombinant albumin/heat shock protein complex retains significant ATPase activity (FIG. 4C) consistent with the presence of functional heat shock proteins. This increased activity was further confirmed as providing a growth promoting effect in Example 9A and 9B. The interaction of HSA and Hsp70 proteins was further demonstrated in FIG. 4B, which revealed a significant amount of contaminating albumin even though albumin does not bind to an ATP-agarose column to any appreciable extent. The most likely explanation is that the Hsp70 and other proteins, and more specifically recombinant albumin in this case, interact with an easily observable affinity. FIG. 4C further substantiates these conclusions that the growth stimulating property of Cellastim derives at least in part from contaiminating heat shock proteins by showing that the ATP purified fraction retains high ATPase activity, suggesting that the Hsps are functional.

Example 7

Influence of HSP and Albumin Addition on Cell Viability

To test the hypothesis that Hsp70 contaminants identified in Cellastim occur at the correct level relative to albumin to act as a positive growth modulator of albumin, Hsp70 was added to control cells and cells treated with a non recombinant commercial source of albumin (Seracare) at concentrations of 0.5, 1.0, 5.0, and 10 ug/ml or 1/1000 the concentration of the Seracare albumin. This is also 1/1000 the normal concentration of Cellastim that is typically used in routine tissue culture, corresponding to 0.1%. The cells were grown out for three days and the concentration of viable cells was determined. The objective of this experiment was to verify whether very low amounts of hsp can act to cause measureable and significant changes in viable cell concentration.

Methods: Specially conditioned Hybridoma cells AE1 were seeded in DF12/ITSE at a density of $0.5 \times 10^5$ cells per ml of media after washing twice with same media to remove residual media as described previously. The media and cells were then left untreated (negative control), treated with Hsp 70, treated with Seracare albumin, and treated with Hsp70 and Seracare albumin in combination at the concentrations given. The cells were grown under 5% CO2 and 37° C. for approximately 70 hours after which the viability for each culture was measured. The samples were tested in duplicate.

Results: The molar concentrations used in the experiment shown in FIG. 5 were: 7 nM, 14 nM, 70 nM, 140 nM, and 280 nM Hsp70. The difference between the average of the negative control and the samples is as follows: 34.1% increased, 34.1% increased, 43.9% increased, 34.1% increased, and 48.8% increased (respectively). The signal to noise ratio of the replicates for the negative control is: $4.1 \times 10^5 +/- 0.1 \times 10^5$. The signal to noise ratio for the sample replicates is: $6.1 \times 10^5 +/- 0.1 \times 10^5$, $6.0 \times 10^5 +/- 0.1 \times 10^5$, $6.5 \times 10^5 +/- 0.25 \times 10^5$, $6.2 \times 10^5 + 1 - 0.1 \times 10^5$, and $6.65 \times 10^5 +/- 0.05 \times 10^5$. As described previously, the difference of 34.1%, 43.9% and 48.8% are much greater than the signal to noise ratio among the replicates and therefore a difference of greater than 20% is considered significant with 95% confidence (p=0.05 for addition of Hsp 70 at the 5 concentrations tested, n=5×2 replicates for samples and n=4 for negative control). Only four of five of the concentrations used are shown for illustration purposes.

Figure 5:
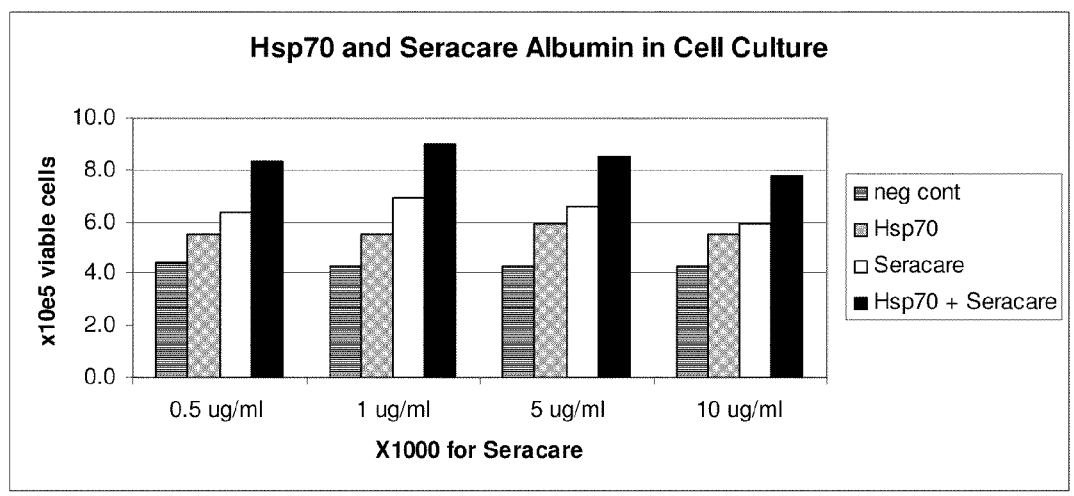
FIG. 5: Shows a comparison and analysis of the effects of addition of exogenous Hsp70 either alone, or added to a blood serum purified (non-recombinant) albumin (Seracare Albumin) compared to Seracare albumin alone on cell growth and viability.

Discussion: Hsp70 when added to Seracare at 1 part Hsp70 per thousand parts Seracare albumin, the concentration of viable cells of the cell culture increased significantly over negative control (FIG. 5). The significant increase in the concentration of viable cells can be attributed to the combination of albumin and Hsp70. While both have activity that is measureable, the combination of the two factors provides a statistically significant synergistic increase in viable cell concentration as compared to either factor alone or the negative control.

Although Hsp70 was added at the very low concentration of 0.5, 1.0, 5.0, and 10.0 μg/ml (1/1000 the concentration of Seracare), it improved the concentration of viable cells significantly, producing a similar improvement in cell concentration as Seracare plasma albumin but at 1000 fold less concentration. This demonstrates that Hsp70 although only occurring at 1 part per 1000 parts albumin is active at the concentrations commonly used in cell culture. Albumin is commonly used at concentrations of 0.1 mg/ml to 10 mg/ml which corresponds to 0.1 ug/ml to 10 ug/ml Hsp70—or the low to mid nanomolar range. This is in a similar range of Hsp70 concentration that we found to be effective in cell culture (FIG. 5). Taken together, these results suggest that the Hsp70 found in Cellastim occurs in the product at a relevant concentration such that the Hsp70 is expected to have measureable activity. Furthermore, it demonstrates that Hsp70, when added to the competitor albumin at 0.05, 0.1, 0.5, 1.0, and 2.0% relative to albumin, the Hsp70 significantly improves the concentration of viable cells of the resulting cell culture. Hsp70 when added to Seracare at 1 part Hsp70 per thousand parts Seracare albumin, caused the concentration of viable cells to increase nearly to levels normally seen only with Cellastim.

Example 8

Dose Response Curves for HSP70 and Albumin

Figure 6:
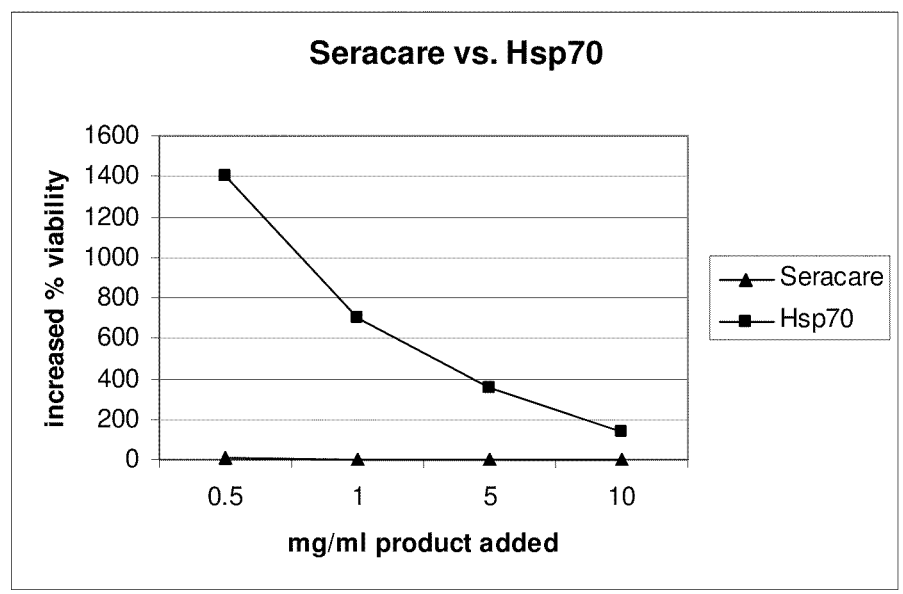
FIG. 6: Shows a comparison of the effects of serum purified (Seracare) albumin alone and exogenous Hsp70 alone on cell growth and viability when added at the same concentrations.

Cells were plated as described as Example 3, and varying amounts of either serum dervived albumin (*Seracare albumin*) or human hsp70 alone were added to the cultures at the concentrations shown in FIG. 6.

Results: Both HSP70 and Seracare albumin promoted an improvement in cell viability when added alone to the cells. (FIG. 6). However, when the comparison is made with the mass normalized amounts of both proteins, it is evident that Hsp70 is far more potent at promoting cell viability compared to Seracare. In fact 1/1000 the amount of Hsp70 relative relative to albumin is enough to cause a similar performance increase in cell culture as Seracare albumin.

This result demonstrates the very high potency of Hsp70, and reinforces the hypothesis that Hsp70, although occurring at only low amounts, is potent enough at the levels found in Cellastim to cause a significant increase in viability. Furthermore, the most significant gain in viability is seen at the very lowest concentrations of Hsp70, demonstrating that a small mass of Hsp70 that could be economically produced is all that is necessary to increase the viability of cell culture cells.

Example 9

Figure 7:
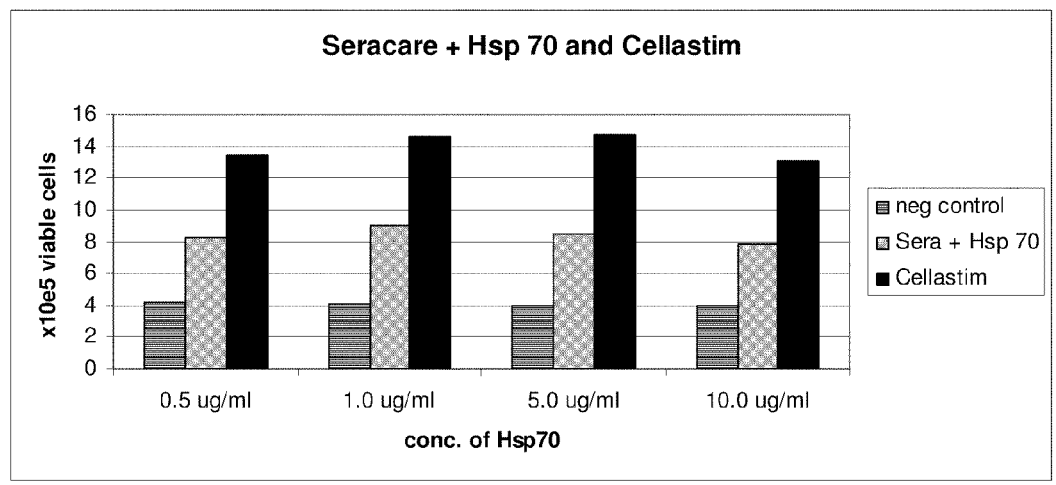
FIG. 7: Shows a comparison of the effect of exogenous Hsp70 mixed with Seracare albumin compared with Cellastim albumin made using the new process on cell growth and viability.

Comparison of the Effect of Cellastim with the Separate Addition of Albumin and HSP70 on Cell Viability Cells were plated as described in Example 3, and varying amounts of either Seracare albumin with varying amounts of admixed hsp70 or Cellastim (P0153) were added to the cultures at the concentrations shown in FIG. 7.

Results: As shown in FIG. 7, the addition of HSP70 to Seracare caused the supplemented Seracare albumin to perform more similarly to Cellastim albumin (hsp70 added at 1 part per thousand parts Seracare): Compared to the performance of Seracare alone, Seracare with added Hsp70 increased the performance significantly. The viability of Seracare alone compared with Seracare and Hsp70 added at 1/1000 relative to Seracare caused the concentration of viable cells to increase 29.7%, 30.4%, 28.8%, and 32.2% respectively at the 4 concentrations tested. While hsp70 addition increased the performance of the Seracare albumin, it is evident that the addition of hsp70 alone is not sufficient to create a supplement that performs as well as Cellastim.

Discussion: Hsp 70 seems to be most active in the 0.01 to 0.1% concentration range and occurs in Cellastim at these levels. Hsp 70 is therefore about 100-1000 times more potent in promoting viability than Seracare plasma albumin. When added to Seracare, Hsp70 significantly improved viability over Seracare alone. It is evident that there is a synergistic effect of combining both albumin and Hsp70 on improving the cell viability in a statistically and economically significant manner.

The results presented are consistent with the idea that hsp70 acts as a positive cell growth promoting agent in Cellastim and is responsible at least in part for the superior properties of Cellastim compared to other commercial preparations of albumin.

Example 10

Impact of the Removal of Hsps from Cellastim on Cell Viability

Figure 8:
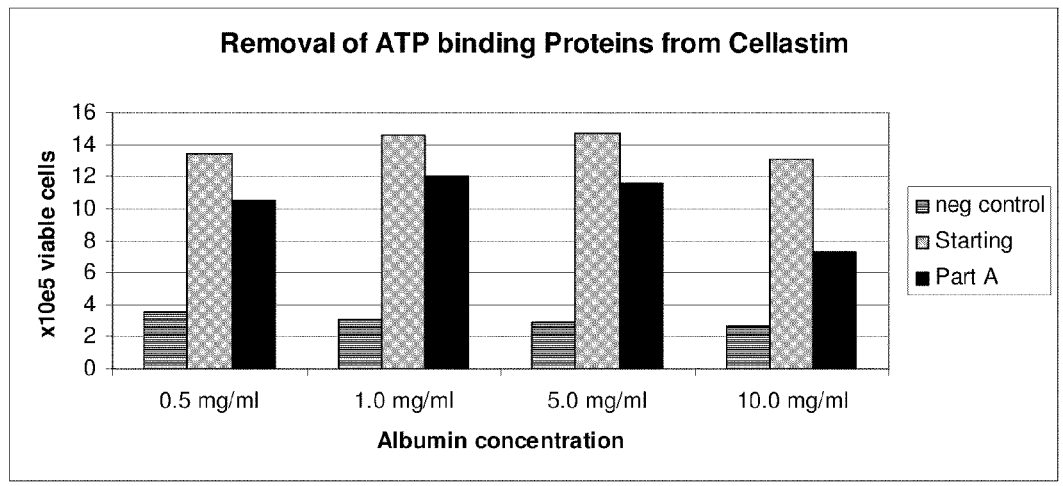
FIG. 8.
Figure 8:
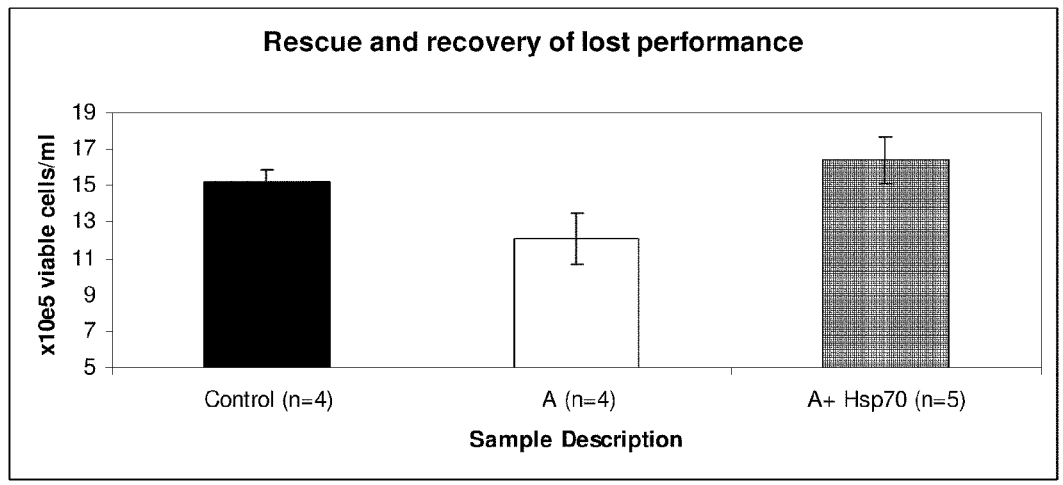

Methods: The separation scheme described in Example 5 was also used to produce fraction A suitable for Cell culture testing (FIG. 8A). The method involves minimal manipulation of fraction A, as it is flowed through an ATP agarose column and then concentrated by diafiltration and buffered with PBS that is suitable for cell culture. The intent of this protocol was to minimize the introduction of new variables into the experiment such that a loss of viability is seen but due to some other reason or cause beyond the removal of ATP binding proteins. Fraction A was tested against the unadulterated control (starting material) for ability to promote hybridoma cell culture viability. The results of the test are shown in FIG. 8A

In FIG. 8B, the ATP-agarose affinity purified fraction was added back to the Cellastim that had been deleted of hsps (Fraction A) after flowing through the column. In this case the purified Hsp70 fraction was concentrated to about 5-10 mg/ml. This experiment was repeated at least six times with similar results.

Results: As shown in FIG. 8A, the Cellastim starting material (cross hatched bars), and Part A (solid bars) were tested at the same concentration and compared to the negative control (striped bars). A statistically significant decrease is observable at all four concentrations tested. The result indicates that there was a significant loss in the performance of Cellastim after ATP agarose treatment. The treatment resulted in a 28.0, 21.7, 26.7, and 79.5% loss as compared to Cellastim before removal of ATP binding proteins. In this experiment, care was taken in the design and handling of the samples to ensure that any inadvertent losses in performance due to sample handling or the accidental introduction of new contaminants were minimized. In FIG. 8B, the results for the addition of the affinity purified Hsp70 fraction back to Cellastim treated with ATP-agarose shows that the loss in performance can be retrieved by the simple mixing of the fractions back together. In six experiments the decrease seen in Fraction A varied which made it hard to determine the effects of adding back the Hsp70 fraction. In no case however did adding the fraction back appear to have a toxic effect. The results of one such experiment with 5 data points is given in FIG. 8B.

Discussion: The cell culture results (FIG. 8A) demonstrate that it is possible to reduce the performance of Cellastim by simply passing it over an ATP binding column. This data, when combined with the results shown in Example 5 demonstrates that the depletion of the hsps from albumin by the ATP agarose column directly reduces the cell growth promoting properties of the albumin. This result therefore demonstrates that the superior properties of the albumin arise, at least in part, from the contaminating heat shock proteins in the albumin.

As shown in FIG. 8B, it is further evident that similar to the result shown in FIG. 5, the performance could be re-constituted by mixing the ATP-agarose treated Cellastim and the affinity purified Hsp70 fractions together. Many different concentrations were attempted and in no case was the Hsp70 fraction toxic to the cells.

The results shown in FIG. 8B were from one such experiment in which the loss in performance was not dramatic but significant (20%), and in 10 separate culture wells with 5 separate samples the performance was recovered to 100% or above. It is clear from six separate experiments that the amount of loss in performance in fraction A varied from dramatic (75%) to significant (10-20%) depending on the level of viability of the control and several other factors. It was also observed during this work that Stressgen Hsp70 could substitute for fraction B in recovering the lost activity (data not shown).

Thus it is clear that hsps are at least partially responsible for the enhanced performance of Cellastim albumin compared to either yeast or plasma derived albumins. However, at the same time, the data presented in FIG. 7 clearly establishes that there is a discrepancy observed between Hsp70 supplemented Seracare and Cellastim with regard to cell culture performance. Specifically the addition of Hsp70 is not able to fully restore the activity of Seracare albumin to the levels seen with Cellastim, thus suggesting that other factor(s) are also important for enhancing the growth promoting ability of Cellastim. Accordingly a detailed lipid analysis of Cellastim compared to plasma derived and yeast derived albumins was conducted. The results of this analysis are described in Example 11.

Example 11

Lipid Analysis of Cellastim, Plasma Derived Albumin and Yeast Derived Albumin Fatty Acid Determination of Albumins Fatty acid content determination was made by a method based on the work of D. L. Palmquist and others (Palmquist et al. J. Agric. Food. Chem. (1988) 36:1202-1206). Briefly, the protein solution or powder was extracted with benzene including an internal standard and methanolic-HCl. The sample was then heated to 80° C. for 2 hr. 15 min and then neutralized with potassium carbonate. After centrifugation, the upper organic layer was transferred to a GC vial. The sample was separated on a Supelco SP-2560 capillary and quantified according to the internal standards supplied by Supelco # 47885-U. Delipidation Cellastim was defatted according to the method of Chen, (R. F. Chen. J. Biol. Chem. (1907) 242: 173-181).

Results: As shown in Tables E7 to E11, there were also dramatic differences in the lipid content of Cellastim produced using the new process compared to the old process. These results are consistent with the hypothesis that part of the growth promoting activity of Cellastim derives from its high fatty acid content. More specifically Cellastim is enriched in oleic, palmitic, as well as linoleic and alpha linoleic acids. Furthermore the total fatty acid content of Cellastim made using the new process comprises significantly high total fatty acid content, compared to that prepared with the old process.

TABLE E7

Comparison of fatty acid content of old and new methods for producing albumin C12 to C16 fatty Acids

| Sample ID | C12:0 | C14:0 | C14:1 | C15:0 | C15:1 | C16:0 Palmitic | C16:1 |
|---|---|---|---|---|---|---|---|
| Albumin prepared with Old Process ||||||||
| P124 | 0.002 | 0.010 | 0.000 | 0.000 | 0.000 | 0.073 | 0.006 |
| P125 | 0.002 | 0.011 | 0.000 | 0.000 | 0.000 | 0.096 | 0.005 |
| P126 | 0.002 | 0.012 | 0.000 | 0.000 | 0.000 | 0.109 | 0.006 |
| P145 | 0.001 | 0.016 | 0.001 | 0.001 | 0.000 | 0.222 | 0.005 |
| P146 | 0.001 | 0.017 | 0.002 | 0.001 | 0.000 | 0.267 | 0.005 |
| P147 | 0.002 | 0.021 | 0.001 | 0.001 | 0.000 | 0.185 | 0.009 |
| Albumin prepared with New Process ||||||||
| P167 | 0.002 | 0.023 | 0.002 | 0.002 | 0.000 | 0.243 | 0.008 |
| P171 | 0.003 | 0.023 | 0.001 | 0.003 | 0.000 | 0.275 | 0.008 |
| P176 | 0.003 | 0.024 | 0.000 | 0.002 | 0.000 | 0.310 | 0.008 |
| P183 | 0.007 | 0.024 | 0.001 | 0.003 | 0.001 | 0.282 | 0.007 |
| P189 | 0.003 | 0.024 | 0.001 | 0.002 | 0.002 | 0.282 | 0.006 |
| P190 | 0.002 | 0.023 | 0.001 | 0.002 | 0.001 | 0.287 | 0.006 |

TABLE E8

Comparison of fatty acid content of old and new methods for producing albumin C17 to C18 fatty Acids

| Sample ID | C17:0 | C17:1 | C18:0 | C18:1n9t | C18:1n11 | C18:1n9c (oleic) | C18:1n7 | C18:2n6t |
|---|---|---|---|---|---|---|---|---|
| Albumin prepared with Old Process |||||||||
| P124 | 0.000 | 0.000 | 0.004 | 0.000 | 0.000 | 0.246 | 0.000 | 0.000 |
| P125 | 0.000 | 0.000 | 0.004 | 0.000 | 0.000 | 0.241 | 0.000 | 0.000 |
| P126 | 0.000 | 0.000 | 0.004 | 0.000 | 0.000 | 0.311 | 0.000 | 0.000 |
| P145 | 0.000 | 0.000 | 0.006 | 0.000 | 0.000 | 0.281 | 0.000 | 0.000 |
| P146 | 0.000 | 0.000 | 0.007 | 0.000 | 0.000 | 0.289 | 0.000 | 0.000 |
| P147 | 0.000 | 0.000 | 0.004 | 0.000 | 0.000 | 0.410 | 0.000 | 0.000 |
| Albumin prepared with New Process |||||||||
| P167 | 0.001 | 0.001 | 0.010 | 0.001 | 0.000 | 0.422 | 0.017 | 0.001 |
| P171 | 0.002 | 0.001 | 0.008 | 0.001 | 0.000 | 0.363 | 0.015 | 0.002 |
| P176 | 0.003 | 0.000 | 0.010 | 0.002 | 0.000 | 0.369 | 0.015 | 0.001 |
| P183 | 0.002 | 0.001 | 0.010 | 0.001 | 0.000 | 0.303 | 0.013 | 0.001 |
| P189 | 0.001 | 0.001 | 0.009 | 0.001 | 0.000 | 0.284 | 0.011 | 0.002 |
| P190 | 0.002 | 0.001 | 0.008 | 0.001 | 0.000 | 0.287 | 0.012 | 0.002 |

TABLE E9

Comparison of fatty acid content of old and new methods for producing albumin C18 to C29 fatty Acids

| Sample ID | linoleic C18:2n6c (Linoleic) | C18:3n6 | α-linoleic C18:3n3 (α-linoleic) | C20:0 | C20:1 | C20:2 | C20:3n6 | C20:4n6 |
|---|---|---|---|---|---|---|---|---|
| Albumin prepared with Old Process |||||||||
| P124 | 0.304 | 0.000 | 0.024 | 0.000 | 0.000 | 0.000 | 0.000 | 0.000 |
| P125 | 0.325 | 0.000 | 0.025 | 0.000 | 0.000 | 0.000 | 0.000 | 0.000 |
| P126 | 0.367 | 0.000 | 0.031 | 0.000 | 0.000 | 0.000 | 0.000 | 0.000 |
| P145 | 0.411 | 0.000 | 0.045 | 0.000 | 0.000 | 0.000 | 0.000 | 0.000 |
| P146 | 0.311 | 0.000 | 0.032 | 0.000 | 0.000 | 0.000 | 0.000 | 0.000 |
| P147 | 0.450 | 0.000 | 0.043 | 0.000 | 0.000 | 0.000 | 0.000 | 0.000 |
| Albumin prepared with New Process |||||||||
| P167 | 0.834 | 0.002 | 0.084 | 0.002 | 0.003 | 0.001 | 0.001 | 0.000 |
| P171 | 0.683 | 0.001 | 0.068 | 0.001 | 0.003 | 0.002 | 0.001 | 0.000 |
| P176 | 0.791 | 0.001 | 0.076 | 0.001 | 0.002 | 0.001 | 0.001 | 0.000 |
| P183 | 1.017 | 0.002 | 0.086 | 0.001 | 0.002 | 0.002 | 0.001 | 0.000 |

TABLE E9-continued

Comparison of fatty acid content of old and new methods for producing albumin C18 to C29 fatty Acids

| Sample ID | linoleic C18:2n6c (Linoleic) | C18:3n6 | α-linoleic C18:3n3 (α-linoleic) | C20:0 | C20:1 | C20:2 | C20:3n6 | C20:4n6 |
|---|---|---|---|---|---|---|---|---|
| P189 | 0.984 | 0.007 | 0.084 | 0.003 | 0.004 | 0.002 | 0.000 | 0.000 |
| P190 | 0.977 | 0.001 | 0.081 | 0.000 | 0.001 | 0.001 | 0.000 | 0.000 |

TABLE E10

Comparison of fatty acid content of old and new methods for producing albumin C18 to C29 fatty Acids

| Sample ID | C20:5n3 | C21:0 | C22:0 | C22:5n3 | C22:6n3 | C24:0 | C24:1 |
|---|---|---|---|---|---|---|---|
| Albumin prepared with Old Process | | | | | | | |
| P124 | 0.000 | 0.000 | 0.000 | 0.000 | 0.000 | 0.000 | 0.000 |
| P125 | 0.000 | 0.000 | 0.000 | 0.000 | 0.000 | 0.000 | 0.000 |
| P126 | 0.000 | 0.000 | 0.000 | 0.000 | 0.000 | 0.000 | 0.000 |
| P145 | 0.000 | 0.000 | 0.000 | 0.000 | 0.000 | 0.000 | 0.000 |
| P146 | 0.000 | 0.000 | 0.000 | 0.000 | 0.000 | 0.000 | 0.000 |
| P147 | 0.000 | 0.000 | 0.000 | 0.000 | 0.000 | 0.000 | 0.000 |
| Albumin prepared with New Process | | | | | | | |
| P167 | 0.006 | 0.002 | 0.000 | 0.003 | 0.001 | 0.000 | 0.005 |
| P171 | 0.007 | 0.002 | 0.001 | 0.002 | 0.001 | 0.001 | 0.005 |
| P176 | 0.004 | 0.001 | 0.001 | 0.004 | 0.016 | 0.000 | 0.005 |
| P183 | 0.003 | 0.003 | 0.001 | 0.002 | 0.000 | 0.001 | 0.003 |
| P189 | 0.002 | 0.003 | 0.000 | 0.002 | 0.000 | 0.001 | 0.003 |
| P190 | 0.002 | 0.001 | 0.001 | 0.001 | 0.005 | 0.000 | 0.002 |

TABLE E11

Comparison of most common lipids in Cellastim

| Sample ID | Palmitic C16:0 | oleic C18:1n9c | linoleic C18:2n6c | α-linoleic C18:3n3 | Total % fatty acids | AVG |
|---|---|---|---|---|---|---|
| Albumin prepared with Old Process | | | | | | |
| P124 | 0.073 | 0.246 | 0.304 | 0.024 | 0.67 | |
| P125 | 0.096 | 0.241 | 0.325 | 0.025 | 0.71 | |
| P126 | 0.109 | 0.311 | 0.367 | 0.031 | 0.84 | |
| P145 | 0.222 | 0.281 | 0.411 | 0.045 | 0.99 | |
| P146 | 0.267 | 0.289 | 0.311 | 0.032 | 0.93 | |
| P147 | 0.185 | 0.410 | 0.450 | 0.043 | 1.13 | 0.88 |
| Albumin prepared with New Process | | | | | | |
| P167 | 0.243 | 0.422 | 0.834 | 0.084 | 1.69 | |
| P171 | 0.275 | 0.363 | 0.683 | 0.068 | 1.49 | |
| P176 | 0.310 | 0.369 | 0.791 | 0.076 | 1.66 | |
| P183 | 0.282 | 0.303 | 1.017 | 0.086 | 1.79 | |
| P189 | 0.282 | 0.284 | 0.984 | 0.084 | 1.74 | |
| P190 | 0.287 | 0.287 | 0.977 | 0.081 | 1.72 | 1.68 |

In FIG. 9A, the results for the total long chain fatty acid analysis is given for Cellastim, compared to plasma derived albumin and yeast derived albumin. The results show significantly higher long chain lipid fatty acid content for Cellastim compared to either plasma derive albumin or yeast derived albumin. FIG. 9B shows the results broken down by the actual fatty acid composition. Cellastim preferentially contained C18:2n6c, C18:1n9c and C16:0 fatty acids.

In FIG. 9C, the results of an experiment are shown where we attempted to add back exogenous lipid to de-lipidated Cellastim. In this experiment, linoleic acid (the most abundant long chain fatty acid) (Sigma Aldrich), was added back to completely defatted Cellastim. The results showed that the exogenous lipids were not able to restore the activity of the defatted Cellastim to the levels observed with the normal Cellastim.

Example 12

Differential Scanning Calorimetry Analysis of Cellastim, Plasma Derived Albumin and Yeast Derived Albumin Differential scanning calorimetry was used to compare the thermodynamic stability of Cellastim, plasma derived HSA, and yeast derived HSA. A Microcal Differential Scanning calorimeter was utilized to obtain the scans. One ml of reference buffer was placed in the reference cell and 1 ml of 1 mg/ml of each sample was placed in the sample cell after standard degassing. The cells and samples were allowed to reach equilibrium starting temperature before the samples were scanned from 25° C. to 95° C. over 70 minutes. The major transition temperatures for the albumin samples was determined from the peak change in heat capacity for the three samples.

Figure 10:
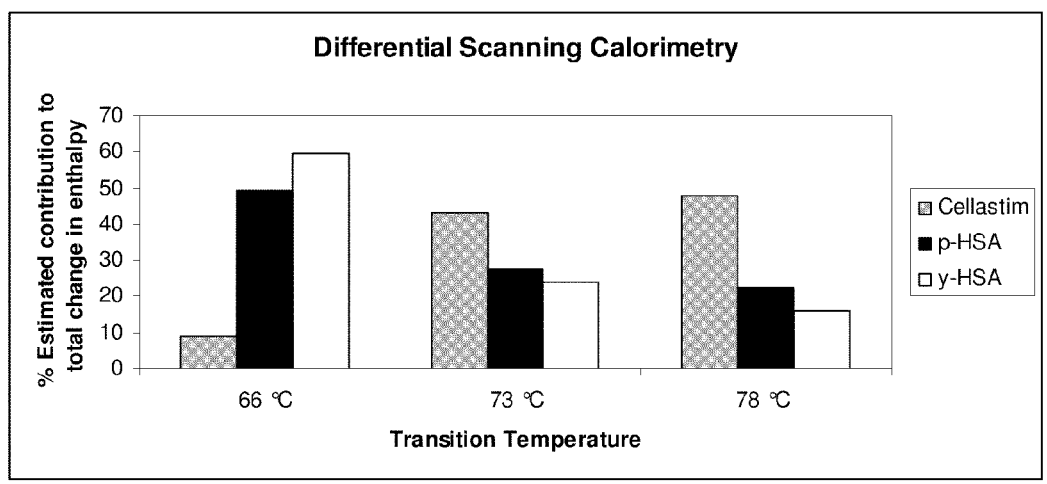
FIG. 10 shows the results for Differential Scanning calorimetry for Cellastim and albumin from plasma and yeast derived albumin.

The results, shown in FIG. 10 demonstrate a significant difference in the overall thermodynamic stability in Cellastim compared to the plasma derived and yeast derived albumins. Specifically Cellastim displayed a significantly higher transition temperature compared to either of the yeast derived or plasma derived albumins, thus demonstrating that Cellastim exhibits enhanced stability compared to the other albumins tested.

Discussion: The results presented are consistent with the idea that hsp70 acts as a positive cell growth promoting agent in Cellastim and is responsible at least in part for the superior properties of Cellastim compared to other commercial preparations of albumin.

Figure 9:
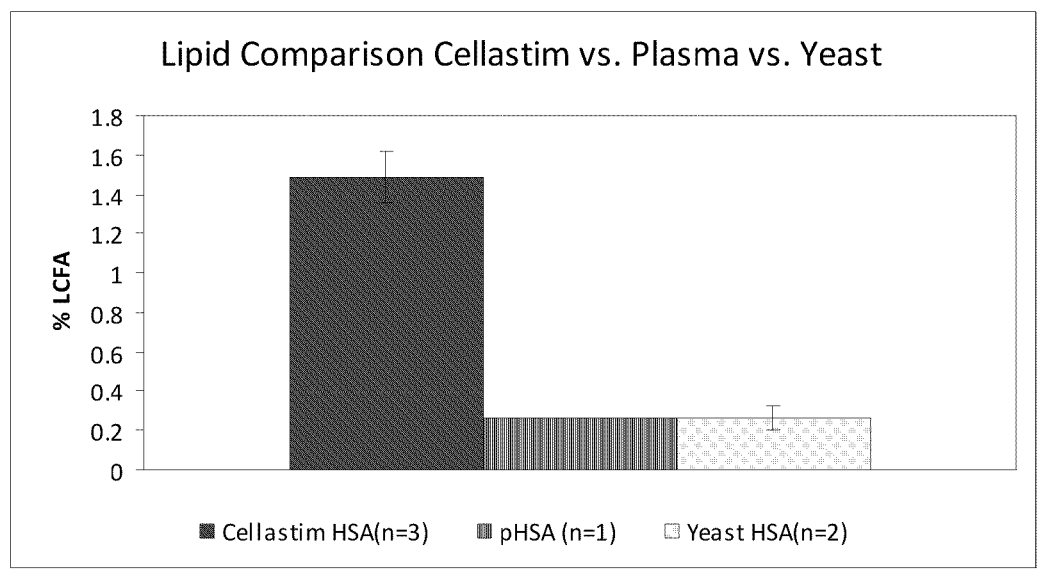
FIG. 9.
Figure 9:
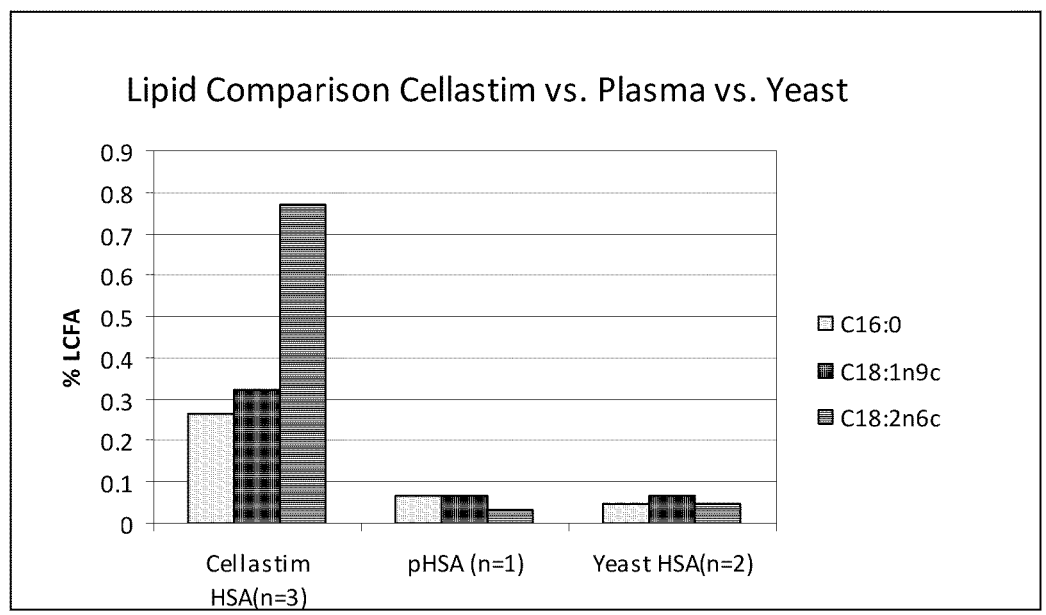
Figure 9:
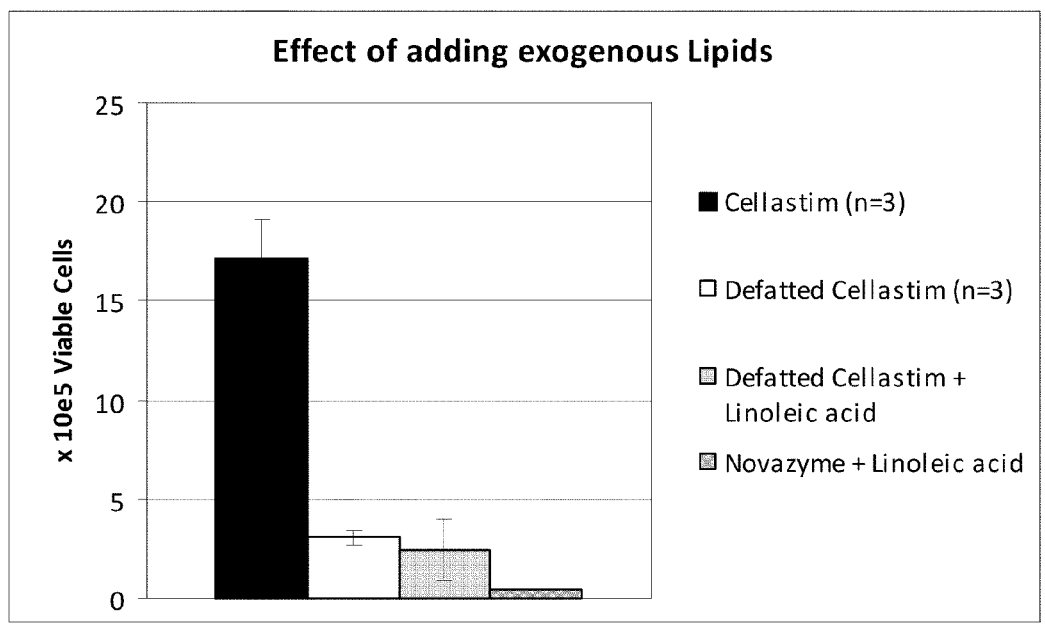

The remainder of the descrepency remaining between Hsp70 supplemented Seracare and Cellastim albumins (FIG. 7) is likely explained by the results presented in Tables E7 to E11 and FIGS. 9 and 10. These results suggest that the factor, and reveal the likely mechanism responsible for improved performance for Cellastim in cell culture when compared to other albumins.

In FIG. 9C, the results are shown for the effect of defatting the albumin on the ability of Cellastim to promote the growth of cells in culture. From this study it is clear that complete removal of the fatty acids from Cellastim causes a toxic effect on the cultured cells—most likely due to the sequesteration of free fatty acids from the culture media and cells, caused by the stripped albumin.

In an effort to recover the lost viability, linoleic acid at a ratio of 1% (wt/wt) of the albumin was added back to defatted albumin to see if the original product characteristics could be reproduced. As is shown in FIG. 9C, these attempts were not successful, and the results are consistent with the mixed results that have been reported previously with regard to the effects of adding long chain fatty acids to essentially fat free albumin and delivering such mixtures to cells (Garcia-Gonzalo et al. PLoS ONE 3(1): e1384). Without being bound to any one particular theory of operation, it is possible that the affinity, and binding mode of fatty acids to albumin differs between the addition of exogenous fatty acids to the mature fully folded protein, compared to lipid binding that occurs during translation and folding of the immature protein in the presence of lipids in vivo. The best evidence for this comes from the fact that lipids added to albumin in titration experiments demonstrate binding to different classes of binding sites with different affinities and do not result in the same activity as the lipid rich albumin produced de novo (Keenan et al. Cytotechnology (1997) 24(3): 243-252 and Garcia-Gonzalo et al. PLOS ONE 3(1): e1384). Cellastim lipids that are bound to albumin may be bound either during translation, directly thereafter, or during transport between different cellular compartments, and appear to be bound to mainly high affinity sites. We were unable to remove these lipids from their binding sites except with the Chen method. Using other methods we were able to remove other substances such as endotoxin (estimated Kd in 1-10 uM range, David et al, J. Endo. Res. (1995) 2, 99-106) and Triton X-100 or X-114 (estimated Kd in 0.1 mM range, Sukow et al, Biochemistry. (1980) 19(5):912-7) from similar binding sites on the albumin molecule (Nguyen et al. Mol. Pharm. (2008) 5(6):1131-7) with no change in fat content.

Furthermore, apparent defatting of the rice flour before processing by complete removal of the germ and bran layer did not change the fatty acid content of the final albumin product and purification based on the well known method of Cohn using ethanol only reduces the fat content of Cellastim by 30-40% (Data not shown).

The effect of the tightly bound long chain fatty acids in Cellastim has a clear effect on the stability of recombinant albumin as measured by DSC (FIG. 10). As the data in FIG. 10 demonstrates, the enthalpy of unfolding patterns for the three sources of proteins compared are strikingly different. In fact, the profile seen for Cellastim is expected to make it more stable than albumin prepared from plasma or yeast and the increased stability by bound ligands as well as the increased stability provided by Hsp70 proteins point to a similar mechanism of promoting viability in cell culture conditions. This mechanism of action, which stems from the binding of both Hsp70 and 2) long chain fatty acids is consistent with several recent publications; Stability in Times of Stress, Nature. 463 (28): 2010, and the previous work of Shrake et al. Biopolymers. (1988) 81(4): 235-248, respectively.

Example 13

Use of Albumin/HSP Supplements to Increase Viability of Stem Cells

HUMAN EMBRYONIC STEM CELL CULTURE The human embryonic stem cell lines H1, H7 and H9 are obtained from WiCell Research Institute, Inc., (Madison, Wis.) and cultured according to instructions provided by the source institute. Briefly, cells are cultured on mouse embryonic fibroblast (MEF) feeder cells in ES cell medium consisting of DMEM/F12 (Invitrogen/GIBCO) supplemented with 20% knockout serum replacement, 100 nM MEM nonessential amino acids, 0.5 mM beta-mercaptoethanol, 2 mM L-glutamine with 4 ng/ml human basic fibroblast growth factor (bFGF) (all from Invitrogen/GIBCO). MEF cells, derived from E13 to 13.5 mouse embryos, were purchased from Charles River. MEF cells are expanded in DMEM medium supplemented with 10% FBS (Hyclone), 2 mM glutamine, and 100 mM MEM nonessential amino acids. Sub-confluent MEF cell cultures are treated with 10 μg/ml mitomycin C (Sigma, St. Louis, Mo.) for 3 h to arrest cell division, trypsinized and plated at 2×107/cm2 on 0.1% bovine gelatin-coated dishes. MEF cells from passage two through four are used as feeder layers. Human embryonic stem cells plated on MEF cell feeder layers are cultured at 37° C. in an atmosphere of 5% $CO_2$ within a humidified tissue culture incubator. When confluent (approximately 5-7 days after plating), human embryonic stem cells are treated with 1 mg/ml collagenase type IV (Invitrogen/GIBCO) for 5-10 min and are gently scraped off the surface using a 5-ml pipette. Cells are centrifuged at 900 rpm for 5 min, and the pellet is resuspended and re-plated at a 1:3 to 1:4 ratio of cells in fresh culture medium.

In parallel, H1, H7, and H9 human embryonic stem cells are also seeded on plates coated with a 1:30 dilution of growth factor reduced MATRIGEL (BD Biosciences) and cultured in MEF-conditioned media supplemented with 8 ng/ml bFGF. The cells cultured on MATRIGEL are routinely passaged with collagenase IV (Invitrogen/GIBCO), Dispase (BD Biosciences) or LIBERASE enzyme.

1. Embryonic stem cells are cultured either of the above media containing 20%, 10%, 5% or 0% KSR in the presence of various concentrations of Cellastim (0%, 1%, 2% or 5%).

2. At various times, the embryonic stem cells are removed from the dish using microdissection and a dissecting scope. The number of viable cells in each condition is determined by trypan blue exclusion. In addition, the total number of visible colonies can be documented.

In a similar manner, adult stem cells from bone marrow or peripheral blood can be isolated and cultured. CD34+ cells are isolated and cultured in Iscove's Modified Dulbecco's Medium (IMDM), 20% Fetal Bovine Serum (FBS), stem cell factor (100 ng/ml), IL-3 (50 ng/ml) and GM-CSF (25 ng/ml) as a control at an initial density of $2×10^4$ cells/well in 24-well plates. In the experimental arm, FBS is decreased to 10%, 5% and 0% and the media is supplemented with Cellastim at 0%, 1%, 2% and 5% at each FBS concentration. Cell viability is measured using typan blue at various time points Mesenchymal stem cell, neuronal stem cell and induced pluripotent stem cell viability can also be determined in a similar manner. Basal media for each cell type is commercially available from Invitrogen. As described above, cell viability can be determined at different FBS concentrations in the presence of increasing concentrations of Cellastim to demonstrate the optimum amount of Cellastim needed to enhance the viability of these different stem cell groups under different FBS conditions including the absence of FBS.

Example 14

Use of Albumin/HSP Supplements to Increase Viability of CHO Cells

Stock CHO-DUXB11 or CHO-K1 cells (CCL-61, ATCC) are harvested and washed three times in serum free media before plating at various densities in 12-well dishes in the DMEM/10% FBS/PenStrep in the control arm. In the experimental arm, the amount of FBS is decreased from 10% to 5% to 2.5% to 1% to 0% in separate cultures while the supplement of the invention is added at various concentrations at each FBS step. The supplement concentration is 0%, 1%, 2%, and 5%. The viability of the CHO cells under the different conditions is determined on various days. Measuring viability sooner after plating will measure viability under subconfluent conditions while later measurements can measure viability under confluent conditions. Viability is determined using trypan blue exclusion with 0.4% trypan blue.

Example 15

Use of Albumin/HSP Supplements to Increase the Yield of a Recombinant Product

CHO-DUXB11 cells engineered to express a protein of interest under control of the strong HCMV immediate early constitutive promoter are washed three times in serum free media and are seeded at $1\times10^3$ cells per well in a 96 well tissue culture plate in 100 microliters DMEM/Penstrep media supplemented with 10% FBS as the positive control. The media in the experimental wells contains 10%, 5% or 2% or 0% FBS with 0%, 1% 2%, or 5% of the supplement of the invention. Media is changed again on the second day and the media and the cells in a well are harvested each day thereafter for 5 days. Each harvested sample is serially diluted in PBS and assayed for the protein of interest using an ELISA. The viable cells from each well are counted. The amount of the protein of interest which is produced at each time point per viable cell is determined.

Example 16

Improvement of Antibody Producing Cell Survival in Stationary Batch Culture By the Addition of Hsp Supplements Summary: A cell clone is generated to express a monoclonal antibody. The clone is developed by gene amplification with methotrexate and subcloning to enhance the maximum antibody productivity. Following weaning off serum supplementation in the culture medium the antibody productivity of the clone is decreased. To improve the productivity of the antibody producing clone, supplements of the invention are added to the culture medium during one or more of the growth phase, transition phase and production phases of the culture.

A CHO cell is transfected with an expression vector encoding a monoclonal antibody, (for example as disclosed in Gillies et al., J. Immunol Methods 125 191-196 (1989)). The expression vector provides expression of both IgG heavy and light genes that are independently controlled by two metallothionine promoters and IgH enhancers. Transfected can be obtained by electroporation with linearized vector, and selection can be initiated 48 hours after transfection by incubating cells with medium containing 0.05 to 0.1 uM methotrexate (MTX). Amplification of inserted antibody sequences is achieved by a stepwise increase in MTX concentration up to 5 µM.

The resulting clones are weaned into serum free media. The cells are adapted to a customized formulation of hybridoma serum free medium (HSFM) (Immunomedics PN 10070) containing 3 µM MTX by continuous subculture in T-flasks for several months. The adapted cells are scaled up from T-flasks to roller bottles for banking. A master cell bank is created to provide a consistent source of experimental cells.

The fed-batch experiments are conducted in two 3-L Bellco spinner-flask bioreactor systems (Bellco glasses, Vineland, N.J.) with 2 L of working volume, using the above cells expanded from the master cell bank. The bioreactor temperature, pH and dissolved oxygen (DO) is monitored and controlled by single loop controllers. The reactor temperature is controlled at 37 C by a heating blanket. The culture pH is controlled at 7.3 by the addition of $CO_2$ or 6% $Na_2CO_3$. Aeration was performed through a cylindrical sintered sparger at 10 ml/min. Dissolved oxygen was controlled above 40% of air saturation by intermittent sparging of $O_2$ into the medium. A constant agitation rate of 50 to about 60 rpm is used throughout the cultivation.

A frozen vial from the master cell bank is thawed and recovered in T-flasks in approximately 1 to 2 weeks. The cells are then expanded from T-flasks to roller bottles prior to inoculation into the bioreactors. Cells are cultured at 37 C in a 5% $CO_2$ atmosphere and maintained in the exponential growth phase throughout the expansion process.

Prior to the inoculation, 1.2 liters of Basal media is pump-transferred into the bioreactor aseptically. In one bioreactor the media also contains the supplement of the invention at a final concentration of about 0.01 to 0.1% wt/wt.

The medium is air saturated to calibrate the dissolved oxygen (DO) probe. A medium sample is also taken to calibrate the pH probe. Once pH probes and DO probes are calibrated, both controllers are set to AUTO modes. Once the system reaches set points of pH (7.3) and temperature (37° C.), calculated amounts of inoculum from the roller bottles are pump transferred into the bioreactor. The post-inoculation viable cell density (VCD) is around $2\times10^5$ vial cells/ml.

The feeding strategy is as follows. During the cultivation, concentrated nutrient solutions are fed into the bioreactor to provide the cells with necessary and non-excessive nutrients. Concentrated nutrient solutions are delivered to the culture via continuous feeding and pulse feeding. The continuous feeding solutions are pump transferred into the reactor continuously using peristaltic pumps (Watson-Marlow 101U/R). The pulse feeding solutions are pulse fed once a day into the culture. In the case of the cells grown with the supplements of the invention, the feeding solutions also included additional amounts of the supplements of the invention.

During the cultivation, bioreactor samples are taken periodically for off-line analysis. The viable cell density (VCD) and the cell viability are measured by microscopic counting using a hemocytometer after staining with 0.4% trypan blue dye. The glucose, lactate, glutamine, ammonia concentrations are measured using a Nova Bioprofile 200. The antibody concentration is determined by HPLC using a protein A affinity chromatography column (Applied Biosystems, P/N 2-1001-00). Cells grown in the presence of the supplements of the invention showed significantly higher rates of cell growth, and produced more antibody, compared to cells grown in the absence of the supplements of the invention.

I claim:

1. A cell culture medium supplement composition comprising: a first protein and a second protein, wherein the composition is produced in a plant, wherein said first protein is a protein cell culture component and said second protein is a heat shock protein; and wherein said protein cell culture component comprises at least 0.01% wt/wt of said heat shock protein; and wherein said protein cell culture component has less than 1 EU of endotoxin/mg of said protein cell culture component.

2. The supplement of claim 1, wherein said heat shock protein is bound to said protein cell culture component.

3. The supplement of claim 2, wherein said protein cell culture component comprises at least 1% wt/wt of bound long chain fatty acids.

4. The supplement of claim 3, wherein said supplement provides a cell viability of greater than $10 \times 10^5$ cells/ml AE1 hybridoma cells after 70 hours of culture when said AE1 cells are seeded at an initial density of $0.5 \times 10^5$ cells per ml in serum free DMEM with 5 mg/ml supplement and grown under standard culture conditions of humidity and temperature.

5. The supplement of claim 3, wherein said first protein is albumin.

6. The supplement of claim 5, wherein said albumin is recombinant albumin.

7. The supplement of claim 6, wherein said albumin comprises less than 2% wt/wt of aggregated albumin.

8. The supplement of claim 6, wherein said albumin comprises about 1% to about 2% wt/wt of long chain fatty acids.

9. The supplement of claim 3, wherein said heat shock protein is a HSP70 family member.

10. A supplement for use in serum free culture, comprising monomeric albumin to which is bound about 1% to about 2% wt/wt of long chain fatty acids and about 0.01% to about 0.1% wt/wt of heat shock proteins.

11. A method for improving the viability of cells in culture comprising the addition of a supplement of any of claims 1 through 3, or 10 to the cell culture medium.

12. A method for improving the viability of cells grown in culture under serum free conditions, comprising adding the supplement of any one of claims 1 through 3, or 10 to a cell culture medium used for growing said cells in culture.

13. A method for improving the viability of cells when plated at low density comprising the addition of a supplement of any of claims 1 through 3, or 10 to the cell culture medium.

14. A method for improving the viability of cells grown in culture from single cell clones comprising the addition of a supplement of any of claims 1 through 3, or 10 to the cell culture medium.

15. A method for improving the viability of primary cells grown in culture comprising the addition of a supplement of any of claims 1 through 3, or 10 to the cell culture medium.

16. A method for improving the viability of cells after transfection comprising the addition of a supplement of any of claims 1 through 3, or 10 to the cell culture medium prior to, during, or immediately after transfection.

17. A method for improving the viability of cells after cryopreservation comprising the addition of a supplement of any of claims 1 through 3, or 10 to the cell culture medium prior to, during, or immediately after cryopreservation or thawing.

18. A method for improving the yield of a recombinant product produced from cells in culture comprising the addition of a supplement of any of claims 1 through 3, or 10 to the cell culture medium.

19. The supplement of any one of claims 1 through 3, or 10, wherein said first protein is recombinant human serum albumin.

20. The method of claim 12, wherein the cells are stem cells, or other progenitor cells.

21. The method of claim 17, wherein the cells are tissue culture cells.

22. The method of claim 18, wherein the cells are CHO cells.

23. The method of claim 18, wherein the cells are hybridoma cells.

24. The method of claim 18, wherein the cells are vero cells or other epithelial cells.

25. The supplement of claim 1 which improves the viability of cells grown in a cell culture medium comprising said supplement.

* * * * *

UNITED STATES PATENT AND TRADEMARK OFFICE
CERTIFICATE OF CORRECTION

| | | |
|---|---|---|
| PATENT NO. | : 8,609,416 B2 | Page 1 of 1 |
| APPLICATION NO. | : 12/972112 | |
| DATED | : December 17, 2013 | |
| INVENTOR(S) | : Barnett | |

It is certified that error appears in the above-identified patent and that said Letters Patent is hereby corrected as shown below:

Title page, Item [75], delete:

Michael E. Barnett

And substitute the following:

Micheal E. Barnett

Signed and Sealed this

Fifteenth Day of April, 2014

Michelle K. Lee
*Deputy Director of the United States Patent and Trademark Office*

SEQUENCE LISTING

<160> NUMBER OF SEQ ID NOS: 22

<210> SEQ ID NO 1
<211> LENGTH: 9
<212> TYPE: PRT
<213> ORGANISM: Homo sapiens

<400> SEQUENCE: 1

Asp Ala His Lys Ser Glu Val Ala His
1               5

<210> SEQ ID NO 2
<211> LENGTH: 609
<212> TYPE: PRT
<213> ORGANISM: Homo sapiens

<400> SEQUENCE: 2

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

```
Lys Pro Leu Leu Glu Lys Ser His Cys Ile Ala Glu Val Glu Asn Asp
305                 310                 315                 320

Glu Met Pro Ala Asp Leu Pro Ser Leu Ala Asp Phe Val Glu Ser
            325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 3
<211> LENGTH: 476
<212> TYPE: PRT
<213> ORGANISM: Homo sapiens

<400> SEQUENCE: 3

Met Ala Lys Ala Ala Ala Ile Gly Ile Asp Leu Gly Thr Thr Tyr Ser
1               5                   10                  15

Cys Val Gly Val Phe Gln His Gly Lys Gly Glu Arg Asn Val Leu Ile
            20                  25                  30

Phe Asp Leu Gly Gly Gly Thr Phe Asp Val Ser Ile Leu Thr Ile Asp
        35                  40                  45

Asp Gly Ile Phe Glu Val Lys Ala Thr Ala Gly Asp Thr His Leu Gly
    50                  55                  60

Gly Glu Asp Phe Asp Asn Arg Leu Val Asn His Phe Val Glu Glu Phe
```

```
                65                  70                  75                  80
Lys Arg Lys His Lys Asp Ile Ser Gln Asn Lys Arg Ala Val Arg
                    85                  90                  95

Arg Leu Arg Thr Ala Cys Glu Arg Ala Lys Arg Thr Leu Ser Ser Ser
                100                 105                 110

Thr Gln Ala Ser Leu Glu Ile Asp Ser Leu Phe Glu Gly Ile Asp Phe
                115                 120                 125

Tyr Thr Ser Ile Thr Arg Ala Arg Phe Glu Glu Leu Cys Ser Asp Leu
                130                 135                 140

Phe Arg Ser Thr Leu Glu Pro Val Glu Lys Ala Leu Arg Asp Ala Lys
145                 150                 155                 160

Leu Asp Lys Ala Gln Ile His Asp Leu Val Leu Val Gly Gly Ser Thr
                165                 170                 175

Arg Ile Pro Lys Val Gln Lys Leu Leu Gln Asp Phe Phe Asn Gly Arg
                180                 185                 190

Asp Leu Asn Lys Ser Ile Asn Pro Asp Glu Ala Val Ala Tyr Gly Ala
                195                 200                 205

Ala Val Gln Ala Ala Ile Leu Met Gly Asp Lys Ser Glu Asn Val Gln
                210                 215                 220

Asp Leu Leu Leu Leu Asp Val Ala Pro Leu Ser Leu Gly Leu Glu Thr
225                 230                 235                 240

Ala Gly Gly Val Met Thr Ala Leu Ile Lys Arg Asn Ser Thr Ile Pro
                245                 250                 255

Thr Lys Gln Thr Gln Ile Phe Thr Thr Tyr Ser Asp Asn Gln Pro Gly
                260                 265                 270

Val Leu Ile Gln Val Tyr Glu Gly Glu Arg Ala Met Thr Lys Asp Asn
                275                 280                 285

Asn Leu Leu Gly Arg Phe Glu Leu Ser Gly Ile Pro Pro Ala Pro Arg
                290                 295                 300

Gly Val Pro Gln Ile Glu Val Thr Phe Asp Ile Asp Ala Asn Gly Ile
305                 310                 315                 320

Leu Asn Val Thr Ala Thr Asp Lys Ser Thr Gly Lys Ala Asn Lys Ile
                325                 330                 335

Thr Ile Thr Asn Asp Lys Gly Arg Leu Ser Lys Glu Ile Glu Arg
                340                 345                 350

Met Val Gln Glu Ala Glu Lys Tyr Lys Ala Glu Asp Glu Val Gln Arg
                355                 360                 365

Glu Arg Val Ser Ala Lys Asn Ala Leu Glu Ser Tyr Ala Phe Asn Met
                370                 375                 380

Lys Ser Ala Val Glu Asp Glu Gly Leu Lys Gly Lys Ile Ser Glu Ala
385                 390                 395                 400

Asp Lys Lys Lys Val Leu Asp Lys Cys Gln Glu Val Ile Ser Trp Leu
                405                 410                 415

Asp Ala Asn Thr Leu Ala Glu Lys Asp Glu Phe Glu His Lys Arg Lys
                420                 425                 430

Glu Leu Glu Gln Val Cys Asn Pro Ile Ile Ser Gly Leu Tyr Gln Gly
                435                 440                 445

Ala Gly Gly Pro Gly Pro Gly Gly Phe Gly Ala Gln Gly Pro Lys Gly
                450                 455                 460

Gly Ser Gly Ser Gly Pro Thr Ile Glu Glu Val Asp
465                 470                 475

<210> SEQ ID NO 4
<211> LENGTH: 642
```

```
<212> TYPE: PRT
<213> ORGANISM: Drosophila melanogaster

<400> SEQUENCE: 4

Met Pro Ala Ile Gly Ile Asp Leu Gly Thr Thr Tyr Ser Cys Val Gly
1               5                   10                  15

Val Tyr Gln His Gly Lys Val Glu Ile Ile Ala Asn Asp Gln Gly Asn
            20                  25                  30

Arg Thr Thr Pro Ser Tyr Val Ala Phe Thr Asp Ser Glu Arg Leu Ile
        35                  40                  45

Gly Asp Pro Ala Lys Asn Gln Val Ala Met Asn Pro Arg Asn Thr Val
    50                  55                  60

Phe Asp Ala Lys Arg Leu Ile Gly Arg Lys Tyr Asp Asp Pro Lys Ile
65                  70                  75                  80

Ala Glu Asp Met Lys His Trp Pro Phe Lys Val Val Ser Asp Gly Gly
                85                  90                  95

Lys Pro Lys Ile Gly Val Glu Tyr Lys Gly Glu Ser Lys Arg Phe Ala
            100                 105                 110

Pro Glu Glu Ile Ser Ser Met Val Leu Thr Lys Met Lys Glu Thr Ala
        115                 120                 125

Glu Ala Tyr Leu Gly Glu Ser Ile Thr Asp Ala Val Ile Thr Val Pro
    130                 135                 140

Ala Tyr Phe Asn Asp Ser Gln Arg Gln Ala Thr Lys Asp Ala Gly His
145                 150                 155                 160

Ile Ala Gly Leu Asn Val Leu Arg Ile Ile Asn Glu Pro Thr Ala Ala
                165                 170                 175

Ala Leu Ala Tyr Gly Leu Asp Lys Asn Leu Lys Gly Glu Arg Asn Val
            180                 185                 190

Leu Ile Phe Asp Leu Gly Gly Gly Thr Phe Asp Val Ser Ile Leu Thr
        195                 200                 205

Ile Asp Glu Gly Ser Leu Phe Glu Val Arg Ser Thr Ala Gly Asp Thr
    210                 215                 220

His Leu Gly Gly Glu Asp Phe Asp Asn Arg Leu Val Thr His Leu Ala
225                 230                 235                 240

Asp Glu Phe Lys Arg Lys Tyr Lys Lys Asp Leu Arg Ser Asn Pro Arg
                245                 250                 255

Ala Leu Arg Arg Leu Arg Thr Ala Ala Glu Arg Ala Lys Arg Thr Leu
            260                 265                 270

Ser Ser Ser Thr Glu Ala Thr Ile Glu Ile Asp Ala Leu Phe Glu Gly
        275                 280                 285

Gln Asp Phe Tyr Thr Lys Val Ser Arg Ala Arg Phe Glu Glu Leu Cys
    290                 295                 300

Ala Asp Leu Phe Arg Asn Thr Leu Gln Pro Val Glu Lys Ala Leu Asn
305                 310                 315                 320

Asp Ala Lys Met Asp Lys Gly Gln Ile His Asp Ile Val Leu Val Gly
                325                 330                 335

Gly Ser Thr Arg Ile Pro Lys Val Gln Ser Leu Leu Gln Asp Phe Phe
            340                 345                 350

His Gly Lys Asn Leu Asn Leu Ser Ile Asn Pro Asp Glu Ala Val Ala
        355                 360                 365

Tyr Gly Ala Ala Val Gln Ala Ala Ile Leu Ser Gly Asp Gln Ser Gly
    370                 375                 380

Lys Ile Gln Asp Val Leu Leu Val Asp Val Ala Pro Leu Ser Leu Gly
385                 390                 395                 400
```

```
Ile Glu Thr Ala Gly Gly Val Met Thr Lys Leu Ile Glu Arg Asn Cys
            405                 410                 415

Arg Ile Pro Cys Lys Gln Thr Lys Thr Phe Ser Thr Tyr Ala Asp Asn
        420                 425                 430

Gln Pro Gly Val Ser Ile Gln Val Tyr Glu Gly Glu Arg Ala Met Thr
            435                 440                 445

Lys Asp Asn Asn Ala Leu Gly Thr Phe Asp Leu Ser Gly Ile Pro Pro
450                 455                 460

Ala Pro Arg Gly Val Pro Gln Ile Glu Val Thr Phe Asp Leu Asp Ala
465                 470                 475                 480

Asn Gly Ile Leu Asn Val Ser Ala Lys Glu Met Ser Thr Gly Lys Ala
            485                 490                 495

Lys Asn Ile Thr Ile Lys Asn Asp Lys Gly Arg Leu Ser Gln Ala Glu
        500                 505                 510

Ile Asp Arg Met Val Asn Glu Ala Glu Lys Tyr Ala Asp Glu Asp Glu
            515                 520                 525

Lys His Arg Gln Arg Ile Thr Ser Arg Asn Ala Leu Glu Ser Tyr Val
        530                 535                 540

Phe Asn Val Lys Gln Ala Val Glu Gln Ala Pro Ala Gly Lys Leu Asp
545                 550                 555                 560

Glu Ala Asp Lys Asn Ser Val Leu Asp Lys Cys Asn Asp Thr Ile Arg
            565                 570                 575

Trp Leu Asp Ser Asn Thr Thr Ala Glu Lys Glu Glu Phe Asp His Lys
        580                 585                 590

Leu Glu Glu Leu Thr Arg His Cys Ser Pro Ile Met Thr Lys Met His
            595                 600                 605

Gln Gln Gly Ala Gly Ala Gly Ala Gly Gly Pro Gly Ala Asn Cys Gly
        610                 615                 620

Gln Gln Ala Gly Gly Phe Gly Gly Tyr Ser Gly Pro Thr Val Glu Glu
625                 630                 635                 640

Val Asp

<210> SEQ ID NO 5
<211> LENGTH: 649
<212> TYPE: PRT
<213> ORGANISM: Saccharomyces cerevisiae

<400> SEQUENCE: 5

Met Ser Arg Ala Val Gly Ile Asp Leu Gly Thr Thr Tyr Ser Cys Val
1               5                   10                  15

Ala His Phe Ser Asn Asp Arg Val Glu Ile Ile Ala Asn Asp Gln Gly
            20                  25                  30

Asn Arg Thr Thr Pro Ser Tyr Val Ala Phe Thr Asp Thr Glu Arg Leu
        35                  40                  45

Ile Gly Asp Ala Ala Lys Asn Gln Ala Ala Ile Asn Pro His Asn Thr
    50                  55                  60

Val Phe Asp Ala Lys Arg Leu Ile Gly Arg Lys Phe Asp Asp Pro Glu
65                  70                  75                  80

Val Thr Thr Asp Ala Lys His Phe Pro Phe Lys Val Ile Ser Arg Asp
            85                  90                  95

Gly Lys Pro Val Val Gln Val Glu Tyr Lys Gly Glu Thr Lys Thr Phe
        100                 105                 110

Thr Pro Glu Glu Ile Ser Ser Met Val Leu Ser Lys Met Lys Glu Thr
    115                 120                 125

Ala Glu Asn Tyr Leu Gly Thr Thr Val Asn Asp Ala Val Val Thr Val
```

```
                130                 135                 140
Pro Ala Tyr Phe Asn Asp Ser Gln Arg Gln Ala Thr Lys Asp Ala Gly
145                 150                 155                 160

Thr Ile Ala Gly Met Asn Val Leu Arg Ile Ile Asn Glu Pro Thr Ala
                165                 170                 175

Ala Ala Ile Ala Tyr Gly Leu Asp Lys Lys Gly Arg Ala Glu His Asn
            180                 185                 190

Val Leu Ile Phe Asp Leu Gly Gly Thr Phe Asp Val Ser Leu Leu
        195                 200                 205

Ser Ile Asp Glu Gly Val Phe Glu Val Lys Ala Thr Ala Gly Asp Thr
210                 215                 220

His Leu Gly Gly Glu Asp Phe Asp Asn Arg Leu Val Asn His Leu Ala
225                 230                 235                 240

Thr Glu Phe Lys Arg Lys Thr Lys Lys Asp Ile Ser Asn Asn Gln Arg
                245                 250                 255

Ser Leu Arg Arg Leu Arg Thr Ala Ala Glu Arg Ala Lys Arg Ala Leu
            260                 265                 270

Ser Ser Ser Ser Gln Thr Ser Ile Glu Ile Asp Ser Leu Phe Glu Gly
        275                 280                 285

Met Asp Phe Tyr Thr Ser Leu Thr Arg Ala Arg Phe Glu Glu Leu Cys
290                 295                 300

Ala Asp Leu Phe Arg Ser Thr Leu Glu Pro Val Glu Lys Val Leu Lys
305                 310                 315                 320

Asp Ser Lys Leu Asp Lys Ser Gln Ile Asp Glu Ile Val Leu Val Gly
                325                 330                 335

Gly Ser Thr Arg Ile Pro Lys Ile Gln Lys Leu Val Ser Asp Phe Phe
            340                 345                 350

Asn Gly Lys Glu Pro Asn Arg Ser Ile Asn Pro Asp Glu Ala Val Ala
        355                 360                 365

Tyr Gly Ala Ala Val Gln Ala Ala Ile Leu Thr Gly Asp Gln Ser Thr
370                 375                 380

Lys Thr Gln Asp Leu Leu Leu Leu Asp Val Ala Pro Leu Ser Leu Gly
385                 390                 395                 400

Ile Glu Thr Ala Gly Gly Ile Met Thr Lys Leu Ile Pro Arg Asn Ser
                405                 410                 415

Thr Ile Pro Thr Lys Lys Ser Glu Thr Phe Ser Thr Tyr Ala Asp Asn
            420                 425                 430

Gln Pro Gly Val Leu Ile Gln Val Phe Glu Gly Glu Arg Thr Arg Thr
        435                 440                 445

Lys Asp Asn Asn Leu Leu Gly Lys Phe Glu Leu Ser Gly Ile Pro Pro
450                 455                 460

Ala Pro Arg Gly Val Pro Gln Ile Asp Val Thr Phe Asp Ile Asp Ala
465                 470                 475                 480

Asn Gly Ile Leu Asn Val Ser Ala Leu Glu Lys Gly Thr Gly Lys Ser
                485                 490                 495

Asn Lys Ile Thr Ile Thr Asn Asp Lys Gly Arg Leu Ser Lys Asp Asp
            500                 505                 510

Ile Asp Arg Met Val Ser Glu Ala Glu Lys Tyr Arg Ala Asp Asp Glu
        515                 520                 525

Arg Glu Ala Glu Arg Val Gln Ala Lys Asn Gln Leu Glu Ser Tyr Ala
530                 535                 540

Phe Thr Leu Lys Asn Thr Ile Asn Glu Ala Ser Phe Lys Glu Lys Val
545                 550                 555                 560
```

```
Gly Glu Asp Asp Ala Lys Arg Leu Glu Thr Ala Ser Gln Glu Thr Ile
            565                 570                 575

Asp Trp Leu Asp Ala Ser Gln Ala Ala Ser Thr Asp Glu Tyr Lys Asp
            580                 585                 590

Arg Gln Lys Glu Leu Glu Gly Ile Ala Asn Pro Ile Met Thr Lys Phe
            595                 600                 605

Tyr Gly Ala Gly Ala Gly Ala Gly Pro Gly Ala Gly Glu Ser Gly Gly
            610                 615                 620

Phe Pro Gly Ser Met Pro Asn Ser Gly Ala Thr Gly Gly Gly Glu Asp
625                 630                 635                 640

Thr Gly Pro Thr Val Glu Glu Val Asp
            645

<210> SEQ ID NO 6
<211> LENGTH: 649
<212> TYPE: PRT
<213> ORGANISM: Oryza sativa

<400> SEQUENCE: 6

Met Ala Gly Lys Gly Glu Gly Pro Ala Ile Gly Ile Asp Leu Gly Thr
1               5                   10                  15

Thr Tyr Ser Cys Val Gly Val Trp Gln His Asp Arg Val Glu Ile Ile
            20                  25                  30

Ala Asn Asp Gln Gly Asn Arg Thr Thr Pro Ser Tyr Val Gly Phe Thr
            35                  40                  45

Asp Ser Glu Arg Leu Ile Gly Asp Ala Ala Lys Asn Gln Val Ala Met
        50                  55                  60

Asn Pro Ile Asn Thr Val Phe Asp Ala Lys Arg Leu Ile Gly Arg Arg
65                  70                  75                  80

Phe Ser Asp Ala Ser Val Gln Ser Asp Ile Lys Leu Trp Pro Phe Lys
                85                  90                  95

Val Ile Ala Gly Pro Gly Asp Lys Pro Met Ile Val Gln Tyr Lys
            100                 105                 110

Gly Glu Glu Lys Gln Phe Ala Ala Glu Glu Ile Ser Ser Met Val Leu
            115                 120                 125

Ile Lys Met Arg Glu Ile Ala Glu Ala Tyr Leu Gly Thr Thr Ile Lys
            130                 135                 140

Asn Ala Val Val Thr Val Pro Ala Tyr Phe Asn Asp Ser Gln Arg Gln
145                 150                 155                 160

Ala Thr Lys Asp Ala Gly Val Ile Ala Gly Leu Asn Val Met Arg Ile
                165                 170                 175

Ile Asn Glu Pro Thr Ala Ala Ala Ile Ala Tyr Gly Leu Asp Lys Lys
            180                 185                 190

Ala Thr Ser Val Gly Glu Lys Asn Val Leu Ile Phe Asp Leu Gly Gly
            195                 200                 205

Gly Thr Phe Asp Val Ser Leu Leu Thr Ile Glu Glu Gly Ile Phe Glu
            210                 215                 220

Val Lys Ala Thr Ala Gly Asp Thr His Leu Gly Gly Glu Asp Phe Asp
225                 230                 235                 240

Asn Arg Met Val Asn His Phe Val Gln Glu Phe Lys Arg Lys Asn Lys
                245                 250                 255

Lys Asp Ile Thr Gly Asn Pro Arg Ala Leu Arg Arg Leu Arg Thr Ala
            260                 265                 270

Cys Glu Arg Ala Lys Arg Thr Leu Ser Ser Thr Ala Gln Thr Thr Ile
            275                 280                 285
```

```
Glu Ile Asp Ser Leu Tyr Glu Gly Ile Asp Phe Tyr Ser Thr Ile Thr
            290                 295                 300

Arg Ala Arg Phe Glu Glu Leu Asn Met Asp Leu Phe Arg Lys Cys Met
305                 310                 315                 320

Glu Pro Val Glu Lys Cys Leu Arg Asp Ala Lys Met Asp Lys Ser Ser
                325                 330                 335

Val His Asp Val Val Leu Val Gly Gly Ser Thr Arg Ile Pro Arg Val
                340                 345                 350

Gln Gln Leu Leu Gln Asp Phe Phe Asn Gly Lys Glu Leu Cys Lys Asn
            355                 360                 365

Ile Asn Pro Asp Glu Ala Val Ala Tyr Gly Ala Ala Val Gln Ala Ala
            370                 375                 380

Ile Leu Ser Gly Glu Gly Asn Glu Lys Val Gln Asp Leu Leu Leu Leu
385                 390                 395                 400

Asp Val Thr Pro Leu Ser Leu Gly Leu Glu Thr Ala Gly Gly Val Met
                405                 410                 415

Thr Val Leu Ile Pro Arg Asn Thr Thr Ile Pro Thr Lys Lys Glu Gln
                420                 425                 430

Val Phe Ser Thr Tyr Ser Asp Asn Gln Pro Gly Val Leu Ile Gln Val
            435                 440                 445

Tyr Glu Gly Glu Arg Thr Arg Thr Arg Asp Asn Asn Leu Leu Gly Lys
450                 455                 460

Phe Glu Leu Ser Gly Ile Pro Pro Ala Pro Arg Gly Val Pro Gln Ile
465                 470                 475                 480

Thr Val Cys Phe Asp Ile Asp Ala Asn Gly Ile Leu Asn Val Ser Ala
                485                 490                 495

Glu Asp Lys Thr Thr Gly Gln Lys Asn Lys Ile Thr Ile Thr Asn Asp
                500                 505                 510

Lys Gly Arg Leu Ser Lys Glu Glu Ile Glu Lys Met Val Gln Glu Ala
                515                 520                 525

Glu Lys Tyr Lys Ser Glu Asp Glu Glu His Lys Lys Lys Val Glu Ser
            530                 535                 540

Lys Asn Ala Leu Glu Asn Tyr Ala Tyr Asn Met Arg Asn Thr Ile Lys
545                 550                 555                 560

Asp Glu Lys Ile Ala Ser Lys Leu Pro Ala Ala Asp Lys Lys Lys Ile
                565                 570                 575

Glu Asp Ala Ile Asp Gln Ala Ile Gln Trp Leu Asp Gly Asn Gln Leu
                580                 585                 590

Ala Glu Ala Asp Glu Phe Asp Asp Lys Met Lys Glu Leu Glu Gly Ile
            595                 600                 605

Cys Asn Pro Ile Ile Ala Lys Met Tyr Gln Gly Ala Gly Ala Asp Met
610                 615                 620

Ala Gly Gly Met Asp Glu Asp Ala Pro Ala Gly Gly Ser Gly
625                 630                 635                 640

Ala Gly Pro Lys Ile Glu Glu Val Asp
                645

<210> SEQ ID NO 7
<211> LENGTH: 653
<212> TYPE: PRT
<213> ORGANISM: Oryza sativa

<400> SEQUENCE: 7

Met Ala Gly Asn Lys Gly Glu Gly Pro Ala Ile Gly Ile Asp Leu Gly
1               5                   10                  15
```

```
Thr Thr Tyr Ser Cys Val Gly Val Trp Gln His Asp Arg Val Glu Ile
             20                  25                  30

Ile Ala Asn Asp Gln Gly Asn Arg Thr Thr Pro Ser Tyr Val Ala Phe
             35                  40                  45

Thr Asp Thr Glu Arg Leu Ile Gly Asp Ala Ala Lys Asn Gln Val Ala
 50                  55                  60

Met Asn Pro Thr Asn Thr Val Phe Asp Ala Lys Arg Leu Ile Gly Arg
 65                  70                  75                  80

Arg Phe Ser Asp Pro Ser Val Gln Ala Asp Met Lys Met Trp Pro Phe
                 85                  90                  95

Lys Val Val Pro Gly Pro Ala Asp Lys Pro Met Ile Val Val Thr Tyr
             100                 105                 110

Lys Gly Glu Glu Lys Lys Phe Ser Ala Glu Glu Ile Ser Ser Met Val
             115                 120                 125

Leu Thr Lys Met Lys Glu Ile Ala Glu Ala Phe Leu Ser Thr Thr Ile
             130                 135                 140

Lys Asn Ala Val Ile Thr Val Pro Ala Tyr Phe Asn Asp Ser Gln Arg
145                 150                 155                 160

Gln Ala Thr Lys Asp Ala Gly Val Ile Ser Gly Leu Asn Val Met Arg
                 165                 170                 175

Ile Ile Asn Glu Pro Thr Ala Ala Ala Ile Ala Tyr Gly Leu Asp Lys
             180                 185                 190

Lys Ala Ala Ser Thr Gly Glu Lys Asn Val Leu Ile Phe Asp Leu Gly
             195                 200                 205

Gly Gly Thr Phe Asp Val Ser Ile Leu Thr Ile Glu Glu Gly Ile Phe
             210                 215                 220

Glu Val Lys Ala Thr Ala Gly Asp Thr His Leu Gly Gly Glu Asp Phe
225                 230                 235                 240

Asp Asn Arg Met Val Asn His Phe Val Gln Glu Phe Lys Arg Lys His
                 245                 250                 255

Lys Lys Asp Ile Thr Gly Asn Pro Arg Ala Leu Arg Arg Leu Arg Thr
             260                 265                 270

Ala Cys Glu Arg Ala Lys Arg Thr Leu Ser Ser Thr Ala Gln Thr Thr
             275                 280                 285

Ile Glu Ile Asp Ser Leu Tyr Glu Gly Ile Asp Phe Tyr Ala Thr Ile
             290                 295                 300

Thr Arg Ala Arg Phe Glu Glu Leu Asn Met Asp Leu Phe Arg Arg Cys
305                 310                 315                 320

Met Glu Pro Val Glu Lys Cys Leu Arg Asp Ala Lys Met Asp Lys Ala
                 325                 330                 335

Gln Ile His Asp Val Val Leu Val Gly Gly Ser Thr Arg Ile Pro Lys
             340                 345                 350

Val Gln Gln Leu Leu Gln Asp Phe Phe Asn Gly Lys Glu Leu Cys Lys
             355                 360                 365

Ser Ile Asn Pro Asp Glu Ala Val Ala Tyr Gly Ala Ala Val Gln Ala
             370                 375                 380

Ala Ile Leu Ser Gly Gly Asn Gln Arg Val Gln Asp Leu Leu Leu Leu
385                 390                 395                 400

Leu Asp Val Thr Pro Leu Ser Leu Gly Leu Thr Ala Gly Gly Val
                 405                 410                 415

Met Thr Val Leu Ile Pro Arg Asn Thr Thr Ile Pro Thr Lys Lys Glu
             420                 425                 430

Gln Val Phe Ser Thr Tyr Ser Asp Asn Gln Pro Gly Val Leu Ile Gln
             435                 440                 445
```

```
Val Tyr Glu Gly Glu Arg Thr Arg Thr Lys Asp Asn Asn Leu Leu Gly
        450                 455                 460

Lys Phe Glu Leu Thr Gly Ile Pro Pro Ala Pro Arg Gly Val Pro Gln
465                 470                 475                 480

Ile Asn Val Thr Phe Asp Ile Asp Ala Asn Gly Ile Leu Asn Val Ser
                485                 490                 495

Ala Glu Asp Lys Thr Thr Gly Lys Lys Asn Lys Ile Thr Ile Thr Asn
            500                 505                 510

Asp Lys Gly Arg Leu Ser Lys Glu Glu Ile Glu Arg Met Val Gln Glu
        515                 520                 525

Ala Glu Lys Tyr Lys Ala Glu Asp Glu Gln Val Arg His Lys Val Glu
    530                 535                 540

Ala Arg Asn Ala Leu Glu Asn Tyr Ala Tyr Asn Met Arg Asn Thr Val
545                 550                 555                 560

Arg Asp Glu Lys Ile Ala Ser Lys Leu Pro Ala Asp Asp Lys Lys Lys
                565                 570                 575

Ile Glu Asp Ala Ile Glu Asp Ala Ile Lys Trp Leu Asp Gly Asn Gln
            580                 585                 590

Leu Ala Glu Ala Asp Glu Phe Glu Asp Lys Met Lys Glu Leu Glu Ser
        595                 600                 605

Leu Cys Asn Pro Ile Ile Ser Lys Met Tyr Gln Gly Gly Ala Gly Gly
    610                 615                 620

Pro Ala Gly Met Asp Glu Asp Ala Pro Asn Gly Ser Ala Gly Thr Gly
625                 630                 635                 640

Gly Gly Ser Gly Ala Gly Pro Lys Ile Glu Glu Val Asp
                645                 650

<210> SEQ ID NO 8
<211> LENGTH: 648
<212> TYPE: PRT
<213> ORGANISM: Nicotiana tabacum

<400> SEQUENCE: 8

Met Ala Gly Lys Gly Glu Gly Pro Ala Ile Gly Ile Asp Leu Gly Thr
1               5                   10                  15

Thr Tyr Ser Cys Val Gly Val Trp Gln His Asp Arg Val Glu Ile Ile
                20                  25                  30

Ala Asn Asp Gln Gly Asn Arg Thr Thr Pro Ser Tyr Val Gly Phe Thr
            35                  40                  45

Asp Ser Glu Arg Leu Ile Gly Asp Ala Ala Lys Asn Gln Val Ala Met
        50                  55                  60

Asn Pro Ile Asn Thr Val Phe Asp Ala Lys Arg Leu Ile Gly Arg Arg
65                  70                  75                  80

Phe Ser Asp Ala Ser Val Gln Ser Asp Ile Lys Leu Trp Pro Phe Lys
                85                  90                  95

Val Ile Ser Gly Pro Gly Asp Lys Pro Met Ile Val Val Asn Tyr Lys
            100                 105                 110

Gly Glu Glu Lys Gln Phe Ala Ala Glu Glu Ile Ser Ser Met Val Leu
        115                 120                 125

Ile Lys Met Lys Glu Ile Ala Glu Ala Phe Leu Gly Ser Thr Val Lys
    130                 135                 140

Asn Ala Val Val Thr Val Pro Ala Tyr Phe Asn Asp Ser Gln Arg Gln
145                 150                 155                 160

Ala Thr Lys Asp Ala Gly Val Ile Ser Gly Leu Asn Val Met Arg Ile
                165                 170                 175
```

```
Ile Asn Glu Pro Thr Ala Ala Ala Ile Ala Tyr Gly Leu Asp Lys Lys
            180                 185                 190

Ala Thr Ser Val Gly Glu Lys Asn Val Leu Ile Phe Asp Leu Gly Gly
        195                 200                 205

Gly Thr Phe Asp Val Ser Leu Leu Thr Ile Glu Gly Ile Phe Glu
        210                 215                 220

Val Lys Ala Thr Ala Gly Asp Thr His Leu Gly Gly Glu Asp Phe Asp
225                 230                 235                 240

Asn Arg Met Val Asn His Phe Val Gln Glu Phe Lys Arg Lys His Lys
                245                 250                 255

Lys Asp Ile Thr Gly Asn Pro Arg Ala Leu Arg Arg Leu Arg Thr Ala
                260                 265                 270

Cys Glu Arg Ala Lys Arg Thr Leu Ser Ser Thr Ala Gln Thr Thr Ile
                275                 280                 285

Glu Ile Asp Ser Leu Tyr Glu Gly Val Asp Phe Tyr Ser Thr Ile Thr
                290                 295                 300

Arg Ala Arg Phe Glu Glu Leu Asn Met Asp Leu Phe Arg Lys Cys Met
305                 310                 315                 320

Glu Pro Val Glu Lys Cys Leu Arg Asp Ala Lys Met Asp Lys Ser Thr
                325                 330                 335

Val His Asp Val Val Leu Val Gly Gly Ser Thr Arg Ile Pro Lys Val
                340                 345                 350

Gln Gln Leu Leu Gln Asp Phe Phe Asn Gly Lys Glu Leu Cys Lys Ser
                355                 360                 365

Ile Asn Pro Asp Glu Ala Val Ala Tyr Gly Ala Ala Val Gln Ala Ala
370                 375                 380

Ile Leu Ser Gly Gly Asn Glu Lys Val Gln Asp Leu Leu Leu Leu
385                 390                 395                 400

Asp Val Thr Pro Leu Ser Leu Gly Leu Glu Thr Ala Gly Gly Val Met
                405                 410                 415

Thr Val Leu Ile Pro Arg Asn Thr Thr Ile Pro Thr Lys Lys Glu Gln
                420                 425                 430

Val Phe Ser Thr Tyr Ser Asp Asn Gln Pro Gly Val Leu Ile Gln Val
                435                 440                 445

Tyr Glu Gly Glu Arg Ala Arg Thr Arg Asp Asn Asn Leu Leu Gly Lys
                450                 455                 460

Phe Glu Leu Ser Gly Ile Pro Pro Ala Pro Arg Gly Val Pro Gln Ile
465                 470                 475                 480

Thr Val Cys Phe Asp Ile Asp Ala Asn Gly Ile Leu Asn Val Ser Ala
                485                 490                 495

Glu Asp Lys Thr Thr Gly Gln Lys Asn Lys Ile Thr Ile Thr Asn Asp
                500                 505                 510

Lys Gly Arg Leu Ser Lys Glu Glu Ile Glu Lys Met Val Gln Glu Ala
                515                 520                 525

Glu Lys Tyr Lys Ala Glu Asp Glu His Lys Lys Val Glu Ala
                530                 535                 540

Lys Asn Ala Leu Glu Asn Tyr Ala Tyr Asn Met Arg Asn Thr Ile Lys
545                 550                 555                 560

Asp Glu Lys Ile Gly Ser Lys Leu Ser Ser Asp Asp Lys Lys Ile
                565                 570                 575

Glu Asp Ala Ile Asp Gln Ala Ile Ser Trp Leu Asp Ser Asn Gln Leu
                580                 585                 590

Ala Glu Ala Asp Glu Phe Glu Asp Lys Met Lys Glu Leu Glu Ser Ile
```

```
                595             600             605
Cys Asn Pro Ile Ile Ala Lys Met Tyr Gln Gly Ala Gly Gly Glu Ala
        610             615             620

Gly Ala Pro Met Asp Asp Ala Pro Pro Ala Gly Gly Ser Ser Ala
625             630             635             640

Gly Pro Lys Ile Glu Glu Val Asp
                645

<210> SEQ ID NO 9
<211> LENGTH: 587
<212> TYPE: PRT
<213> ORGANISM: Homo sapiens

<400> SEQUENCE: 9

Ala Met Asn Pro Thr Asn Thr Val Phe Asp Ala Lys Arg Leu Ile Gly
1               5                   10                  15

Arg Arg Phe Asp Asp Ala Val Val Gln Ser Asp Met Lys His Trp Pro
            20                  25                  30

Phe Met Val Val Asn Asp Ala Gly Arg Pro Lys Val Gln Val Glu Tyr
        35                  40                  45

Lys Gly Glu Thr Lys Ser Phe Tyr Pro Glu Glu Val Ser Ser Met Val
50                  55                  60

Leu Thr Lys Met Lys Glu Ile Ala Glu Ala Tyr Leu Gly Lys Thr Val
65                  70                  75                  80

Thr Asn Ala Val Val Thr Val Pro Ala Tyr Phe Asn Asp Ser Gln Arg
                85                  90                  95

Gln Ala Thr Lys Asp Ala Gly Thr Ile Ala Gly Leu Asn Val Leu Arg
            100                 105                 110

Ile Ile Asn Glu Pro Thr Ala Ala Ala Ile Ala Tyr Gly Leu Asp Lys
        115                 120                 125

Lys Val Gly Ala Glu Arg Asn Val Leu Ile Phe Asp Leu Gly Gly Gly
130                 135                 140

Thr Phe Asp Val Ser Ile Leu Thr Ile Glu Asp Gly Ile Phe Glu Val
145                 150                 155                 160

Lys Ser Thr Ala Gly Asp Thr His Leu Gly Gly Glu Asp Phe Asp Asn
                165                 170                 175

Arg Met Val Asn His Phe Ile Ala Glu Phe Lys Arg Lys His Lys Lys
            180                 185                 190

Asp Ile Ser Glu Asn Lys Arg Ala Val Arg Arg Leu Arg Thr Ala Cys
        195                 200                 205

Glu Arg Ala Lys Arg Thr Leu Ser Ser Ser Thr Gln Ala Ser Ile Glu
210                 215                 220

Ile Asp Ser Leu Tyr Glu Gly Ile Asp Phe Tyr Thr Ser Ile Thr Arg
225                 230                 235                 240

Ala Arg Phe Glu Glu Leu Asn Ala Asp Leu Phe Arg Gly Thr Leu Asp
                245                 250                 255

Pro Val Glu Lys Ala Leu Arg Asp Ala Lys Leu Asp Lys Ser Gln Ile
            260                 265                 270

His Asp Ile Val Leu Val Gly Gly Ser Thr Arg Ile Pro Lys Ile Gln
        275                 280                 285

Lys Leu Leu Gln Asp Phe Phe Asn Gly Lys Glu Leu Asn Lys Ser Ile
290                 295                 300

Asn Pro Asp Glu Ala Val Ala Tyr Gly Ala Ala Val Gln Ala Ala Ile
305                 310                 315                 320

Leu Ser Gly Asp Lys Ser Glu Asn Val Gln Asp Leu Leu Leu Leu Asp
```

```
                    325                 330                 335
Val Thr Pro Leu Ser Leu Gly Ile Glu Thr Ala Gly Val Met Thr
                340                 345                 350

Val Leu Ile Lys Arg Asn Thr Thr Ile Pro Thr Lys Gln Thr Gln Thr
            355                 360                 365

Phe Thr Thr Tyr Ser Asp Asn Gln Pro Gly Val Leu Ile Gln Val Tyr
        370                 375                 380

Glu Gly Glu Arg Ala Met Thr Lys Asp Asn Asn Leu Leu Gly Lys Phe
385                 390                 395                 400

Glu Leu Thr Gly Ile Pro Pro Ala Pro Arg Gly Val Pro Gln Ile Glu
                405                 410                 415

Val Thr Phe Asp Ile Asp Ala Asn Gly Ile Leu Asn Val Ser Ala Val
            420                 425                 430

Asp Lys Ser Thr Gly Lys Glu Asn Lys Ile Thr Ile Thr Asn Asp Lys
        435                 440                 445

Gly Arg Leu Ser Lys Glu Asp Ile Glu Arg Met Val Gln Glu Ala Glu
    450                 455                 460

Lys Tyr Lys Ala Glu Asp Glu Lys Gln Arg Asp Lys Val Ser Ser Lys
465                 470                 475                 480

Asn Ser Leu Glu Ser Tyr Ala Phe Asn Met Lys Ala Thr Val Glu Asp
                485                 490                 495

Glu Lys Leu Gln Gly Lys Ile Asn Asp Glu Asp Lys Gln Lys Ile Leu
            500                 505                 510

Asp Lys Cys Asn Glu Ile Ile Asn Trp Leu Asp Lys Asn Gln Thr Ala
        515                 520                 525

Glu Lys Glu Glu Phe Glu His Gln Lys Glu Leu Glu Lys Val Cys
    530                 535                 540

Asn Pro Ile Ile Thr Lys Leu Tyr Gln Ser Ala Gly Gly Met Pro Gly
545                 550                 555                 560

Gly Met Pro Gly Gly Phe Pro Gly Gly Gly Ala Pro Pro Ser Gly Gly
                565                 570                 575

Ala Ser Ser Gly Pro Thr Ile Glu Glu Val Asp
            580                 585

<210> SEQ ID NO 10
<211> LENGTH: 804
<212> TYPE: PRT
<213> ORGANISM: Drosophila melanogaster

<400> SEQUENCE: 10

Met Ser Val Ile Gly Ile Asp Phe Gly Asn Glu Ser Cys Tyr Val Ala
1               5                   10                  15

Ala Ala Arg Ser Gly Gly Ile Glu Thr Leu Ala Asn Asp Tyr Ser Leu
            20                  25                  30

Arg Ala Thr Pro Ser Phe Val Ala Phe Asp Gly Lys Lys Arg Ile Ile
        35                  40                  45

Gly Val Ala Ala Lys Asn Gln Gln Val Thr Asn Met Lys Asn Thr Val
    50                  55                  60

Gly Gly Phe Lys Arg Leu Leu Gly Arg Lys Phe Asn Asp Pro His Val
65                  70                  75                  80

Gln His Glu Leu Thr Ser Ile Pro Ala Arg Val Glu Ala Arg Gly Asp
                85                  90                  95

Gly Ser Ile Gly Ile Lys Val Asn Tyr Leu Gly Glu Asp Gln His Phe
            100                 105                 110

Gly Pro Glu Gln Leu Thr Ala Met Leu Phe Thr Lys Leu Lys Glu Thr
```

```
                 115                 120                 125
Ser Ala Ala Met Gln Thr Gln Val Asn Asp Cys Val Ile Ala Cys
130                 135                 140

Pro Val Phe Phe Thr Asn Ala Glu Arg Lys Ala Leu Leu Asp Ala Ala
145                 150                 155                 160

Gln Ile Ala Gly Leu Asn Val Leu Arg Leu Met Asn Glu Thr Thr Ala
                165                 170                 175

Thr Ala Leu Ala Tyr Gly Phe Tyr Lys Asn Asp Leu Phe Glu Asp Lys
                180                 185                 190

Pro Arg Asn Val Ile Phe Val Asp Phe Gly His Ser Ser Leu Gln Ala
            195                 200                 205

Ser Ala Cys Ala Phe Thr Lys Gly Lys Leu Lys Met Leu Ala Ser Thr
210                 215                 220

Trp Asp Gln Ile Gly Gly Arg Asp Ile Asp Leu Ala Leu Gly Asp Tyr
225                 230                 235                 240

Phe Ala Lys Glu Phe Gln Glu Arg Tyr Lys Ile Asn Ala Lys Thr Asn
                245                 250                 255

Ala Arg Ala Asn Leu Arg Leu Leu Thr Glu Ile Glu Lys Leu Lys Lys
            260                 265                 270

Gln Met Ser Ala Asn Ser Thr Lys Leu Pro Leu Asn Ile Glu Cys Phe
        275                 280                 285

Leu Asp Asp Ile Asp Val Ser Ser Met Gln Arg Ser Gln Met Glu
290                 295                 300

Glu Leu Cys Ala Pro Val Leu Gln Arg Val Glu Gln Thr Phe Lys Arg
305                 310                 315                 320

Leu Leu Ala Glu Ser Lys Leu Gln Leu Asp Asp Ile His Ser Val Glu
                325                 330                 335

Ile Val Gly Gly Ser Ser Arg Ile Pro Ser Val Lys Gln Leu Ile Glu
            340                 345                 350

Gln Val Phe Asn Lys Pro Ala Ser Thr Thr Leu Asn Gln Asp Glu Ala
        355                 360                 365

Val Ser Arg Gly Ala Ala Leu Gln Cys Ala Ile Met Ser Pro Ala Val
370                 375                 380

Arg Val Arg Glu Phe Gly Val Thr Asp Ile Gln Asn Tyr Ala Val Lys
385                 390                 395                 400

Val Leu Trp Asp Ser Glu Gly Ser Ala Ala Pro Gly Glu Ile Glu Ile
                405                 410                 415

Phe Pro Gln Tyr His Ala Ser Pro Phe Ser Arg Leu Leu Thr Ile Asn
            420                 425                 430

Arg Lys Gly Pro Phe Asn Val Ser Ile Val Tyr Gly Gln Gln Val Pro
        435                 440                 445

Tyr Pro Asp Gln Thr Ile Gly Val Trp Lys Val Lys Asp Val Lys Pro
    450                 455                 460

Thr Glu Arg Gly Glu Gly Gln Asp Val Lys Leu Lys Val Arg Ile Asn
465                 470                 475                 480

Asn Asn Gly Ile Val Leu Ile Ser Ser Ala Thr Leu Val Glu Lys Lys
                485                 490                 495

Glu Ala Glu Glu Ala Ala Ala Ala Glu Gln Ala Ala Ser Glu Glu
            500                 505                 510

Lys Pro Gly Asp Gln Thr Asn Asn Thr Gly Glu Pro Ala Asp Gly Gln
        515                 520                 525

Gln Glu Gly Ala Asp Lys Lys Lys Ala Ser Lys Ala Thr Glu Leu
    530                 535                 540
```

```
Pro Leu Glu Cys Thr Thr His Gly Phe Ser Pro Val Asp Leu Ser Asn
545                 550                 555                 560

Tyr Thr Gln Gln Glu Ser Lys Met Ile Gly Asn Asp Gln Lys Glu Thr
                565                 570                 575

Glu Arg Ile Asp Ala Lys Asn Ala Leu Glu Glu Phe Val Tyr Asp Met
            580                 585                 590

Arg Asn Lys Leu Gln Gly Gly Pro Phe Glu Arg Tyr Val Val Glu Ala
        595                 600                 605

Glu Arg Glu Lys Ile Val Ser Gln Leu Asn Asp Leu Glu Asn Trp Leu
610                 615                 620

Tyr Glu Asp Gly Glu Asp Cys Glu Arg Asp Ile Tyr Thr Ser Arg Leu
625                 630                 635                 640

Gln Ala Leu His Gln Lys Thr Asp Pro Ile Lys Leu Arg Ala Ser Asp
                645                 650                 655

Tyr Glu Gln Gly Pro Ala Ala Phe Asp Glu Leu Lys Asn Ser Ile Ala
            660                 665                 670

Ile Ala Arg Leu Ala Val Ala Glu Phe Arg Lys Gly Val Pro Lys Tyr
        675                 680                 685

Asp His Leu Thr Glu Thr Glu Phe Ile Asn Ile Ser Glu Thr Ala Asp
690                 695                 700

Lys Ala Gln Ser Trp Leu Asp Ala Asn Leu Pro Lys Phe Thr Gln Ser
705                 710                 715                 720

Pro Arg Thr Ala Asp Ser Pro Val Gln Ile Ser Ala Val Arg Gln Glu
                725                 730                 735

Val Gln Thr Leu Asn Ser Cys Val Ser Val Ile Asn Arg Ala Lys
            740                 745                 750

Pro Lys Pro Thr Pro Ala Lys Thr Ala Thr Pro Pro Lys Asp Glu Ala
        755                 760                 765

Asn Ala Glu Gln Asn Gly Gly Glu Pro Ala Ala Asn Ser Gly Asp Lys
770                 775                 780

Met Asp Val Asp Asn Asn Gly Gln Ser Ala Ala Gly Asn Asp Pro Ser
785                 790                 795                 800

Met Glu Val Glu

<210> SEQ ID NO 11
<211> LENGTH: 668
<212> TYPE: PRT
<213> ORGANISM: Saccharomyces cerevisiae

<400> SEQUENCE: 11

Gly Pro Met Ser Thr Pro Phe Gly Leu Asp Leu Gly Asn Asn Asn Ser
1               5                   10                  15

Val Leu Ala Val Ala Arg Asn Arg Gly Ile Asp Ile Val Val Asn Glu
            20                  25                  30

Val Ser Asn Arg Ser Thr Pro Ser Val Val Gly Phe Gly Pro Lys Asn
        35                  40                  45

Arg Tyr Leu Gly Glu Thr Gly Lys Asn Lys Gln Thr Ser Asn Ile Lys
    50                  55                  60

Asn Thr Val Ala Asn Leu Lys Arg Ile Ile Gly Leu Asp Tyr His His
65                  70                  75                  80

Pro Asp Phe Glu Gln Glu Ser Lys His Phe Thr Ser Lys Leu Val Glu
                85                  90                  95

Leu Asp Asp Lys Lys Thr Gly Ala Glu Val Arg Phe Ala Gly Glu Lys
            100                 105                 110

His Val Phe Ser Ala Thr Gln Leu Ala Ala Met Phe Ile Asp Lys Val
```

```
                115              120               125
Lys Asp Thr Val Lys Gln Asp Thr Lys Ala Asn Ile Thr Asp Val Cys
        130              135               140
Ile Ala Val Pro Pro Trp Tyr Thr Glu Glu Gln Arg Tyr Asn Ile Ala
145              150               155                       160
Asp Ala Ala Arg Ile Ala Gly Leu Asn Pro Val Arg Ile Val Asn Asp
                165              170               175
Val Thr Ala Ala Gly Val Ser Tyr Gly Ile Phe Lys Thr Asp Leu Pro
        180              185               190
Glu Gly Glu Glu Lys Pro Arg Ile Val Ala Phe Val Asp Ile Gly His
            195              200               205
Ser Ser Tyr Thr Cys Ser Ile Met Ala Phe Lys Lys Gly Gln Leu Lys
        210              215               220
Val Leu Gly Thr Ala Cys Asp Lys His Phe Gly Gly Arg Asp Phe Asp
225              230               235                       240
Leu Ala Ile Thr Glu His Phe Ala Asp Glu Phe Lys Thr Lys Tyr Lys
                245              250               255
Ile Asp Ile Arg Glu Asn Pro Lys Ala Tyr Asn Arg Ile Leu Thr Ala
        260              265               270
Ala Glu Lys Leu Lys Lys Val Leu Ser Ala Asn Thr Asn Ala Pro Phe
        275              280               285
Ser Val Glu Ser Val Met Asn Asp Val Asp Val Ser Ser Gln Leu Ser
        290              295               300
Arg Glu Glu Leu Glu Glu Leu Val Lys Pro Leu Leu Glu Arg Val Thr
305              310               315                       320
Glu Pro Val Thr Lys Ala Leu Ala Gln Ala Lys Leu Ser Ala Glu Glu
                325              330               335
Val Asp Phe Val Glu Ile Ile Gly Gly Thr Thr Arg Ile Pro Thr Leu
                340              345               350
Lys Gln Ser Ile Ser Glu Ala Phe Gly Lys Pro Leu Ser Thr Thr Leu
        355              360               365
Asn Gln Asp Glu Ala Ile Ala Lys Gly Ala Ala Phe Ile Cys Ala Ile
        370              375               380
His Ser Pro Thr Leu Arg Val Arg Pro Phe Lys Phe Glu Asp Ile His
385              390               395                       400
Pro Tyr Ser Val Ser Tyr Ser Trp Asp Lys Gln Val Glu Asp Glu Asp
                405              410               415
His Met Glu Val Phe Pro Ala Gly Ser Ser Phe Pro Ser Thr Lys Leu
                420              425               430
Ile Thr Leu Asn Arg Thr Gly Asp Phe Ser Met Ala Ala Ser Tyr Thr
        435              440               445
Asp Ile Thr Gln Leu Pro Pro Asn Thr Pro Glu Gln Ile Ala Asn Trp
        450              455               460
Glu Ile Thr Gly Val Gln Leu Pro Glu Gly Gln Asp Ser Val Pro Val
465              470               475                       480
Lys Leu Lys Leu Arg Cys Asp Pro Ser Gly Leu His Thr Ile Glu Glu
                485              490               495
Ala Tyr Thr Ile Glu Asp Ile Glu Val Glu Glu Pro Ile Pro Leu Pro
                500              505               510
Glu Asp Ala Pro Glu Asp Ala Glu Gln Glu Phe Lys Lys Val Thr Lys
        515              520               525
Thr Val Lys Lys Asp Asp Leu Thr Ile Val Ala His Thr Phe Gly Leu
        530              535               540
```

```
Asp Ala Lys Lys Leu Asn Glu Leu Ile Glu Lys Glu Asn Glu Met Leu
545                 550                 555                 560

Ala Gln Asp Lys Leu Val Ala Glu Thr Glu Asp Arg Lys Asn Thr Leu
            565                 570                 575

Glu Glu Tyr Ile Tyr Thr Leu Arg Gly Lys Leu Glu Glu Tyr Ala
                580                 585                 590

Pro Phe Ala Ser Asp Ala Glu Lys Thr Lys Leu Gln Gly Met Leu Asn
            595                 600                 605

Lys Ala Glu Glu Trp Leu Tyr Asp Glu Gly Phe Asp Ser Ile Lys Ala
            610                 615                 620

Lys Tyr Ile Ala Lys Tyr Glu Glu Leu Ala Ser Leu Gly Asn Ile Ile
625                 630                 635                 640

Arg Gly Arg Tyr Leu Ala Lys Glu Glu Lys Lys Gln Ala Ile Arg
                645                 650                 655

Ser Lys Gln Glu Ala Ser Gln Met Ala Ala Met Ala
            660                 665

<210> SEQ ID NO 12
<211> LENGTH: 684
<212> TYPE: PRT
<213> ORGANISM: Oryza sativa

<400> SEQUENCE: 12

Met Ala Ile Gly Ser Leu Ile Ala Ser Arg Leu Ala Arg Ser Thr Gly
1               5                   10                  15

His Ala Leu Ala Ser Ala Ala Ser Gln Ala Pro Met Ala Arg His Ala
                20                  25                  30

Ala Ala Ser Pro Leu Leu Ser Arg Leu Gly Ser Val Ala Arg Ala Phe
            35                  40                  45

Ser Ser Lys Pro Ala Ala Ala Asp Val Ile Gly Ile Asp Leu Gly Thr
        50                  55                  60

Thr Asn Ser Cys Val Ser Val Met Glu Gly Lys Thr Pro Arg Val Ile
65                  70                  75                  80

Glu Asn Ala Glu Gly Ala Arg Thr Thr Pro Ser Ile Val Ala Lys Asn
                85                  90                  95

Gln Asn Gly Asp Leu Leu Val Gly Ile Thr Ala Ser Arg Gln Ala Val
            100                 105                 110

Thr Asn Ala Gln Asn Thr Val Arg Gly Ser Lys Arg Leu Ile Gly Arg
        115                 120                 125

Thr Phe Asp Asp Pro Gln Thr Gln Lys Glu Met Lys Met Val Pro Tyr
130                 135                 140

Lys Ile Val Arg Gly Pro Asn Gly Asp Ala Trp Val Glu Met Gly Gly
145                 150                 155                 160

Gln Gln Tyr Ser Pro Ser Gln Ile Gly Ala Phe Val Leu Thr Lys Met
                165                 170                 175

Lys Glu Thr Ala Glu Ala Phe Leu Gly Lys Thr Val Ser Lys Ala Val
            180                 185                 190

Ile Thr Val Pro Ala Tyr Phe Asn Asp Ala Gln Arg Gln Ala Thr Lys
        195                 200                 205

Asp Ala Gly Arg Ile Ala Gly Leu Glu Val Met Arg Ile Ile Asn Glu
210                 215                 220

Pro Thr Ala Ala Ala Leu Ser Tyr Gly Met Asn Asn Lys Glu Gly Leu
225                 230                 235                 240

Ile Ala Val Phe Asp Leu Gly Gly Gly Thr Phe Asp Val Ser Ile Leu
                245                 250                 255
```

```
Glu Ile Ser Asn Gly Val Phe Glu Val Lys Ala Thr Asn Gly Asp Thr
            260                 265                 270

Phe Leu Gly Gly Glu Asp Phe Asp Gly Ala Leu Leu Asp Tyr Leu Val
            275                 280                 285

Ser Glu Phe Lys Lys Ser Asp Asn Ile Asp Leu Ser Lys Asp Lys Leu
            290                 295                 300

Ala Leu Gln Arg Leu Arg Glu Ala Ala Glu Lys Ala Lys Val Glu Leu
305                 310                 315                 320

Ser Ser Thr Met Gln Thr Glu Ile Asn Leu Pro Phe Ile Thr Ala Asp
            325                 330                 335

Ala Thr Gly Ala Lys His Phe Asn Ile Thr Leu Thr Arg Ser Lys Phe
            340                 345                 350

Glu Ser Leu Val Gln Ser Leu Ile Glu Arg Thr Arg Ile Pro Cys Val
            355                 360                 365

Asn Cys Leu Lys Asp Ala Gly Val Ser Ala Lys Asp Ile Asp Glu Val
            370                 375                 380

Leu Leu Val Gly Gly Met Thr Arg Val Pro Lys Val Gln Asp Ile Val
385                 390                 395                 400

Ser Gln Ile Phe Asn Lys Thr Pro Ser Lys Gly Val Asn Pro Asp Glu
            405                 410                 415

Ala Val Ala Met Gly Ala Ala Ile Gln Gly Gly Ile Leu Arg Gly Asp
            420                 425                 430

Val Lys Glu Leu Leu Leu Leu Asp Val Thr Pro Leu Ser Leu Gly Ile
            435                 440                 445

Glu Thr Leu Gly Gly Ile Phe Thr Arg Leu Ile Asn Arg Asn Thr Thr
            450                 455                 460

Ile Pro Thr Lys Lys Ser Gln Val Phe Ser Thr Ala Ala Asp Asn Gln
465                 470                 475                 480

Thr Gln Val Gly Ile Lys Val Leu Gln Gly Glu Arg Glu Met Ala Thr
            485                 490                 495

Asp Asn Lys Leu Leu Gly Glu Phe Gln Leu Glu Gly Ile Pro Pro Ala
            500                 505                 510

Pro Arg Gly Met Pro Gln Ile Glu Val Thr Phe Asp Ile Asp Ala Asn
            515                 520                 525

Gly Ile Val Lys Val Ser Ala Lys Asp Lys Ser Thr Gly Lys Glu Gln
            530                 535                 540

Glu Ile Thr Ile Lys Ser Ser Gly Gly Leu Ser Glu Ser Asp Ile Glu
545                 550                 555                 560

Lys Met Val Arg Glu Ala Glu Leu His Ser Gln Lys Asp Gln Glu Arg
            565                 570                 575

Lys Ser Leu Ile Asp Leu Lys Asn Ser Ala Asp Thr Thr Ile Tyr Ser
            580                 585                 590

Ile Glu Lys Ser Val Ser Glu Tyr Lys Asp Lys Val Pro Ala Glu Val
            595                 600                 605

Thr Asn Glu Ile Gln Ser Ala Val Ser Asp Leu Arg Ala Ala Met Ala
            610                 615                 620

Glu Asp Asp Leu Glu Lys Ile Lys Gln Lys Leu Glu Ala Ala Asn Lys
625                 630                 635                 640

Ala Val Ser Lys Ile Gly Glu His Met Gln Gln Gly Gly Gly Gly
            645                 650                 655

Ser Gly Gly Gly Ser Ser Ser Ser Gly Gly Asp Gln Thr Pro Glu
            660                 665                 670

Ala Glu Tyr Gln Asp Ala Ala Lys Glu Ala Lys Met
            675                 680
```

<210> SEQ ID NO 13
<211> LENGTH: 648
<212> TYPE: PRT
<213> ORGANISM: Nicotiana tabacum

<400> SEQUENCE: 13

```
Met Ala Gly Lys Gly Glu Gly Pro Ala Ile Gly Ile Asp Leu Gly Thr
1               5                   10                  15

Thr Tyr Ser Cys Val Gly Val Trp Gln His Asp Arg Val Glu Ile Ile
            20                  25                  30

Ala Asn Asp Gln Gly Asn Arg Thr Thr Pro Ser Tyr Val Gly Phe Thr
        35                  40                  45

Asp Ser Glu Arg Leu Ile Gly Asp Ala Ala Lys Asn Gln Val Ala Met
    50                  55                  60

Asn Pro Ile Asn Thr Val Phe Asp Ala Lys Arg Leu Ile Gly Arg Arg
65                  70                  75                  80

Phe Ser Asp Ala Ser Val Gln Ser Asp Ile Lys Leu Trp Pro Phe Lys
                85                  90                  95

Gly Ile Ser Gly Pro Gly Asp Lys Pro Met Ile Val Val Asn Tyr Lys
            100                 105                 110

Gly Glu Glu Lys Gln Phe Ala Ala Glu Glu Ile Ser Ser Met Gly Leu
        115                 120                 125

Ile Lys Met Lys Glu Met Ala Glu Ala Phe Leu Gly Ser Thr Val Lys
    130                 135                 140

Asn Ala Val Val Thr Val Pro Ala Tyr Phe Asn Asp Ser Gln Arg Gln
145                 150                 155                 160

Ala Thr Lys Asp Ala Gly Val Ile Ser Gly Leu Asn Val Met Arg Ile
                165                 170                 175

Ile Asn Glu Pro Thr Ala Ala Ala Ile Ala Tyr Gly Leu Asp Lys Lys
            180                 185                 190

Ala Thr Ser Val Gly Glu Lys Asn Val Leu Ile Phe Asp Leu Gly Gly
        195                 200                 205

Gly Thr Phe Asp Val Ser Leu Leu Thr Ile Glu Glu Gly Ile Phe Glu
    210                 215                 220

Val Lys Ala Thr Ala Gly Asp Thr His Leu Gly Gly Glu Asp Phe Asp
225                 230                 235                 240

Asn Arg Met Val Asn His Phe Val Gln Glu Phe Lys Arg Lys His Lys
                245                 250                 255

Lys Asp Ile Thr Gly Asn Pro Arg Ala Leu Arg Arg Leu Arg Thr Ala
            260                 265                 270

Cys Glu Arg Ala Lys Arg Thr Leu Ser Ser Thr Ala Gln Thr Thr Ile
        275                 280                 285

Glu Ile Asp Ser Leu Tyr Glu Gly Val Asp Phe Tyr Ser Thr Ile Thr
    290                 295                 300

Arg Ala Arg Phe Glu Glu Leu Asn Met Asp Leu Phe Arg Lys Cys Met
305                 310                 315                 320

Glu Pro Val Glu Lys Cys Leu Arg Asp Ala Lys Met Asp Lys Ser Thr
                325                 330                 335

Val His Asp Val Val Leu Val Gly Gly Ser Thr Arg Ile Pro Lys Val
            340                 345                 350

Gln Gln Leu Leu Gln Asp Phe Phe Asn Gly Lys Glu Leu Cys Lys Ser
        355                 360                 365

Ile Asn Pro Asp Glu Ala Val Ala Tyr Gly Ala Ala Val Gln Ala Ala
    370                 375                 380
```

```
Ile Leu Ser Gly Glu Gly Asn Glu Lys Val Gln Asp Leu Leu Leu Leu
385                 390                 395                 400

Asp Val Thr Pro Leu Ser Leu Gly Leu Glu Thr Ala Gly Gly Val Met
            405                 410                 415

Thr Val Leu Ile Pro Arg Asn Thr Thr Ile Pro Thr Lys Lys Glu Gln
            420                 425                 430

Val Phe Ser Thr Tyr Ser Asp Asn Gln Pro Gly Val Leu Ile Gln Val
        435                 440                 445

Tyr Glu Gly Glu Arg Ala Arg Thr Arg Ala Asn Asn Leu Leu Gly Lys
    450                 455                 460

Phe Glu Leu Ser Gly Ile Pro Pro Ala Pro Arg Gly Val Pro Gln Ile
465                 470                 475                 480

Thr Val Cys Phe Asp Ile Asp Ala Asn Gly Ile Leu Asn Val Ser Ala
            485                 490                 495

Glu Asp Lys Thr Thr Gly Gln Lys Asn Lys Ile Thr Ile Thr Asn Asp
            500                 505                 510

Lys Gly Arg Leu Ser Lys Glu Glu Ile Glu Lys Met Val Gln Glu Ala
        515                 520                 525

Glu Lys Tyr Lys Ala Glu Asp Glu His Lys Lys Lys Val Glu Ala
    530                 535                 540

Lys Asn Ala Leu Glu Asn Tyr Ala Tyr Asn Met Arg Asn Thr Ile Lys
545                 550                 555                 560

Asp Glu Lys Ile Gly Ser Lys Leu Ser Ser Asp Lys Lys Lys Ile
            565                 570                 575

Glu Asp Ala Ile Asp Gln Ala Ile Ser Trp Leu Asp Ser Asn Gln Leu
            580                 585                 590

Ala Glu Ala Asp Glu Phe Glu Asp Lys Met Lys Glu Leu Glu Ser Ile
        595                 600                 605

Cys Asn Pro Ile Ile Ala Lys Met Tyr Gln Gly Ala Gly Gly Glu Ala
    610                 615                 620

Gly Ala Pro Met Asp Asp Asp Ala Pro Pro Ala Gly Gly Ser Ser Ala
625                 630                 635                 640

Gly Pro Lys Ile Glu Glu Val Asp
                645

<210> SEQ ID NO 14
<211> LENGTH: 654
<212> TYPE: PRT
<213> ORGANISM: Homo sapiens

<400> SEQUENCE: 14

Met Lys Leu Ser Leu Val Ala Ala Met Leu Leu Leu Leu Ser Ala Ala
1               5                   10                  15

Arg Ala Glu Glu Glu Asp Lys Lys Glu Asp Val Gly Thr Val Val Gly
            20                  25                  30

Ile Asp Leu Gly Thr Thr Tyr Ser Cys Val Gly Val Phe Lys Asn Gly
        35                  40                  45

Arg Val Glu Ile Ile Ala Asn Asp Gln Gly Asn Arg Ile Thr Pro Ser
    50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
            85                  90                  95

Arg Leu Ile Gly Arg Thr Trp Asn Asp Pro Ser Val Gln Gln Asp Ile
        100                 105                 110
```

-continued

```
Lys Phe Leu Pro Phe Lys Val Val Glu Lys Thr Lys Pro Tyr Ile
            115                 120                 125
Gln Val Asp Ile Gly Gly Gln Thr Lys Thr Phe Ala Pro Glu Glu
        130                 135                 140
Ile Ser Ala Met Val Leu Thr Lys Met Lys Glu Thr Ala Glu Ala Tyr
145                 150                 155                 160
Leu Gly Lys Lys Val Thr His Ala Val Val Thr Val Pro Ala Tyr Phe
                    165                 170                 175
Asn Asp Ala Gln Arg Gln Ala Thr Lys Asp Ala Gly Thr Ile Ala Gly
                180                 185                 190
Leu Asn Val Met Arg Ile Ile Asn Glu Pro Thr Ala Ala Ile Ala
            195                 200                 205
Tyr Gly Leu Asp Lys Arg Glu Gly Glu Lys Asn Ile Leu Val Phe Asp
        210                 215                 220
Leu Gly Gly Gly Thr Phe Asp Val Ser Leu Leu Thr Ile Asp Asn Gly
225                 230                 235                 240
Val Phe Glu Val Val Ala Thr Asn Gly Asp Thr His Leu Gly Gly Glu
                    245                 250                 255
Asp Phe Asp Gln Arg Val Met Glu His Phe Ile Lys Leu Tyr Lys Lys
                260                 265                 270
Lys Thr Gly Lys Asp Val Arg Lys Asp Asn Arg Ala Val Gln Lys Leu
            275                 280                 285
Arg Arg Glu Val Glu Lys Ala Lys Arg Ala Leu Ser Ser Gln His Gln
        290                 295                 300
Ala Arg Ile Glu Ile Glu Ser Phe Tyr Glu Gly Glu Asp Phe Ser Glu
305                 310                 315                 320
Thr Leu Thr Arg Ala Lys Phe Glu Glu Leu Asn Met Asp Leu Phe Arg
                    325                 330                 335
Ser Thr Met Lys Pro Val Gln Lys Val Leu Glu Asp Ser Asp Leu Lys
                340                 345                 350
Lys Ser Asp Ile Asp Glu Ile Val Leu Val Gly Gly Ser Thr Arg Ile
            355                 360                 365
Pro Lys Ile Gln Gln Leu Val Lys Glu Phe Phe Asn Gly Lys Glu Pro
        370                 375                 380
Ser Arg Gly Ile Asn Pro Asp Glu Ala Val Ala Tyr Gly Ala Ala Val
385                 390                 395                 400
Gln Ala Gly Val Leu Ser Gly Asp Gln Asp Thr Gly Asp Leu Val Leu
                    405                 410                 415
Leu Asp Val Cys Pro Leu Thr Leu Gly Ile Glu Thr Val Gly Gly Val
                420                 425                 430
Met Thr Lys Leu Ile Pro Arg Asn Thr Val Pro Thr Lys Lys Ser
            435                 440                 445
Gln Ile Phe Ser Thr Ala Ser Asp Asn Gln Pro Thr Val Thr Ile Lys
        450                 455                 460
Val Tyr Glu Gly Glu Arg Pro Leu Thr Lys Asp Asn His Leu Leu Gly
465                 470                 475                 480
Thr Phe Asp Leu Thr Gly Ile Pro Pro Ala Pro Arg Gly Val Pro Gln
                    485                 490                 495
Ile Glu Val Thr Phe Glu Ile Asp Val Asn Gly Ile Leu Arg Val Thr
                500                 505                 510
Ala Glu Asp Lys Gly Thr Gly Asn Lys Asn Lys Ile Thr Ile Thr Asn
            515                 520                 525
Asp Gln Asn Arg Leu Thr Pro Glu Glu Ile Glu Arg Met Val Asn Asp
```

```
                    530              535              540
Ala Glu Lys Phe Ala Glu Asp Lys Leu Lys Glu Arg Ile Asp
545                 550              555              560

Thr Arg Asn Glu Leu Glu Ser Tyr Ala Tyr Ser Leu Lys Asn Gln Ile
            565                 570              575

Gly Asp Lys Glu Lys Leu Gly Gly Lys Leu Ser Ser Glu Asp Lys Glu
                580              585              590

Thr Met Glu Lys Ala Val Glu Glu Lys Ile Glu Trp Leu Glu Ser His
            595              600              605

Gln Asp Ala Asp Ile Glu Asp Phe Lys Ala Lys Lys Glu Leu Glu
            610              615              620

Glu Ile Val Gln Pro Ile Ile Ser Lys Leu Tyr Gly Ser Ala Gly Pro
625             630              635              640

Pro Pro Thr Gly Glu Glu Asp Thr Ala Glu Lys Asp Glu Leu
                645              650
```

<210> SEQ ID NO 15
<211> LENGTH: 682
<212> TYPE: PRT
<213> ORGANISM: Saccharomyces cerevisiae

<400> SEQUENCE: 15

```
Met Phe Phe Asn Arg Leu Ser Ala Gly Lys Leu Leu Val Pro Leu Ser
1               5                   10                  15

Val Val Leu Tyr Ala Leu Phe Val Ile Leu Pro Leu Gln Asn Ser
            20                  25                  30

Phe His Ser Ser Asn Val Leu Val Arg Gly Ala Asp Val Glu Asn
        35                  40                  45

Tyr Gly Thr Val Ile Gly Ile Asp Leu Gly Thr Thr Tyr Ser Cys Val
50                  55                  60

Ala Val Met Lys Asn Gly Lys Thr Glu Ile Leu Ala Asn Glu Gln Gly
65                  70                  75                  80

Asn Arg Ile Thr Pro Ser Tyr Val Ala Phe Thr Asp Asp Glu Arg Leu
                85                  90                  95

Ile Gly Asp Ala Ala Lys Asn Gln Val Ala Ala Asn Pro Gln Asn Thr
            100                 105                 110

Ile Phe Asp Ile Lys Arg Leu Ile Gly Leu Lys Tyr Asn Asp Arg Ser
        115                 120                 125

Val Gln Lys Asp Ile Lys His Leu Pro Phe Asn Val Val Asn Lys Asp
130                 135                 140

Gly Lys Pro Ala Val Glu Val Ser Val Lys Gly Glu Lys Lys Val Phe
145                 150                 155                 160

Thr Pro Glu Glu Ile Ser Gly Met Ile Leu Gly Lys Met Lys Gln Ile
                165                 170                 175

Ala Glu Asp Tyr Leu Gly Thr Lys Val Thr His Ala Val Val Thr Val
            180                 185                 190

Pro Ala Tyr Phe Asn Asp Ala Gln Arg Gln Ala Thr Lys Asp Ala Gly
        195                 200                 205

Thr Ile Ala Gly Leu Asn Val Leu Arg Ile Val Asn Glu Pro Thr Ala
    210                 215                 220

Ala Ala Ile Ala Tyr Gly Leu Asp Lys Ser Asp Lys Glu His Gln Ile
225                 230                 235                 240

Ile Val Tyr Asp Leu Gly Gly Gly Thr Phe Asp Val Ser Leu Leu Ser
                245                 250                 255

Ile Glu Asn Gly Val Phe Glu Val Gln Ala Thr Ser Gly Asp Thr His
```

-continued

```
                260                 265                 270
Leu Gly Gly Glu Asp Phe Asp Tyr Lys Ile Val Arg Gln Leu Ile Lys
            275                 280                 285
Ala Phe Lys Lys Lys His Gly Ile Asp Val Ser Asp Asn Asn Lys Ala
        290                 295                 300
Leu Ala Lys Leu Lys Arg Glu Ala Glu Lys Ala Lys Arg Ala Leu Ser
305                 310                 315                 320
Ser Gln Met Ser Thr Arg Ile Glu Ile Asp Ser Phe Val Asp Gly Ile
                325                 330                 335
Asp Leu Ser Glu Thr Leu Thr Arg Ala Lys Phe Glu Glu Leu Asn Leu
            340                 345                 350
Asp Leu Phe Lys Lys Thr Leu Lys Pro Val Glu Lys Val Leu Gln Asp
        355                 360                 365
Ser Gly Leu Glu Lys Lys Asp Val Asp Ile Val Leu Val Gly Gly
        370                 375                 380
Ser Thr Arg Ile Pro Lys Val Gln Gln Leu Leu Glu Ser Tyr Phe Asp
385                 390                 395                 400
Gly Lys Lys Ala Ser Lys Gly Ile Asn Pro Asp Glu Ala Val Ala Tyr
                405                 410                 415
Gly Ala Ala Val Gln Ala Gly Val Leu Ser Gly Glu Glu Gly Val Glu
            420                 425                 430
Asp Ile Val Leu Leu Asp Val Asn Ala Leu Thr Leu Gly Ile Glu Thr
        435                 440                 445
Thr Gly Gly Val Met Thr Pro Leu Ile Lys Arg Asn Thr Ala Ile Pro
    450                 455                 460
Thr Lys Lys Ser Gln Ile Phe Ser Thr Ala Val Asp Asn Gln Pro Thr
465                 470                 475                 480
Val Met Ile Lys Val Tyr Glu Gly Glu Arg Ala Met Ser Lys Asp Asn
                485                 490                 495
Asn Leu Leu Gly Lys Phe Glu Leu Thr Gly Ile Pro Pro Ala Pro Arg
            500                 505                 510
Gly Val Pro Gln Ile Glu Val Thr Phe Ala Leu Asp Ala Asn Gly Ile
        515                 520                 525
Leu Lys Val Ser Ala Thr Asp Lys Gly Thr Gly Lys Ser Glu Ser Ile
    530                 535                 540
Thr Ile Thr Asn Asp Lys Gly Arg Leu Thr Gln Glu Ile Asp Arg
545                 550                 555                 560
Met Val Glu Glu Ala Glu Lys Phe Ala Ser Glu Asp Ala Ser Ile Lys
                565                 570                 575
Ala Lys Val Glu Ser Arg Asn Lys Leu Glu Asn Tyr Ala His Ser Leu
            580                 585                 590
Lys Asn Gln Val Asn Gly Asp Leu Gly Glu Lys Leu Glu Glu Glu Asp
        595                 600                 605
Lys Glu Thr Leu Leu Asp Ala Ala Asn Asp Val Leu Glu Trp Leu Asp
    610                 615                 620
Asp Asn Phe Glu Thr Ala Ile Ala Glu Asp Phe Asp Glu Lys Phe Glu
625                 630                 635                 640
Ser Leu Ser Lys Val Ala Tyr Pro Ile Thr Ser Lys Leu Tyr Gly Gly
                645                 650                 655
Ala Asp Gly Ser Gly Ala Ala Asp Tyr Asp Asp Glu Asp Glu Asp Asp
            660                 665                 670
Asp Gly Asp Tyr Phe Glu His Asp Glu Leu
        675                 680
```

-continued

```
<210> SEQ ID NO 16
<211> LENGTH: 642
<212> TYPE: PRT
<213> ORGANISM: Drosophila melanogaster

<400> SEQUENCE: 16

Met Pro Ala Ile Gly Ile Asp Leu Gly Thr Thr Tyr Ser Cys Val Gly
1               5                   10                  15

Val Tyr Gln His Gly Lys Val Glu Ile Ile Ala Asn Asp Gln Gly Asn
            20                  25                  30

Arg Thr Thr Pro Ser Tyr Val Ala Phe Thr Asp Ser Glu Arg Leu Ile
        35                  40                  45

Gly Asp Pro Ala Lys Asn Gln Val Ala Met Asn Pro Arg Asn Thr Val
    50                  55                  60

Phe Asp Ala Lys Arg Leu Ile Gly Arg Lys Tyr Asp Asp Pro Lys Ile
65                  70                  75                  80

Ala Glu Asp Met Lys His Trp Pro Phe Lys Val Val Ser Asp Gly Gly
                85                  90                  95

Lys Pro Lys Ile Gly Val Glu Tyr Lys Gly Glu Ser Lys Arg Phe Ala
            100                 105                 110

Pro Glu Glu Ile Ser Ser Met Val Leu Thr Lys Met Lys Glu Thr Ala
        115                 120                 125

Glu Ala Tyr Leu Gly Glu Ser Ile Thr Asp Ala Val Ile Thr Val Pro
    130                 135                 140

Ala Tyr Phe Asn Asp Ser Gln Arg Gln Ala Thr Lys Asp Ala Gly His
145                 150                 155                 160

Ile Ala Gly Leu Asn Val Leu Arg Ile Ile Asn Glu Pro Thr Ala Ala
                165                 170                 175

Ala Leu Ala Tyr Gly Leu Asp Lys Asn Leu Lys Gly Glu Arg Asn Val
            180                 185                 190

Leu Ile Phe Asp Leu Gly Gly Gly Thr Phe Asp Val Ser Ile Leu Thr
        195                 200                 205

Ile Asp Glu Gly Ser Leu Phe Glu Val Arg Ser Thr Ala Gly Asp Thr
    210                 215                 220

His Leu Gly Gly Glu Asp Phe Asp Asn Arg Leu Val Thr His Leu Ala
225                 230                 235                 240

Asp Glu Phe Lys Arg Lys Tyr Lys Lys Asp Leu Arg Ser Asn Pro Arg
                245                 250                 255

Ala Leu Arg Arg Leu Arg Thr Ala Ala Glu Arg Ala Lys Arg Thr Leu
            260                 265                 270

Ser Ser Ser Thr Glu Ala Thr Ile Glu Ile Asp Ala Leu Phe Glu Gly
        275                 280                 285

Gln Asp Phe Tyr Thr Lys Val Ser Arg Ala Arg Phe Glu Glu Leu Cys
    290                 295                 300

Ala Asp Leu Phe Arg Asn Thr Leu Gln Pro Val Glu Lys Ala Leu Asn
305                 310                 315                 320

Asp Ala Lys Met Asp Lys Gly Gln Ile His Asp Ile Val Leu Val Gly
                325                 330                 335

Gly Ser Thr Arg Ile Pro Lys Val Gln Ser Leu Leu Gln Asp Phe Phe
            340                 345                 350

His Gly Lys Asn Leu Asn Leu Ser Ile Asn Pro Asp Glu Ala Val Ala
        355                 360                 365

Tyr Gly Ala Ala Val Gln Ala Ala Ile Leu Ser Gly Asp Gln Ser Gly
    370                 375                 380
```

```
Lys Ile Gln Asp Val Leu Leu Val Asp Val Ala Pro Leu Ser Leu Gly
385                 390                 395                 400

Ile Glu Thr Ala Gly Val Met Thr Lys Leu Ile Glu Arg Asn Cys
                405                 410                 415

Arg Ile Pro Cys Lys Gln Thr Lys Thr Phe Ser Thr Tyr Ala Asp Asn
                420                 425                 430

Gln Pro Gly Val Ser Ile Gln Val Tyr Glu Gly Arg Ala Met Thr
                435                 440                 445

Lys Asp Asn Asn Ala Leu Gly Thr Phe Asp Leu Ser Gly Ile Pro Pro
450                 455                 460

Ala Pro Arg Gly Val Pro Gln Ile Glu Val Thr Phe Asp Leu Asp Ala
465                 470                 475                 480

Asn Gly Ile Leu Asn Val Ser Ala Lys Glu Met Ser Thr Gly Lys Ala
                485                 490                 495

Lys Asn Ile Thr Ile Lys Asn Asp Lys Gly Arg Leu Ser Gln Ala Glu
                500                 505                 510

Ile Asp Arg Met Val Asn Glu Ala Glu Lys Tyr Ala Asp Glu Asp
                515                 520                 525

Lys His Arg Gln Arg Ile Thr Ser Arg Asn Ala Leu Glu Ser Tyr Val
                530                 535                 540

Phe Asn Val Lys Gln Ala Val Glu Gln Ala Pro Ala Gly Lys Leu Asp
545                 550                 555                 560

Glu Ala Asp Lys Asn Ser Val Leu Asp Lys Cys Asn Asp Thr Ile Arg
                565                 570                 575

Trp Leu Asp Ser Asn Thr Thr Ala Glu Lys Glu Glu Phe Asp His Lys
                580                 585                 590

Leu Glu Glu Leu Thr Arg His Cys Ser Pro Ile Met Thr Lys Met His
                595                 600                 605

Gln Gln Gly Ala Gly Ala Gly Ala Gly Pro Gly Ala Asn Cys Gly
                610                 615                 620

Gln Gln Ala Gly Gly Phe Gly Gly Tyr Ser Gly Pro Thr Val Glu Glu
625                 630                 635                 640

Val Asp

<210> SEQ ID NO 17
<211> LENGTH: 667
<212> TYPE: PRT
<213> ORGANISM: Nicotiana tabacum

<400> SEQUENCE: 17

Met Ala Gly Gly Ala Trp Asn Arg Arg Thr Ser Leu Ile Val Phe Gly
1               5                   10                  15

Ile Val Leu Phe Gly Cys Leu Phe Ala Phe Ser Ile Ala Thr Glu Glu
                20                  25                  30

Ala Thr Lys Leu Gly Thr Val Ile Gly Ile Asp Leu Gly Thr Thr Tyr
                35                  40                  45

Ser Cys Val Gly Val Tyr Lys Asn Gly His Val Glu Ile Ile Ala Asn
                50                  55                  60

Asp Gln Gly Asn Arg Ile Thr Pro Ser Trp Val Ala Phe Thr Asp Gly
65                  70                  75                  80

Glu Arg Leu Ile Gly Glu Ala Ala Lys Asn Leu Ala Ala Val Asn Pro
                85                  90                  95

Glu Arg Thr Val Phe Asp Val Lys Arg Leu Ile Gly Arg Lys Phe Asp
                100                 105                 110

Asp Lys Glu Val Gln Arg Asp Met Lys Leu Val Pro Tyr Lys Ile Val
```

-continued

```
            115                 120                 125
Asn Lys Asp Gly Lys Pro Tyr Ile Gln Val Lys Ile Lys Asp Gly Glu
            130                 135                 140
Thr Lys Ile Phe Ser Pro Glu Glu Ile Ser Ala Met Ile Leu Thr Lys
145                 150                 155                 160
Met Lys Glu Thr Ala Glu Ala Tyr Leu Gly Lys Ile Lys Asp Ala
            165                 170                 175
Val Val Thr Val Pro Ala Tyr Phe Asn Asp Ala Gln Arg Gln Ala Thr
            180                 185                 190
Lys Asp Ala Gly Val Ile Ala Gly Leu Asn Val Ala Arg Ile Ile Asn
            195                 200                 205
Glu Pro Thr Ala Ala Ala Ile Ala Tyr Gly Leu Asp Lys Lys Gly Gly
            210                 215                 220
Glu Lys Asn Ile Leu Val Phe Asp Leu Gly Gly Gly Thr Phe Asp Val
225                 230                 235                 240
Ser Ile Leu Thr Ile Asp Asn Gly Val Phe Glu Val Leu Ser Thr Asn
            245                 250                 255
Gly Asp Thr His Leu Gly Gly Glu Asp Phe Asp Gln Arg Ile Met Glu
            260                 265                 270
Tyr Phe Ile Lys Leu Ile Lys Lys Lys His Gly Lys Asp Ile Ser Lys
            275                 280                 285
Asp Asn Arg Ala Leu Gly Lys Leu Arg Arg Glu Ala Glu Arg Ala Lys
            290                 295                 300
Arg Ala Leu Ser Ser Gln His Gln Val Arg Val Glu Ile Glu Ser Leu
305                 310                 315                 320
Phe Asp Gly Val Asp Phe Ser Glu Pro Leu Thr Arg Ala Arg Phe Glu
            325                 330                 335
Glu Leu Asn Asn Asp Leu Phe Arg Lys Thr Met Gly Pro Val Lys Lys
            340                 345                 350
Ala Met Asp Asp Ala Gly Leu Glu Lys Thr Gln Ile Asp Glu Ile Val
            355                 360                 365
Leu Val Gly Gly Ser Thr Arg Ile Pro Lys Val Gln Gln Leu Leu Lys
            370                 375                 380
Asp Tyr Phe Asp Gly Lys Glu Pro Asn Lys Gly Val Asn Pro Asp Glu
385                 390                 395                 400
Ala Val Ala Tyr Gly Ala Ala Val Gln Gly Ile Leu Ser Gly Glu
            405                 410                 415
Gly Gly Asp Glu Thr Lys Asp Ile Leu Leu Leu Asp Val Ala Pro Leu
            420                 425                 430
Thr Leu Gly Ile Glu Thr Val Gly Gly Val Met Thr Lys Leu Ile Pro
            435                 440                 445
Arg Asn Thr Val Ile Pro Thr Lys Lys Ser Gln Val Phe Thr Thr Tyr
            450                 455                 460
Gln Asp Gln Gln Thr Thr Val Thr Ile Gln Val Phe Glu Gly Glu Arg
465                 470                 475                 480
Ser Leu Thr Lys Asp Cys Arg Leu Leu Gly Lys Phe Asp Leu Thr Gly
            485                 490                 495
Ile Ala Pro Ala Pro Arg Gly Thr Pro Gln Ile Glu Val Thr Phe Glu
            500                 505                 510
Val Asp Ala Asn Gly Ile Leu Asn Val Lys Ala Glu Asp Lys Ala Ser
            515                 520                 525
Gly Lys Ser Glu Lys Ile Thr Ile Thr Asn Asp Lys Gly Arg Leu Ser
            530                 535                 540
```

```
Gln Glu Glu Ile Glu Arg Met Val Lys Glu Ala Glu Phe Ala Glu
545                 550                 555                 560

Glu Asp Lys Lys Val Lys Glu Arg Ile Asp Ala Arg Asn Ser Leu Glu
                565                 570                 575

Thr Tyr Val Tyr Asn Met Arg Asn Gln Ile Asn Asp Lys Asp Lys Leu
            580                 585                 590

Ala Asp Lys Leu Glu Ser Asp Glu Lys Glu Lys Ile Glu Thr Ala Thr
        595                 600                 605

Lys Glu Ala Leu Glu Trp Leu Asp Asp Asn Gln Ser Ala Glu Lys Glu
610                 615                 620

Asp Tyr Glu Glu Lys Leu Lys Glu Val Glu Ala Val Cys Asn Pro Ile
625                 630                 635                 640

Ile Thr Ala Val Tyr Gln Lys Ser Gly Gly Ala Pro Gly Gly Glu Ser
                645                 650                 655

Gly Ala Ser Glu Asp Asp Asp His Asp Glu Leu
            660                 665
```

<210> SEQ ID NO 18
<211> LENGTH: 663
<212> TYPE: PRT
<213> ORGANISM: Oryza sativa

<400> SEQUENCE: 18

```
Met Asp Arg Val Arg Gly Ser Ala Phe Leu Leu Gly Val Leu Leu Ala
1               5                   10                  15

Gly Ser Leu Phe Ala Phe Ser Val Ala Lys Glu Glu Thr Lys Lys Leu
            20                  25                  30

Gly Thr Val Ile Gly Ile Asp Leu Gly Thr Thr Tyr Ser Cys Val Gly
        35                  40                  45

Val Tyr Lys Asn Gly His Val Glu Ile Ile Ala Asn Asp Gln Gly Asn
    50                  55                  60

Arg Ile Thr Pro Ser Trp Val Ala Phe Thr Asp Ser Glu Arg Leu Ile
65                  70                  75                  80

Gly Glu Ala Ala Lys Asn Gln Ala Ala Val Asn Pro Glu Arg Thr Ile
                85                  90                  95

Phe Asp Val Lys Arg Asp Ile Gly Arg Lys Phe Glu Glu Lys Glu Val
            100                 105                 110

Gln Arg Asp Met Lys Leu Val Pro Tyr Lys Ile Val Asn Lys Ile Gly
        115                 120                 125

Lys Pro Tyr Ile Gln Val Lys Ile Lys Asp Gly Glu Asn Lys Val Phe
    130                 135                 140

Ser Pro Glu Glu Val Ser Ala Met Ile Leu Gly Lys Met Lys Glu Thr
145                 150                 155                 160

Ala Glu Ala Tyr Leu Gly Lys Lys Ile Asn Asp Ala Val Val Thr Val
                165                 170                 175

Pro Ala Tyr Phe Asn Asp Ala Gln Arg Gln Ala Thr Lys Asp Ala Gly
            180                 185                 190

Val Ile Ala Gly Leu Asn Val Ala Arg Ile Ile Asn Glu Pro Thr Ala
        195                 200                 205

Ala Ala Ile Ala Tyr Gly Leu Asp Lys Lys Gly Gly Glu Lys Asn Ile
    210                 215                 220

Leu Val Phe Asp Leu Gly Gly Gly Thr Phe Asp Val Ser Ile Leu Thr
225                 230                 235                 240

Ile Asp Asn Gly Val Phe Glu Val Leu Ala Thr Asn Gly Asp Thr His
                245                 250                 255
```

Leu Gly Gly Glu Asp Phe Asp Gln Arg Ile Met Glu Tyr Phe Ile Lys
            260                 265                 270

Leu Ile Lys Lys Tyr Ser Lys Asp Ile Ser Lys Asp Asn Arg Ala
275                 280                 285

Leu Gly Lys Leu Arg Arg Glu Ala Glu Arg Ala Lys Arg Ala Leu Ser
            290                 295                 300

Asn Gln His Gln Val Arg Val Glu Ile Glu Ser Leu Phe Asp Gly Thr
305                 310                 315                 320

Asp Phe Ser Glu Pro Leu Thr Arg Ala Arg Phe Glu Glu Leu Asn Asn
            325                 330                 335

Asp Leu Phe Arg Lys Thr Met Gly Pro Val Lys Ala Met Asp Asp
            340                 345                 350

Ala Gly Leu Glu Lys Ser Gln Ile His Glu Ile Val Leu Val Gly Gly
            355                 360                 365

Ser Thr Arg Ile Pro Lys Val Gln Gln Leu Leu Arg Asp Tyr Phe Glu
370                 375                 380

Gly Lys Glu Pro Asn Lys Gly Val Asn Pro Asp Glu Ala Val Ala Tyr
385                 390                 395                 400

Gly Ala Ala Val Gln Gly Ser Ile Leu Ser Gly Glu Gly Gly Asp Glu
            405                 410                 415

Thr Lys Asp Ile Leu Leu Leu Asp Val Ala Pro Leu Thr Leu Gly Ile
            420                 425                 430

Glu Thr Val Gly Gly Val Met Thr Lys Leu Ile Pro Arg Asn Thr Val
            435                 440                 445

Ile Pro Thr Lys Lys Ser Gln Val Phe Thr Thr Tyr Gln Asp Gln Gln
450                 455                 460

Thr Thr Val Ser Ile Gln Val Phe Glu Gly Glu Arg Ser Met Thr Lys
465                 470                 475                 480

Asp Cys Arg Leu Leu Gly Lys Phe Asp Leu Ser Gly Ile Pro Ala Ala
            485                 490                 495

Pro Arg Gly Thr Pro Gln Ile Glu Val Thr Phe Glu Val Asp Ala Asn
            500                 505                 510

Gly Ile Leu Asn Val Lys Ala Glu Asp Lys Gly Thr Gly Lys Ser Glu
            515                 520                 525

Lys Ile Thr Ile Thr Asn Glu Lys Gly Arg Leu Ser Gln Glu Glu Ile
530                 535                 540

Asp Arg Met Val Arg Glu Ala Glu Glu Phe Ala Glu Glu Asp Lys Lys
545                 550                 555                 560

Val Lys Glu Arg Ile Asp Ala Arg Asn Gln Leu Glu Thr Tyr Val Tyr
            565                 570                 575

Asn Met Lys Asn Thr Val Gly Asp Lys Asp Lys Leu Ala Asp Lys Leu
            580                 585                 590

Glu Ser Glu Glu Lys Glu Lys Val Glu Glu Ala Leu Lys Glu Ala Leu
            595                 600                 605

Glu Trp Leu Asp Glu Asn Gln Thr Ala Glu Lys Glu Glu Tyr Glu Glu
            610                 615                 620

Lys Leu Lys Glu Val Glu Ala Val Cys Asn Pro Ile Ile Ser Ala Val
625                 630                 635                 640

Tyr Gln Arg Thr Gly Gly Ala Pro Gly Gly Arg Arg Gly Arg Leu
            645                 650                 655

Asp Asp Glu His Asp Glu Leu
            660

<210> SEQ ID NO 19

```
<211> LENGTH: 69
<212> TYPE: PRT
<213> ORGANISM: Oryza sativa

<400> SEQUENCE: 19

Ala Thr Ala Gly Asp Thr His Leu Gly Gly Glu Asp Phe Asp Asn Arg
1               5                   10                  15

Val Val Pro Gly Pro Ala Asp Lys Ser Pro Met Ile Val Val Thr Tyr
            20                  25                  30

Lys Gly Glu Glu Lys Asn Ala Val Ile Thr Val Pro Ala Tyr Phe Asn
        35                  40                  45

Asp Ser Gln Arg Ile Ile Asn Glu Pro Thr Ala Ala Ile Ala Tyr
    50                  55                  60

Gly Leu Asp Lys Lys
65

<210> SEQ ID NO 20
<211> LENGTH: 93
<212> TYPE: PRT
<213> ORGANISM: Oryza sativa

<400> SEQUENCE: 20

Asn Gln Ala Ala Val Asn Pro Glu Arg Asn Gly His Val Glu Ile Ile
1               5                   10                  15

Ala Asn Asp Gln Gly Asn Arg Ile Val Asn Lys Asp Gly Lys Pro Tyr
            20                  25                  30

Ile Gln Val Lys Ile Ile Asn Glu Pro Thr Ala Ala Ile Ala Tyr
        35                  40                  45

Gly Leu Asp Lys Lys Lys Leu Gly Thr Val Ile Gly Ile Asp Leu Gly
    50                  55                  60

Thr Thr Tyr Ser Cys Val Gly Val Tyr Lys Val Glu Ile Glu Ser Leu
65                  70                  75                  80

Phe Asp Gly Thr Asp Ser Phe Ser Glu Pro Leu Thr Arg
                85                  90

<210> SEQ ID NO 21
<211> LENGTH: 56
<212> TYPE: PRT
<213> ORGANISM: Oryza sativa

<400> SEQUENCE: 21

Asn Gln Ala Asp Ser Val Val Tyr Gln Thr Glu Lys Lys Gln Asp Ile
1               5                   10                  15

Thr Ile Thr Gly Ala Ser Thr Leu Pro Lys Asp Glu Val Glu Arg Asp
            20                  25                  30

Val Val Leu Leu Asp Val Thr Pro Leu Ser Leu Ser Gly Leu Glu
        35                  40                  45

Thr Leu Gly Gly Val Met Thr Lys
    50                  55

<210> SEQ ID NO 22
<211> LENGTH: 715
<212> TYPE: PRT
<213> ORGANISM: Oryza sativa

<400> SEQUENCE: 22

Met Ala Ser Phe Thr Ser Gln Leu Gly Ala Met Ala Cys Gly Ala Ala
1               5                   10                  15

Pro Ser Thr Ser Pro Leu Ala Ala Arg Arg Ser Gly Gln Leu Phe Val
            20                  25                  30
```

-continued

Gly Arg Lys Pro Ala Ala Ser Val Gln Met Arg Val Pro Arg Ala
              35                  40                  45

Gly Arg Ala Arg Gly Val Ala Met Arg Val Ala Cys Glu Lys Val Val
 50                  55                  60

Gly Ile Asp Leu Gly Thr Thr Asn Ser Ala Val Ala Ala Met Glu Gly
 65                  70                  75                  80

Gly Lys Pro Thr Val Ile Thr Asn Ala Glu Gly Gln Arg Thr Thr Pro
              85                  90                  95

Ser Val Val Ala Tyr Thr Lys Gly Glu Arg Leu Val Gly Gln Ile
                100                 105                 110

Ala Lys Arg Gln Ala Val Val Asn Pro Glu Asn Thr Phe Phe Ser Val
                115                 120                 125

Lys Arg Phe Ile Gly Arg Lys Met Ala Glu Val Asp Asp Glu Ala Lys
                130                 135                 140

Gln Val Ser Tyr His Val Val Arg Asp Asp Asn Gly Asn Val Lys Leu
145                 150                 155                 160

Asp Cys Pro Ala Ile Gly Lys Gln Phe Ala Ala Glu Ile Ser Ala
                     165                 170                 175

Gln Val Leu Arg Lys Leu Val Asp Asp Ala Ser Lys Phe Leu Asn Asp
                180                 185                 190

Lys Ile Thr Lys Ala Val Val Thr Val Pro Ala Tyr Phe Asn Asp Ser
                195                 200                 205

Gln Arg Thr Ala Thr Lys Asp Ala Gly Arg Ile Ala Gly Leu Glu Val
                210                 215                 220

Leu Arg Ile Ile Asn Glu Pro Thr Ala Ala Ser Leu Ala Tyr Gly Phe
225                 230                 235                 240

Glu Lys Lys Asn Asn Glu Thr Ile Leu Val Phe Asp Leu Gly Gly Gly
                245                 250                 255

Thr Phe Asp Val Ser Val Leu Glu Val Gly Asp Gly Val Phe Glu Val
                260                 265                 270

Leu Ser Thr Ser Gly Asp Thr His Leu Gly Gly Asp Phe Asp Lys
                275                 280                 285

Phe Tyr Phe Cys Trp Val Phe Tyr Phe Gly Ala Met Thr His Glu Thr
                290                 295                 300

Pro Lys Val Val Asp Trp Leu Ala Ser Asn Phe Lys Lys Asp Glu Gly
305                 310                 315                 320

Ile Asp Leu Leu Lys Asp Lys Gln Ala Leu Gln Arg Leu Thr Glu Ala
                325                 330                 335

Ala Glu Lys Ala Lys Met Glu Leu Ser Thr Leu Ser Gln Thr Asn Ile
                340                 345                 350

Ser Leu Pro Phe Ile Thr Ala Thr Ala Asp Gly Pro Lys His Ile Glu
                355                 360                 365

Thr Thr Leu Ser Arg Ala Lys Phe Glu Glu Leu Cys Ser Asp Leu Ile
                370                 375                 380

Asp Arg Leu Lys Thr Pro Val Thr Asn Ala Leu Arg Asp Ala Lys Leu
385                 390                 395                 400

Ser Val Asp Asn Leu Asp Glu Val Ile Leu Val Gly Gly Ser Thr Arg
                405                 410                 415

Ile Pro Ser Val Gln Glu Leu Val Lys Lys Ile Thr Gly Lys Asp Pro
                420                 425                 430

Asn Val Thr Val Asn Pro Asp Glu Val Val Ser Leu Gly Ala Ala Val
                435                 440                 445

Gln Gly Gly Val Leu Ala Gly Asp Val Lys Asp Val Val Leu Leu Asp

-continued

```
            450                 455                 460
Val Thr Pro Leu Ser Leu Gly Leu Glu Thr Leu Gly Gly Val Met Thr
465                 470                 475                 480

Lys Ile Ile Pro Arg Asn Thr Thr Leu Pro Thr Ser Lys Ser Glu Val
                485                 490                 495

Phe Ser Thr Ala Ala Asp Gly Gln Thr Ser Val Glu Ile Asn Val Leu
                500                 505                 510

Gln Gly Glu Arg Glu Phe Val Arg Asp Asn Lys Ser Leu Gly Ser Phe
                515                 520                 525

Arg Leu Asp Gly Ile Pro Pro Ala Pro Arg Gly Val Pro Gln Ile Glu
530                 535                 540

Val Lys Phe Asp Ile Asp Ala Asn Gly Ile Leu Ser Val Ala Ala Ile
545                 550                 555                 560

Asp Lys Gly Thr Gly Lys Lys Gln Asp Ile Thr Ile Thr Gly Ala Ser
                565                 570                 575

Thr Leu Pro Lys Asp Glu Val Glu Arg Met Val Glu Glu Ala Asp Lys
                580                 585                 590

Phe Ala Gln Glu Asp Lys Glu Lys Arg Asp Ala Ile Asp Thr Lys Asn
                595                 600                 605

Gln Ala Asp Ser Val Val Tyr Gln Thr Glu Lys Gln Leu Lys Glu Leu
                610                 615                 620

Gly Asp Lys Val Pro Ala Pro Val Lys Glu Lys Val Asp Ala Lys Leu
625                 630                 635                 640

Asn Glu Leu Lys Glu Ala Ile Ala Gly Gly Ser Thr Gln Ser Met Lys
                645                 650                 655

Asp Ala Met Ala Ala Leu Asn Glu Glu Val Met Gln Ile Gly Gln Ala
                660                 665                 670

Met Tyr Asn Gln Gln Pro Asn Ala Gly Ala Ala Gly Pro Thr Pro Gly
                675                 680                 685

Ala Asp Ala Gly Pro Thr Ser Ser Gly Gly Lys Gly Pro Asn Asp Gly
                690                 695                 700

Asp Val Ile Asp Ala Asp Phe Thr Asp Ser Asn
705                 710                 715
```